Figure 1B:
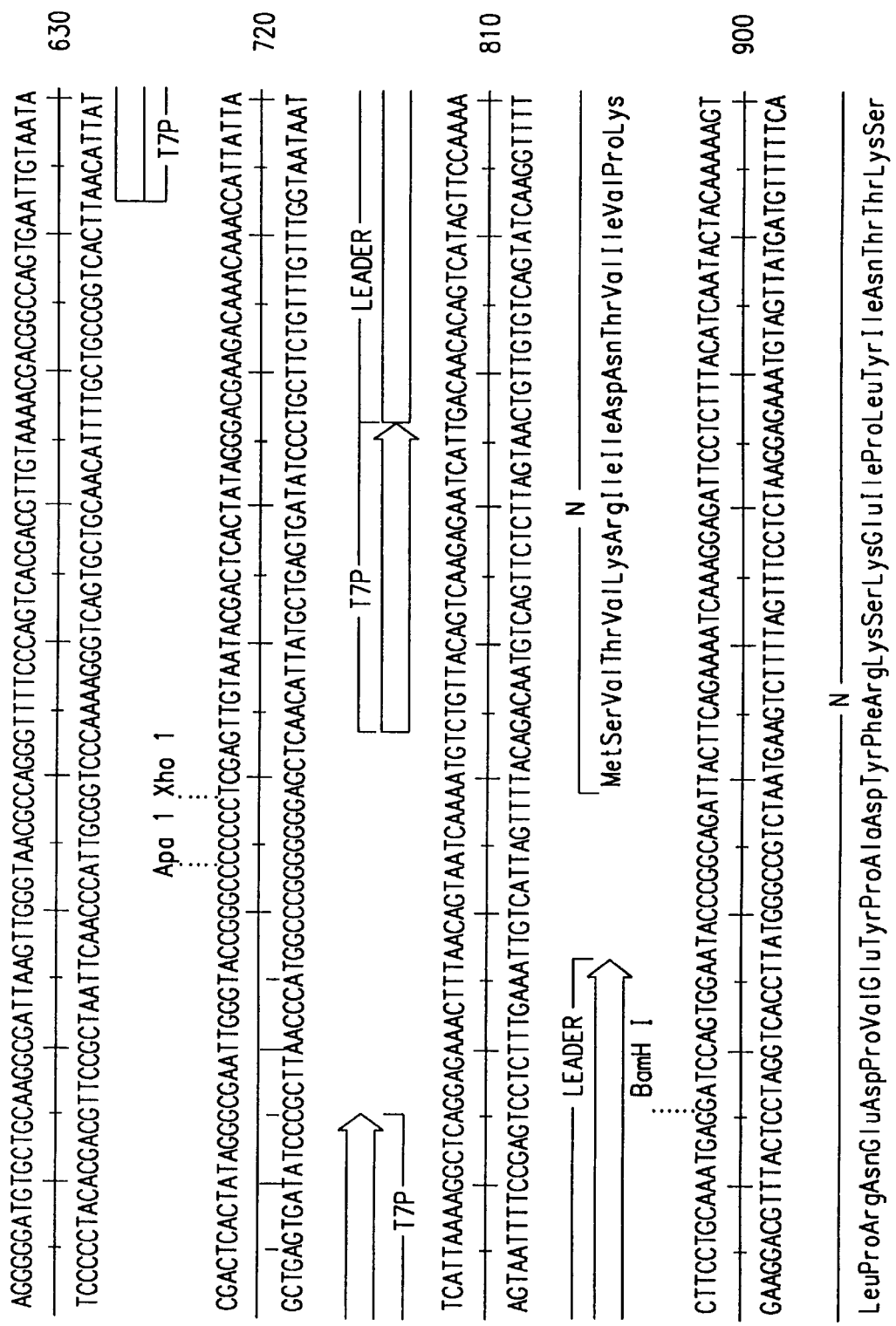

US006168943B1

(12) United States Patent
Rose

(10) Patent No.: US 6,168,943 B1
(45) Date of Patent: Jan. 2, 2001

(54) METHODS FOR MAKING MODIFIED RECOMBINANT VESICULOVIRUSES

(75) Inventor: John K. Rose, Guil

```
CCATATTCTTCCGTCAAAAACCCTGCCTTCCACTTCTGGGGCAATTGACAGCTCTTCTGCTCAGATCCACCAGAGCAAGGAATGCCCGA
                                                                                        ————————+ 1710
GGTATAAGAAGGCAGTTTTTGGGACGGAAGGTGAACTGTCGAGAAGACGAGTCTAGGTGGTCTCGTTCCTTACGGGCT
                                    N
ProTyrSerSerValLysAsnProAlaPheHisPheTrpGlyGlnLeuThrAlaLeuLeuArgSerThrArgAlaArgAsnAlaArg

Bst1107 1                                          Bam H 1
CAGCCTGATGACATTGAGTATACATCTCTTACTACACAGGTTTGTTGTACGCTTATGCAGTAGGATCCTCTGCCGACTTGGCACAACAG
                                                                                        ————————+ 1800
GTCGGACTACTGTAACTCATATGTAGAGAATGATGTGTCCAAACAACATGCGAATACGTCATCCTAGGAGACGGCTGAACCGTGTTGTC
                                    N
GlnProAspAspIleGluTyrThrSerLeuThrThrAlaGlyLeuLeuTyrAlaValGlySerSerAlaAspLeuAlaGlnGln

TTTTGTGTTGGAGATAACAAATACACTCCAGATGATAGTACCGGAGATTGACGACTAATGCACCGCCACAAGGCAGAGATGTGGTCGAA
                                                                                        ————————+ 1890
AAAACACAACCTCTATTGTTTATGTGAGGTCTACTATCATGGCCTCTAACTGCTGATTACGTGGCGGTGTTCCGTCTCTACACCAGCTT
                                    N
PheCysValGlyAspAsnLysTyrThrProAspAspSerThrGlyLeuThrThrAsnAlaProProGlnGlyArgAspValValGlu
```

FIG.1E

```
TGCCTCGGATGGTTTGAAGATCAAAACAGAAAACCGACTCCTGATATGATGCAGTATGCCAAAAGAGCAGTCATGTCACTGCAAGGCCTA
         +         +         +         +         +         +         +         +         +   1980
ACCGAGCCTACCAAACTTCTAGTTTTGTCTTTTGGCTGAGGACTATACTACGTCATACGGTTTTCTCGTCAGTACGTGACGTCCGGAT
          TrpLeuGlyTrpPheGluAspGlnAsnArgLysProThrProAspMetMetGlnTyrAlaLysArgAlaValMetSerLeuGlnGlyLeu
          ────────────────────────── N ─────────────────────────────────────────────────────

AGAGAGAGACAATTGGCCAAGTATGCTAAGTCAGAATTTGACAAATGACCCTATAATTCTCAGATCACCTATTATATATTATGCTACATA
         +         +         +         +         +         +         +         +         +   2070
TCTCTCTCTGTTAACCGTTCATACGATTCAGTCTTAAACTGTTTACTGGGATATTAAGAGTCTAGTGGATAATATATAATACGATGTAT
          ArgGluLysThrIleGlyLysTyrAlaLysSerGluPheAspLys *
          ───────────────────────── N ───────────────────

TGAAAAAACTAACAGATATCATGGATAATCTCACAAAAGTTCGTGAGTATCTCAAGTCCTATTCTCGTCTGGATCAGGCGGTAGGAGAG
         +         +         +         +         +         +         +         +         +   2160
ACTTTTTTGATTGTCTATAGTACCTATTAGAGTGTTTCAAGCACTCAGTCAAGGATAAGAGCAGACTAGTCCGCCATCCTCTC
             MetAspAsnLeuThrLysValArgGluTyrLeuLysSerTyrSerArgLeuAspGlnAlaValGlyGlu
             ──────────────────────── P ────────────────────────────────────────

ATAGATGAGATCGAAGCACAACGAGCTGAAAGTCCAATTATGAGTTGTTCCAAGAGGATGGAAGAGCATACTAAGCCCTCTTAT
         +         +         +         +         +         +         +         +         +   2250
TATCTACTCTAGCTTCGTGTTGCTCGACTTTTCAGGTTAATACTCAACAAGGTTCTCCTACCTTCTCCGTAGATTCGGGAGAATA
          IleAspGluIleGluAlaGlnArgAlaGluLysSerAsnTyrGluLeuPheGlnGluAspGlyValGluHisThrLysProSerTyr
          ──────────────────────── P ────────────────────────────────────────────────────────
```

FIG.1F

FIG. 1G

```
ACTCCCGGATGTATATAAGGTCACTCCAGTGATGAACACACATCCGTCCCAATCAGAAGCAGTATCAGATGTTGGTCTCTCAAAGACA
                                                                                        2700
TGAGGCCTACATATATTCCAGTGAGGTCACTACTTGTGTGTAGGCAGGGTTAGTCTTCGTCATAGTCTACAAACCAGAGAGTTTCTGT
                            |————————————————————— p —————————————————————|
    ThrProAspValTyrLysValThrProValMetAsnThrHisProSerGlnSerGluAlaValSerAspValTrpSerLeuSerLysThr

Xba 1
                                                ····
TCCATGACTTTCCAACCCAAGAAAGCAAGTCTTTCAGCCTCTCACCATATCCTTGGATGAATTGTCTCCATCTAGAGGAGAGTTCATCTCT
                                                                                         2790
AGGTACTGAAAGGTTGGGTTCTTTCGTTCAGAAGTCGGAGAGTGGTATAGGAACCTACTTAACAGAGTAGATCTCCTCTCAAGTAGAGA
                    |————————————————————— p —————————————————————|
    SerMetThrPheGlnProLysLysAlaSerLeuGlnProLeuThrIleSerLeuAspGluLeuPheSerSerArgGlyGluPheIleSer

GTCGGAGGTGACGGAGGATTCATAAAGAGGCCCATCCTGCTCCGGCCTGAGATACAAAAAGTTGTACAATCAGGCCGAGAGTCAAATAT
                                                                                        2880
CAGCCTCCACTGCCTCCTAAGTATTTCTCCGGTAGGACGAGGCCGGACTCTATGTTTTTCAACATGTTAGTCCGGCTCTCAGTTTATA
               |————————————————————— p —————————————————————|
    ValGlyAspGlyArgMetSerHisLysGluAlaIleLeuLeuGlyLeuArgTyrLysLysLeuTyrAsnGlnAlaArgValLysTyr
```

FIG.1H

FIG.11

```
CAGGGAAACGTCCCTTCTACAAATCTTGGCTTTTTTGGGTTCTTCTAATCTAAAGGCCACTCCAGCGGTATTGGCAGATCAAGGTCAAC
       +         +         +         +         +         +         +         +         + 3330
GTCCCTTTGCAGGGAAGATGTTTAGAACCGAAAAAACCCAAGAGATTAGATTTCCGGTGAGGTCGCCATAACCGTCTAGTTCCAGTTG
                                         ————————————— M —————————————
AlaGlyLysArgProPheTyrLysIleLeuAlaPheLeuGlySerSerAsnLeuLysAlaThrProAlaValLeuAlaAspGlnGlyGln

CAGAGTATCACACTCACTGCGAAGGCAGGGCTTATTGCCACATAGGAGAAGACCCCTCCATGCTCAATGTACCAGAGCACTTCA
       +         +         +         +         +         +         +         +         + 3420
GTCTCATAGTGTGAGTGACGCTTCCGTCCCGAATAACGGTGTATCCTCCTTCTGGGGAGGTACGAGTTACATGGTCTCGTGAAGT
                                         ————————————— M —————————————
ProGluTyrHisThrHisCysGluGlyArgAlaTyrLeuProHisArgMetGlyLysThrProProMetLeuAsnValProGluHisPhe
                                                                Sac 1
                                                                ....
GAAGACCATTCAATATAGGTCTTTACAAGGGAACGATTGAGCTCACAATGACCATCTACGATGATGAGTCACTGGAAGCAGCTCCTATGA
       +         +         +         +         +         +         +         +         + 3510
CTTCTGGTAAGTTATATCCAGAAATGTTCCCTTGCTAACTCGAGTGTTACTGGTAGATGCTACTACTCAGTGACTTCGTCGAGGATACT
                                         ————————————— M —————————————
ArgArgProPheAsnIleGlyLeuTyrLysGlyThrIleGluLeuThrMetThrIleTyrAspAspGluSerLeuGluAlaAlaProMet
```

FIG.1J

```
TCTGGGATCATTCAATTCTTCCAAATTTCTCTGATTCAGAGAGAAGGCCTTAATGTTGTTGGCCTGATTGTGTCGAGAAAAGGCATCTGGAG
                                                                                         3600
AGACCCTAGTAAAGTTAAGAAGTTTAAAGACTAAAGTCTCTCTTCCGGAATTACAACCGACTAACAGCTCTTTTCCGTAGACCTC
                                    |————————————————————————————— M —————————————————————————————
                                    IleTrpAspHisPheAsnSerSerLysPheSerAspPheArgGluLysAlaLeuMetPheGlyLeuIleValGluLysLysAlaSerGly
                                                                                                 3690
CGTGGGTCCTGGATTCTATCAGCCACTTCAAATGAGCTAACTTCTAGCTTCTGAACAATCCCGGTTTACTCAGTCTCTCCTAAT

GCACCCAGGACCTAAGATAGTCGGTGAAGTTTACTCGATCAGATTGAAGATCGAAGACTTGTTAGGGGCCAAATGAGTCAGAGAGGATTA
|————————————— M ——————————————|
AlaTrpValLeuAspSerIleSerHisPheLys *
                                                          Mlu 1
                                                          ⋮
TCCAGCCTCTCGAACAACTAATATCCTGTCTTTTCTATCCCTATGAAAAAACTAACAGAGATCGATCTGTTTACGCGTCACTATGAAGT
                                                                                         3780
AGGTCGGAGAGCTTGTTGATTATAGGACAGAAAAGATAGGATACTTTTTTGATTGTCTCTAGCTAGACAAATGCGCAGTGATACTTCA
                                                                              ┌— G —
                                                                               MetLys
```

FIG.1K

```
GCCTTTTGTACTTAGCCTTTTTATTCATTGGGGTGAATTGCAAGTTCACCATAGTTTTTCCACACAAAAGGAAACTGAAAAATG
                                                                                        3870
CGGAAACATGAATCGGAAAATAAGTAACCCACTTAACGTTCAAGTGTATCAAAAGGTGTTGGTTTTTCCTTTTGACCTTTTTAC
      CysLeuLeuTyrLeuAlaPheLuePheIleGlyValAsnCysLysPheThrIleValPheProHisAsnGlnLysGlyAsnTrpLysAsn
                                              G
                                          Swa 1
TTCCTTCTAATTACCATTATTGCCCGTCAAGCTCAGATTTAAATTGGCATAATGACTTAATAGGCACAGCCATACAAGTCAAAATGCCCA
                                                                                        3960
AAGGAAGATTAATGGTAATAACGGGCAGTTCGAGTCTAAATTTAACCGTATTACTGAATTATCCGTGTCGGTATGTTCAGTTTTACGGGT
     ValProSerAsnTyrHisTyrCysProSerSerSerAspLeuAsnTrpHisAsnAspLeuIleGlyThrAlaIleGlnValLysMetPro
                                              G
AGAGTCACAAGGCTATTCAAGCAGATCGAGTTCGATGTGTCATGCTTCCAAATGGGTCACTACTGTGATTTCCGCTGGTATGGACCGAAGT
                                                                                        4050
TCTCAGTGTTCCGATAAGTTCGTCTAGCTCAAGCTACACAGTACGAAGGTTTACCCAGTGATGAACACTAAAGGCGACCATACCTGGCTTCA
      LysSerHisLysAlaIleGlnAlaAspGlyTrpMetCysHisAlaSerLysTrpValThrThrCysAspPheArgTrpTyrGlyProLys
                                              G
```

FIG. 1L

FIG. 1M

```
CCCTGGGAAAGGAGGGCACAGGGTTCAGAAGTAACTACTTTGCTTTATGAAACTGGAGGCAAGGCCTGCAAAATGCAATACTGCAAGCATT
                                                                                          4500
     +         +         +         +         +         +         +         +         +
GGGACCCTTTCCTCCGTGTCCCAAGTCTTCATTGATGAAACGAATACTTTGACCTCCGTTCCGGACGTTTTACGTTATGACGTTCGTAA
                                                G
SerLeuGlyLysGluGlyThrGlyPheArgSerAsnTyrPheAlaTyrGluThrGlyLysAlaCysLysLysMetGlnTyrCysLysHis

GGGGAGTCAGACTCCCATCAGGTCTCTCGTTCCGAGATGGCTGATAAGGATCTCTTTGCTGCAGCCAGATTCCCTGAATGCCCAGAAGGT
                                                                                          4590
     +         +         +         +         +         +         +         +         +
CCCCTCAGTCTGAGGGTAGTCCACAGACCAAGCTCTACCGACTATTCCTAGAGAAACGACGTCGGTCTAAGGGACTTACGGGTCTTCCCA
                                                G
TrpGlyValArgLeuProSerGlyValMetAlaAspLeuPheAlaAlaArgPheProGluCysProGluGly

CAAGTATCTCTGCTCCATCTCAGACCTCCAGTGGATGTAAGTCTAATTCAGGACGTTGAGAGGATCTTGGATTATTCCCTCTGCCAAGAAA
                                                                                          4680
     +         +         +         +         +         +         +         +         +
GTTCATAGAGACGAGGTAGAGTCTGGAGTCCACCTACATTCAGATTAAGTCCTGCAACTCTCCTAGAACCTAATAAGGGAGACGGTTCTTT
                                                G
SerSerIleSerAlaProSerGlnThrSerValAspValSerLeuIleArgIleLeuAspTyrSerLeuCysGlnGlu

CCTGGAGCAAATCAGAGCGGGTCTTCCAATCTCTCCAGTGGATCTCAGCTATCTGCCTCCTAAAAACCAGGAACCGGTCCTGCTTTCA
                                                                                          4770
     +         +         +         +         +         +         +         +         +
GGACCTCGTTTTAGTCTCGCCCAGAAGGTTAGAGAGGTCACCTAGAGTCGATAGAACGAGGATTTTTGGTCCTTGGCCAGGACGAAAGT
                                                G
ThrTrpSerLysIleArgAlaGlyLeuProIleSerProValAspLeuSerTyrLeuAlaProLysAsnProGlyThrGlyProAlaPhe
```

FIG.1N

```
CCATAATCAATGGTACCCTAAAATACTTTGAGACCAGATACATCAGAGTCGATATATTGCTGCTCCAATCCTCTCAAGAATGGTCGGAATGA
                                                                                              4860
GGTATTAGTTACCATGGGATTTTATGAAACTCTGGTCTATAGTCTCAGCTATAACGACGAGGTTAGGAGAGTTCTTACCAGCTTACT
                                        ────G────
ThrIleIleAsnGlyThrLeuLysTyrPheGluThrArgTyrIleArgValAspIleAlaAlaProIleLeuSerArgMetValGluMet

TCAGTGGAACTACCACAGAAAGGAACTGTGGGATGACTGGGCACCATATGAAGACGTGAAATTGGACCCATGAGTTCTGAGGACCA
                                                                                        4950
AGTCACCTTGATGGTGTCTTTCCCTTGACACCCTACTGACCCCTACTGACCCGTGTATACTTCTGCACCTTTAACCTGGGTTACCTCAAGACTCCTGGT
                                                       ────G────
IleSerGlyThrThrThrGluArgLeuArgGluLeuTrpAspAspTrpAlaProTyrGluIleGlyValLeuArgThr

GTTCAGGATATAAGTTCCTTTATACATGATTGGACATGGTATGTTGGACTCCGATCTTCATCTTAGCTCAAGGCTCAGGTGTTCGAAC
                                                                                          5040
CAAGTCCTATATTCAAAGGAAATATGTACTAACCTGTACCATACAACCTGAGGCTAGAAGTAGAATCGAGTTCCGAGTCCACAAGCTTG
                                                   ────G────
SerSerGlyTyrLysPheProLeuTyrMetIleGlyHisGlyMetLeuAspSerAspLeuHisLeuAspSerAspLeuGlnValPheGlu

ATCCTCACATTCAAGACGCTGCTTCGCCAACTTCCTGATGATGAGAGTTTATTTTTGGTGATACTGGGCTATCCAAAATCCAATCGAGC
                                                                                           5130
TAGGAGTGTAAGTTCTGCGACGAAGCGGTTGAAGGACTACTACTCTCAAATAAAAAACCACTATGACCCGATAGGTTTTAGGTTAGCTCG
                                                     ────G────
HisProHisIleGlnAspAlaAlaSerGlnLeuProAspAspGluSerLeuPhePheGlyAspThrGlyLeuSerLysAsnProIleGlu
```

FIG.10

FIG.1P

```
AAGAGAATTCCTGAATCCCGATGAGGCGCATGACGTACTTGAATTCTCCTCTAATTAGTGATGATATTGA
                                                                      +5580
TTCTCTTAAGGACTTAGGGCTACTCGCGTACTGCATGAACTTAGTACGACTAATGTTAAACTTAAGAGGAGATTAATCACTACTATAACT
  ArgGluPheLeuAsnProAspGluArgMetThrTyrLeuAsnHisAlaAspTyrAsnLeuAsnSerProLeuIleAsp

CAATTTGATCAGGAAATTCAATTCTCTTCCGATTCCCTCCGATGGGATAGTAAGAACTGGGATAGTAAGAACTGGGATGAAGTTCTTGAGATGTTAACATCATG
                                                                      +5670
GTTAAACTAGTCCTTTAAGTTAAGAGAAGGCTAAGGGAGCTACACCCTATCATTCTTGACCCTACCTCAAGAACTCTACAATTGTAGTAC
  AsnLeuIleArgLysPheAsnSerLeuProIleProSerMetTrpAspSerLysAsnTrpAspGlyValIleGluMetLeuThrSerCys

TCAAGCCAATCCCCATCTCAACATCTCAGATGCATAAATGGAAGTTGGTTAATGTCTGATAATCATGATGCCAGTCAAGGGTATAG
                                                                      +5760
AGTTCGGTTAGGGTAGAGTTGTAGAGTCTACGTATTTACCTTCAACCAATTACAGACTATTAGTACTACGGTCAGTTCCCATATC
  GlnAlaAsnProIleSerThrSerGlnMetHisLysTrpMetGlySerAspAsnHisAspAlaSerGlnGlyTyrSer
```

FIG. 1Q

```
                                                          Sac 11
                                                          ....
TTTTTACATGAAGTGGACAAAGAGGCAGAAATAACATTTGACGTGGTGGAGACCTTCATCCGGGCTGGGCAACAAACCATTGAATA
      +         +         +         +         +         +         +         +         + 5850
AAAAATGTACTTCACCTGTTTCTCCGTCTTTATTGTAAACTGCACCACCTCTGGAAGTAGGCGCCGACCCCGTTGTTTGGTTAACTTAT
                      └─────────────────────────────┘
 PheLeuHisGluValAspLysGluAlaGluIleThrPheAspValValGluThrPheIleArgGlyTrpGlyAsnLysProIleGluTyr

CATCAAAAAGGAAAGATGGACTGACTGAATTCTCGCTTCATTCAAAATTTGTGTCAAAAGTTTTTTGACTTACACAAGTTGACATTAATCTT
       +         +         +         +         +         +         +         +         + 5940
GTAGTTTTTCCTTTCTACCTGACTGAGTAAGTTTAAGAGCGAATAAACACAGTTTTCAAAAACTGAATGTGTTCAACTGTAATTAGAA
                      └─────────────────────────────┘
 IleLysLysGluArgTrpThrAspSerPheLysIleLeuAlaTyrLeuCysGlnLysPheLeuAspLeuHisLysLeuThrLeuIleLeu

AAATGCTGTCTCTGAGGTGGAATTGCTCAAACGAGTTGAACCGCTCCACCTTAACGAGTTCCGTTTCAGTCTCTTCAAGAGTACTTGCTTGTATACGTC
       +         +         +         +         +         +         +         +         + 6030
TTTACGACAGAGACTCCACCTTAACGAGTTGGCTCAAGGTGGAATTGCTCAACGAGTTTGCTCAAGAAGTCAGAGAAGTCTCATGAACGAACATATGCAG
                      └─────────────────────────────┘
 AsnAlaValSerGluValGluLeuLeuAsnLeuAlaArgThrPheLysGlyLeuValArgArgSerHisGlyThrAsnIleCysArg

GATTAGGGTTCCCAAGGTTCCCAGCTTGGGTCCTACTTTTTATTTCAGAAGGATGGGCTTACTTCAAGAAACTTCTAATGGACCGAAACTTTCT
       +         +         +         +         +         +         +         +         + 6120
CTAATCCCAAGGGTCGAACCCAGGATGAAAATAAAGTCTTCCTACCCGAATGAAGTTCTTTGAACTATAAGATTACCTGGCTTTGAAAGA
                      └─────────────────────────────┘
 IleArgValProSerLeuGlyProThrPheIleSerGluGlyTrpAlaTyrPheLysGlyTrpAlaTyrPheLysLysLeuAspIleLeuMetAspArgAsnPheLeu
```

FIG.1R

```
GTTAATGGTCAAAGATGTGATTATAGGAGGATGCAAACGTGTCTATCCATGTATGTAGAATAGACAACCTGTTCTCAGAGCAAGACAT
                                                                                      6210
CAATTACCAGTTTCTACACTAATATCCCTCCTACGTTTGCCACGATAGGTACCATACATCTTATCTGTTGGACAAGAGTCTCGTTCTGTA
        LeuMetValLysAspValIleIleGlyArgMetGlnThrValLeuSerMetValCysArgIleAspAsnLeuPheSerGlnAspIle
```

```
CTTCTCCCTTCTAAATATCTACAGATTGGAGAGAGGCACGGAAATTTTCTTATGACTTGATTAAAATGGTGAACC
                                                                           6300
GAAGAGGGAAGATTTATAGATGTCTTAACCTCTATTTAACACCTCTCCGTCCCTTTAAAAGAATACTGAACTAATTTTACCACCTTGG
        PheSerLeuLeuAsnIleTyrArgIleGlyAspLysIleValGluArgGlnGlyAsnPheSerTyrAspLeuIleLysMetValGluPro
```

```
GATATGCAACTTGAAGCTGATGAAATAGCAAGAGAATTCCTCCACAATTCCCTCCATTTGAAAATCATATCAAGACTTC
                                                                               6390
CTATACGTTGAACTTCGACTACTTTAATCGTTCCTTAAGGAGGTGTTAAGGAGTAAAACTTTTAGTATAGTTCTGAAG
        IleCysAsnLeuLysLeuMetLysLeuAlaArgGluSerArgProLeuValProGlnPheProHisPheGluAsnHisIleLysThrSer
```

```
TGTTGATGAAGGGCAAAAATTGACCGAGGTATAAGAGATTCCTCCATGATCAGATAATGAGTGTGAAAACAGTGGATCTCACACTGGTGAT
                                                                                              6480
ACAACTACTTCCCGTTTTTAACTGGCTCCATATTCTAAGGAGGTACTAGTCTATTACTCACACTTTTGTCACCTAGAGTGTGACCACTA
        ValAspGluGlyAlaLysIleAspArgGlyIleArgPheLeuHisAspGlnIleMetSerValLysThrValAspLeuThrLeuValIle
```

FIG.1S

```
TTATGGATCGTTCAGACATTGGGGTCATCCTTTTATAGATTATTACACTGGACTAGAAAAATTACATTCCAAGTAACCATGAAGAAAGA
                                                                                         ──┼── 6570
AATACCTAGCAAGTCTGTAACCCAGTAGGAAAATATCTAATAATGTGACCTGATCTTTTAATGTAAGGGTTCATGGTACTTCTTTCT

TyrGlySerPheArgHisTrpGlyHisProPheIleAspTyrTyrThrGlyLeuGluLysLeuHisSerGlnValThrMetLysLysAsp
TATTGATGTGTCATATGCAAAAGCACTTGCAAGTGTTCGAAGTCCAAGATTGTTCTATTTCAACAGTTCATGATGATCATAAAAAGTGGTTCGT
                                                                                         ──┼── 6660
ATAACTACACAGTATACGTTTTCGTGAACGTTCACTAAGTTCAACAGATAAAGTGTCAAGTACTAGTATTTTCACCAAGCA

IleAspValSerTyrAlaLysAlaLeuAlaSerAspLeuAlaArgIleValLeuPheGlnPheAsnAspHisLysLysTrpPheVal
GAATGGAGACTTGCTCCCTCATGATCATCCCTTTAAAAGTCATGTTAAAGAAAATACATGGCCCACAGCTGCTCGAAGTTCAAGATTTTGG
                                                                                         ──┼── 6750
CTTACCTCTGAACGAGGAGTACTAGTAGGGAAATTTTCAGTACAATTCTTTTATGTACCGGGTGTCGACGAGTTCAAGTTCTAAAACC

AsnGlyProHisAspHisProPheLysSerHisValLysAsnThrTrpProThrAlaAlaGlnValGlnAspPheGly
AGATAAATGGCCATGAACTTCCGCTGATTAAATGTTTGAAATGCCCGACTTACTAGACCCATGATAATACTCTGACAAAGTCATTC
                                                                                         ──┼── 6840
TCTATTTACCGGTACTTGAAGGCGACTAATTTACAAACTTTATGGGCTGAATGATCTGGGTAGCTATTATGAGACTGTTTCAGTAAG

AspLysTrpHisGluLeuProLeuIleLysCysPheGluIleProAspLeuLeuAspProSerIleIleTyrSerAspLysSerHisSer
```

FIG.1T

```
AATGAATAGGTCAGAGGTGTTGAAACATGTCCGAATGAATCCGAACACTCCTAGTAAAAGGTGTTGCAGACTATGTTGGACAC
                                                                                    + 6930
TTACTTATCCAGTCTCCACAACTTTGTACACGGTTACTTGTGAGGATAGGATCATTTTCCACAACGTCTGATACAACCTGTG

MetAsnArgSerGluValLeuLysHisValArgMetAsnProSerLysLysValLeuGlnThrMetLeuAspThr

AAAGGCTACCAATTGGAAAGAATTTCTTAAAGAGATTGATGAGAAGGGCTTAGATGATGATCTAATTATTGGTCTTAAAGGAAAGGA
                                                                                    + 7020
TTTCCGATGGTTAACCTTTCTTAAAGAATTTCTCTAACTACTCTTCCCGAATCTACTACTAGATTAATAACCAGAATTCCTTTCCT

LysAlaThrAsnTrpLysGluPheLeuLysGluIleAspGluLysGlyLeuAspAspAspLeuIleIleGlyLeuLysGlu

GAGGGAACTGAAGTGGCAGGTAGATTTTTCTCCCTAATGTCTTGGAAATTGCGAGAATACTTTGTAATTACCGAATATTGATAAAGAC
                                                                                    + 7110
CTCCCTTGACTTCAACCGTCCATCTAAAAGAGGGATTACAGAACCTTTAACGCTCTTATGAAACATTAATGGCTTATAACTATTTCTG

ArgGluLeuLysLeuAlaGlyArgPheSerLeuMetSerTrpLysLeuArgGluTyrPheValIleThrGluTyrLeuIleLysThr

TCATTTCGTCCCTATGTTTAAAGGCCTGACAATGGGCACGGATCTAACTGCAGTCATTAAAAAGATGTTAGATTCCTCATCCGGCCAAGG
                                                                                    + 7200
AGTAAAGCAGGGATACAAATTTCCGGACTGTTACCGCTGCTAGATTGAGGTCAGTAATTTTCTACAATCTAAGGAGTAGGCCGGTTCC

HisPheValProMetPheLysGlyLeuThrMetAlaAspAspLeuThrAlaValIleLysLysMetLeuAspSerSerSerGlyGlnGly
```

FIG.1U

```
ATTGAAGTCATATGAGGCAATTTGCATAGCCAATCACATTGATTACGAAAAATGGAATAACCACCAAAGGAAGTTATCAAACGGCCCAGT
                                                                                        ┼ 7290
TAACTTCAGTATACTCCGTTAAACGTATCGGTTAGTGTAACTAATGCTTTTTACCTTATGGTGGTTTCCTTCAATAGTTTGCCGGGTCA

LeuLysSerTyrGluAlaIleCysIleAlaAsnHisIleAspTyrGluLysTrpAsnAsnHisGlnArgLysLeuSerAsnGlyProVal

GTTCCGAGTTATGGGCCAGTTCTTAGGTTATCCATCCTTAATCGAGAGAACTCATGAATTTTTGAGAAAAGTCTTATATACTACAATGG
                                                                                        ┼ 7380
CAAGGCTCAATACCCGTCAAGAATCCAATAGGCAGTTCAAGAATTAGTCTCTGAGTACTTAAAAAACTCTTTTCAGAATATATGATGTTACC

PheArgValMetGlyGlnPheLeuGlyTyrProSerLeuIleGluArgThrHisGluPheGluLysSerLeuIleTyrTyrAsnGly

AAGACCAGACTTGATGCGTGTTCACACAACAACACTGATCAATTCAACCTCCAACGAGTTTGTTGGCAAGGACAAGAGGGTGGACTGGA
                                                                                        ┼ 7470
TTCTGGTCTGAACTACGCACAAGTGTTGTTGTTGACTAGTTAAGTTGGAGGGTGCTCAAACAACCGTTCCTGTTCTCCCACCTGACCT

ArgProAspLeuMetArgValHisAsnAsnThrLeuIleAsnSerThrSerGlnArgValCysTrpGlnGlyGlyLeuGlu

AGGTCTACGGCAAAAGGATGGAACATGGACTATCCTCAATACTACTGGTTATTCAAAGAGAGGCTAAAATCAGAAACACTGCTGTCAAAGTCTTGGC
                                                                                        ┼ 7560
TCCAGATGCCGTTTTTCCTACCTTGTACCTGATAGGAGTTAGATGACCAATAAGTTCTCTCCGATTTTAGTCTTTGTGACGACAGTTCAGAACCG

GlyLeuArgGlnLysGlyTrpThrIleLeuAsnLeuValIleGlnArgGluAlaLysIleArgAsnThrAlaValLysValLeuAla
```

FIG.1V

```
ACAAGGTGATAATCAAGTTATTTGCACACAGTATAAAACGAGAAATCGAGAAGAACGTTGTAGAATTACAGGGTGCTCTCAATCAAATGGT
                                                                                        7650
TGTTCCACTATTAGTTCAATAAACGTGTGTCATATTTGCTCTTCTTTGCAACATCTTAATGTCCCACGAGAGTTAGTTTACCA
         GlnGlyAspAsnGlnValIleCysThrGlnTyrLysThrLysLysSerArgAsnValValGluLeuGlnGlyAlaLeuAsnGlnMetVal
TTCTAATAATGAGAAAATTATGACTGCAATCAAAATAGGGACAGGAAGTTAGGACTTTTGATAAATGACGATGAGACTATGCAATCTGC
                                                                                        7740
AAGATTATTACTCTTTAATACTGACGTTAGTTTTATCCCTGTTTTTATCCCGTCCCTTCAATCCTGAAAACTATTTACTGCTACTCTGATACGTTAGACG
         SerAsnAsnGluLysIleMetThrAlaIleLysIleGlyThrGlyLysLeuLeuLeuIleGlyLeuGlyLysLeuLeuLeuIleAsnAspAspGluThrMetGlnSerAla
AGATTACTTGAATTATGGAAAAATACCGATTTCCGTGGAGTGATTAGAGGGTTAGAGACCAAGATGGTCACCGAGTGACTTGTGTCAC
                                                                                        7830
TCTAATGAACTTAATACCTTTTATGGCTAAAAGGCACCTCACTAATCTCCCAATCTCTGGTTCTCTACCAGTGCTCACTGAACACAGTG
         AspTyrLeuAsnTyrGlyLysIleProIlePheArgGlyValIleArgGlyLeuGluThrLysArgGlyLeuGluThrLysArgTrpSerArgValThrCysValThr
```

FIG.1W

```
Sac 1
CAATGACCAAATACCCACTTGTGCTAATATAATGAGCTCAGTTTCCACAAATGCTCTCACCGTAGCTCATTTGCTGAGAACCCAATCAA
                                                                                      +7920
GTTACTGGTTTATGGGTGAACACGATTATTACTCGAGTCAAAGGTGTTTACGAGAGTGGCATCGAGTAAAACGACTCTTGGGTTAGTT
              AsnAspGlnIleProThrCysAlaAsnIleMetSerSerValSerThrAsnAlaLeuThrValAlaHisPheAlaGluAsnProIleAsn
TGCCATGATACAGTACAATTATATTTGGGACATTTGCTAGACTCTCTGTTGATGATGCATGACAACTACTACTAGGACGAGAAGCAGTTAGTAACATACTTCA
                                                                                      +8010
ACGGTACTATGTCATGTTAATAAACCCTGTAAACGATCTGAGAACACTACTACGTACTGATGATGATCCTGCTACGTACAATCATTGTATGAAGT
                      AlaMetIleGlnTyrAsnTyrPheGlyThrPheAlaArgLeuLeuMetMetHisAspProAlaLeuArgGlnSerLeuTyrGluVal
TCAAGATAAGATACCCGGGCTTGCACAGTTCTCTACTTTCAAATAGCCATGTTGTATTTGGACCCTTCCATTGGAGGAGTGTCGGGCATGTC
                                                                                      +8100
AGTTCTATTCTATGGCCCGAACGTGTCAAGAGAAGTTTATGCGGTACAACATAAACCTGGGAAGGTAACCTCCTCACAGCCCGTACAG
            GlnAspLysIleProGlyLeuHisSerSerThrPheLysTyrAlaMetLeuTyrLeuAspProSerIleGlyGlyValSerGlyMetSer
```

FIG.1X

```
TTTGTCCAGGTTTTTGATTAGAGCCTTCCCAGATCCCGTAACAGAAAGTCTCTCATTCTGGAGATTCATCCATGTACATGCTCGAAGTGA
                                                                                        ──────── 8190
AAACAGGTCCAAAAACTAATCTCGGAAGGGTCTAGGGCATTGTCTTTCAGAGAGTAAGACCTCTAAGTAGTACATGTACGAGCTTCACT

LeuSerArgPheLeuIleArgAlaPheProAspProValThrGluSerPheTrpArgPheIleHisValHisAlaArgSerGlu
                                                                 └─────────┘
                                                                    Bsg 1

GCATCTGAAGGAGATGAGTGCAGTATTTGGAAACCCCGAGATAGCCAAGTTTCGAATAACTCACATAGAGAAGCTAGTAGAAGATCCAAC
                                                                                        ──────── 8280
CGTAGACTTCCTCTACTCACGTCATAAACCTTTGGGGCTCTATCGGTTCAAAGCTTATTGAGTATCTGTTCGATCATCTTCTAGGTTG

HisLeuLysGluMetSerAlaValPheGlyAsnProGluIleAlaLysPheArgIleThrHisIleAspLysLeuValGluAspProThr

CTCTCTGAACATGCTATGGGAATGAGTCCAGCGAACTTGTTAAAGACTGAGTTAAAAAATGCTTAATCGAATCAAGACAAACCATCAG
                                                                                        ──────── 8370
GAGAGACTTGTAGGATACCCTTACTCAGGTCGCCTTGAACAATTTCTGACTCAAATTTTTACGAATTAGCTTAGTTCTGTTTGGTAGTC

SerLeuAsnIleAlaMetGlyMetSerProAlaAsnLeuLeuLysThrGluValLysLysCysLeuIleGluSerArgGlnThrIleArg
```

FIG.1Y

```
GAACCAGGTGATTAAGGATGCAACCATATATTTGTATCATGAAGAGGATCGGCTCAGAAGTTTCTTATGGTCAATAAATCCTCTGTTCCC
                                                                                          8460
CTTGGTCCACTAATTCCTACGTTGGTATATAAACATAGTACTTCCTCTAGCCGAGTCTTCAAAGAATACCAGTTATTAGGAGACAAGG
        AsnGlnValIleLysAspAlaThrIleTyrLeuTyrHisGluAspArgLeuArgSerPheLeuTrpSerIleAsnProLeuPhePro

TAGATTTTAAGTGAATTCAAATCAGGCACTTTTTTGGGAGTCGCAGACGGGCTCATCAGTAGTCTATTTCAAAATTCTCGTACTATTCGGAA
                                                                                          8550
ATCTAAAAATTCACTTAAGTTTAGTCCGTGAAAAAACCCTCAGCAGCGTCTGCCCGAGTAGTCAGATAAAGTTTTAAGAGCATGATAAGCCTT
        ArgPheLeuSerGluPheLysSerGlyThrPheLeuGlyValAlaAspGlyLeuIleSerLeuPheGlnAsnSerArgThrIleArgAsp

CTCCTTTAAGAAAAGTATCATAGGGAATTGATTGTGAGGAGTATCCTCTTTGACACATTTAGGAAACTTCATT
                                                                                          8640
GAGGAAATCTTTTCATAGTATCCCTTAACCTACTAAACTAACACTCCACTCCATAGGAGAAACTGTAAATCCCTTGAAGTAAA
        SerPheLysLysTyrHisArgGluLeuAspAspLeuIleValArgSerGluValSerSerLeuThrHisLeuGlyLysLeuHisLeu

GAGAAGGGGATCATGTAAAATGTGGACATGTTCAGCTACTCATGCTGACACATTAAGATACAAATCCTGGGGCCGTACAGTTATTGGGAC
                                                                                          8730
CTCTTCCCCTAGTACATTTTACACCTGTACAAGTCGATGAGTACGACTGTGTAATTCTATGTTTAGGACCCGGCATGTCAATAACCCTG
        ArgArgGlySerCysLysMetTrpThrCysSerAlaThrHisAlaAspThrLeuArgTyrLysSerTrpGlyArgThrValIleGlyThr
```

```
GGACTCAAGTATGGACTACACGCCCCCAGATGTATCCCATGTGCTGAAGACATGGAGGAATGGGGAAGGTTCGTGGGGACAAGAGATAAA
     |         |         |         |         |         |         |         |         |
CCTGAGTTCATACCTGATGTGCGGGGGTCTACATAGGGTACGACTTCTGTACCCCTTCCAAGCACCCGTCTCTATTT                9450

AspSerMetAspTyrThrProProAspValSerHisValLeuLysThrTrpArgAsnGlyGluGlyLysSerTrpGlyGlnGluIleLys

ACAGATCTATCCTTTAGAAGGGAATTGGAAGCACCTGCTGAGCAATCCTATCAAGTCGGCAGATGTATAGGTTTTCTATATGG
     |         |         |         |         |         |         |         |         |
TGTCTAGATAGGAAATCTTCCCTTAACCTTCGTGGACGACTCGTTAGGATAGTTCAGCCGTCTACATATCCAAAGATATACC            9540

GlnIleTyrProLeuGluGlyAsnTrpLysAsnLeuAlaAlaProAlaGluGlnSerTyrGlnValGlyArgCysIleGlyPheLeuTyrGly

AGACTTGGGCGTATAGAGAAATCTCTACTCATGCCGAGGACAGTTCTCTATCTATACAAGGTGTATTAGAGGTCGAGGTTTCTT
     |         |         |         |         |         |         |         |         |
TCTGAACCCGCATATCTCTTTAGAGATGAGTACGGCTCCTGTCAAGAGATAGATATGTTCCACATAATCTCCAGTCCAAAGAA         9630

AspLeuAlaTyrArgLysSerThrHisAlaGluAspSerSerLeuPheProLeuSerIleGlnGlyArgIleArgGlyPheLeu
```

FIG. 1C1

FIG.1D1

```
ATGCCGTCTAATTGAAAAGGGAAAATACAGATCACATTATTCACAATTATGGTTATTCTCAGATGTCTTATCCATAGACTTCATTGGACC
                                                                                        9990
TACGGCAGATTAACTTTTCCCTTTTATGTCTAGTGTAATAAGAGTCTACAGAATAGGTATCTGAAGTAACCTGG
CysArgLeuIleGluLysGlyLysTyrArgSerHisTyrSerGlnLeuTrpLeuPheSerAspValLeuSerIleAspPheIleGlyPro

ATTCTCTATTTCCACCCTCTTGCAAATCCTATACAAGCCATTTTTATCTGGAAAGATAAGAGTGAGAGACTGGCAAATCT
                                                                                       10080
TAAGAGATAAAGGTGGGAGAACGTTTAGGATATGTTCGGTAAAAATAGACCCTTTCTATTCTTACTCAACTCTCGACCGTTTAGA
PheSerIleSerThrThrLeuLeuGlnIleLeuTyrLysProPheLeuSerGlyLysAspLysAsnGluLeuArgGluLeuAlaAsnLeu

TTCTTCATTGCTAAGATCAGAGAGGGGTGAGGTCCTCCCCACCCTTCTGTACACTTTAAGAAGTGGTTCCTGTATAATAACAGGTCTCCTTTAGTC
                                                                                        10170
AAGAAGTAACGATTCTAGTCTCTCCCCACTCCAGGAGGGGTGGGAAGACATGTGAAATTCTTCACCAAGGAGATATTATTGTGTCCAGAGGAAATCAG
SerSerLeuLeuArgSerGlyGluGlyTrpGluGlyTrpAspIleHisValLysPhePheThrLysAspIleLeuLeuCysProGluGluIleArg

ACATGCTTGCAAGTTCGGGATTGCTAAGGATAATAATAAAGACATGAGCTATCCCCCTTGGGGAAGGAATCCAGAGGGACAATTACAAC
                                                                                       10260
TGTACGAACGTTCAAGCCCTAACGATTCCTATTATTATTTCTGTACTCGATAGGGGAACCCCTTCCCTTAGTCTCCCTGTTAATGTTG
HisAlaCysLysPheGlyIleAlaLysAspAsnAsnLysAspMetSerTyrProProTrpGlyArgGluSerArgGlyThrIleThrThr
```

FIG.1E1

FIG.1F1

Nar 1
CATGCGGAGGCGCCTCTCCTGAGCCCCCAGTGCCCTAGAAACTTTAGGAGGAGATAAATCGAGATGTGTAAATGTGAAACATGTTGGA
GTACGGCTCCCGGGAGAGGACTCGGGGGGGCTCACGGGATCTTTGAAATCCTCCTCTATTTAGCTCTACACATTTACCACTTTGTACAACCCT
———————————————————————————————————
MetArgGlyAlaSerProGluProProSerAlaLeuGluThrLeuGlyGlyAspLysSerArgCysValAsnGlyGluThrCysTrpGlu
ATATCCATCTGACTTATGTGACCCAAGGACTTGGGACTATTTCCTCCGACTCAAAGCAGGCTTGGGCCTTCAAATTGATTTAATTGTAAT
TATAGGTAGACTGAATACACTGGGTTCCTGAACCCTGATAAAGGAGGCTGAGTTTCGTCCGAACCCGAAGTTTAACTAAATTAACATTA
———————————————————————————————————
TyrProSerAspLeuCysAspProArgThrTrpAspTyrPheLeuArgLeuLysAlaGlyTyrLeuGlyLeuGlnIleAspLeuIleValMet
GGATATGGAAGTTCGGGGATTCTTCTACTAGCCTGAAAATTGAGACGAATGTTAGAAATTATGTGCACCGGATTTTGGATGAGCAAGGAGT
CCTATACCTTCAAGCCCTAAGAGAGATCGACTTTTAACTCTGCTTACAATCTTTAATACGGTGGCCTAAAACCTACTCGTTCCTCA
———————————————————————————————————
AspMetGluValArgAspSerSerThrSerLeuLysIleGluThrAsnValArgAsnTyrValHisArgIleLeuAspGluGlnGlyVal

FIG.1G1

```
                                                                    Sal 1
TTTAATCTACAAGACTTATGGAACATATATTTGTGAGAGCGAAAAGAATGCAGTAACAATCCTTGGTCTCCCATGTTCAAGACACGGTCGACTT
                                                                                              10890
AAATTAGATGTTCTGAATACCTTGTATATAAACACTCTCGCTTTTCTTACGTCATTGTTAGGAACCAGGTACAAGTTCTGCCAGCTGAA
          LeuIleTyrLysThrTyrIleCysGluSerGluLysAsnAlaValThrIleLeuGlyProMetPheLysThrValAspLeu
AGTTCAAACAGAATTTAGTAGTTCTCAAACGTCTGAAGTATATGGTATGTAAAGGTTTGAAGAAATTAATCGATGAACCCAATCCCGA
                                                                                          10980
TCAAGTTGTCTTAAATCATCAAGAGTTTGCAGACTTCATATATACCATACATTTCCAAACTTCTTAATTAGCTACTGGGTTAGGGCT
          ValGlnThrSerSerGlnThrSerGlnValPheSerSerGluValCysLysGlyIleLeuLysLysLeuIleAspGluProAsnProAsp
TTGGTCTCTTCCATCAATGAATCCTGGAAAAACCTGTACCATTCCAGTCATCCAGACAGGAATTTGCCAGAGCAAAGAAGGTTAGTACATA
                                                                                              11070
AACCAGAGGTAGTTACTTAGGACCTTTTTGGACATGCCTAAGGTCAGTAGTCTGTGCCTTAAACGTCTCGTTTCTTCCAATCATGTAT
          TrpSerSerIleAsnGluSerTrpLysAsnLeuTyrAlaPheGlnSerSerGluGlnPheAlaArgAlaLysLysValSerThrTyr
```

FIG.1H1

```
CTTTACCTTGACAGGTATTCCCTCCCAATTCATTCCTGATCCTTTTGTAAACATTGAGACTATGCTACAAATATTCGGAGTACCCACGGG
                                                                                        ----+ 11160
GAAATGGAACTGTCCATAAGGGAGGGTTAAGTAAGGACTAGGAAAACATTTGTAACTCTGATACGATGTTTATAAGCCTCATGGGTGCCC
         PheThrLeuThrGlyIleProSerGlnPheIleProAspProPheValAsnIleProAspProPheValAsnIlePheGlyValProThrGly
TGTGTCTCATGGGCTGCCTTAAAATCATCTGATAGACCTGCAGATTTATTGACCATTAGCCTTTTTTATATGGCATTATATCGTATTA
                                                                                       ----+ 11250
ACACAGAGTACGCCGACGGAATTTTAGTAGACTATCTGGACGTCTAAATAACTGGTAATCGGAAAAATATACCGTAATATAGCATAAT
         ValSerHisAlaAlaLeuLysSerSerAspArgProAlaAspLeuLeuThrIleSerLeuPheTyrMetAlaIleIleSerTyrTyr
TAACATCAATCATCATATCAGAGTAGGACCGATACCTCCGAACCCCATCAGATGAATTGCACAAAATGTGGGGATCGCTATAACTGGTAT
                                                                                          ----+ 11340
ATTGTAGTTAGTATAGTCTCATCCTGGCTATGGAGGCTTGGGGGTAGTCTACCTTAACGTGTTTTACACCCCTAGGATATTGACCATA
         AsnIleAsnHisIleArgValGlyProIleProProAsnProSerAspGlyIleAlaIleAlaGlnAsnValGlyIleAlaIleThrGlyIleIle
```

FIG.111

FIG. 1J1

```
TCGTACAGTGGATAATCATTTGAAATGGTCAAATTTGCAAGAAACACAGGAATGATTGAATGATCAATAGACGAATTCAAAGAAGA
                                                                                        ——+—— 11700
AGCATGTCACCTATTAGTAAACTTTACCAGTTTAAACGCTTCTTTGTCCTTACTAACTTACCTAGTTATCTGCTTAAAGTTTCTCT

ArgThrValAspAsnHisLeuLysTrpSerAsnLeuArgArgAsnThrGlyMetIleGluTrpIleAsnArgArgIleSerLysGluAsp
CCGGTCTATACTGATGTTGAAGAGTGACCTACACGAGAAAACTCTTGGAGAGATTAAAAAATCATGAGAGGACTCCAAACTTTAAGTAT
                                                                                        ——+—— 11790
GGCCAGATATGACTACAACTTCTCACTGGATGTGCCTCCTTTTGAGAACCTCTCTAATTTTTTAGTACTCTCCTGAGGTTTGAAATTCATA
                                                ┌──────────────────────────────
         ArgSerIleLeuMetLeuLysSerAspLeuHisGluGluAsnSerTrpArgAsp *
         Afl 11
GAAAAAAACTTTGATCCTTAAGACCCTCTCTGTGGTTTTATTCTGGTTTGTGGTCTTCGTGGGTCGGCATGGCATCTCCACCT
                                                                                        ——+—— 11880
CTTTTTTGAAACTAGGAATTCTGGGAGAACACCAAAATAAGACCAAAACACCAGAAGCACCAGCCGTACGCTAGAGGTGGA
                                                              ────── RBZ
Rsr 11      Tth 1                                 Apa 1 Sac 11
CCTCGCGGTCCGACCTGGGCATCCGAAGGAGGACGTCGTCCACTCGGAGTGCTAAGGGAGGGCCCCGCGGGGCTGCTAACAAAGCCCG
                                                                                        ——+—— 11970
GGAGCGCCAGGCTGGACCCGTAGGCTTCCTCCTGCAGCAGGTGAGCCTCACGATTCCCTCCCGGGGCGCCCCGACGATTGTTTCGGGC
```

FIG.1K1

```
                                                                                                    ─ T7 Ter ─
─ RBZ ─
AAAGGAAGCTGAGTTGGCTGCTCCACCGCTGAGCAATAAACTAGCATAAACCCCTTGGGGCCTCTAAACGGGTCTTGAGGGGTTTTTTGCT
                                                                                                                    12060
      +         +         +         +         +         +         +         +         +
TTTCCTTCGACTCAACGACGACGGTGGCGACTCGTTATTGATCGTATTTGGGGAACCCCGGAGATTTGCCCAGAACTCCCCAAAAAACGA

─ T7 Ter ─
                            Spe 1           Sac 1
GAAAGGAGGAACTATATCCGGATCGAGACCTCGATACTAGTGCGGTGGAGCTCCAGCTTTTGTTCCCTTTAGTGAGGGTTAATTTCGAGC
                                                                                                                    12150
      +         +         +         +         +         +         +         +         +
CTTTCCTCCTTGATATAGGCCTAGCTCTGGAGCTATGATCACGCCACCTCGAGGTCGAAAACAAGGGAGTCGAAAATCACTCCCAATTAAAGCTCG
    ── T7 Ter ──

TTGGGGTAATCATGTCATAGCTGTTTCCTGTGTGAAATTGTTATCCGCTCACAATTCCACACAACATACGAGCCGGAAGCATAAAGTGT
                                                                                                                    12240
      +         +         +         +         +         +         +         +         +
AACCCGCATTAGTACCAGTATCGACAAAGGACACACTTTAACAATAGGCGAGTGTTAAGGTGTGTTGTATGCTCGGCCTTCGTATTTCACA

AAAGCCTGGGGTGCCTAATGAGTGAGCTAACTCACATTAATTGCGTTGCCTCACTGCCCGCTTTCCAGTCGGGAAACCTGTCGTGCCAG
                                                                                                                    12330
      +         +         +         +         +         +         +         +         +
TTTCGGACCCCACGGATTACTCACTCGATTGAGTGTAATTAACGCAACGGAGTGACGGGCGAAAGGTCAGCCCTTTGGACAGCACGGTC

CTGCATTAATGAATCGGCCAACGCGCGGGGAGAGGCGGTTTGCGTATTGGGCGCTCTTCCGCTTCCTCGCTCACTGACTCGCTGCGCTCG
                                                                                                                    12420
      +         +         +         +         +         +         +         +         +
GACGTAATTACTTAGCCGGTTGCGCGCCCCTCTCCGCCAAACGCATAACCCGCGAGAAGGCGAAGGAGCGAGTGACTGAGCGACGCGAGC
```

FIG.1L1

```
GTCGTTCGGCTGCGGGGAGCGGTATCAGCTCACTCAAAGGCGGGTAATACGGTTATCCACAGAATCAGGGGATAACCGGAGAAAGAACATG
                                                                                          12510
CAGCAAGCCGACCCGCCCTCGCCATCGAGTGAGTTTCCGCCATTATGCCAGTTCTTAGTCCCCTATTGCGTCCTTCTTTCTGTAC
                                                                                          12600
TGAGCAAAAGGCCAGCAAAGGCCAGGAACCGTAAAAAGGCCGCGTTGCTGGCGTTTTTCCATAGGCTCCGCCCCCCTGACGAGCATCAC

ACTCCGTTTTCCGCGTCGTTTCCGGTCCTTGGCCATTTTTCCGGGTCCAACGCGCAAAAGTATCCGAGGCGGGACTGCTCGTAGTG
                                                                                          12690
AAAAATCGACGCTCAAGTCAGAGGTGGCGAAACCCGACACAGGACTATAAAGATACCAGGCGTTTCCCCCTGGAAGCTCCCTGTGCGCTCT

TTTTAGCTGCGAGTTCAGTCTCCACCGCCTTGGGCTGTCCTGATATTTCTATGGTGTCCGCAAAGGGGGACCTTCGAGGGAGCACGCGAGA
                                                                                          12780
CCTGTTCCGACCCTGCCGCTTACCGGATACCTGTCCGCCTTTCTCCCTTCGGGAAGCGTGGCGCTTTCTCATAGCTCACGCTGTAGGTAT

GGACAAGGCTGGGACGCTGGGAATGGCCTATGGCCACAGCCCTTCGCACCGGGAAAGAGTATCGAGTGCCACATCCATA
                                                                                          12870
CTCAGTTCGGTGTAGGTCGTTCGCTCCAAGCTGGGCTGTGTGCACGAACCCCCCGTTCAGCCCGACCGCTGCGCCTTATCCGGTAACTAT

GAGTCAAGCCACATCCAGCAAGCGAGTTCGACCGGCTGCTTGGGGCAAGTCGGCTGGCGACGCGGAATAGGCCATTGATA
                                                                                          12960
CGTCTTGAGTCCAACCCGGTTAAGACACGACTTATCGCCACTGGCAGCAGCCACTGGTAACAGGATTAGCAGAGCGAGGTATGTAGGCGGT

GCAGAACTCAGGTTGGGCCATTCTGTGCTGAATAGCGGTGCGTCGTGACCATTGTCCTAATCGTCTCGCTCCTCCATACATCCGCCA
```

FIG.1M1

```
GCTACAGAGTTCTTGAAGTGGTGGCCCTAACTACGGCCTACACTAGAAGGACAGTATTTGGTATCTGCGCTCTCGCTGAAGCCAGTTACCTTC
                                                                                              13050
CGATGTCTCAAGAACTTCACCACCGGATTGATGCCGATGTCTTCCTGTCATAAACCATAGACGCGAGACGACTTCGTCAATGAAG

GGAAAAGAGTTGGTAGCTCTTGATCCGGCAAACAACACCGGCTGGTACGGCGGTGGTTTTTTTGTTTGCAAGCAGCAGATTACCCGCAGA
                                                                                              13140
CCTTTTTCTCAACCATCGAGAACTAGGCCGTTTGTTTGGTGGGACCATCCGCCACCAAAAAACAAACGTTCGTCGTCTAATGCGCGTCT

AAAAAAGGATCTCAAGAAGATCCTTTGATCTTTTCTACGGGGTCTGACGCTCAGTGGAACGAAAACTCACGTTAAGGGATTTTGGTCATG
                                                                                              13230
TTTTTCCTAGAGTTCTTCTAGGAAACTAGAAAAGATGCCCCAGACTGCGAGTCACCTTGCTTTGAGTGCAATTCCTAAAACCAGTAC

AGATTATCAAAAGGATCTTCACCTAGATCCTTTTAAATTAAAAATGAAGTTTTAAATCAATCTAAAGTATATATGAGTAAACTTGGTCT
                                                                                              13320
TCTAATAGTTTTTCCTAGAAGTGGATCTAGGAAATCGCTAGCAGGCACCTATCTCAGCGATCGTCTATTCGTTCATCCATAGTTAGATTTCATATATACTCATTGAACCAGA

GACAGTTACCAATGCTTAATCAGTGAGGGCTTACCATCTGGCCCCAGTGCTGCAATGATACCGCGAGACCCACGCTCACCGGCTCCAGATTTATCAGTAG
                                                                                              13410
CTGTCAATGGTTACGAATTAGTCACTCCGTGGATAGAGTCGCTAGACAGATAAAGCAAGTAGGTATCAACGGACTGAGGGCAGCACATC

ATAACTACGATACGGGAGGGCTTACCGAGACCCACGCTCACCGGCTCCAGATTTATCAGCA
                                                                                              13500
TATTGATGCTATCGCCTCCCGAATCGGTAGACCGGGTCACGACGTTACTATGGGCGTCTGGTGCGAGTGGCCGAGTTCTAAATAGTCGT

ATAAACCAGCCAGCCCGGAAGGGCCGAGCCCGAGCAGAAGTGCCTCGCAACTTATCCCTCCATCCAGTCTATTAATTGTTGCCGGGAAGCT
                                                                                              13590
TATTTGGTCGGCCTTCCCCGGCTCTTCCACCAGGACGTTGAAATAGGCGGAGGTAGGTCAGATAATTAACAACGGCCCTTCGA
```

FIG.1N1

```
AGAGTAAGTAGTTCGGCCAGTTAATAGTTTGCGCAACGTTGTTGCCATTGCTACACGGCATCGTCGTGGTCACCCTCGTCGTTTGGTATGGCT
                                                                                                        13680
TCTCATTCATCAAGCGGTCAATTATCAAACGCGTTGCAACAACGGTAACGATGTCCGTAGCACCACAGTGCCGAGCAGCAAACCATACCGA
                                                                                                        13770
TCATTCAGCTCCGGTTCCCAACGATCAAGGCGAGTTACATGATCCCCATGTGTGCAAAAAGCGGTTAGCTCCTTCGGTCCTCCGATC
                                                                                                        13860
AGTAAGTCGAGGCCAAGGTTGCTAGTTCCGCTCAATGTACTAGGGGTACAACACGTTTTTTCGCCAATCGAGGAAGCCAGGAGGCTAG
                                                                                                        13860
GTTGTCAGAAGTAAGTTGGCCGCAGTGTTATCACTCATGGTTATGGCAGCACTGCATAATTCTCTTACTGTCATGCCATCCGTAAGATGC

CAACAGTCTCTTCATTCAACCGGGTCACAATAGTGAGTACCAATACCGTCGTGACGTATTAAGAGAATGACAGTAGGCATTCTACG
                                                                                                        13950
TTTCTGTGACTGGTGAGTACTCAACCAGTCATTCTGAGTAAGACTCTTATCACATACGCCGTCTTGCCCGGTCAATACGGGAT

AAAAGACACTGACCACTCATGAGTCAGAACTTTAAAAGTGCTCATCATTGGAAAACGTTCTTCCGGGGCGAAAACTCTCAAGGATCTTACCGCTGTTG
                                                                                                        14040
AATACCCGCCACATAGCAGAACTTTAAAAGTGCTCATCATTGGAAAACGTTCTTCCGGGGCGAAAACTCTCAAGGATCTTACCGCTGTTG

TTATGGCGGGTGTATCGTCTTGAACCCAGTAGTAACCTTTTGCACGAGTAGTAACCTTTTGCAAGAAGCCCCGTTTCGAAGTTCCTAGAATGGCACAAC
                                                                                                        14130
AGATCCAGTTCGATGTAACCCACTCGTGCACCAACTGATCTTCAGCATCTTTACTTTCACCAGGCGTTCGAGCAGCCAAAGACGGA

TCTAGGTCAAGCTACATTGGGTGAGCACGTGGGTTGACTAGAAGTCGTAGAAAATGAAGTGGTCGCAAAGACCCACCACTCGTTTTTGTCCT
```

FIG.101

AGGCAAAATGCCGCAAAAAAGGGAATAAGGGGCCACACGGAAATGTTGAATACTCATACTCTTCCTTTTCAATATTATTGAAGCATTTAT
                                                                                        14220
TCCGTTTTACGGGGTTTTTCCCTTATCCCGCTGTGCCTTTACAACTTATGAGTATGAGAAGGAAAAAGTTATAATAACTTCGTAAATA
                                                                                        14310
CAGGGTTATTGTCTCATGACGGGATACATATTTGAATGTATTTAGAAAAATAAACAAATAGGGGTTCCGCCACATTTCCCCGAAAAGTG

GTCCCAATAACAGAGTACTCGCCTATGTATAAACTTACATAAATCTTTTTATTGTTTATCCCCAAGGCGCGTGTAAAGGGGCTTTTCAC
C
+ 14311
G

FIG. 1P1

```
                           G 3' NON-CODING                                    MetGluVal
ACGATTTTGAGACCGACGAGTTCAATGATTTCAATGAAGATGCCACAAGAGAATTCCTGAATCCCGATGAGGCATGACGTACT
                              +         +         +         +         +         5580
TGCTAAAACTCTGGCTGCTCAAGTTACTAAAGTTACTTCTACTGATACGGTGTTCTCTTAAGGACTTAGGGCTACTCCGTACTGCATGA
 HisAspPheGluThrAspTyrAlaThrArgGluPheLeuAsnProAspGluArgMetThrTyr

TGAATCATGCTGATTACAATTTGAATTCTCCTCTAATTAGTGATGATATTGACAATTTGATCAGGAAATTCAATTCTCTTCCGATTCCCT
                              +         +         +         +         +         5670
ACTTAGTACGACTAATGTTAAACTTAAGAGGAGATTAATCACTACTATAACTGTTAAACTAGTCCTTTAAGTTAAGAGAAGGCTAAGGA
 LeuAsnHisAlaAspTyrAsnLeuAsnSerProLeuIleSerAspAspIleAspAsnLeuIleArgLysPheAsnSerLeuProIlePro

CGATGTGGGATAGTAAGAACTGGGATGGAGTTCTTGAGATGTTAACATCATGTCAAGCCAATCCATCTCAACATCTCAGATGCATAAAT
                              +         +         +         +         +         5760
GCTACACCCTATCATTCTTGACCCTACCTCAAGAACTCTACAATTGTAGTACAGTTCGGTTAGGGTAGAGTTGTAGAGTCTACGTATTTA
 SerMetTrpAspSerLysAsnTrpAspGlyValLeuGluMetLeuThrSerCysGlnAlaAsnProIleSerThrSerGlnMetHisLys
```

FIG.2B

| | | SEQUENCE IS NO: |
|---|---|---|
| LEADER RNA | 5'.UCAGGAGAAAC $^{G}{}_{P}{}^{P}{}_{P}$ ᴵAACAGUAAUC.3' (I / N) | 15, 16 |
| vRNA | 3'.AGUCCUCUUUGAAAUUGUCAUUAG.5' | 17 |
| mRNAs | 5'.GCUACAUAUG-poly(A) $^{G}{}_{P}{}^{P}{}_{P}$ AACAGAUAUC.3' (N / NS) | 18, 19 |
| vRNA | 3'.CGAUGUAUACUUUUUUUGAUUGUCUAUAG.5' | 20 |
| mRNAs | 5'.GUAGACUAUG-poly(A) $^{G}{}_{P}{}^{P}{}_{P}$ AACAGAUAUC.3' (NS / M) | 21, 22 |
| vRNA | 3'.CAUCUGAUACUUUUUUCAUUGUCUAUAG.5' | 23 |
| mRNAs | 5'.UAUCCCUAUG-poly(A) $^{G}{}_{P}{}^{P}{}_{P}$ AACAGAGAUC.3' (M / G) | 24, 25 |
| vRNA | 3'.AUAGGGAUACUUUUUUUGAUUGUCUCUAG.5' | 26 |
| mRNAs | 5'.AAUUUUUAUG-poly(A) $^{G}{}_{P}{}^{P}{}_{P}$ AACAGCAAUC.3' (G / L) | 27, 28 |
| vRNA | 3'.UUAAAAAUACUUUUUUUGAUUGUCGUUAG.5' | 29 |
| mRNAs | 5'.UUUAAGUAUG-poly(A) (L) | 30 |
| vRNA | 3'.AAAUUCAUACUUUUUUUGAAACUAGGA.5' | 31 |

FIG. 3

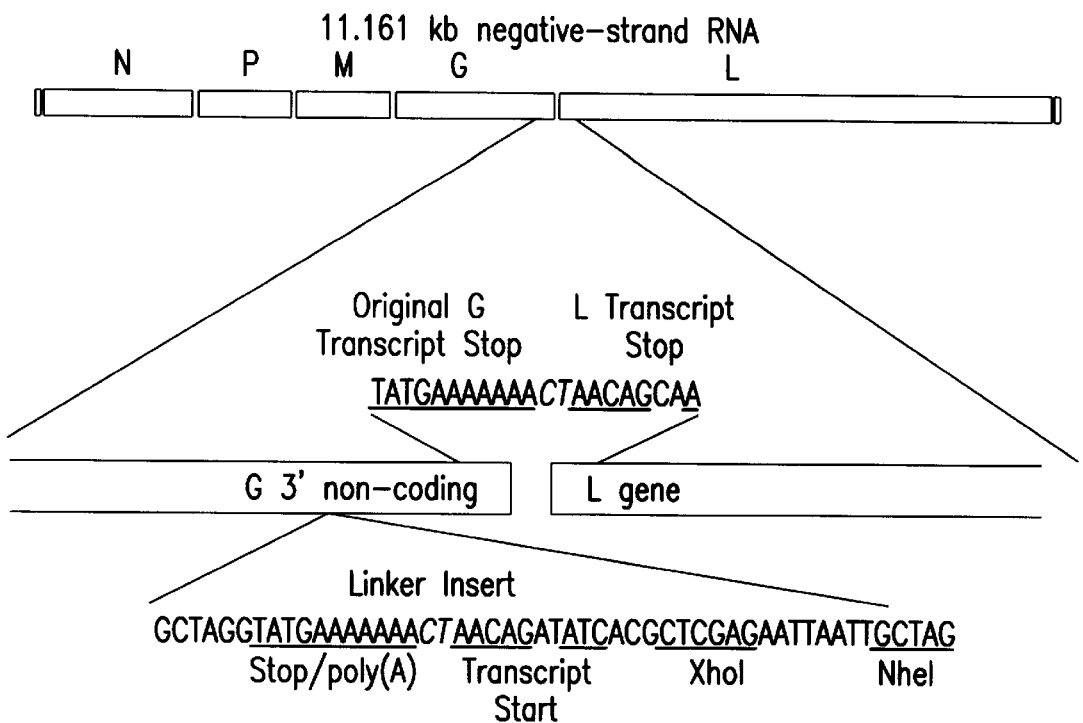
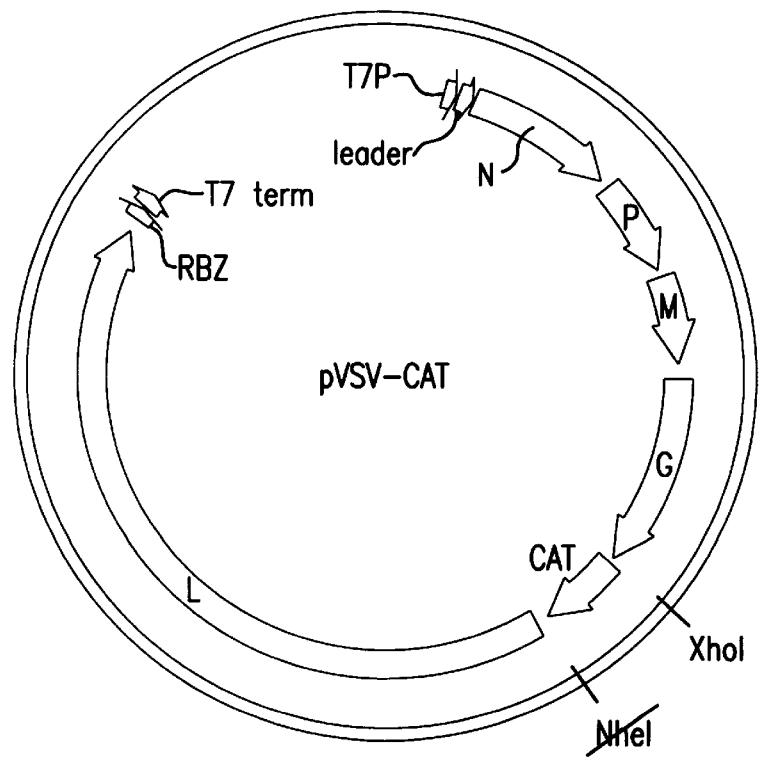
FIG. 9A
FIG. 9B 1 2 3 4 5 6 7 8 9 10 11 12 wt

METHODS FOR MAKING MODIFIED RECOMBINANT VESICULOVIRUSES

This application is a continuation-in-part of copending application Ser. No. 08/435,032 filed May 4, 1995, which is incorporated by reference herein in its entirety.

This invention was made with government support under grant number R37 AI243245 awarded by the National Institutes of Health. The government has certain rights in the invention.

1. INTRODUCTION

The present invention relates to recombinant vesiculoviruses which are replicable and capable of expressing foreign nucleic acid contained in their genome. Also provided are inactivated forms of the recombinant viruses. The vesiculoviruses are useful in vaccine formulations to prevent or treat various diseases and disorders.

2. BACKGROUND OF THE INVENTION

2.1. RHABDOVIRUSES

Rhabdoviruses are membrane-enveloped viruses that are widely distributed in nature where they infect vertebrates, invertebrates, and plants. There are two distinct genera within the rhabdoviruses, the Lyssavirus genus and the Vesiculovirus genus. Rhabdoviruses have single, negative-strand RNA genomes of 11–12,000 nucleotides (Rose and Schubert, 1987, Rhabdovirus genomes and their products, in *The Viruses: The Rhabdoviruses*, Plenum Publishing Corp., NY, pp. 129–166). The virus particles contain a helical, nucleocapsid core composed of the genomic RNA and protein. Generally, three proteins, termed N (nucleocapsid, which encases the genome tightly), P (formerly termed NS, originally indicating nonstructural), and L (large) are found to be associated with the nucleocapsid. An additional matrix (M) protein lies within the membrane envelope, perhaps interacting both with the membrane and the nucleocapsid core. A single glycoprotein (G) species spans the membrane and forms the spikes on the surface of the virus particle. G is responsible for binding to cells and membrane fusion. Because the genome is the negative sense [i.e., complementary to the RNA sequence (positive sense) that functions as mRNA to directly produce encoded protein], rhabdoviruses must encode and package an RNA-dependent RNA polymerase in the virion (Baltimore et al., 1970, Proc. Natl. Acad. Sci. USA 66: 572–576), composed of the P and L proteins. This enzyme transcribes genomic RNA to make subgenomic mRNAS encoding the 5–6 viral proteins and also replicates full-length positive and negative sense RNAs. The genes are transcribed sequentially, starting at the 3' end of the genomes. The same basic genetic system is also employed by the paramyxoviruses and filoviruses.

The prototype rhabdovirus, vesicular stomatitis virus (VSV), grows to very high titers in most animal cells and can be prepared in large quantities. As a result, VSV has been widely used as a model system for studying the replication and assembly of enveloped RNA viruses. The complete sequences of the VSV mRNAs and genome have been known for many years (Gallione et al. 1981, J. Virol. 39:529–535; Rose and Gallione, 1981, J. Virol. 39:519–528; Rose and Schubert, 1987, Rhabdovirus genomes and their products, p.129–166, in R. R. Wagner (ed.), The Rhabdoviruses. Plenum Publishing Corp., NY; Schubert et al., 1985, Proc. Natl. Acad. Sci. USA 82:7984–7988). However, the study of VSV and related negative strand viruses has been limited by the inability to perform direct genetic manipulation of the virus using recombinant DNA technology. The difficulty in generating VSV from DNA is that neither the full-length genomic nor antigenomic RNAs are infectious. The minimal infectious unit is the genomic RNA tightly bound to 1,250 subunits of the nucleocapsid (N) protein (Thomas et al., 1985, J. Virol. 54:598–607) and smaller amounts of the two virally encoded polymerase subunits, L and P. To reconstitute infectious virus from the viral RNA, it is necessary first to assemble the N protein-RNA complex that serves as the template for transcription and replication by the VSV polymerase. Although smaller negative-strand RNA segments of the influenza virus genome can be packaged into nucleocapsids in vitro, and then rescued in influenza infected cells (Enami et al., 1990, Proc. Natl. Acad. Sci. USA 87:3802–3805; Luytjes et al., 1989, Cell 59:1107–1113), systems for packaging the much larger rhabdoviral genomic RNAs in vitro are not yet available.

Recently, systems for replication and transcription of DNA-derived minigenomes or small defective RNAs from rhabdoviruses (Conzelmann and Schnell, 1994, J. Virol. 68:713–719; Pattnaik et al., 1992, Cell 69:1011–1120) and paramyxoviruses (Calain et al., 1992, Virology 191:62–71; Collins et al., 1991, Proc. Natl. Acad. Sci. USA 88:9663–9667; Collins et al., 1993, Virology 195:252–256; De and Banerjee, 1993, Virology 196:344–348; Dimock and Collins, 1993, J. Virol. 67:2772–2778; Park et al., 1991, Proc. Natl. Acad. Sci. USA 88:5537–5541) have been described. In these systems, RNAs are assembled into nucleocapsids within cells that express the viral N protein and polymerase proteins. Although these systems have been very useful, they do not allow genetic manipulation of the full-length genome of infectious viruses.

The recovery of rabies virus from a complete cDNA clone was published recently (Schnell et al., 1994, EMBO J. 13:4195–4203). The infectious cycle was initiated by expressing the antigenomic (full-length positive strand) RNA in cells expressing the viral N, P, and L proteins. Although rabies virus is a rhabdovirus, it is structurally and functionally different from the vesiculoviruses. Rabies virus is a Lyssavirus, not a Vesiculovirus. Lyssaviruses invade the central nervous system. Vesiculoviruses invade epithelial cells, predominantly those of the tongue, to produce vesicles. Rabies virus causes encephalitis in a variety of animals and in humans, while VSV causes an epidemic but self-limiting disease in cattle. In sharp contrast to VSV-infected cells, rabies virus produces little or no cytopathic effect in infected cell culture, replicates less efficiently than VSV in cell culture, and causes little depression of cellular DNA, RNA or protein synthesis in infected cell cultures (see Baer et al., 1990, in *Virology*, 2d ed., Fields et al. (eds.), Raven Press, Ltd., NY, pp. 883, 887). Indeed, there is no cross-hybridization observed between the genomes of rabies virus and VSV, and sequence homology between the two genomes is generally discernable only with the aid of computer run homology programs. The differences between vesiculoviruses and rabies virus, and the extremely rare nature of rabies virus recovery from cDNA (~$10^8$ cells are transfected to yield one infectious cell), renders it unpredictable whether the strategy used with rabies virus would be successful for viruses of a different genus, i.e., the vesiculoviruses.

The recovery of infectious measles virus, another negative strand RNA virus, from cloned cDNA has been attempted, without success (see Ballart et al., 1990, EMBO J. 9(2):379–384 and the retraction thereof by Eschle et al., 1991, EMBO J. 10(11):3558).

2.2. VACCINES

The development of vaccines for the prevention of viral, bacterial, or parasitic diseases is the focus of much research effort.

Traditional ways of preparing vaccines include the use of inactivated or attenuated pathogens. A suitable inactivation of the pathogenic microorganism renders it harmless as a biological agent but does not destroy its immunogenicity. Injection of these "killed" particles into a host will then elicit an immune response capable of preventing a future infection with a live microorganism. However, a major concern in the use of killed vaccines (using inactivated pathogen) is failure to inactivate all the microorganism particles. Even when this is accomplished, since killed pathogens do not multiply in their host, or for other unknown reasons, the immunity achieved is often incomplete, short lived and requires multiple immunizations. Finally, the inactivation process may alter the microorganism's antigens, rendering them less effective as immunogens.

Attenuation refers to the production of strains of pathogenic microorganisms which have essentially lost their disease-producing ability. One way to accomplish this is to subject the microorganism to unusual growth conditions and/or frequent passage in cell culture. Mutants are then selected which have lost virulence but yet are capable of eliciting an immune response. Attenuated pathogens often make good immunogens as they actually replicate in the host cell and elicit long lasting immunity. However, several problems are encountered with the use of live vaccines, the most worrisome being insufficient attenuation and the risk of reversion to virulence.

An alternative to the above methods is the use of subunit vaccines. This involves immunization only with those components which contain the relevant immunological material.

Vaccines are often formulated and inoculated with various adjuvants. The adjuvants aid in attaining a more durable and higher level of immunity using small amounts of antigen or fewer doses than if the immunogen were administered alone. The mechanism of adjuvant action is complex and not completely understood. However, it may involve the stimulation of cytokine production, phagocytosis and other activities of the reticuloendothelial system as well as a delayed release and degradation of the antigen. Examples of adjuvants include Freund's adjuvant (complete or incomplete), Adjuvant 65 (containing peanut oil, mannide monooleate and aluminum monostearate), the pluronic polyol L-121, Avridine, and mineral gels such as aluminum hydroxide, aluminum phosphate, etc. Freund's adjuvant is no longer used in vaccine formulations for humans because it contains nonmetabolizable mineral oil and is a potential carcinogen.

3. SUMMARY OF THE INVENTION

The present invention provides recombinant replicable vesiculoviruses. The prior art has unsuccessfully attempted to produce replicable vesiculoviruses from cloned DNA. In contrast, the invention provides a method which, for the first time, has successfully allowed the production and recovery of replicable vesiculoviruses, as well as recombinant replicable vesiculoviruses, from cloned DNA.

The vesiculoviruses of the invention are produced by providing in an appropriate host cell: (a) DNA that can be transcribed to yield (encodes) vesiculovirus antigenomic (+) RNA (complementary to the vesiculovirus genome), (b) a recombinant source of vesiculovirus N protein, (c) a recombinant source of vesiculovirus P protein, and (d) a recombinant source of vesiculovirus L protein; under conditions such that the DNA is transcribed to produce the antigenomic RNA, and a vesiculovirus is produced that contains genomic RNA complementary to the antigenomic RNA produced from the DNA.

The invention provides an infectious recombinant vesiculovirus capable of replication in an animal into which the recombinant vesiculovirus is introduced, in which the genome of the vesiculovirus comprises foreign RNA which is not naturally a part of the vesiculovirus genome. The recombinant vesiculovirus is formed by producing vesiculoviruses according to the method of the invention, in which regions of the DNA encoding vesiculovirus antigenomic (+) RNA that are nonessential for viral replication have been inserted into or replaced with foreign DNA.

In a preferred embodiment, the foreign RNA contained within the genome of the recombinant vesiculovirus (originally encoded by the foreign DNA), upon expression in an appropriate host cell, produces a protein or peptide that is antigenic or immunogenic.

The recombinant vesiculoviruses of the invention have use as vaccines. In one embodiment, where the foreign RNA directs production of an antigen that induces an immune response against a pathogen, the vaccines of the invention have use in the treatment or prevention of infections by such a pathogen (particularly a pathogenic microorganism), and its clinical manifestations, i.e., infectious disease. In a preferred embodiment, such an antigen displays the antigenicity or immunogenicity of an envelope glycoprotein of a virus other than a vesiculovirus, and the antigen is incorporated into the vesiculovirus envelope. The recombinant vesiculoviruses also have uses in diagnosis, and monitoring progression of infectious disorders, including response to vaccination and/or therapy.

In another embodiment, where the foreign RNA directs production of an antigen that induces an immune response against a tumor, the recombinant viruses of the invention have uses in cancer immunoprophylaxis, immunotherapy, and diagnosis, and monitoring of tumor progression or regression.

The recombinant vesiculoviruses can be used as live vaccines, or can be inactivated for use as killed vaccines. The recombinant viruses can also be used to produce large quantities of readily purified antigen, e.g., for use in subunit vaccines.

The invention also provides vaccine formulations, kits, and recombinant host cells.

4. DESCRIPTION OF THE FIGURES

Figure 1M:
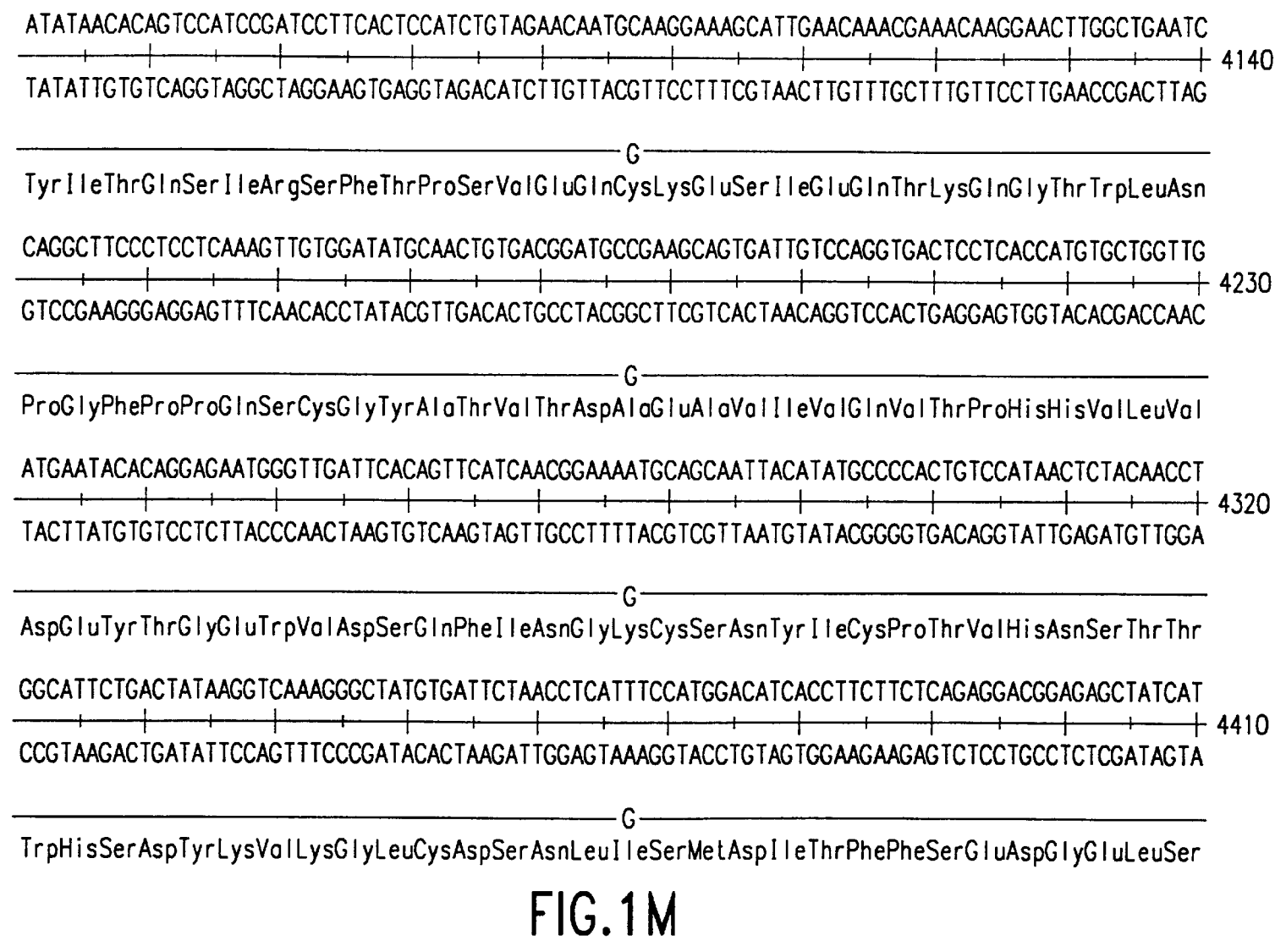
Figure 1A1:
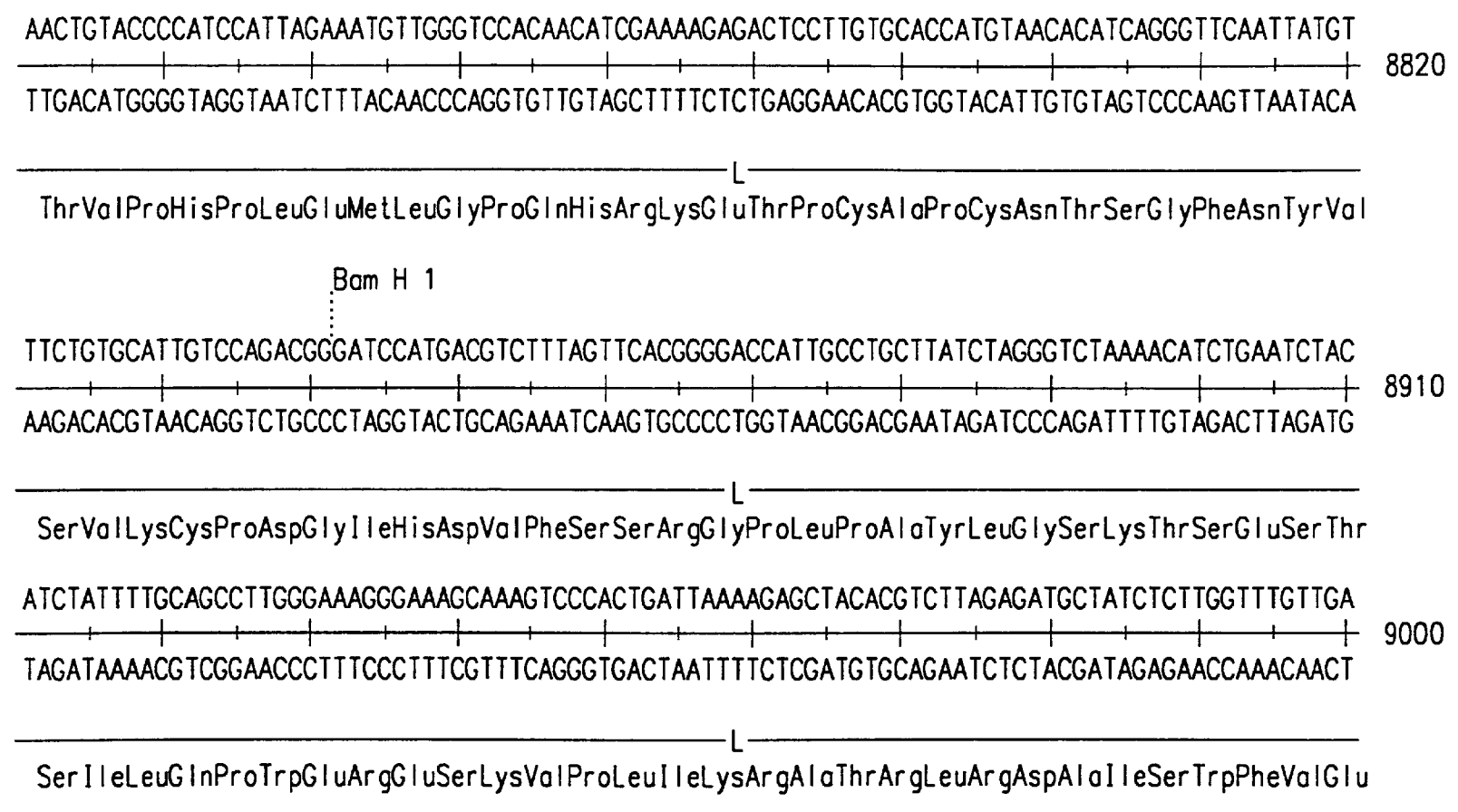
Figure 1D1:
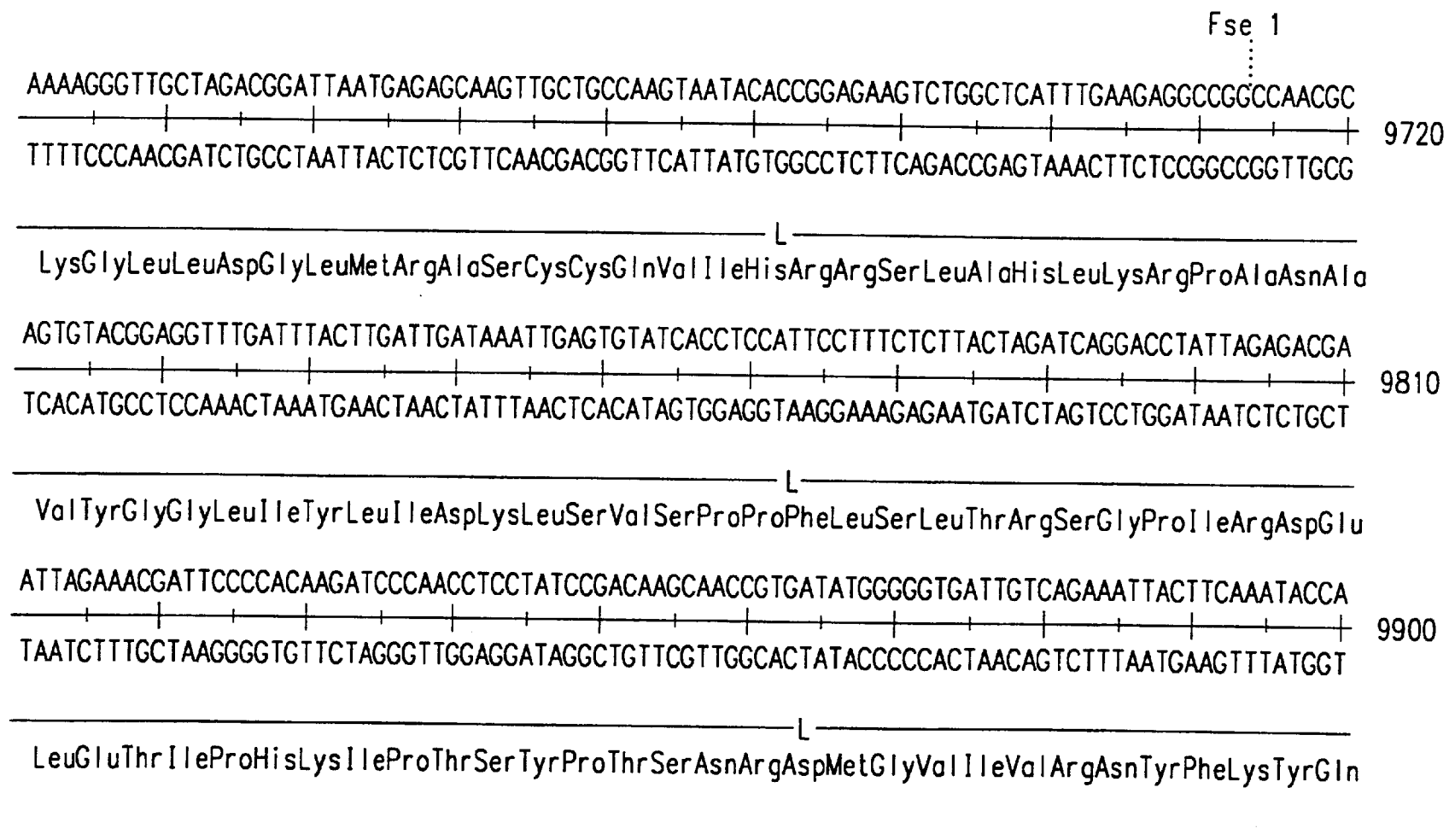
Figure 1F1:
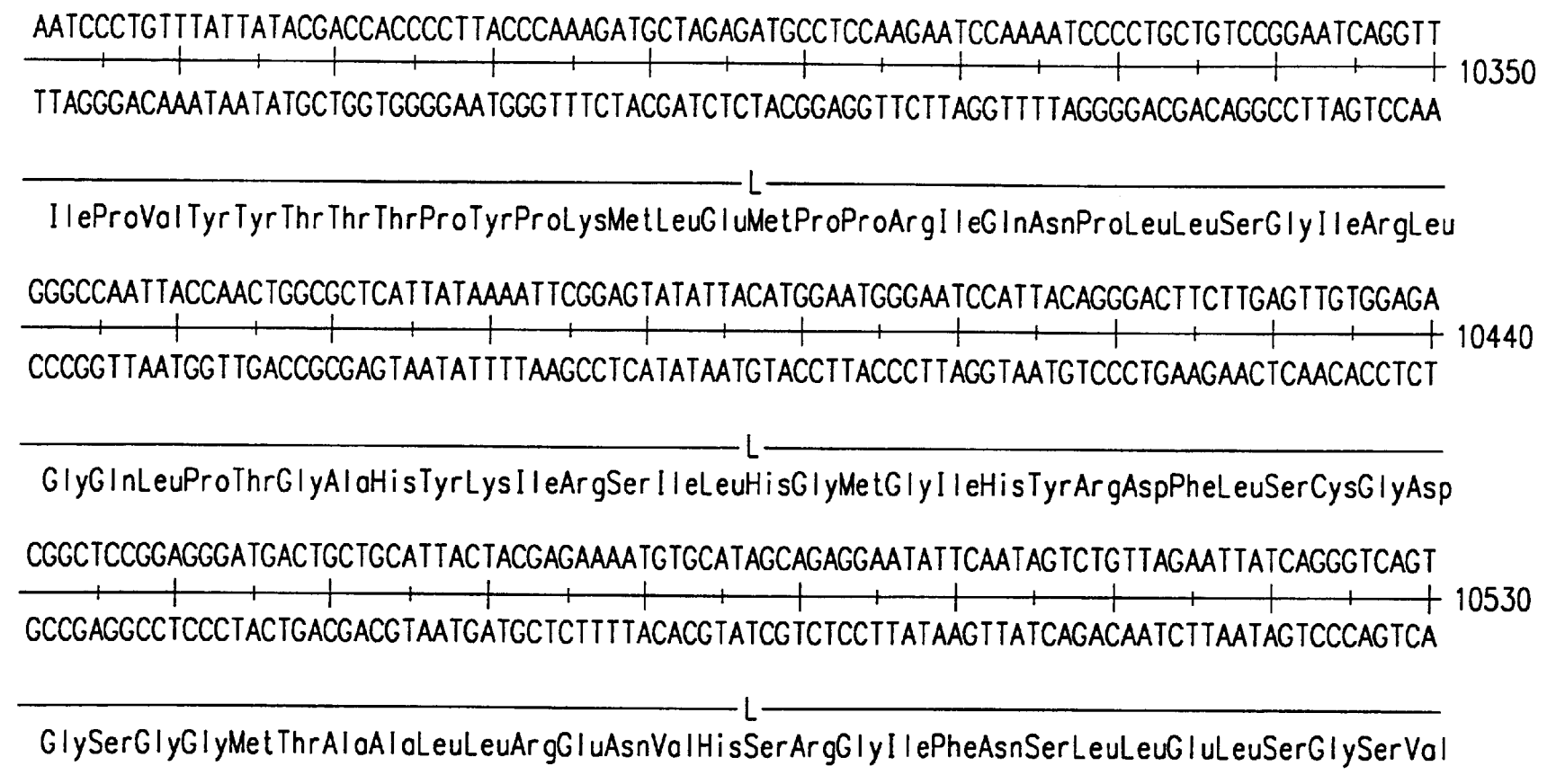
Figure 1J1:
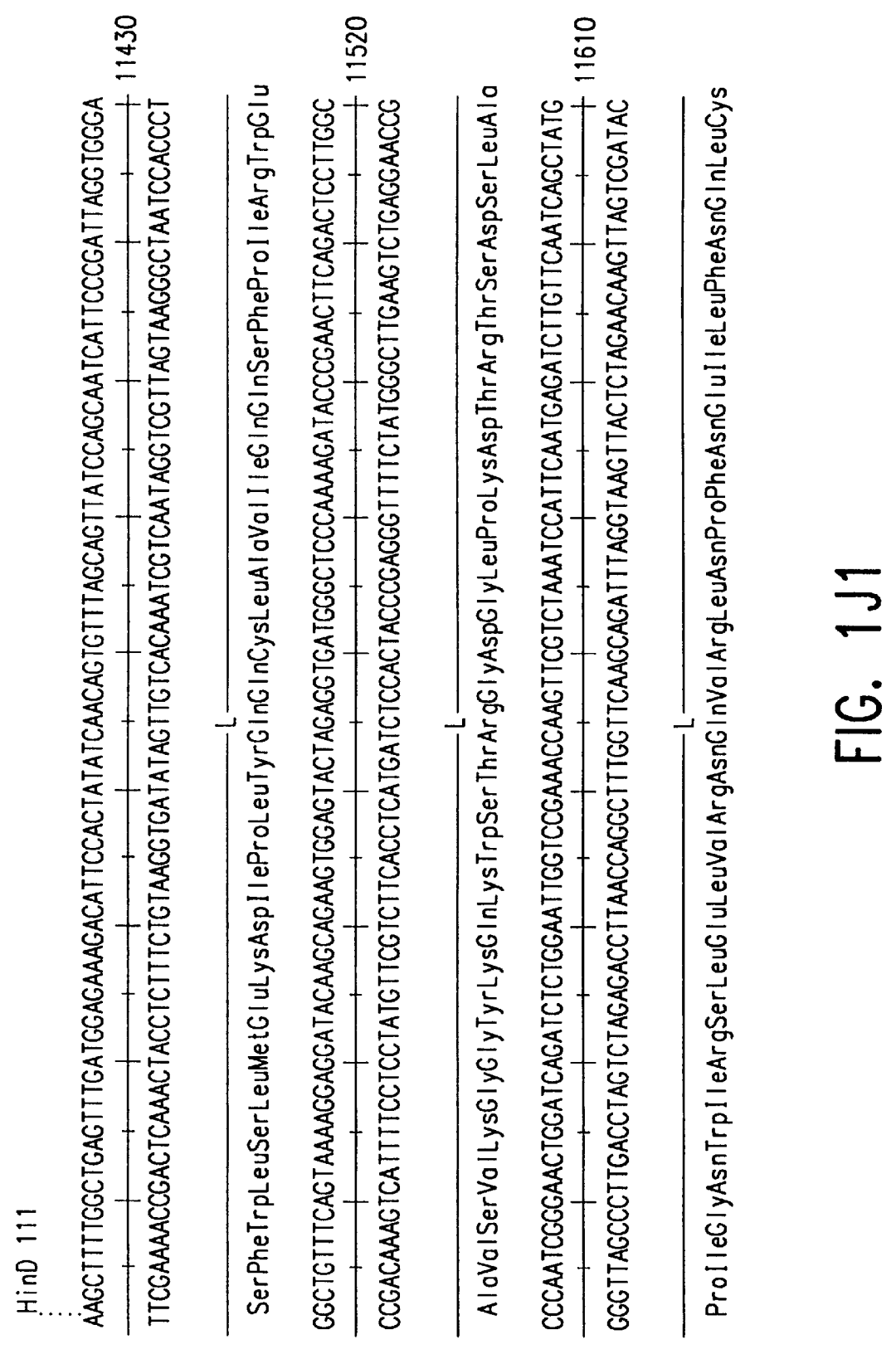

FIGS. 1A–1S. Nucleotide sequence of plasmid pVSVFL (+), showing the complete DNA sequence that is transcribed to produce VSV antigenomic (+) RNA, and predicted sequences of the encoded VSV proteins. [N protein: SEQ ID NO:2; P protein: SEQ ID NO:3; M protein: SEQ ID NO:4; G protein: SEQ ID NO:5; L protein: SEQ ID NO:6] The noncoding and intergenic regions are observable. The upper line of sequence (SEQ ID NO:1) is the VSV antigenomic positive strand; lower line=SEQ ID NO:7. Restriction sites are indicated. The transmembrane and cytoplasmic domains of the G protein are also indicated. The sequences of the first T7 RNA polymerase promoter (SEQ ID NO:8), the second T7 RNA polymerase promoter (SEQ ID NO:9); leader sequence (SEQ ID NO:10), T7 RNA polymerase transcription termination signal (SEQ ID NO:11), and the sequence that is transcribed to produce the HDV ribozyme (SEQ ID NO:12) are shown.

FIG. 2. Nucleotide sequence of a portion of plasmid pVSVSS1, showing the synthetic DNA insert containing the polylinker region inserted between the G and L coding regions (3' of G and 5' of L) containing unique restriction enzyme recognition sites, namely, XmaI, NotI, and SmaI. Upper line of sequence: SEQ ID NO:13; lower line of sequence: SEQ ID NO:14.

FIG. 3. Gene junctions of VSV. The nucleotide sequences at the 3' end of the leader RNA and the 5' and 3' ends of each mRNA are shown along with the corresponding genomic sequences (VRNA) (SEQ ID NO:15–31). The intergenic dinucleotides are indicated by bold letters. From Rose and Schubert, 1987, in *The Viruses: The Rhabdoviruses*, Plenum Press, NY, pp. 129–166, at p. 136.

Figure 4A:
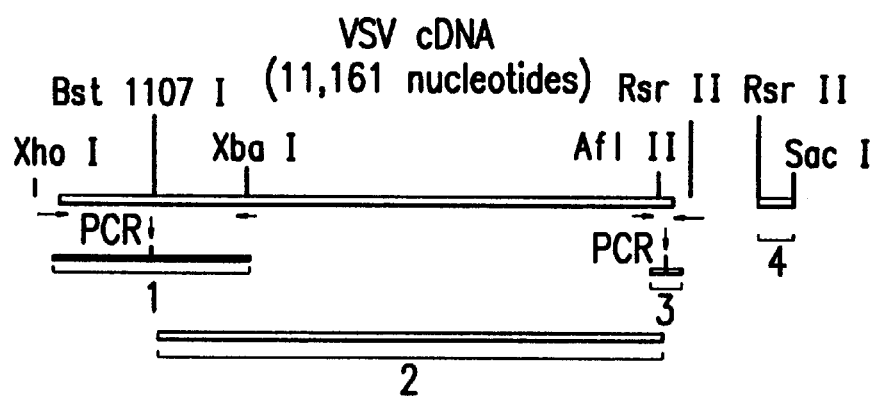
Figure 4B:
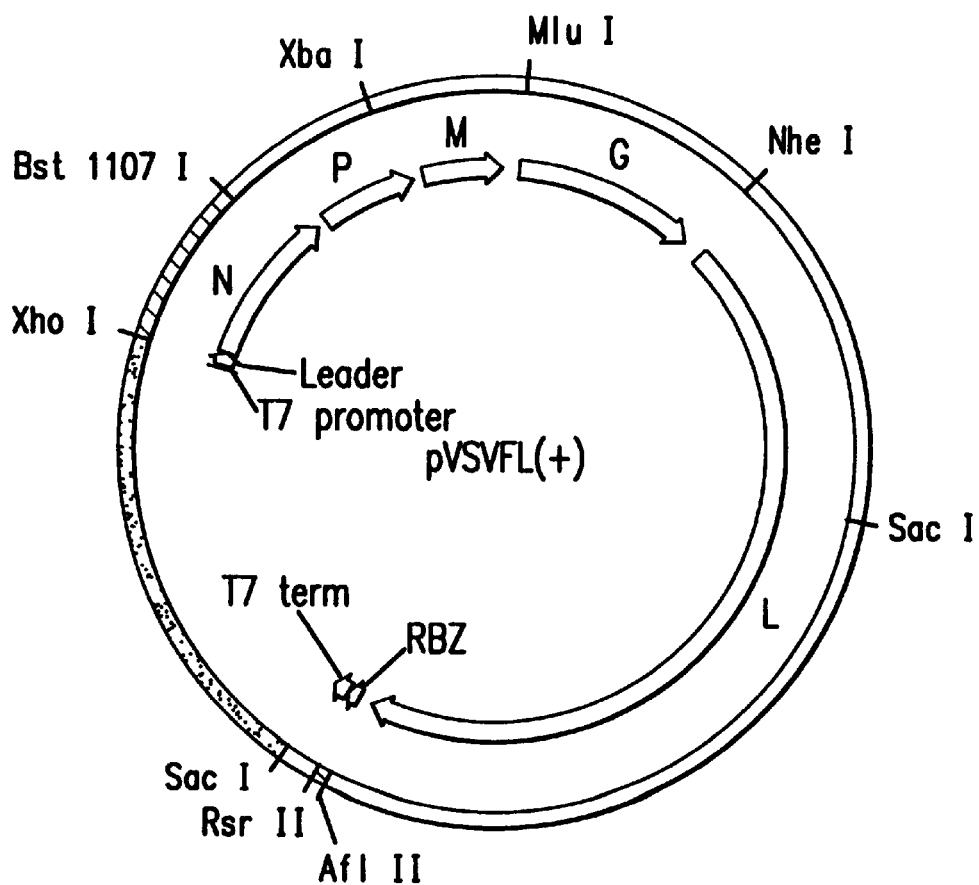

FIGS. 4A and 4B. Plasmid DNA construction. A. The diagram illustrates the cloned VSV genomic sequence and the four DNA fragments (numbered 1–4) that were used to generate the plasmid pVSVFL(+). The horizontal arrows represent PCR primers used to generate fragments 1 and 3. B. Diagram of the plasmid pVSVFL(+) that gives rise to infectious VSv. The locations of the VSV genes encoding the five proteins N, P, M, G, and L are shown. The stippled region from Sac I to Xho I represents the pBSSK$^+$ vector sequence, and the hatched segments represent the regions of the VSV genome generated by PCR. Transcription from the T7 promoter generates the complete (+) strand VSV RNA.

Figure 5:
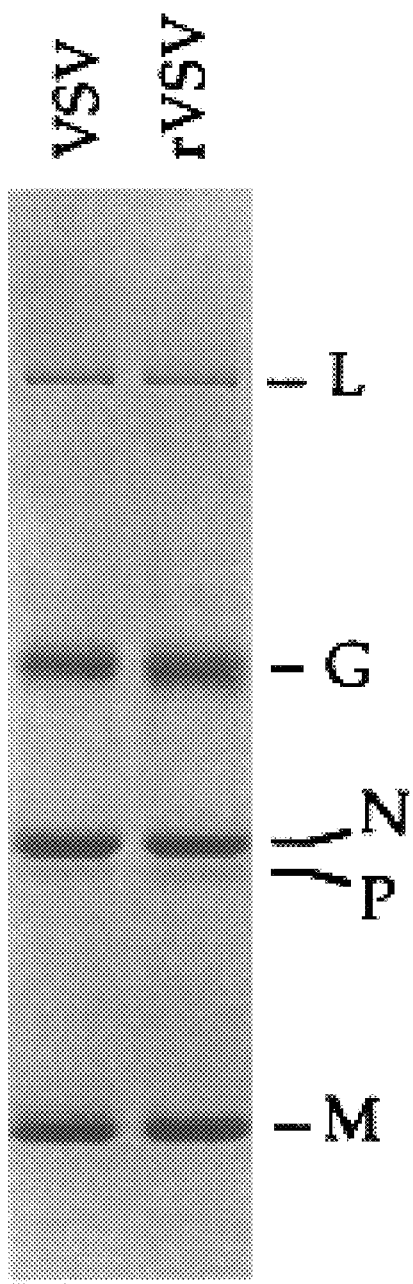

FIG. 5. Proteins present in wild-type and recombinant VSVs. Proteins from 1% of the virus recovered from approximately 5×10$^6$ infected BHK cells were separated by SDS-PAGE (10% acrylamide) and visualized by staining with Coomassie brilliant blue. Positions of the five VSV proteins are indicated.

Figure 6:
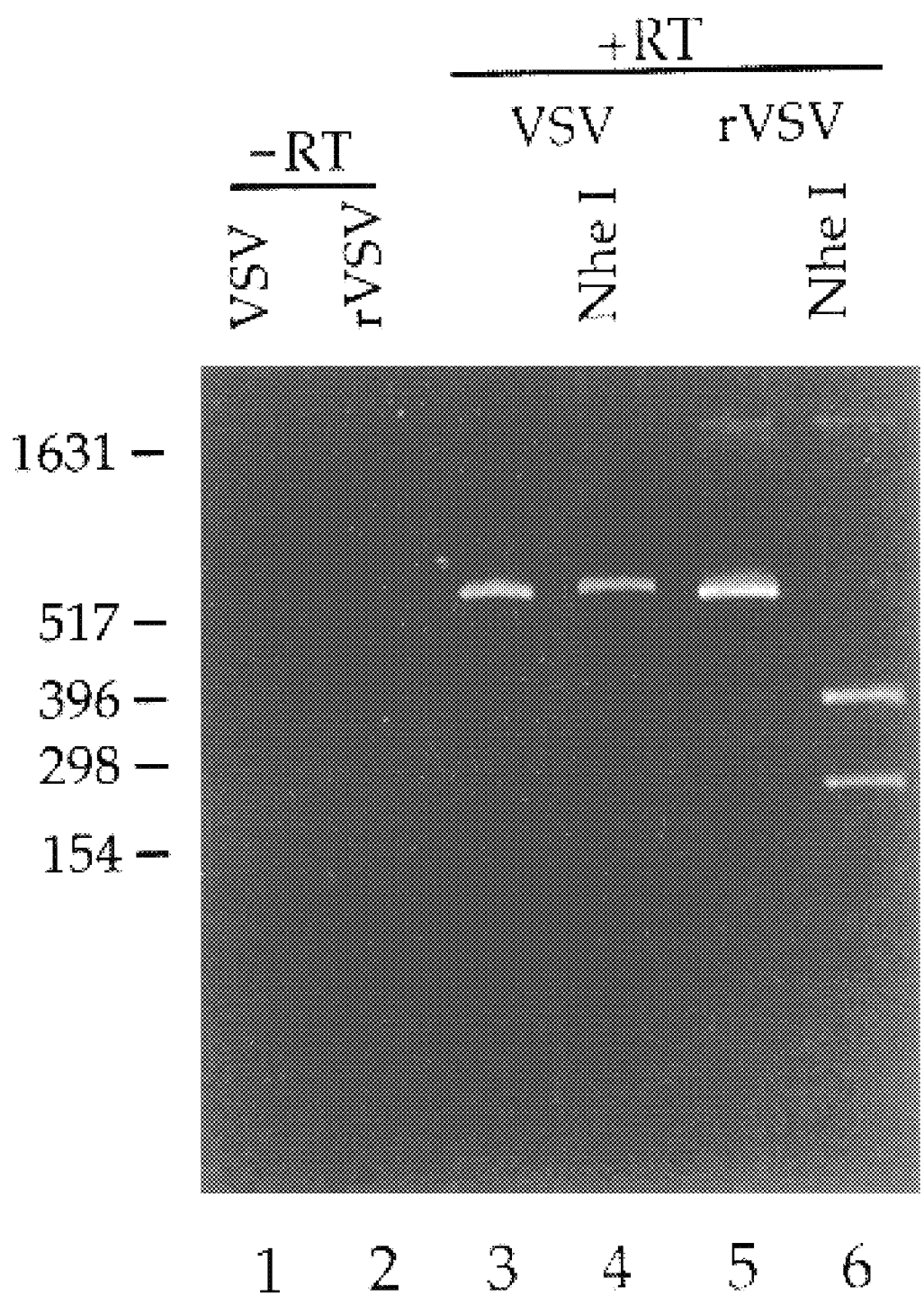

FIG. 6. Identification of a restriction enzyme recognition sequence in the recombinant VSV. A 620 nucleotide segment of genomic RNA isolated from wildtype and recombinant VSV was amplified by reverse transcription and PCR using the primers 5'-CATTCAAGACGCTGCTTCGCAACTTCC (SEQ ID NO:32) and 5'-CATGAATGTTAACATCTCAAGA (SEQ ID NO:33). Controls in which reverse transcriptase was omitted from the reaction are indicated. DNA samples were either digested with Nhe I or left undigested prior to electrophoresis on a 6% polyacrylamide gel as indicated. DNA was detected by staining with ethidium bromide. Sizes of DNA markers are indicated on the left.

Figure 7:
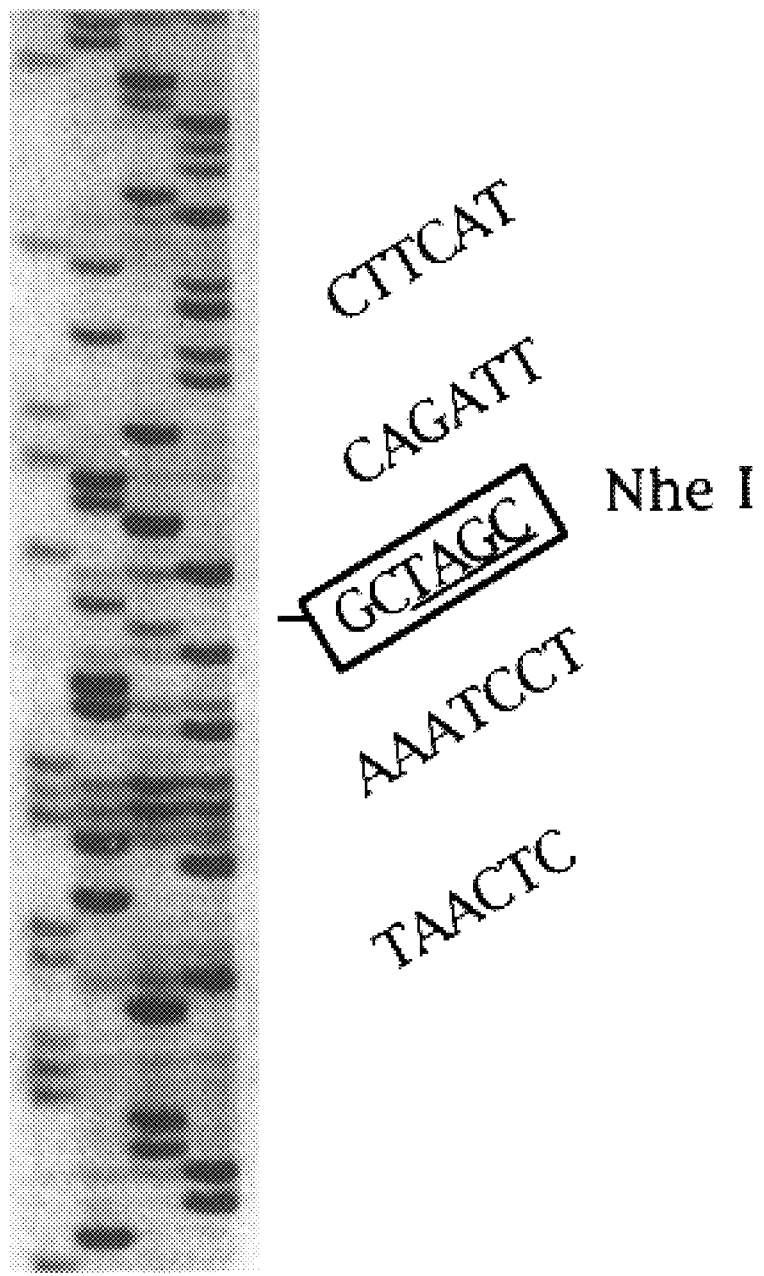

FIG. 7. Autoradiogram showing the sequence of genomic RNA from recombinant VSV. RNA prepared from recombinant VSV was sequenced by the dideoxy method using reverse transcriptase. The written sequence corresponds to nucleotides 1563–1593 in the G mRNA (Rose and Gallione, 1981, J. Virol. 39:519–528). The underlined sequence represents the four nucleotides that were changed to generate the Nhe I site.

Figure 8:
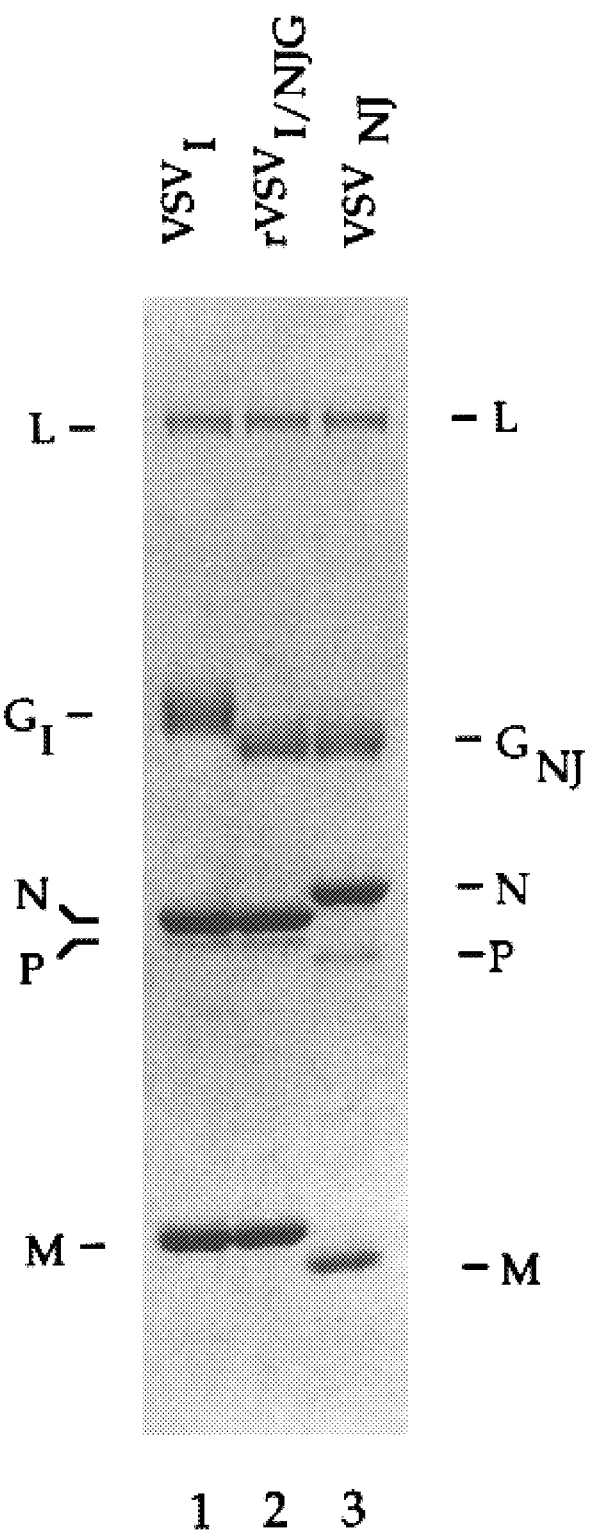

FIG. 8. Protein analysis of recombinant VSV expressing the glycoprotein from the New Jersey serotype. Proteins from 1% of the virus pelleted from the medium of approximately 5×10$^6$ BHK cells infected for 24 hours with wildtype VSV$_I$ (lane 1), recombinant VSV$_{I/NJG}$ (lane 2) or wildtype VSV$_{NJ}$ (lane 3) were separated by SDS-PAGE (10% acrylamide). The proteins were visualized by staining with Coomassie brilliant blue. Positions of viral proteins are indicated.

FIGS. 9A–9B. Construction of VSV-CAT. A. VSV genome diagram and sequence of the synthetic linker encoding minimal, consensus transcription start/stop sequences. The letters in boldface type represent the nucleotides within the consensus sequence that are conserved at all four gene junctions. Intergenic dinucleotides are italicized. The putative stop/poly(A) sequences as well as the transcription start sequences are labeled. The linker was cloned at the unique NheI site introduced in the 31-noncoding region of the VSV gene, and eliminates the upstream NheI site. B. The diagram shows the pVSV-CAT plasmid with the positions of the T7 RNA polymerase promoter (T7P) and terminator (T7-term) and hepatitis virus delta ribozyme (RBZ) indicated. The NheI site was eliminated when joined to the XbaI site in the CAT PCR product.

Figure 10A:
Figure 10B:
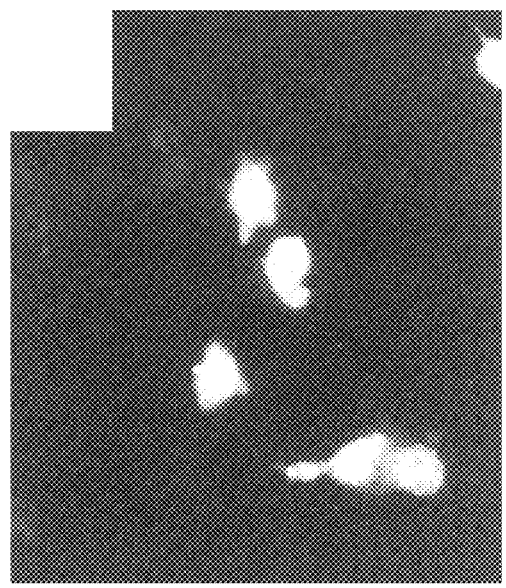

FIGS. 10A–10B. Co-expression of G and CAT in VSV-CAT infected cells. Double-label indirect immunofluorescence microscopy was used to examine co-expression of CAT and VSV G protein in VSV-CAT infected cells. Cells infected at a multiplicity of infection (MOI) of approximately 1 were fixed, permeabilized and stained as described in Section 7.1. A. Detection of VSV G protein (fluorescein isothiocyanate (FITC) stain). B. Detection of CAT protein (rhodamine stain).

Figure 11:
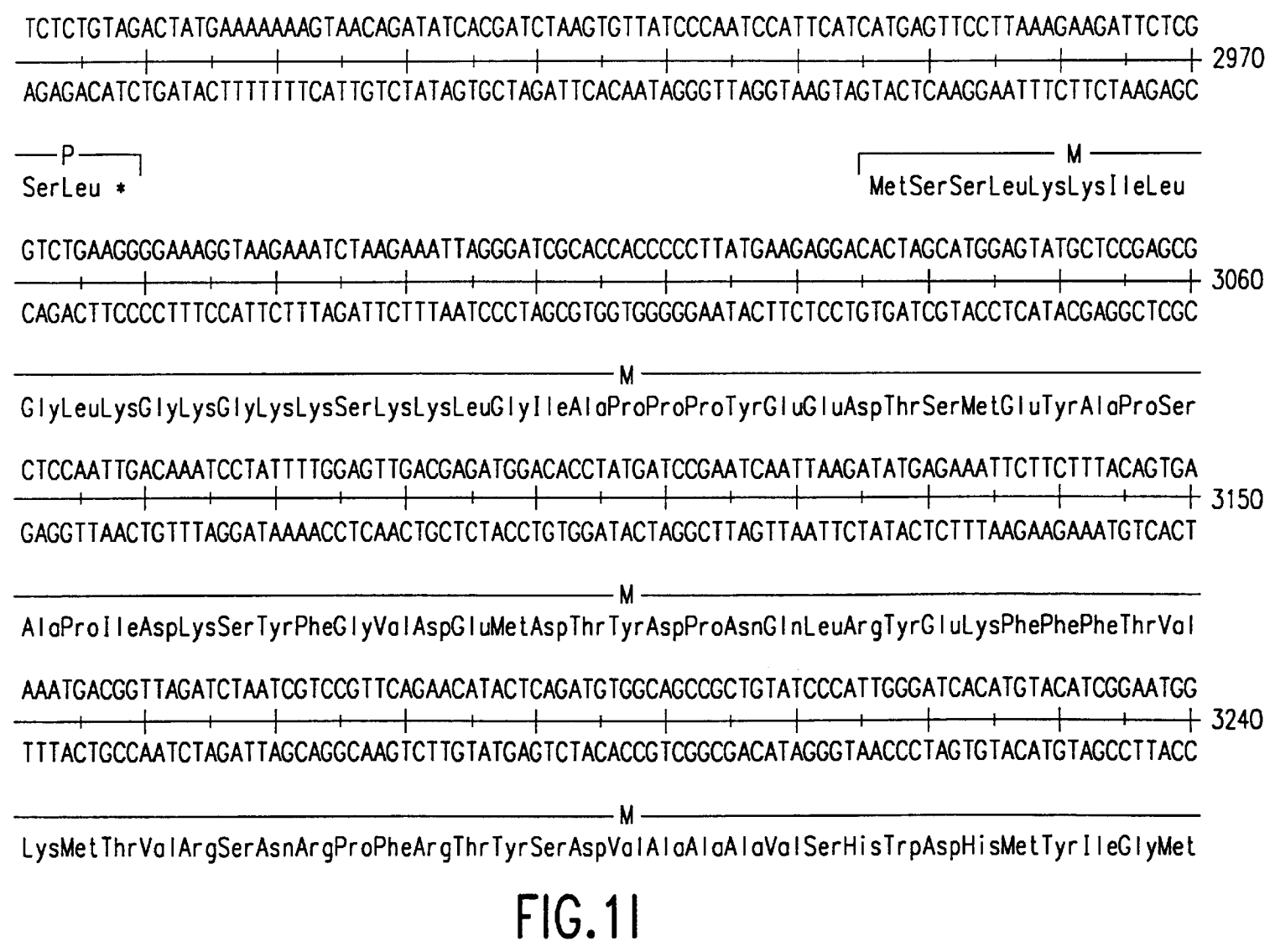
Figure 11A:
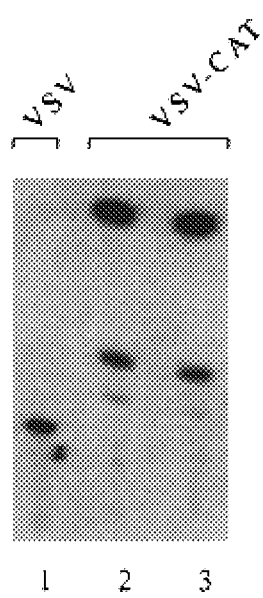
Figure 11B:
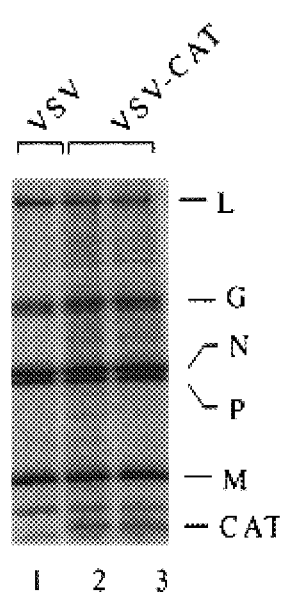
Figure 11C:
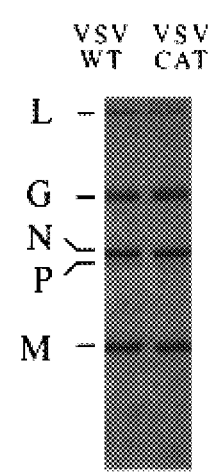

FIGS. 11A–11C. Analysis of CAT protein activity and expression. A. PhosphorImager results of CAT assay performed on lysates of cells infected with two independent VSV-CAT viruses or with wild-type (wt) VSV. B. Extracts from [$^{35}$S]-methionine labeled cells infected with VSV or two VSV-CAT viruses were separated by SDS-PAGE and detected on the PhosphorImager. Positions of VSV proteins and CAT protein are indicated. C. Coomassie blue stained gel of proteins found in VSV virions or in VSV-CAT virions.

Figure 12:
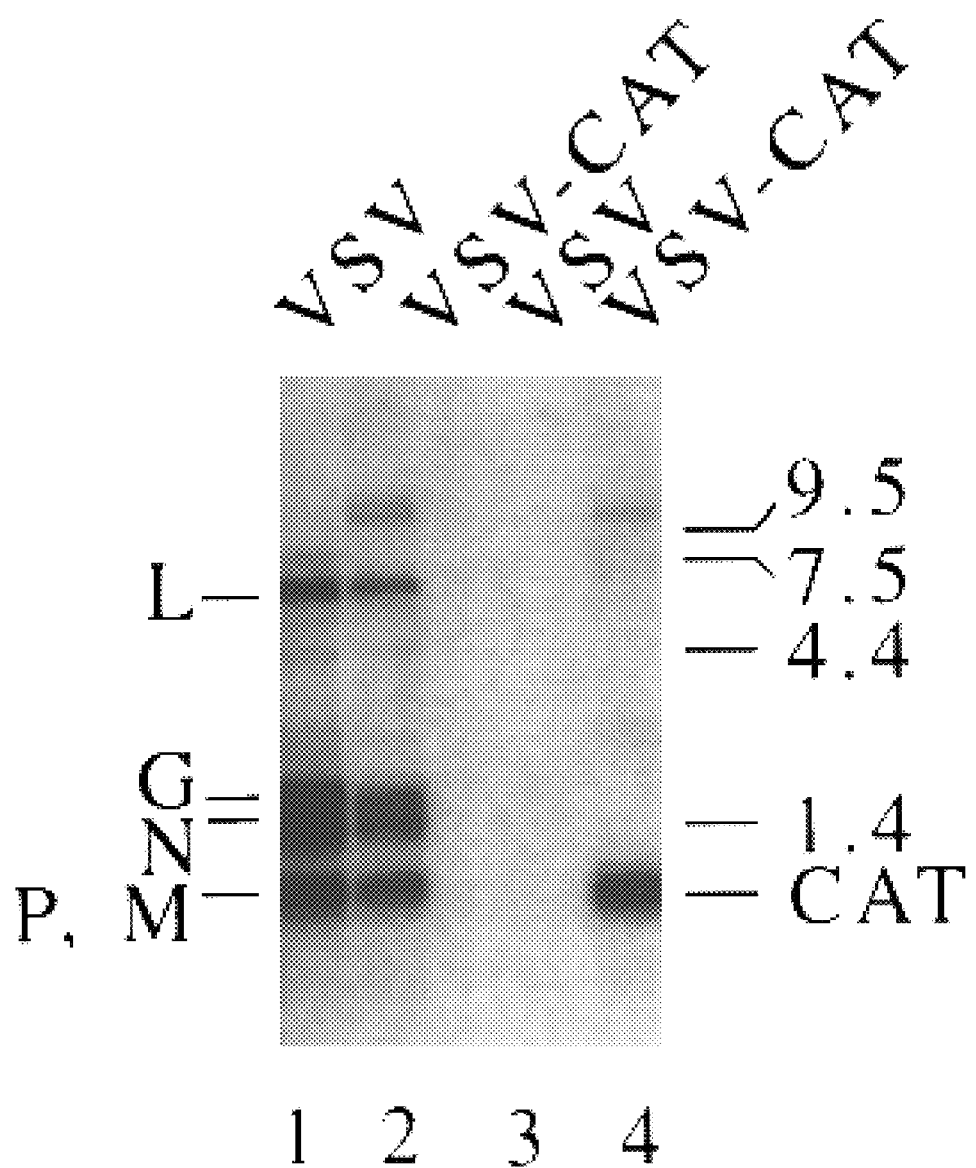

FIG. 12. Detection of VSV mRNAs and mRNA encoding CAT protein. Total RNA from VSV (lanes 1 and 3) or VSV-CAT (lanes 2 and 4)-infected cells was separated by gel electrophoresis and detected by Northern blotting with VSV probe (lanes 1 and 2) or CAT probe (lanes 3 and 4). Positions of molecular size markers (in kilobases) are indicated to the right of the gel.

Figure 13:
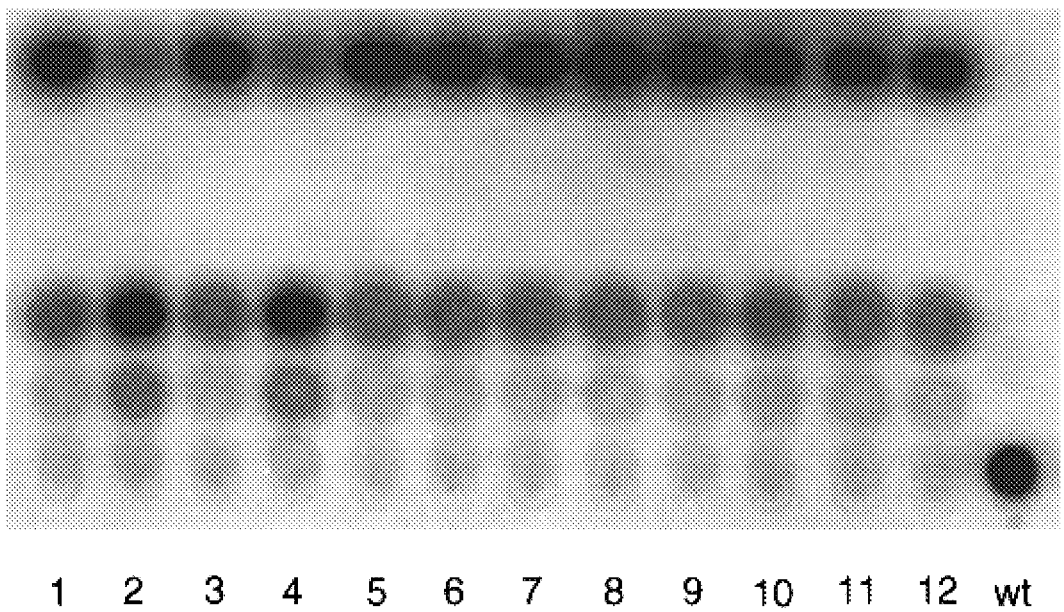

FIG. 13. Detection of CAT expression after 15 passages. Individual plaques of VSV-CAT virus were picked after fifteen passages and used to infect twelve dishes of BHK cells. CAT assays were performed on lysates from these cells (lanes 1–12) and on a lysate from VSV infected cells (lane wt).

5. DETAILED DESCRIPTION OF THE INVENTION

The present invention provides recombinant replicable vesiculoviruses. The prior art has unsuccessfully attempted to produce replicable vesiculoviruses from cloned DNA. In contrast, the invention provides a method which, for the first time, has successfully allowed the production and recovery of replicable vesiculoviruses, as well as recombinant replicable vesiculoviruses, from cloned DNA. Expression of the full-length positive-strand vesiculovirus RNA in host cells has successfully allowed the generation of recombinant vesiculoviruses from DNA, providing recombinant viruses that do not cause serious pathology in humans and that can be obtained in high titers, that have use as vaccines.

The vesiculoviruses of the invention are produced by providing in an appropriate host cell: (a) DNA that can be transcribed to yield (encodes) vesiculovirus antigenomic (+) RNA (complementary to the vesiculovirus genome), (b) a recombinant source of vesiculovirus N protein, (c) a recombinant source of vesiculovirus P protein, and (d) a recombinant source of vesiculovirus L protein; under conditions such that the DNA is transcribed to produce the antigenomic RNA, and a vesiculovirus is produced that contains genomic RNA complementary to the antigenomic RNA produced from the DNA.

The invention provides an infectious recombinant vesiculovirus capable of replication in an animal into which the recombinant vesiculovirus is introduced, in which the genome of the vesiculovirus comprises foreign RNA which is not naturally a part of the vesiculovirus genome. The recombinant vesiculovirus is formed by producing vesiculoviruses according to the method of the invention, in which regions of the DNA encoding vesiculovirus antigenomic (+) RNA that are nonessential for viral replication have been inserted into or replaced with foreign DNA.

Since the viruses are replicable (i.e., not replication-defective), they encode all the vesiculovirus machinery necessary for replication in a cell upon infection by the virus.

In a preferred embodiment, the recombinant vesiculovirus is a recombinant vesicular stomatitis virus (VSV).

In another preferred embodiment, the foreign RNA contained within the genome of the recombinant vesiculovirus (originally encoded by the foreign DNA), upon expression in an appropriate host cell, produces a protein or peptide that is antigenic or immunogenic. Such an antigenic or immunogenic protein or peptide whose expression is directed by the foreign RNA (present in the negative sense) within the vesiculovirus genome (by expression from the (+) antigenomic message) shall be referred to hereinafter as the "Antigen." Appropriate Antigens include but are not limited to known antigens of pathogenic microorganisms or of tumors, as well as fragments or derivatives of such antigens displaying the antigenicity or immunogenicity of such antigens. A protein displays the antigenicity of an antigen when the protein is capable of being immunospecifically bound by an antibody to the antigen. A protein displays the immunogenicity of an antigen when it elicits an immune response to the antigen (e.g., when immunization with the protein elicits production of an antibody that immunospecifically binds the antigen or elicits a cell-mediated immune response directed against the antigen).

The recombinant vesiculoviruses of the invention have use as vaccines. In one embodiment, where the foreign RNA directs production of an Antigen (originally encoded by the foreign DNA used to produce the recombinant vesiculovirus or its predecessor) that induces an immune response against a pathogen, the vaccines of the invention have use in the treatment or prevention of infections by such a pathogen (particularly a pathogenic microorganism), and its clinical manifestations, i.e., infectious disease. The invention thus provides methods of prevention or treatment of infection and infectious disease comprising administering to a subject in which such treatment or prevention is desired one or more of the recombinant vesiculoviruses of the invention. The recombinant vesiculoviruses also have uses in diagnosis, and monitoring progression of infectious disorders, including response to vaccination and/or therapy.

In another embodiment, where the Antigen induces an immune response against a tumor, the recombinant viruses of the invention have uses in cancer immunoprophylaxis, immunotherapy, and diagnosis, and monitoring of tumor progression or regression.

The recombinant vesiculoviruses can be used as live vaccines, or can be inactivated for use as killed vaccines. The recombinant viruses can also be used to produce large quantities of readily purified antigen, e.g., for use in subunit vaccines.

In a specific embodiment, the foreign DNA used initially for production of the recombinant vesiculoviruses can also comprise a sequence encoding a detectable marker, e.g., β-galactosidase, β-glucuronidase, β-geo (Friedrich & Soriano, 1991, Genes Dev. 5:1513–1523).

In another specific embodiment, the foreign DNA can also comprise a sequence encoding a cytokine capable of stimulating an immune response. Such cytokines include but are not limited to, interleukin-2, interleukin-6, interleukin-12, interferons, and granulocyte-macrophage colony stimulating factors.

In a preferred aspect, upon infection with a recombinant vesiculovirus of the invention, the Antigen is expressed as a nonfusion protein. In a less preferred embodiment, the Antigen is expressed as a fusion protein, e.g., to the viral G protein. "Fusion protein," as used herein, refers to a protein comprising an amino acid sequence from a first protein covalently linked via a peptide bond at its carboxy terminus to the amino terminus of an amino acid sequence from a second, different protein.

In one embodiment, a vaccine formulation of the invention contains a single type of recombinant vesiculovirus of the invention. In another embodiment, a vaccine formulation comprises a mixture of two or more recombinant viruses of the invention.

The vaccine formulations of the invention provide one or more of the following benefits: stability for long periods without refrigeration; ease of production; low cost and high titer of production; ability to be administered by local workers without advanced medical training; and involving administration of a microorganism that is known not to cause serious disease in humans.

The present invention also provides a host cell infected with a recombinant vesiculovirus capable of replication. In one embodiment, the host cell is a mammalian cell. Preferably, the mammalian cell is a hamster kidney cell.

5.1. DNA THAT CAN BE TRANSCRIBED TO PRODUCE VESICULOVIRUS ANTIGENOMIC (+) RNA

Many vesiculoviruses are known in the art and can be made recombinant according to the methods of the invention. Examples of such vesiculoviruses are listed in Table I.

TABLE I

MEMBERS OF THE VESICULOVIRUS GENUS

| Virus | Source of virus in nature |
|---|---|
| VSV-New Jersey | Mammals, mosquitoes, midges, blackflies, houseflies |
| VSV-Indiana | Mammals, mosquitoes, sandflies |
| Alagoas | Mammals, sandflies |
| Cocal | Mammals, mosquitoes, mites |
| Jurona | Mosquitoes |
| Carajas | Sandflies |
| Maraba | Sandflies |
| Piry | Mammals |
| Calchaqui | Mosquitoes |
| Yug Bogdanovac | Sandflies |
| Isfahan | Sandflies, ticks |
| Chandipura | Mammals, sandflies |
| Perinet | Mosquitoes, sandflies |
| Porton-S | Mosquitoes |

Any DNA that can be transcribed to produce vesiculovirus antigenomic (+) RNA (complementary to the VSV genome) can be used for the construction of a recombinant DNA containing foreign DNA encoding an Antigen, for use in producing the recombinant vesiculoviruses of the invention. DNA that can be transcribed to produce vesiculovirus antigenomic (+) RNA (such DNA being referred to herein as "vesiculovirus (−) DNA") is available in the art and/or can be obtained by standard methods. In particular, plasmid pVSVFL(+), containing VSV (−) DNA that is preferred for use in the present invention, has been deposited with the ATCC and assigned accession no. 97134. In a preferred aspect, DNA that can be transcribed to produce VSV (+) RNA, [i.e., VSV (−) DNA], is used. VSV (−) DNA for any serotype or strain known in the art, e.g., the New Jersey or Indiana serotypes of VSV, can be used. The complete nucleotide and deduced protein sequence of the VSV genome is known, and is available as Genbank VSVCG, Accession No. JO2428; NCBI Seq ID 335873; and is published in Rose and Schubert, 1987, in *The Viruses: The Rhabdoviruses*, Plenum Press, NY, pp. 129–166.

Partial sequences of other vesiculovirus genomes have been published and are available in the art. The complete sequence of the VSV(−) DNA that is used in a preferred embodiment is contained in plasmid pVSVFL(+) and is shown in FIG. 1; also shown are with the predicted sequences of the VSV proteins (this sequence contains several sequence corrections relative to that obtainable from Genbank). Vesiculovirus (−) DNA, if not already available, can be prepared by standard methods, as follows: If vesiculoviral cDNA is not already available, vesiculovirus genomic RNA can be purified from virus preparations, and reverse transcription with long distance polymerase chain reaction used to generate the vesiculovirus (−) DNA. Alternatively, after purification of genomic RNA, VSV mRNA can be synthesized in vitro, and cDNA prepared by standard methods, followed by insertion into cloning vectors (see, e.g., Rose and Gallione, 1981, J. Virol. 39(2):519–528). Individual cDNA clones of vesiculovirus RNA can be joined by use of small DNA fragments covering the gene junctions, generated by use of reverse transcription and polymerase chain reaction (RT-PCR) (Mullis and Faloona, 1987, Meth. Enzymol. 155:335–350) from VSV genomic RNA (see Section 6, infra). Vesiculoviruses are available in the art. For example, VSV can be obtained from the American Type Culture Collection.

In a preferred embodiment, one or more, preferably unique, restriction sites (e.g., in a polylinker) are introduced into the vesiculovirus (−) DNA, in intergenic regions, or 5' of the sequence complementary to the 3' end of the vesiculovirus genome, or 3' of the sequence complementary to the 5' end of the vesiculovirus genome, to facilitate insertion of the foreign DNA.

In a preferred method of the invention, the vesiculovirus (−) DNA is constructed so as to have a promoter operatively linked thereto. The promoter should be capable of initiating transcription of the (−) DNA in an animal or insect cell in which it is desired to produce the recombinant vesiculovirus. Promoters which may be used include, but are not limited to, the SV40 early promoter region (Bernoist and Chambon, 1981, Nature 290:304–310), the promoter contained in the 3' long terminal repeat of Rous sarcoma virus (Yamamoto, et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al., 1982, Nature 296:39–42); heat shock promoters (e.g., hsp70 for use in Drosophila S2 cells); the ADC (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift et al., 1984, Cell 38:639–646; Ornitz et al., 1986, Cold Spring Harbor Symp. Quant. Biol. 50:399–409; MacDonald, 1987, Hepatology 7:425–515); insulin gene control region which is active in pancreatic beta cells (Hanahan, 1985, Nature 315:115–122), immunoglobulin gene control region which is active in lymphoid cells (Grosschedl et al., 1984, Cell 38:647–658; Adames et al., 1985, Nature 318:533–538; Alexander et al., 1987, Mol. Cell. Biol. 7:1436–1444), mouse mammary tumor virus control region which is active in testicular, breast, lymphoid and mast cells (Leder et al., 1986, Cell 45:485–495), albumin gene control region which is active in liver (Pinkert et al., 1987, Genes and Devel. 1:268–276), alpha-fetoprotein gene control region which is active in liver (Krumlauf et al., 1985, Mol. Cell. Biol. 5:1639–1648; Hammer et al., 1987, Science 235:53–58; alpha 1-antitrypsin gene control region which is active in the liver (Kelsey et al., 1987, Genes and Devel. 1:161–171), beta-globin gene control region which is active in myeloid cells (Mogram et al., 1985, Nature 315:338–340; Kollias et al., 1986, Cell 46:89–94; myelin basic protein gene control region which is active in oligodendrocyte cells in the brain (Readhead et al., 1987, Cell 48:703–712); and myosin light chain-2 gene control region which is active in skeletal muscle (Sani, 1985, Nature 314:283–286). Preferably, the promoter is an RNA polymerase promoter, preferably a bacteriophage or viral or insect RNA polymerase promoter, including but not limited to the promoters for T7 RNA polymerase, SP6 RNA polymerase, and T3 RNA polymerase. If an RNA polymerase promoter is used in which the RNA polymerase is not endogenously produced by the host cell in which it is desired to produce the recombinant vesiculovirus, a recombinant source of the RNA polymerase must also be provided in the host cell.

The vesiculovirus (−) DNA can be operably linked to a promoter before or after insertion of foreign DNA encoding an Antigen. Preferably, a transcriptional terminator is situated downstream of the vesiculovirus (−) DNA. In another preferred embodiment, a DNA sequence that can be transcribed to produce a ribozyme sequence is situated at the immediate 3' end of the vesiculovirus (−) DNA, prior to the transcriptional termination signal, so that upon transcription a self-cleaving ribozyme sequence is produced at the 3' end of the antigenomic RNA, which ribozyme sequence will autolytically cleave (after a U) this fusion transcript to release the exact 3' end of the vesiculovirus antigenomic (+) RNA. Any ribozyme sequence known in the art may be used, as long as the correct sequence is recognized and cleaved. (It is noted that hammerhead ribozyme is probably not suitable for use.) In a preferred aspect, hepatitis delta virus (HDV) ribozyme is used (Perrotta and Been, 1991, Nature 350:434–436; Pattnaik et al., 1992, Cell 69:1011–1020).

A preferred VSv(−) DNA for use, for insertion of foreign DNA, is that shown in FIG. 1 and contained in plasmid pVSVFL(+), in which a T7 RNA polymerase promoter is present 5' of the sequence complementary to the 3' end of the VSV genome. Plasmid pVSVFL(+) thus comprises (in 5' to 3' order) the following operably linked components: the T7 RNA polymerase promoter, VSV (−) DNA, a DNA sequence that is transcribed to produce an HDV ribozyme sequence (immediately downstream of the VSV (−) DNA), and a T7 RNA polymerase transcription termination site. A plasmid that can also be made and used is plasmid pVSVSS1, a portion of the sequence of which is shown in FIG. 2, in which a synthetic DNA polylinker, facilitating insertion of foreign DNA, has been inserted into pVSVFL(+) between the G and L coding regions. The polylinker was synthesized on a DNA synthesizer so as to have ends compatible for ligation into an NheI site, and to contain the unique restriction enzyme recognition sites XmaI, SmaI, and NotI, facilitating insertion of foreign DNA generated by cleavage with one of these enzymes or ligated to a linker containing a recognition site for one of these enzymes (which is then subjected to cleavage prior to insertion).

The foreign DNA encoding an Antigen is inserted into any region, or replaces any region, of the vesiculovirus (−) DNA that is not essential for vesiculovirus replication. In a preferred embodiment, the foreign DNA is thus inserted into an intergenic region, or a portion of the vesiculovirus (−) DNA that is transcribed to form the noncoding region of a viral mRNA. In a preferred embodiment, the invention provides a nucleic acid comprising the DNA sequence of plasmid pVSVFL(+) as depicted in FIG. 1 from nucleotide numbers 623–12088 (a portion of SEQ ID NO:1), in which a region nonessential for vesiculovirus replication has been inserted into or replaced by foreign DNA.

Vesiculoviruses have a defined intergenic structure. Extensive homologies are found around the intergenic dinucleotides (FIG. 3). These regions have the common structure (3')AUACUUUUUUU<u>N</u>AUUGUCNNUAG(5') (SEQ ID NO:34), in which N indicates any nucleotide (thus three variable positions are present) and the intergenic dinucleotide is underlined. These dinucleotide spacers are GA, except at the NS-M junction, where the dinucleotide is CA. The first 11 nucleotides of the common sequence are complementary to the sequence (5') . . . UAUGAAAAAAA . . . (3') (SEQ ID NO:35) that occurs at the mRNA-polyadenylate[poly(A)] junction in each mRNA including L. Reiterative copying of the U residues by the VSV polymerase presumably generates the poly(A) tail on each mRNA (McGeoch, 1979, Cell 17:3199; Rose, 1980, Cell 19:415; Schubert et al., 1980, J. Virol. 34:550). The sequence complementary to the 5' end of the mRNA follows the intergenic dinucleotide. The L mRNA also terminates with the sequence UAUG-poly(A) encoded by the sequence (3')AUACUUUUUUU (SEQ ID NO:36) and is presumably also polyadenylated by a polymerase "slippage" mechanism (Schubert et al., 1980, J. Virol. 34:550; Schubert and Lazarini, 1981, J. Virol. 38:256).

Thus, intergenic regions in vesiculovirus (−) DNA consist of three parts, triggering transcriptional termination and reinitiation present both 5' and 3' to each gene (presented as the 5' to 3' sequence of the positive sense strand of vesiculovirus (−) DNA): (a) TATGAAAAAAA (SEQ ID NO:37), followed by (b) the dinucleotide GT or CT, followed by (c) AACAG. Therefore, in a preferred aspect, foreign DNA encoding an Antigen can readily be expressed as a nonfusion protein from intergenic regions, simply by ensuring that this three-part intergenic region is reconstituted—i.e., that this intergenic region appears 5' and 3' to the foreign DNA and also 5' and 3' to the adjacent genes. For example, in a preferred embodiment, DNA consisting of (a) this three-part intergenic region, fused to (b) foreign DNA coding for a desired Antigen (preferably including the Antigen gene's native start and stop codons for initiation), is inserted into a portion of the vesiculovirus (−) DNA that is transcribed to form the 3' noncoding region of any vesiculovirus mRNA. In a particularly preferred aspect, the foreign DNA is inserted in the noncoding region between G and L.

In an alternative embodiment, the foreign DNA can be inserted into the G gene, so as to encode a fusion protein with G, for resultant surface display of the Antigen on the vesiculovirus particle. Selection should be undertaken to ensure that the foreign DNA insertion does not disrupt G protein function.

In a preferred embodiment, an Antigen expressed by a recombinant vesiculovirus is all or a portion of an envelope glycoprotein of a virus other than a vesiculovirus. Such an Antigen can replace the endogenous vesiculovirus G protein in the vesiculovirus, or can be expressed as a fusion with the endogenous G protein, or can be expressed in addition to the endogenous G protein either as a fusion or nonfusion protein. In a specific embodiment, such an Antigen forms a part of the vesiculovirus envelope and thus is surface-displayed in the vesiculovirus particle. By way of example, gp160 or a fragment thereof of Human Immunodeficiency Virus can be the Antigen, which is cleaved to produce gp120 and gp41 (see Owens and Rose, 1993, J. Virol. 67(1):360–365). In a specific embodiment, the G gene of VSV in the VSV (−) DNA of plasmid pVSVFL(+) can be easily excised and replaced, by cleavage at the NheI and MluI sites flanking the G gene and insertion of the desired sequence. In another specific embodiment, the Antigen is a foreign envelope glycoprotein or portion thereof that is expressed as a fusion protein comprising the cytoplasmic domain (and, optionally, also the transmembrane region) of the native vesiculovirus G protein (see Owens and Rose, 1993, J. Virol. 67(1):360–365). Such a fusion protein can replace or be expressed in addition to the endogenous vesiculovirus G protein. As shown by way of example in Section 6 below, the entire native G coding sequence can be replaced by a coding sequence of a different G to produce recombinant replicable vesiculoviruses that express a non-native glycoprotein. While recombinant vesiculoviruses that express and display epitope(s) of envelope glycoproteins of other viruses can be used as live vaccines, such vesiculoviruses also are particularly useful as killed vaccines, as well as in the production of subunit vaccines containing the vesiculovirus-produced protein comprising such epitope(s).

In a specific embodiment, a recombinant vesiculovirus of the invention expresses in a host to which it is administered one or more Antigens. In one embodiment, a multiplicity of Antigens are expressed, each displaying different antigenicity or immunogenicity.

5.2. DNA SEQUENCES ENCODING ANTIGENS

The invention provides recombinant vesiculoviruses capable of replication that have a foreign RNA sequence inserted into or replacing a site of the genome nonessential for replication, wherein the foreign RNA sequence (which is in the negative sense) directs the production of an Antigen capable of being expressed in a host infected by the recombinant virus. This recombinant genome is originally produced by insertion of foreign DNA encoding the Antigen into the vesiculovirus (−) DNA. Any DNA sequence which encodes an immunogenic (capable of provoking an immune response) Antigen, which produces prophylactic or therapeutic immunity against a disease or disorder, when expressed as a fusion or, preferably, nonfusion protein in a recombinant vesiculovirus of the invention, alone or in combination with other Antigens expressed by the same or a different vesiculovirus recombinant, can be isolated for use in the vaccine formulations of the present invention.

In a preferred embodiment, expression of an Antigen by a recombinant vesiculovirus induces an immune response against a pathogenic microorganism. For example, an Antigen may display the immunogenicity or antigenicity of an antigen found on bacteria, parasites, viruses, or fungi which are causative agents of diseases or disorders. In a preferred embodiment, Antigens displaying the antigenicity or immunogenicity of antigens of animal viruses of veterinary importance (for example, which cause diseases or disorders in non-human animals such as domestic or farm animals, e.g., cows, chickens, horses, dogs, cats, etc.) are used. In another embodiment, Antigens displaying the antigenicity or immunogenicity of an antigen of a human pathogen are used.

To determine immunogenicity or antigenicity by detecting binding to antibody, various immunoassays known in the art can be used, including but not limited to competitive and non-competitive assay systems using techniques such as radioimmunoassays, ELISA (enzyme linked immunosorbent assay), "sandwich" immunoassays, immunoradiometric assays, gel diffusion precipitin reactions, immunodiffusion assays, in situ immunoassays (using colloidal gold, enzyme or radioisotope labels, for example), western blots, immunoprecipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labelled. Many means are known in the art for detecting binding in an immunoassay and are envisioned for use. In one embodiment for detecting immunogenicity, T cell-mediated responses can be assayed by standard methods, e.g., in vitro cytoxicity assays or in vivo delayed-type hypersensitivity assays.

Parasites and bacteria expressing epitopes (antigenic determinants) that can be expressed by recombinant vesiculoviruses (wherein the foreign RNA directs the production of an antigen of the parasite or bacteria or a derivative thereof containing an epitope thereof) include but are not limited to those listed in Table II.

TABLE II

PARASITES AND BACTERIA EXPRESSING EPITOPES THAT CAN BE EXPRESSED BY RECOMBINANT VESICULOVIRUSES

PARASITES:

plasmodium spp.
Eimeria spp.

BACTERIA:

Vibrio cholerae
Streptococcus pneumoniae
Neisseria mennigitidis
Neisseria gonorrhoeae
Corynebacteria diphtheriae
Clostridium tetani
Bordetella pertussis
Haemophilus spp. (e.g., influenzae)
Chlamydia spp*
Enterotoxigenic Escherichia coli In another embodiment, the Antigen comprises an epitope of an antigen of a nematode, to protect against disorders caused by such worms.

In another specific embodiment, any DNA sequence which encodes a Plasmodium epitope, which when expressed by a recombinant vesiculovirus, is immunogenic in a vertebrate host, can be isolated for insertion into vesiculovirus (−) DNA according to the present invention. The species of Plasmodium which can serve as DNA sources include but are not limited to the human malaria parasites P. falciparum, P. malariae, P. ovale, P. vivax, and the animal malaria parasites P. berghei, P. yoelii, P. knowlesi, and P. cynomolgi. In a particular embodiment, the epitope to be expressed is an epitope of the circumsporozoite (CS) protein of a species of Plasmodium (Miller et al., 1986, Science 234:1349).

In yet another embodiment, the Antigen comprises a peptide of the β subunit of Cholera toxin (Jacob et al., 1983, Proc. Natl. Acad. Sci. USA 80:7611).

Viruses expressing epitopes (antigenic determinants) that can be expressed by recombinant vesiculoviruses (wherein the foreign RNA directs the production of an antigen of the virus or a derivative thereof comprising an epitope thereof) include but are not limited to those listed in Table III, which lists such viruses by family for purposes of convenience and not limitation (see 1990, Fields Virology, 2d ed., Fields and Knipe (eds.), Raven Press, NY).

TABLE III

VIRUSES EXPRESSING EPITOPES THAT CAN BE EXPRESSED BY RECOMBINANT VESICULOVIRUSES

I. Picornaviridae
  Enteroviruses
  Poliovirus
  Coxsackievirus
  Echovirus
  Rhinoviruses
  Hepatitis A Virus
II. Caliciviridae
  Norwalk group of viruses
III. Togaviridae and Flaviviridae
  Togaviruses (e.g., Dengue virus)
  Alphaviruses
  Flaviviruses (e.g., Hepatitis C virus)
  Rubella virus
IV. Coronaviridae
  Coronaviruses
V. Rhabdoviridae
  Rabies virus
VI. Filoviridae
  Marburg viruses
  Ebola viruses
VII. Paramyxoviridae
  Parainfluenza virus
  Mumps virus
  Measles virus
  Respiratory syncytial virus
VIII. Orthomyxoviridae
  Orthomyxoviruses (e.g., Influenza virus)
IX. Bunyaviridae
  Bunyaviruses
X. Arenaviridae
  Arenaviruses
XI. Reoviridae
  Reoviruses
  Rotaviruses
  Orbiviruses
XII. Retroviridae
  Human T Cell Leukemia Virus type I
  Human T Cell Leukemia Virus type II
  Human Immunodeficiency Viruses (e.g., type I and type II)
  Simian Immunodeficiency Virus
  Lentiviruses
XIII. Papoviridae
  Polyomaviruses
  Papillomaviruses
XIV. Parvoviridae
  Parvoviruses
XV. Herpesviridae
  Herpes Simplex Viruses
  Epstein-Barr virus
  Cytomegalovirus
  Varicella-Zoster virus
  Human Herpesvirus-6
  Cercopithecine Herpes Virus 1 (B virus)

TABLE III-continued

VIRUSES EXPRESSING EPITOPES THAT CAN
BE EXPRESSED BY RECOMBINANT VESICULOVIRUSES
XVI. Poxviridae
Poxviruses
XVIII. Hepadnaviridae
Hepatitis B virus In specific embodiments, the Antigen encoded by the foreign sequences that is expressed upon infection of a host by the recombinant vesiculovirus, displays the antigenicity or immunogenicity of an influenza virus hemagglutinin (Genbank accession no. J02132; Air, 1981, Proc. Natl. Acad. Sci. USA 78:7639–7643; Newton et al., 1983, Virology 128:495–501); human respiratory syncytial virus G glycoprotein (Genbank accession no. Z33429; Garcia et al., 1994, J. Virol.; Collins et al., 1984, Proc. Natl. Acad. Sci. USA 81:7683); core protein, matrix protein or other protein of Dengue virus (Genbank accession no. M19197; Hahn et al., 1988, Virology 162:167–180), measles virus hemagglutinin (Genbank accession no. M81899; Rota et al., 1992, Virology 188:135–142); and herpes simplex virus type 2 glycoprotein gB (Genbank accession no. M14923; Bzik et al., 1986, Virology 155:322–333).

In another embodiment, one or more epitopes of the fusion protein of respiratory synctyial virus (RSV) can be expressed as an Antigen.

Other Antigens that can be expressed by a recombinant vesiculovirus include but are not limited to those displaying the antigenicity or immunogenicity of the following antigens: Poliovirus I VP1 (Emini et al., 1983, Nature 304:699); envelope glycoproteins of HIV I (Putney et al., 1986, Science 234:1392–1395); Hepatitis B surface antigen (Itoh et al., 1986, Nature 308:19; Neurath et al., 1986, Vaccine 4:34); Diptheria toxin (Audibert et al., 1981, Nature 289:543); streptococcus 24M epitope (Beachey, 1985, Adv. Exp. Med. Biol. 185:193); and gonococcal pilin (Rothbard and Schoolnik, 1985, Adv. Exp. Med. Biol. 185:247).

In other embodiments, the Antigen expressed by the recombinant vesiculovirus displays the antigenicity or immunogenicity of pseudorabies virus g50 (gpD), pseudorabies virus II (gpB), pseudorabies virus gIII (gpC), pseudorabies virus glycoprotein H, pseudorabies virus glycoprotein E, transmissible gastroenteritis glycoprotein 195, transmissible gastroenteritis matrix protein, swine rotavirus glycoprotein 38, swine parvovirus capsid protein, *Serpulina hydodysenteriae* protective antigen, Bovine Viral Diarrhea glycoprotein 55, Newcastle Disease Virus hemagglutinin-neuraminidase, swine flu hemagglutinin, or swine flu neuraminidase.

In various embodiments, the Antigen expressed by the recombinant vesiculovirus displays the antigenicity or immunogenicity of an antigen derived from *Serpulina hyodysenteriae*, Foot and Mouth Disease Virus, Hog Colera Virus, swine influenza virus, African Swine Fever Virus, *Mycoplasma hyopneumoniae*, infectious bovine rhinotracheitis virus (e.g., infectious bovine rhinotracheitis virus glycoprotein E or glycoprotein G), or infectious laryngotracheitis virus (e.g., infectious laryngotracheitis virus glycoprotein G or glycoprotein I).

In another embodiment, the Antigen displays the antigenicity or immunogenicity of a glycoprotein of La Crosse Virus (Gonzales-Scarano et al., 1982, Virology 120:42), Neonatal Calf Diarrhea Virus (Matsuno and Inouye, 1983, Infection and Immunity 39:155), Venezuelan Equine Encephalomyelitis Virus (Mathews and Roehrig, 1982, J. Immunol. 129:2763), Punta Toro Virus (Dalrymple et al., 1981, in Replication of Negative Strand Viruses, Bishop and Compans (eds.), Elsevier, NY, p. 167), Murine Leukemia Virus (Steeves et al., 1974, J. Virol. 14:187), or Mouse Mammary Tumor Virus (Massey and Schochetman, 1981, Virology 115:20).

In another embodiment, the Antigen displays the antigenicity or immunogenicity of an antigen of a human pathogen, including but not limited to human herpesvirus, herpes simplex virus-1, herpes simplex virus-2, human cytomegalovirus, Epstein-Barr virus, Varicella-Zoster virus, human herpesvirus-6, human herpesvirus-7, human influenza virus, human immunodeficiency virus, rabies virus, measles virus, hepatitis B virus, hepatitis C virus, *Plasmodium falciparum*, and *Bordetella pertussis*.

In a specific embodiment of the invention, a recombinant vesiculovirus expresses hepatitis B virus core protein and/or hepatitis B virus surface antigen or a fragment or derivative thereof (see, e.g., U.K. Patent Publication No. GB 2034323A published Jun. 4, 1980; Ganem and Varmus, 1987, Ann. Rev. Biochem. 56:651–693; Tiollais et al., 1985, Nature 317:489–495). The HBV genome (subtype adw) is contained in plasmid pAM6 (Moriarty et al., 1981, Proc. Natl. Acad. Sci. USA 78:2606–2610, available from the American Type Culture Collection (ATCC), Accession No. 45020), a pBR322-based vector that is replicable in *E. coli*.

In another embodiment, the Antigen expressed by the recombinant vesiculovirus displays the antigenicity or immunogenicity of an antigen of equine influenza virus or equine herpesvirus. Examples of such antigens are equine influenza virus type A/Alaska 91 neuraminidase, equine influenza virus type A/Miami 63 neuraminidase, equine influenza virus type A/Kentucky 81 neuraminidase equine herpesvirus type 1 glycoprotein B, and equine herpesvirus type 1 glycoprotein D.

In another embodiment, the Antigen displays the antigenicity or immunogenicity of an antigen of bovine respiratory syncytial virus or bovine parainfluenza virus. For example, such antigens include but are not limited to bovine respiratory syncytial virus attachment protein (BRSV G), bovine respiratory syncytial virus fusion protein (BRSV F), bovine respiratory syncytial virus nucleocapsid protein (BRSV N), bovine parainfluenza virus type 3 fusion protein, and the bovine parainfluenza virus type 3 hemagglutinin neuraminidase.

In another embodiment, the Antigen displays the antigenicity or immunogenicity of bovine viral diarrhea virus glycoprotein 48 or glycoprotein 53.

In another embodiment, the Antigen displays the antigenicity or immunogenicity of an antigen of infectious bursal disease virus. Examples of such antigens are infectious bursal disease virus polyprotein and VP2.

Potentially useful antigens or derivatives thereof for use as Antigens expressed by recombinant vesiculoviruses can be identified by various criteria, such as the antigen's involvement in neutralization of a pathogen's infectivity (Norrby, 1985, Summary, in Vaccines85, Lerner et al. (eds.), Cold Spring Harbor Laboratory, Cold Spring Harbor, N.Y., pp. 388–389), type or group specificity, recognition by patients' antisera or immune cells, and/or the demonstration of protective effects of antisera or immune cells specific for the antigen. In addition, the antigen's encoded epitope should preferably display a small or no degree of antigenic variation in time or amongst different isolates of the same pathogen.

In a preferred embodiment, the foreign DNA inserted into the vesiculovirus (−) DNA encodes an immunopotent dominant epitope of a pathogen. Foreign DNA encoding epitopes which are reactive with antibody although incapable of eliciting immune responses, still have potential uses in immunoassays (see Section 5.8, infra).

In another embodiment, foreign RNA of the recombinant vesiculovirus directs the production of an Antigen comprising an epitope, which when the recombinant vesiculovirus is introduced into a desired host, induces an immune response that protects against a condition or disorder caused by an entity containing the epitope. For example, the Antigen can be a tumor specific antigen or tumor-associated antigen, for induction of a protective immune response against a tumor (e.g., a malignant tumor). Such tumor-specific or tumor-associated antigens include but are not limited to KS ¼ pan-carcinoma antigen (Perez and Walker, 1990, J. Immunol. 142:3662–3667; Bumal, 1988, Hybridoma 7(4) :407–415); ovarian carcinoma antigen (CA125) (Yu et al., 1991, Cancer Res. 51(2):468–475); prostatic acid phosphate (Tailor et al., 1990, Nucl. Acids Res. 18(16):4928); prostate specific antigen (Henttu and Vihko, 1989, Biochem. Biophys. Res. Comm. 160(2):903–910; Israeli et al., 1993, Cancer Res. 53:227–230; melanoma-associated antigen p97 (Estin et al., 1989, J. Natl. Cancer Instit. 81(6):445–446); melanoma antigen gp75 (Vijayasardahl et al., 1990, J. Exp. Med. 171(4):1375–1380); high molecular weight melanoma antigen (Natali et al., 1987, Cancer 59:55–63); and prostate specific membrane antigen.

In another embodiment of the invention, the Antigen expressed by the recombinant vesiculovirus comprises large regions of proteins which contain several B cell epitopes (i.e., epitopes capable of enticing a humoral immune response) and T cell epitopes (i.e., epitopes capable of inducing a cell-mediated immune response).

Peptides or proteins which are known to contain antigenic determinants can be used as the Antigen. If specific desired antigens are unknown, identification and characterization of immunoreactive sequences can be carried out. One way in which to accomplish this is through the use of monoclonal antibodies generated to the surface or other molecules of a pathogen or tumor, as the case may be. The peptide sequences capable of being recognized by the antibodies are defined epitopes. Alternatively, small synthetic peptides conjugated to carrier molecules can be tested for generation of monoclonal antibodies that bind to the sites corresponding to the peptide, on the intact molecule (see, e.g., Wilson et al., 1984, Cell 37:767).

In a specific embodiment, appropriate Antigens, including fragments or derivatives of known antigens, can be identified by virtue of their hydrophilicity, by carrying out a hydrophilicity analysis (Hopp and Woods, 1981, Proc. Natl. Acad. Sci. USA 78:3824) to generate a hydrophilicity profile. A hydrophilicity profile can be used to identify the hydrophobic and hydrophilic regions of a protein and the corresponding regions of the gene sequence which encode such proteins. Hydrophilic regions are predicted to be immunogenic/antigenic. Other methods known in the art which may be employed for the identification and characterization of antigenic determinants are also within the scope of the invention.

The foreign DNA encoding the Antigen, that is inserted into a non-essential site of the vesiculovirus (−) DNA, optionally can further comprise a foreign DNA sequence encoding a cytokine capable of being expressed and stimulating an immune response in a host infected by the recombinant vesiculovirus. For example, such cytokines include but are not limited to interleukin-2, interleukin-6, interleukin-12, interferons, granulocyte-macrophage colony stimulating factors, and interleukin receptors.

The foreign DNA optionally can further comprise a sequence encoding and capable of expressing a detectable marker (e.g., β galactosidase).

5.3. CONSTRUCTION OF VESICULOVIRUS (−) DNA CONTAINING FOREIGN DNA

For initial production of a recombinant vesiculovirus, the foreign DNA comprising a sequence encoding the desired antigen is inserted into and/or replaces a region of the vesiculovirus (−) DNA nonessential for replication. Many strategies known in the art can be used in the construction of the vesiculovirus (−) DNA containing the foreign DNA. For example, the relevant sequences of the foreign DNA and of the vesiculovirus (−) DNA can, by techniques known in the art, be cleaved at appropriate sites with restriction endonuclease(s), isolated, and ligated in vitro. If cohesive termini are generated by restriction endonuclease digestion, no further modification of DNA before is ligation may be needed. If, however, cohesive termini of the DNA are not available for generation by restriction endonuclease digestion, or different sites other than those available are preferred, any of numerous techniques known in the art may be used to accomplish ligation of the heterologous DNA at the desired sites. In a preferred embodiment, a desired restriction enzyme site is readily introduced into the desired DNA by amplification of the DNA by use of PCR with primers containing the restriction enzyme site. By way of another example, cleavage with a restriction enzyme can be followed by modification to create blunt ends by digesting back or filling in single-stranded DNA termini before ligation. Alternatively, the cleaved ends of the vesiculovirus (−) DNA or foreign DNA can be "chewed back" using a nuclease such as nuclease Bal 31, exonuclease III, lambda exonuclease, mung bean nuclease, or T4 DNA polymerase exonuclease activity, to name but a few, in order to remove portions of the sequence.

To facilitate insertion of the foreign DNA, an oligonucleotide sequence (a linker) which encodes one or more restriction sites can be inserted in a region of the vesiculovirus (−) DNA (see, e.g., the polylinker in pVSVSS1, FIG. 2) by ligation to DNA termini. A linker may also be used to generate suitable restriction sites in the foreign DNA sequence.

Additionally, vesiculovirus (−) DNA or foreign DNA sequences can be mutated in vitro or in vivo in order to form new restriction endonuclease sites or destroy preexisting ones, to facilitate in vitro ligation procedures. Any technique for mutagenesis known in the art can be used, including but not limited to, in vitro site-directed mutagenesis (Hutchinson et al., 1978, J. Biol. Chem. 253:6551), chemical mutagenesis, etc.

Sequences of the vesiculovirus (−) DNA that have been undesirably modified by such in vitro manipulations can be "restored," if desired, by introduction of appropriate sequences at the desired sites.

The particular strategy for inserting the foreign DNA will depend on the specific vesiculovirus (−) DNA site to be replaced or inserted into, as well as the foreign DNA to be inserted.

The sequences encoding the immunogenic peptides or proteins are preferably present in single copies, but can also be present in multiple copies within the virus genome.

Formation of the desired vesiculovirus (−) DNA containing the foreign DNA can be confirmed by standard methods such as DNA sequence analysis, hybridization analysis, and/or restriction mapping, using methods well known in the art.

Foreign DNA encoding a desired antigen can be obtained from any of numerous sources such as cloned DNA, genomic DNA, or cDNA made from RNA of the desired pathogen or tumor, as the case may be, or chemically synthesized DNA, and manipulated by recombinant DNA methodology well known in the art (see Sambrook et al., 1991, Molecular Cloning, A Laboratory Manual, 2d ed., Cold Spring Harbor Laboratory Press, New York). In a preferred embodiment, polymerase chain reaction (PCR) is used to amplify the desired fragment of foreign DNA from among a crude preparation of DNA or a small sample of the DNA, by standard methods. Appropriate primers for use in PCR can be readily deduced based on published sequences.

In order to generate appropriate DNA fragments, the DNA (e.g., from the pathogen or tumor of interest) may be cleaved at specific sites using various restriction enzymes. Alternatively, one may use DNaseI in the presence of manganese, or mung bean nuclease (McCutchan et al., 1984, Science 225:626), to fragment the DNA, or the DNA can be physically sheared, as for example, by sonication. The linear DNA fragments can then be separated according to size by standard techniques, including, but not limited to, agarose and polyacrylamide gel electrophoresis and column chromatography.

PCR amplification of DNA fragments containing the desired epitope(s) is most preferably carried out, in which the PCR primers contain and thus introduce into the amplified DNA a desired restriction enzyme recognition site. Alternatively, any restriction enzyme or combination of restriction enzymes may be used to generate DNA fragment(s) containing the desired epitope(s), provided the enzymes do not destroy the immunopotency of the encoded product. Consequently, many restriction enzyme combinations may be used to generate DNA fragments which, when inserted into the vesiculovirus (−) DNA, are capable of producing recombinant vesiculoviruses that direct the production of the peptide containing the epitope(s).

Once the DNA fragments are generated, identification of the specific fragment containing the desired sequence may be accomplished in a number of ways. For example, if a small amount of the desired DNA sequence or a homologous sequence is previously available, it can be used as a labeled probe (e.g., nick translated) to detect the DNA fragment containing the desired sequence, by nucleic acid hybridization. Alternatively, if the sequence of the derived gene or gene fragment is known, isolated fragments or portions thereof can be sequenced by methods known in the art, and identified by a comparison of the derived sequence to that of the known DNA or protein sequence. Alternatively, the desired fragment can be identified by techniques including but not limited to mRNA selection, making cDNA to the identified mRNA, chemically synthesizing the gene sequence (provided the sequence is known), or selection on the basis of expression of the encoded protein (e.g., by antibody binding) after "shotgun cloning" of various DNA fragments into an expression system.

The sequences encoding peptides to be expressed in recombinant vesiculoviruses according to the present invention, whether produced by recombinant DNA methods, chemical synthesis, or purification techniques, include but are not limited to sequences encoding all or part (fragments) of the amino acid sequences of pathogen-specific and tumor-specific antigens, as well as other derivatives and analogs thereof displaying the antigenicity or immunogenicity thereof. Derivatives or analogs of antigens can be tested for the desired activity by procedures known in the art, including but not limited to standard immunoassays.

In particular, antigen derivatives can be made by altering the encoding antigen nucleotide sequences by substitutions, additions or deletions that do not destroy the antigenicity or immunogenicity of the antigen. For example, due to the degeneracy of nucleotide coding sequences, other DNA sequences which encode substantially the same amino acid sequence as a native antigen gene or portion thereof may be used in the practice of the present invention. Other examples may include but are not limited to nucleotide sequences comprising all or portions of genes or cDNAs which are altered by the substitution of different codons that encode a functionally equivalent amino acid residue within the sequence, thus producing a silent change. For example, one or more amino acid residues within the sequence can be substituted by another amino acid of a similar polarity which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan, and methionine. The polar neutral amino acids include glycine, serine, threonine, cysteine, tyrosine, asparagine, and glutamine. The positively charged (basic) amino acids include arginine, lysine, and histidine. The negatively charged (acidic) amino acids include aspartic and glutamic acid.

The antigen derivatives and analogs can be produced by various methods known in the art. For example, a cloned gene sequence can be modified by any of numerous strategies known in the art (Sambrook et al., 1989, Molecular Cloning, A Laboratory Manual, 2d ed., Cold Spring Harbor Laboratory, Cold Spring Harbor, N.Y.). The sequence can be cleaved at appropriate sites with restriction endonuclease(s), followed by further enzymatic modification if desired, isolated, and ligated in vitro. In the production of the gene encoding a derivative or analog of an antigen, care should be taken to ensure that the modified gene remains within the same translational reading frame as the antigen, uninterrupted by translational stop signals, in the gene region where the desired epitope(s) are encoded.

Additionally, the antigen-encoding nucleic acid sequence can be mutated in vitro or in vivo, to create and/or destroy translation, initiation, and/or termination sequences, or to create variations in coding regions and/or form new restriction endonuclease sites or destroy preexisting ones, to facilitate further in vitro modification. Any technique for mutagenesis known in the art can be used, including but not limited to, in vitro site-directed mutagenesis (Hutchinson, C., et al., 1978, J. Biol. Chem 253:6551), use of TAB® linkers (Pharmacia), etc.

In another specific embodiment, the encoded antigen derivative is a chimeric, or fusion, protein comprising a first protein or fragment thereof fused to a second, different amino acid sequence. Such a chimeric protein is encoded by a chimeric nucleic acid in which the two coding sequences are joined inframe. Such a chimeric product can be made by ligating the appropriate nucleic acid sequences encoding the desired amino acid sequences to each other by methods known in the art, in the proper coding frame. In a specific embodiment, a fusion protein is produced in which the first protein sequence contains an epitope of an antigen, and the second protein sequence contains an epitope of a different antigen.

Derivatives and fragments of known antigens can be readily tested by standard immunoassay techniques to ascertain if they display the desired immunogenicity or antigenicity, rendering a DNA sequence encoding such a fragment or derivative suitable for insertion into the vesiculovirus (−) DNA.

A DNA sequence encoding an epitope that is a hapten, i.e., a molecule that is antigenic in that it can react selectively with cognate antibodies, but not immunogenic in that it cannot elicit an immune response when administered without adjuvants or carrier proteins, can also be isolated for use, since it is envisioned that, in particular embodiments, presentation by the vesiculoviruses of the invention can confer immunogenicity to the hapten expressed by the virus.

Once identified and isolated, the foreign DNA containing the sequencers) of interest is then inserted into the vesiculovirus (−) DNA, for production of a recombinant vesiculovirus.

5.4. PRODUCTION OF RECOMBINANT VESICULOVIRUSES

The recombinant vesiculoviruses of the invention are produced by providing in an appropriate host cell: vesiculovirus (−) DNA, in which regions nonessential for replication have been inserted into or replaced by foreign DNA comprising a sequence encoding an Antigen, and recombinant sources of vesiculovirus N protein, P protein, and L protein. The production is preferably in vitro, in cell culture.

The host cell used for recombinant vesiculovirus production can be any cell in which vesiculoviruses grow, e.g., mammalian cells and some insect (e.g., Drosophila) cells. Primary cells, or more preferably, cell lines can be used. A vast number of cell lines commonly known in the art are available for use. By way of example, such cell lines include but are not limited to BHK (baby hamster kidney) cells, CHO (Chinese hamster ovary) cells, HeLA (human) cells, mouse L cells, Vero (monkey) cells, ESK-4, PK-15, EMSK cells, MDCK (Madin-Darby canine kidney) cells, MDBK (Madin-Darby bovine kidney) cells, 293 (human) cells, and Hep-2 cells.

The sources of N, P, and L proteins can be the same or different recombinant nucleic acid(s), encoding and capable of expressing the N, P and L proteins in the host cell in which it is desired to produce recombinant vesiculovirus.

The nucleic acids encoding the N, P and L proteins are obtained by any means available in the art. The N, P and L nucleic acid sequences have been disclosed and can be used. For example, see Genbank accession no. J02428; Rose and Schubert, 1987, in *The Viruses: The Rhabdoviruses*, Plenum Press, NY, pp. 129–166. The sequences encoding the N, P and L genes can also be obtained from plasmid pVSVFL(+), deposited with the ATCC and assigned accession no. 97134, e.g., by PCR amplification of the desired gene (PCR; U.S. Pat. Nos. 4,683,202, 4,683,195 and 4,889,818; Gyllenstein et al., 1988, Proc. Natl. Acad. Sci. USA 85:7652–7656; Ochman et al., 1988, Genetics 120:621–623; Loh et al., 1989, Science 243:217–220). If a nucleic acid clone of any of the N, P or L genes is not already available, the clone can be obtained by use of standard recombinant DNA methodology. For example, the DNA may be obtained by standard procedures known in the art by purification of RNA from vesiculoviruses followed by reverse transcription and polymerase chain reaction (Mullis and Faloona, 1987, Methods in Enzymology 155:335–350). Alternatives to isolating an N, P or L gene include, but are not limited to, chemically synthesizing the gene sequence itself. Other methods are possible and within the scope of the invention.

If desired, the identified and isolated gene can then optimally be inserted into an appropriate cloning vector prior to transfer to an expression vector.

Nucleic acids that encode derivatives (including fragments) and analogs of native N, P and L genes, as well as derivatives and analogs of the vesiculovirus (−) DNA can also be used in the present invention, as long as such derivatives and analogs retain function, as exemplified by the ability when used according to the invention to produce a replicable vesiculovirus containing a genomic RNA containing foreign RNA. In particular, derivatives can be made by altering sequences by substitutions, additions, or deletions that provide for functionally active molecules. Furthermore, due to the inherent degeneracy of nucleotide coding sequences, other DNA sequences which encode substantially the same or a functionally equivalent amino acid sequence may be used in the practice of the methods of the invention. Amino acid substitutions may be made on the basis of similarity in polarity, charge, solubility, hydrophobicity, hydrophilicity and/or the amphipathic nature of the residues involved.

The desired N/P/L-encoding nucleic acid is then preferably inserted into an appropriate expression vector, i.e., a vector which contains the necessary elements for the transcription and translation of the inserted protein-coding sequence in the host in which it is desired to produce recombinant vesiculovirus, to create a vector that functions to direct the synthesis of the N/P/L protein that will subsequently assemble with the vesiculovirus genomic RNA containing the foreign sequence (produced in the host cell from antigenomic vesiculovirus (+) RNA produced by transcription of the vesiculovirus (−) DNA). A variety of vector systems may be utilized to express the N, P and L-coding sequences, as well as to transcribe the vesiculovirus (−) DNA containing the foreign DNA, as long as the vector is functional in the host and compatible with any other vector present. Such vectors include but are not limited to bacteriophages, plasmids, or cosmids. In a preferred aspect, a plasmid expression vector is used. The expression elements of vectors vary in their strengths and specificities. Any one of a number of suitable transcription and translation elements may be used, as long as they are functional in the host.

Standard recombinant DNA methods may be used to construct expression vectors containing DNA encoding the N, P, and L proteins, and the vesiculovirus (−) DNA containing the foreign DNA, comprising appropriate transcriptional/ translational control signals (see, e.g., Sambrook et al., 1989, supra, and methods described hereinabove). (Translational control signals are not needed for transcription of the vesiculovirus (−) DNA, and thus may be omitted from a vector containing the vesiculovirus (−) DNA, although such signals may be present in the vector and operably linked to other sequences encoding a protein which it is desired to express). Expression may be controlled by any promoter/enhancer element known in the art. Promoters which may be used to control expression can be constitutive or inducible. In a specific embodiment, the promoter is an RNA polymerase promoter.

Transcription termination signals (downstream of the gene), and selectable markers are preferably also included in a plasmid expression vector. In addition to promoter sequences, expression vectors for the N, P, and L proteins preferably contain specific initiation signals for efficient translation of inserted N/P/L sequences, e.g., a ribosome binding site.

Specific initiation signals are required for efficient translation of inserted protein coding sequences. These signals include the ATG initiation codon and adjacent sequences. In cases where the entire N, P, or L gene including its own initiation codon and adjacent sequences are inserted into the appropriate vectors, no additional translational control signals may be needed. However, in cases where only a portion of the gene sequence is inserted, exogenous translational control signals, including the ATG initiation codon, must be provided. The initiation codon must furthermore be in phase with the reading frame of the protein coding sequences to ensure translation of the entire insert. These exogenous translational control signals and initiation codons can be of a variety of origins, both natural and synthetic.

In a specific embodiment, a recombinant expression vector provided by the invention, encoding an N, P, and/or L protein or functional derivative thereof, comprises the following operatively linked components: a promoter which controls the expression of the N, P, or L protein or functional derivative thereof, a translation initiation signal, a DNA sequence encoding the N, P or L protein or functional derivative thereof, and a transcription termination signal. In a preferred aspect, the above components are present in 5' to 3' order as listed above.

In another specific embodiment, the gene encoding the N, P, or L protein is inserted downstream of the T7 RNA polymerase promoter from phage T7 gene 10, situated with an A in the −3 position. A T7 RNA polymerase terminator and a replicon are also included in the expression vector. In this embodiment, T7 RNA polymerase is provided to transcribe the N/P/L sequence. The T7 RNA polymerase can be produced from a chromosomally integrated sequence or episomally, and is most preferably provided by intracellular expression from a recombinant vaccinia virus encoding the T7 RNA polymerase (see infra). Preferably, the N, P, and L proteins are each encoded by a DNA sequence operably linked to a promoter in an expression plasmid, containing the necessary regulatory signals for transcription and translation of the N, P, and L proteins. Such an expression plasmid preferably includes a promoter, the coding sequence, and a transcription termination/polyadenylation signal, and optionally, a selectable marker (e.g., β-galactosidase). The N, P and L proteins can be encoded by the same or different plasmids, or a combination thereof, and preferably are in different plasmids. Less preferably, one or more of the N, P, and L proteins can be expressed intrachromosomally.

The cloned sequences comprising the vesiculovirus (−) DNA containing the foreign DNA, and the cloned sequences comprising sequences encoding the N, P, and L proteins can be introduced into the desired host cell by any method known in the art, e.g., transfection, electroporation, infection (when the sequences are contained in, e.g., a viral vector), microinjection, etc.

In a preferred embodiment, DNA comprising vesiculovirus (−) DNA containing foreign DNA encoding an Antigen, operably linked to an RNA polymerase promoter (preferably a bacteriophage RNA polymerase promoter); DNA encoding N, operably linked to the same RNA polymerase promoter; DNA encoding P, operably linked to the same polymerase promoter; and DNA encoding L, operably linked to the same polymerase promoter; are all introduced (preferably by transfection) into the same host cell, in which host cell the RNA polymerase has been cytoplasmically provided. The RNA polymerase is cytoplasmically provided preferably by expression from a recombinant virus that replicates in the cytoplasm and expresses the RNA polymerase, most preferably a vaccinia virus (see the section hereinbelow), that has been introduced (e.g., by infection) into the same host cell. Cytoplasmic provision of RNA polymerase is preferred, since this will result in cytoplasmic transcription and processing, of the VSV (−) DNA comprising the foreign DNA and of the N, P and L proteins, avoiding splicing machinery in the cell nucleus, and thus maximizing proper processing and production of N, P and L proteins, and resulting assembly of the recombinant vesiculovirus. For example, vaccinia virus also cytoplasmically provides enzymes for processing (capping and polyadenylation) of mRNA, facilitating proper translation.

In a most preferred aspect, T7 RNA polymerase promoters are employed, and a cytoplasmic source of T7 RNA polymerase is provided by also introducing into the host cell a recombinant vaccinia virus encoding T7 RNA polymerase into the host cell. Such vaccinia viruses can be obtained by well known methods (see section 5.5, infra). In a preferred aspect, a recombinant vaccinia virus such as vTF7-3 (Fuerst et al., 1986, Proc. Natl. Acad. Sci. U.S.A. 83:8122–8126) can be used. In a most preferred aspect, the DNA comprising vesiculovirus (−) DNA containing foreign DNA is plasmid PVSVSS1 in which foreign DNA has been inserted into the polylinker region.

Alternatively, but less preferably, the RNA polymerase (e.g., T7 RNA polymerase) can be provided by use of a host cell that expresses T7 RNA polymerase from a chromosomally integrated sequence (e.g., originally inserted into the chromosome by homologous recombination), preferably constitutively, or that expresses T7 RNA polymerase episomally, from a plasmid.

In another, less preferred, embodiment, the VSV (−) DNA encoding an Antigen, operably linked to a promoter, can be transfected into a host cell that stably recombinantly expresses the N, P, and L proteins from chromosomally integrated sequences.

The cells are cultured and recombinant vesiculovirus is recovered, by standard methods. For example, and not by limitation, after approximately 24 hours, cells and medium are collected, freeze-thawed, and the lysates clarified to yield virus preparations. Alternatively, the cells and medium are collected and simply cleared of cells and debris by low-speed centrifugation.

Confirmation that the appropriate foreign sequence is present in the genome of the recombinant vesiculovirus and directs the production of the desired protein(s) in an infected cell, is then preferably carried out. Standard procedures known in the art can be used for this purpose. For example, genomic RNA is obtained from the vesiculovirus by SDS phenol extraction from virus preparations, and can be subjected to reverse transcription (and PCR, if desired), followed by sequencing, Southern hybridization using a probe specific to the foreign DNA, or restriction enzyme mapping, etc. The virus can be used to infect host cells, which can then be assayed for expression of the desired protein by standard immunoassay techniques using an antibody to the protein, or by assays based on functional activity of the protein. Other techniques are known in the art and can be used.

The invention also provides kits for production of recombinant vesiculoviruses. In one embodiment, the kit comprises in one or more (and most preferably, in separate)

containers: (a) a first recombinant DNA that can be transcribed in a suitable host cell to produce a vesiculovirus antigenomic (+) RNA in which a portion of the RNA nonessential for replication of the vesiculovirus has been inserted into or replaced by a foreign RNA sequence; (b) a second recombinant DNA comprising a sequence encoding a vesiculovirus N protein; (c) a third recombinant DNA comprising a sequence encoding a vesiculovirus L protein; and (d) a fourth recombinant DNA comprising a sequence encoding a vesiculovirus P protein. The second, third and fourth recombinant DNAs can be part of the same or different DNA molecules. In a preferred embodiment, the sequences encoding the N, L, and P proteins are each operably linked to a promoter that controls expression of the N, L, and P proteins, respectively, in the suitable host cell. In various embodiments, the kit can contain the various nucleic acids, e.g., plasmid expression vectors, described hereinabove for use in production of recombinant vesiculoviruses.

In another embodiment, a kit of the invention comprises (a) a first recombinant DNA that can be transcribed in a suitable host cell to produce a vesiculovirus antigenomic DNA in which a portion of the RNA nonessential for replication of the vesiculovirus has been inserted into or replaced by a foreign RNA sequence; and (b) a host cell that recombinantly expresses vesiculovirus N, P and L proteins.

In a preferred embodiment, a kit of the invention comprises in separate containers:

(a) a first plasmid comprising the following operatively linked components: (i) a bacteriophage RNA polymerase promoter, (ii) a DNA comprising a sequence capable of being transcribed in a suitable host cell to produce an RNA molecule comprising a vesiculovirus antigenomic RNA in which a portion of the RNA nonessential for replication of the vesiculovirus has been inserted into or replaced by a foreign RNA sequence, and in which the 3' end of the antigenomic RNA is immediately adjacent to a ribozyme sequence that cleaves at the 3' end of the antigenomic RNA, and (iii) a transcriptional termination signal for the bacteriophage RNA polymerase; and (b) a second plasmid comprising the following operatively linked components: (i) the bacteriophage RNA polymerase promoter, (ii) a DNA comprising a sequence encoding the vesiculovirus N protein, and (ii) a transcriptional termination signal for the bacteriophage RNA polymerase; and (c) a third plasmid comprising the following operatively linked components: (i) the bacteriophage RNA polymerase promoter, (ii) a DNA comprising a sequence encoding the vesiculovirus P protein, and (ii) a transcriptional termination signal for the bacteriophage RNA polymerase; and (d) a fourth plasmid comprising the following operatively linked components: (i) the bacteriophage RNA polymerase promoter, (ii) a DNA comprising a sequence encoding the vesiculovirus L protein, and (ii) a transcriptional termination signal for the bacteriophage RNA polymerase.

In another embodiment, a kit of the invention further comprises in a separate container a recombinant vaccinia virus encoding and capable of expressing the bacteriophage RNA polymerase.

In a preferred embodiment, the components in the containers are in purified form.

5.4.1. RECOMBINANT VACCINIA VIRUSES ENCODING AND CAPABLE OF EXPRESSING FOREIGN RNA POLYMERASES

In a preferred aspect of the invention, transcription of the vesiculovirus (−) DNA containing the foreign DNA encoding an Antigen, and/or transcription of the DNA encoding the N, P, and L proteins in the host cell, is controlled by an RNA polymerase promoter (preferably one in which the RNA polymerase is not endogenous to the host cell), and the RNA polymerase (that initiates transcription from the promoter) is recombinantly provided in the host cell by expression from a recombinant vaccinia virus. DNA sequences encoding RNA polymerases are well known and available in the art and can be used. For example, phage DNA can be obtained and PCR used to amplify the desired polymerase gene.

Insertion of the desired recombinant DNA sequence encoding and capable of expressing the RNA polymerase into a vaccinia virus for expression by the vaccinia virus is preferably accomplished by first inserting the DNA sequence into a plasmid vector which is capable of subsequent transfer to a vaccinia virus genome by homologous recombination. Thus, in a preferred aspect of the invention for constructing the recombinant vaccinia viruses, the desired DNA sequence encoding the polymerase is inserted, using recombinant DNA methodology (see Sambrook et al., 1989, Molecular Cloning, A Laboratory Manual, 2d ed., Cold Spring Harbor Laboratory, Cold Spring Harbor, N.Y.) into an insertion (preferably, plasmid) vector flanked by (preferably) nonessential vaccinia DNA sequences, thus providing for subsequent transfer of its chimeric gene(s) into vaccinia virus by homologous recombination. The sequences are placed in the vector such that they can be expressed under the control of a promoter functional in vaccinia virus.

Expression of foreign DNA in recombinant vaccinia viruses requires the positioning of promoters functional in vaccinia so as to direct the expression of the protein-coding polymerase DNA sequences. Plasmid insertion vectors have been constructed to insert chimeric genes into vaccinia virus for expression therein. Examples of such vectors are described by Mackett (Mackett et al., 1984. J. Virol. 49:857–864). The DNA encoding the polymerase is inserted into a suitable restriction endonuclease cloning site. In addition to plasmid insertion vectors, insertion vectors based on single-stranded M13 bacteriophage DNA (Wilson et al., 1986, Gene 49:207–213) can be used.

The inserted polymerase DNA should preferably not contain introns, and insertion should preferably be so as to place the coding sequences in close proximity to the promoter, with no other start codons in between the initiator ATG and the 5' end of the transcript.

The plasmid insertion vector should contain transcriptional and translational regulatory elements that are active in vaccinia virus. The plasmid should be configured so that the polymerase sequences are under the control of a promoter active in vaccinia virus. Promoters which can be used in the insertion vectors include but are not limited to the vaccinia virus thymidine kinase (TK) promoter, the 7.5K promoter (Cochran et al., 1985, J. Virol. 54:30–37), the 11K promoter (European Patent Publication 0198328), the F promoter (Paoletti et al., 1984, Proc. Natl. Acad. Sci. USA 81:193–197), and various early and late vaccinia promoters (see Moss, 1990, *Virology*, 2d ed., ch. 74, Fields et al., eds., Raven Press, Ltd., New York, pp. 2079–2111).

In a specific embodiment, the plasmid insertion vector contains (for eventual transfer into vaccinia virus) a T7 RNA polymerase coding sequence under the control of a promoter active in vaccinia virus. In another specific embodiment, a plasmid insertion vector contains a co-expression system consisting of divergently oriented promoters, one directing transcription of the polymerase sequences, the other directing transcription of a reporter gene or selectable marker, to facilitate detection or selection of the eventual recombinant vaccinia virus (see, e.g., Fuerst et al., 1987, Mol. Cell. Biol. 5:1918–1924).

As described supra, the plasmid insertion vector contains at least one set of polymerase coding sequences operatively linked to a promoter, flanked by sequences preferably nonessential for vaccinia viral replication. Such nonessential sequences include but are not limited to the TK gene (Mackett et al., 1984, J. Virol. 49:857–864), the vaccinia HindIII-F DNA fragment (Paoletti et al., 1984, Proc. Natl. Acad. Sci. USA 81:193–197), the vaccinia growth factor gene situated within both terminal repeats (Buller et al., 1988, J. Virol. 62:866–874), the N2 and M1 genes (Tamin et al., 1988, Virology 165:141–150), the M1 subunit of the ribonucleotide reductase gene in the vaccinia HindIII-I DNA fragment (Child et al., 1990, Virology 174:625–629), the vaccinia hemagglutinin (Shida et al., 1988, J. Virol. 62:4474–4480), vaccinia 14 kD fusion protein gene (Rodriguez et al., 1989, Proc. Natl. Acad. Sci. USA 86:1287–1291), etc. (see also Buller and Palumbo, 1991, Microbiol. Rev. 55(1):80–122). TK sequences are preferred for use; use of such sequences results in the generation of TK$^-$ recombinant viruses.

Recombinant vaccinia viruses are preferably produced by transfection of the recombinant insertion vectors containing the polymerase sequences into cells previously infected with vaccinia virus. Alternatively, transfection can take place prior to infection with vaccinia virus. Homologous recombination takes place within the infected cells and results in the insertion of the foreign gene into the viral genome, in the region corresponding to the insertion vector flanking regions. The infected cells can be screened using a variety of procedures such as immunological techniques, DNA plaque hybridization, or genetic selection for recombinant viruses which subsequently can be isolated. These vaccinia recombinants preferably retain their essential functions and infectivity and can be constructed to accommodate up to approximately 35 kilobases of foreign DNA.

Transfections may be performed by procedures known in the art, for example, a calcium chloride-mediated procedure (Mackett et al., 1985, The construction and characterization of vaccinia virus recombinants expressing foreign genes, in *DNA Cloning*, Vol. II, Rickwood and Hames (eds.), IRL Press, Oxford-Washington, D.C.) or a liposome-mediated procedure (Rose et al., 1991, Biotechniques 10:520–525).

Where, as is preferred, flanking TK sequences are used to promote homologous recombination, the resulting recombinant viruses thus have a disrupted TK region, permitting them to grow on a TK$^-$ host cell line such as Rat2 (ATCC Accession No. CRL 1764) in the presence of 5-bromo-2'-deoxyuridine (BUDR), under which conditions non-recombinant (TK$^+$) viruses will not grow.

In another embodiment, recombinant vaccinia viruses of the invention can be made by in vitro cloning, and then packaging with a poxvirus sensitive to a selection condition, rather than by homologous recombination (see International Publication No. WO 94/12617 dated Jun. 9, 1994). For example, the HBV DNA sequences can be inserted into vaccinia genomic DNA using standard recombinant DNA techniques in vitro; this recombinant DNA can then be packaged in the presence of a "helper" poxvirus such as a temperature sensitive vaccinia virus mutant or a fowlpox virus which can be selected against under the appropriate conditions.

Various vaccinia virus strains known in the art can be used to generate the recombinant viruses of the invention. A preferred vaccinia virus is the New York City Department of Health Laboratories strain, prepared by Wyeth (available from the American Type Culture Collection (ATCC), Accession No. VR-325). Other vaccinia strains include but are not limited to the Elstree and Moscow strains, the strain of Rivers (CV-1 and CV-2), and the LC16m8 strain of Hashizume.

Selection of the recombinant vaccinia virus can be by any method known in the art, including hybridization techniques (e.g., using polymerase DNA sequences as a hybridization probe), immunological techniques (e.g., assay for binding to antibodies recognizing the encoded polymerase epitope(s)), etc. In a preferred aspect where TK flanking sequences are used in the insertion vector, selection is for TK$^-$ recombinants, as described above; screening for the correct recombinant can then be carried out by standard molecular analyses. In many preferred aspects, the method of choice for selection is dictated by the selectable marker in an insertion vector used to generate the recombinant viruses.

The selected recombinant vaccinia virus is then generally plaque-purified, and preferably subjected to standard nucleic acid and protein analyses to verify its identity and purity, and expression of the inserted polymerase.

5.5. LARGE SCALE GROWTH AND PURIFICATION OF RECOMBINANT REPLICABLE VESICULOVIRUSES

The recovered recombinant vesiculovirus, after plaque-purification, can then be grown to large numbers, by way of example, as follows. Virus from a single plaque (~$10^6$ pfu) is recovered and used to infect ~$10^7$ cells (e.g., BHK cells), to yield, typically, 10 ml at a titer of $10^9$–$10^{10}$ pfu/ml for a total of approximately $10^{11}$ pfu. Infection of ~$10^{12}$ cells can then be carried out (with a multiplicity of infection of 0.1), and the cells can be grown in suspension culture, large dishes, or roller bottles by standard methods.

It is noted that recombinant vesiculoviruses which no longer express the extracellular region of the vesiculovirus G protein (which determine host range) and which, instead, express an envelope glycoprotein of a different virus will need to be grown in cells which are susceptible to infection by the different virus (and which cells thus express a receptor promoting infection by a virus expressing the envelope glycoprotein of the different virus). Thus, for example, where the recombinant vesiculovirus expresses the HIV envelope glycoprotein, the virus is grown in CD4$^+$ cells (e.g., CD4$^+$ lymphoid cells).

Virus for vaccine preparations can then be collected from culture supernatants, and the supernatants clarified to remove cellular debris. If desired, one method of isolating and concentrating the virus that can be employed is by passage of the supernatant through a tangential flow membrane concentration. The harvest can be further reduced in volume by pelleting through a glycerol cushion and by concentration on a sucrose step gradient. An alternate method of concentration is affinity column purification (Daniel et al., 1988, Int. J. Cancer 41:601–608). However, other methods can also be used for purification (see, e.g., Arthur et al., 1986, J. Cell. Biochem. Suppl. 10A:226), and any possible modifications of the above procedure will be readily recognized by one skilled in the art. Purification should be as gentle as possible, so as to maintain the integrity of the virus particle.

5.6. RECOMBINANT REPLICABLE VESICULOVIRUSES FOR USE AS LIVE VACCINES

In one embodiment of the invention, the recombinant replicable vesiculoviruses that express an immunogenic Antigen are used as live vaccines.

The recombinant vesiculoviruses for use as therapeutic or prophylactic live vaccines according to the invention are preferably somewhat attenuated. Most available strains e.g., laboratory strains of VSV, may be sufficiently attenuated for use. Should additional attenuation be desired, e.g., based on pathogenicity testing in animals, attenuation is most preferably achieved simply by laboratory passage of the recombinant vesiculovirus (e.g., in BHK or any other suitable cell line). Generally, attenuated viruses are obtainable by numerous methods known in the art including but not limited to chemical mutagenesis, genetic insertion, deletion (Miller, 1972, Experiments in Molecular Genetics, Cold Spring Harbor Laboratory, Cold Spring Harbor, N.Y.) or recombination using recombinant DNA methodology (Maniatis et al., 1982, Molecular Cloning, A Laboratory Manual, Cold Spring Harbor Laboratory, Cold Spring Harbor, N.Y.), laboratory selection of natural mutants, etc.

In this embodiment of the invention, a vaccine is formulated in which the immunogen is one or several recombinant vesiculovirus(es), in which the foreign RNA in the genome directs the production of an Antigen in a host so as to elicit an immune (humoral and/or cell mediated) response in the host that is prophylactic or therapeutic. In an embodiment wherein the Antigen displays the antigenicity or immunogenicity of an antigen of a pathogen, administration of the vaccine is carried out to prevent or treat an infection by the pathogen and/or the resultant infectious disorder and/or other undesirable correlates of infection. In an embodiment wherein the Antigen is a tumor antigen, administration of the vaccine is carried out to prevent or treat tumors (particularly, cancer).

In a preferred specific embodiment, the recombinant vesiculoviruses are administered prophylactically, to prevent/protect against infection and/or infectious diseases or tumor (e.g., cancer) formation.

In a specific embodiment directed to therapeutics, the recombinant vesiculoviruses of the invention, encoding immunogenic epitope(s), are administered therapeutically, for the treatment of infection or tumor formation. Administration of such viruses, e.g., to neonates and other human subjects, can be used as a method of immunostimulation, to boost the host's immune system, enhancing cell-mediated and/or humoral immunity, and facilitating the clearance of infectious agents or tumors. The viruses of the invention can be administered alone or in combination with other therapies (examples of anti-viral therapies, including but not limited to α-interferon and vidarabine phosphate; examples of tumor therapy including but not limited to radiation and cancer chemotherapy).

5.7. INACTIVATED RECOMBINANT VESICULOVIRUSES FOR VACCINE USE

In a specific embodiment, the recombinant replicable vesiculoviruses of the invention are inactivated (i.e., killed, rendered nonreplicable) prior to vaccine use, to provide a killed vaccine. Since the vesiculovirus envelope is highly immunogenic, in an embodiment wherein one or more foreign proteins (e.g., an envelope glycoprotein of a virus other than a vesiculovirus) is incorporated into the vesiculovirus envelope, such a virus, even in killed form, can be effective to provide an immune response against said foreign protein(s) in a host to which it is administered. In a specific embodiment, a multiplicity of Antigens, each displaying the immunogenicity or antigenicity of an envelope glycoprotein of a different virus, are present in the recombinant vesiculovirus particle.

The inactivated recombinant viruses of the invention differ from defective interfering particles in that, prior to inactivation the virus is replicable (i.e., it encodes all the vesiculovirus proteins necessary to enable it to replicate in an infected cell). Thus, since the virus is originally in a replicable state, it can be easily propagated and grown to large amounts prior to inactivation, to provide a large amount of killed virus for use in vaccines, or for purification of the expressed antigen for use in a subunit vaccine (see Section 5.8, infra).

Various methods are known in the art and can be used to inactivate the recombinant replicable vesiculoviruses of the invention, for use as killed vaccines. Such methods include but are not limited to inactivation by use of formalin, betapropiolactone, gamma irradiation, and psoralen 3 plus ultraviolet light.

In a specific embodiment, recombinant vesiculovirus can be readily inactivated by resuspension of purified virions in a suitable concentration of formaldehyde. While 0.8 formaldehyde may be sufficient, verification of the optimum concentration of formaldehyde can be readily determined for a particular virus by titration of serial dilutions of formaldehyde with infectious virus to determine the inactivation curve of formalin for that virus. This technique has been described in detail by Salk and Gori, 1960, Ann. N.Y. Acad. Sci. 83:609–637). By extrapolation to zero, the concentration expected to inactivate the last infectious particle can be estimated. By utilizing a substantially higher concentration, e.g., 4-fold greater than the estimated concentration, complete inactivation can be assured.

Although formalin inactivation alone has proven to be effective, it may be desirable, for safety and regulatory purposes, to kill the virus twice or more, using one or more of the numerous other methods currently known for virus inactivation. Thus, although not essential, it is contemplated that the virus used in the final formulation will be often inactivated by a second agent after treatment with formalin.

5.8. USE OF RECOMBINANT REPLICABLE VESICULOVIRUSES IN THE PRODUCTION OF SUBUNIT VACCINES

Since the recombinant vesiculoviruses of the invention can be propagated and grown to large amounts, where the recombinant vesiculoviruses express an Antigen, growth of such vesiculoviruses provides a method for large scale production and ready purification of the expressed Antigen, particularly when the Antigen is incorporated into the envelope of the recombinant vesiculovirus. In a specific embodiment, the Antigen is all or a portion of an envelope glycoprotein of another virus, e.g., HIV gp160, expressed as a nonfusion protein, or expressed as a fusion to the cytoplasmic domain of a vesiculovirus G protein.

The Antigens thus produced and purified have use in subunit vaccines.

The recombinant vesiculoviruses that express an Antigen can also be used to recombinantly produce the Antigen in infected cells in vitro, to provide a source of Antigen for use in immunoassays, e.g., to detect or measure in a sample of body fluid from a vaccinated subject the presence of antibodies to the Antigen, and thus to diagnose infection or the presence of a tumor and/or monitor immune response of the subject subsequent to vaccination.

5.9. DETERMINATION OF VACCINE EFFICACY

Immunopotency of the one or more Antigen(s) in its live or inactivated vesiculovirus vaccine formulation, or in is subunit vaccine formulation, can be determined by monitoring the immune response of test animals following immunization with the recombinant vesiculovirus(es) expressing the Antigen(s) or with the subunit vaccine containing the Antigen, by use of any immunoassay known in the art. Generation of a humoral (antibody) response and/or cell-mediated immunity, may be taken as an indication of an immune response. Test animals may include mice, hamsters, dogs, cats, monkeys, rabbits, chimpanzees, etc., and eventually human subjects.

Methods of introduction of the vaccine may include oral, intracerebral, intradermal, intramuscular, intraperitoneal, intravenous, subcutaneous, intranasal or any other standard routes of immunization. The immune response of the test subjects can be analyzed by various approaches such as: the reactivity of the resultant immune serum to the Antigen, as assayed by known techniques, e.g., enzyme linked immunosorbent assay (ELISA), immunoblots, radioimmunoprecipitations, etc.; or, in the case where the Antigen displays the antigenicity or immunogenicity of a pathogen's antigen, by protection of immunized hosts from infection by the pathogen and/or attenuation of symptoms due to infection by the pathogen in immunized hosts; or, in the case where the antigen displays the antigenicity or immunogenicity of a tumor antigen, by prevention of tumor formation or prevention of metastasis, or by regression, or by inhibition of tumor progression, in immunized hosts.

As one example of suitable animal testing of a live vaccine, live vaccines of the invention may be tested in rabbits for the ability to induce an antibody response to the Antigens. Male specific-pathogen-free (SPF) young adult New Zealand White rabbits may be used. The test group of rabbits each receives approximately $5 \times 10^8$ pfu (plaque forming units) of the vaccine. A control group of rabbits receives an injection in 1 mM Tris-HCl pH 9.0 of a non-recombinant vesiculovirus or of a recombinant vesiculovirus which does not express the same Antigen.

Blood samples may be drawn from the rabbits every one or two weeks, and serum analyzed for antibodies to the Antigen(s). The presence of antibodies specific for the Antigen(s) may be assayed, e.g., using an ELISA.

Animals may also be used to test vaccine efficacy (e.g., challenge experiments). For example, in a specific embodiment regarding a live vaccine formulation, monkeys each receive intradermally approximately $5 \times 10^8$ pfu of recombinant vesiculovirus. A control monkey receives (control) non-recombinant virus intradermally. Blood is drawn weekly for 12 weeks, and serum is analyzed for antibodies to the Antigen(s).

5.10. VACCINE FORMULATION AND ADMINISTRATION

The vaccines of the invention may be multivalent or univalent. Multivalent vaccines are made from recombinant viruses that direct the expression of more than one Antigen, from the same or different recombinant viruses.

Many methods may be used to introduce the vaccine formulations of the invention; these include but are not limited to oral, intradermal, intramuscular, intraperitoneal, intravenous, subcutaneous, intranasal routes, and via scarification (scratching through the top layers of skin, e.g., using a bifurcated needle).

The patient to which the vaccine is administered is preferably a mammal, most preferably a human, but can also be a non-human animal including but not limited to cows, horses, sheep, pigs, fowl (e.g., chickens), goats, cats, dogs, hamsters, mice and rats. In the use of a live vesiculovirus vaccine, the patient can be any animal in which vesiculovirus replicates (for example, the above-listed animals).

The virus vaccine formulations of the invention comprise an effective immunizing amount of one or more recombinant vesiculoviruses (live or inactivated, as the case may be) and a pharmaceutically acceptable carrier or excipient. Subunit vaccines comprise an effective immunizing amount of one or more Antigens and a pharmaceutically acceptable carrier or excipient. Pharmaceutically acceptable carriers are well known in the art and include but are not limited to saline, buffered saline, dextrose, water, glycerol, sterile isotonic aqueous buffer, and combinations thereof. One example of such an acceptable carrier is a physiologically balanced culture medium containing one or more stabilizing agents such as stabilized, hydrolyzed proteins, lactose, etc. The carrier is preferably sterile. The formulation should suit the mode of administration.

The composition, if desired, can also contain minor amounts of wetting or emulsifying agents, or pH buffering agents. The composition can be a liquid solution, suspension, emulsion, tablet, pill, capsule, sustained release formulation, or powder. Oral formulation can include standard carriers such as pharmaceutical grades of mannitol, lactose, starch, magnesium stearate, sodium saccharine, cellulose, magnesium carbonate, etc.

Generally, the ingredients are supplied either separately or mixed together in unit dosage form, for example, as a dry lyophilized powder or water free concentrate in a hermetically sealed container such as an ampoule or sachette indicating the quantity of active agent. Where the composition is administered by injection, an ampoule of sterile diluent can be provided so that the ingredients may be mixed prior to administration.

In a specific embodiment, a lyophilized recombinant vesiculovirus of the invention is provided in a first container; a second container comprises diluent consisting of an aqueous solution of 50% glycerin, 0.25% phenol, and an antiseptic (e.g., 0.005% brilliant green).

The precise dose of virus, or subunit vaccine, to be employed in the formulation will also depend on the route of administration, and the nature of the patient, and should be decided according to the judgment of the practitioner and each patient's circumstances according to standard clinical techniques. An effective immunizing amount is that amount sufficient to produce an immune response to the Antigen in the host to which the recombinant vesiculovirus, or subunit vaccine, is administered.

In a specific embodiment, an effective immunizing amount of a live recombinant vesiculovirus of the present invention is within the range of $10^3$ to $10^9$ pfu/dose, more preferably $10^6$ to $10^9$ pfu/dose. Boosting is possible but not preferred. If boosting is desired, one optionally may boost with the Antigen in purified form rather than using a recombinant vesiculovirus of the invention.

For inactivated recombinant vesiculovirus vaccines, the vaccine formulation comprises an effective immunizing amount of the inactivated virus, preferably in combination with an immunostimulant; and a pharmaceutically acceptable carrier. As used in the present context, "immunostimulant" is intended to encompass any compound or composition which has the ability to enhance the activity of the immune system, whether it be a specific potentiating effect in combination with a specific antigen, or simply an independent effect upon the activity of one or more elements of the immune response. Some of the more commonly utilized immunostimulant compounds in vaccine compositions are the adjuvants alum or muramyl dipeptide (MDP) and its analogues. Methods of utilizing these materials are known in the art, and it is well within the ability of the skilled artisan to determine an optimum amount of stimulant for a given virus vaccine. It may also be desired to use more than one immunostimulant in a given formulation.

The exact amount of inactivated virus utilized in a given preparation is not critical, provided that the minimum amount of virus necessary to provoke an immune response is given. A dosage range of as little as about 10 µg, up to amount a milligram or more, is contemplated. As one example, in a specific embodiment, individual dosages may range from about 50–650 µg per immunization.

Use of purified Antigens as subunit vaccines can be carried out by standard methods. For example, the purified protein(s) should be adjusted to an appropriate concentration, formulated with any suitable vaccine adjuvant and packaged for use. Suitable adjuvants may include, but are not limited to: mineral gels, e.g., aluminum hydroxide; surface active substances such as lysolecithin, pluronic polyols; polyanions; peptides; oil emulsions; alum, and MDP. The immunogen may also be incorporated into liposomes, or conjugated to polysaccharides and/or other polymers for use in a vaccine formulation. In instances where the recombinant Antigen is a hapten, i.e., a molecule that is antigenic in that it can react selectively with cognate antibodies, but not immunogenic in that it cannot elicit an immune response, the hapten may be covalently bound to a carrier or immunogenic molecule; for instance, a large protein such as serum albumin will confer immunogenicity to the hapten coupled to it. The hapten-carrier may be formulated for use as a vaccine.

Effective doses (immunizing amounts) of the vaccines of the invention may also be extrapolated from dose-response curves derived from animal model test systems.

The invention also provides a pharmaceutical pack or kit comprising one or more containers comprising one or more of the ingredients of the vaccine formulations of the invention. Associated with such container(s) can be a notice in the form prescribed by a governmental agency regulating the manufacture, use or sale of pharmaceuticals or biological products, which notice reflects approval by the agency of manufacture, use or sale for human administration.

The present invention thus provides a method of immunizing an animal, or treating or preventing various diseases or disorders in an animal, comprising administering to the animal an effective immunizing dose of a vaccine of the present invention.

5.11. USE OF ANTIBODIES GENERATED BY THE VACCINES OF THE INVENTION

The antibodies generated against the Antigen by immunization with the recombinant viruses of the present invention also have potential uses in diagnostic immunoassays, passive immunotherapy, and generation of antiidiotypic antibodies.

The generated antibodies may be isolated by standard techniques known in the art (e.g., immunoaffinity chromatography, centrifugation, precipitation, etc.) and used in diagnostic immunoassays. The antibodies may also be used to monitor treatment and/or disease progression. Any immunoassay system known in the art, such as those listed supra, may be used for this purpose including but not limited to competitive and noncompetitive assay systems using techniques such as radioimmunoassays, ELISA (enzyme-linked immunosorbent assays), "sandwich" immunoassays, precipitin reactions, gel diffusion precipitin reactions, immunodiffusion assays, agglutination assays, complement-fixation assays, immunoradiometric assays, fluorescent immunoassays, protein A immunoassays and immunoelectrophoresis assays, to name but a few.

The vaccine formulations of the present invention can also be used to produce antibodies for use in passive immunotherapy, in which short-term protection of a host is achieved by the administration of pre-formed antibody directed against a heterologous organism.

The antibodies generated by the vaccine formulations of the present invention can also be used in the production of antiidiotypic antibody. The antiidiotypic antibody can then in turn be used for immunization, in order to produce a subpopulation of antibodies that bind the initial antigen of the pathogenic microorganism (Jerne, 1974, Ann. Immunol. (Paris) 125c:373; Jerne, et al., 1982, EMBO J. 1:234).

6. RECOMBINANT VESICULAR STOMATITIS VIRUSES FROM DNA

We assembled a DNA clone containing the 11,161 nucleotide sequence of the prototype rhabdovirus, vesicular stomatitis virus (VSV), such that it could be transcribed by the bacteriophage T7 RNA polymerase to yield a full-length positive strand RNA complementary to the VSV genome. Expression of this RNA in cells also expressing the VSV nucleocapsid protein and the two VSV polymerase subunits resulted in production of VSV with the growth characteristics of wild-type VSV. Recovery of virus from DNA was verified by: 1) the presence of two genetic tags generating novel restriction sites in DNA derived from the genome; 2) direct sequencing of the genomic RNA of the recovered virus, and 3), production of a VSV recombinant in which the glycoprotein was derived from a second serotype. The ability to generate VSV from DNA opens numerous possibilities for the genetic analysis of VSV replication. In addition, because VSV can be grown to very high titers and in large quantities with relative ease, one can genetically engineer recombinant VSVs displaying novel antigens. Such modified viruses can be used as vaccines conferring protection against other viruses or pathogenic microorganisms, or to produce immunity in general against an encoded foreign antigen.

6.1. MATERIALS AND METHODS

Plasmid Construction. The plasmid pVSVFL(+) expressing the 11,161 nucleotide positive strand (antigenomic) VSV RNA sequence was constructed from four DNA fragments cloned into pBluescript SK$^+$ (Stratagene). The starting plasmid for the construction, pVSVFL(−), expressed the complete negative sense VSV genomic RNA (Indiana serotype) from a T7 promoter. This plasmid was generated in a nine step cloning procedure that involved joining the five original cDNA clones of the VSV mRNAs (Gallione et al., 1981, J. Virol. 39:529–535; Rose and Gallione, 1981, J. Virol. 39:519–528; Schubert et al., 1985, Proc. Natl. Acad. Sci. USA 82:7984–7988) with gene junction fragments and terminal fragments. These fragments were generated by reverse transcription and polymerase chain reaction (RT-PCR) (Mullis and Faloona, 1987, Methods in Enzymology 155:335–350) from VSV genomic RNA (M. A. Whitt, R. Burdine, E. A. Stillman and J. K. Rose, manuscript in preparation). To facilitate engineering of the VSV genome and to provide genetic tags, unique Mlu I and Nhe I restriction enzyme sites were introduced by oligonucleotide-directed mutagenesis into the 5' and 3' non-coding regions flanking the VSV glycoprotein gene prior to construction of the full length genome.

In the initial step of constructing pVSVFL(+) we used the primers (5° CCGGCTCGAGT<u>TGTAATACGACTCACTA TAGGG</u>ACGAAGACAAAC AAACCATTATTAT C-3') (SEQ ID NO:38) and (5'GAACTCTCCTCTAGA TGAGAAC-3') (SEQ ID NO:39) to amplify (Mullis and Faloona, 1987, Methods in Enzymology 155:335–350) a 2,124 nucleotide fragment from pVSVFL(−) (#1, FIG. 4A). This fragment corresponds to the 3' end of the VSV genome. The first primer introduced an Xho I site and a T7 promoter (underlined) immediately preceding the sequence complementary to the 3' end of the VSV genome.

The second primer covered a unique Xba I site present in the VSV P gene. The PCR product was digested with Xho I and Xba I and cloned into pBluescript SK$^+$ (Stratagene) that had been digested with Xho I and Xba I. The resulting plasmid carrying the sequence corresponding to the 3' end of the VSV genome preceded by a T7 promoter was designated pBSXX. Note that an additional T7 promoter is also present upstream of the Xho I site in the vector. Next we generated the sequence corresponding to the 5' end of the VSV genome and part of the hepatitis delta virus (HDV) ribozyme (Pattnaik et al., 1992, Cell 69:1011–1120; Perrotta and Been, 1991, Nature 350:434–436). A 147 nucleotide PCR product (#3, FIG. 4A) was amplified from pVSVFL(−) with primers (5'<u>AGGTCGGACCGCGAGGAGGTGGAGATGCCATGC CGACCCACGAAGACCACAAAACCAG</u> -3') (SEQ ID NO:40) and (5'ATGTTGAAGAGTGACCTACACG-3') (SEQ ID NO:41). The first primer contained 39 nucleotides of the sequence encoding the HDV ribozyme (underlined) followed by 19 nucleotides complementary to the 3' end of the VSV antigenomic RNA. The second primer hybridized within the L gene (FIG. 4A). The PCR product was digested with Afl II and Rsr II and the 80 nucleotide Afl II-Rsr II fragment was ligated to a 225 nucleotide Rsr II-Sac I fragment (#4, FIG. 4A) derived from a plasmid designated PBS-GMG (Stillman et al., manuscript submitted). Fragment 4 contained the T7 terminator sequence and the remainder of the sequence encoding the HDV ribozyme. Ligated products were digested with Afl II and Sac I and the 305 nucleotide Afl II-Sac I product was cloned into the Afl II and Sac I sites of a modified pBSXX vector that contained an Afl II site inserted at the unique Not I site within the polylinker. This plasmid containing the Afl II-Sac I fragment was designated PBXXAS. To complete the construction, a 10,077 nucleotide Bst 1107 I to Afl II fragment (#2, FIG. 4A) containing 90% of the VSV sequences from pVSVFL (−) was inserted into the unique Bst 1107 I and AflII sites of pBXXAS. The final plasmid was designated pVSVFL(+). The sequences in this plasmid generated by PCR (hatched sequences, FIG. 4B) were determined and contained no errors. We also prepared a plasmid in which the sequence of the VSV Indiana serotype G gene (MluI-NheI) was replaced with the G gene from the New Jersey serotype of VSV (Gallione and Rose, 1983, J. Virol. 46:162–169). This plasmid is called pVSVFL(+)$_{I/INJG}$ and has only a single T7 promoter.

Transfection and recovery of recombinant VSV. Baby hamster kidney cells (BHK-21, ATCC) were maintained in DME (Dulbecco's modified Eagle's medium) supplemented with 5% fetal bovine serum (FBS). Cells on 10 cm dishes (~70% confluent) were infected at a multiplicity of 10 with vTF7-3 (Fuerst et al., 1986, Proc. Natl. Acad. Sci. USA 83:8122–8126). After 30 min, plasmids encoding the VSV antigenomic RNA and the N, P, and L proteins were transfected into the cells using a calcium phosphate transfection kit according to directions supplied (Stratagene). The coding regions for N, P, and L proteins were each expressed in pBluescript SK(+) from the T7 promoter. Plasmid amounts were 10 μg pVSVFL(+), 5 μg pBS-N, 4 μg pBS-P, and 2 μg PBS-L. After 24–48 h incubation at 37° C. in 3% $CO_2$, cells were scraped from the dish and subjected to three rounds of freeze-thawing (−70° C., 37° C.) to release cell-associated virus. Debris was pelleted from the cell lysates by centrifugation at 1,250× g for 5 min. Five ml of this lysate was added to approximately $10^6$ BHK cells on a 10 cm plate in 10 ml of DME+5% FBS. After 48 h the medium was clarified by centrifugation at 1,250× g for 10 min, and passed through a filter to remove the majority of the vaccinia virus (0.2 μm pore size, Gelman Sciences). One ml was then added directly to BHK cells that had been plated on a coverslip in a 35 mm dish. After four hours, the cells were fixed in 3% paraformaldehyde and stained with monoclonal antibody I1 to the VSV $G_I$protein (Lefrancois and Lyles, 1982, Virology 121:168–174) or 9B5 (Bricker et al., 1987, Virology 161:533–540) to the VSV $G_{NJ}$protein followed by goat anti-mouse rhodamine conjugated antibody (Jackson Research). Cells were then examined by indirect immunofluorescence using a Nikon Microphot-FX microscope equipped with a 40× planapochromat objective. When VSV recovery was successful, 100% of the cells showed the typical bright stain for G protein characteristic of a VSV infection.

Preparation and analysis of VSV RNA and protein. Recombinant VSV and wild-type VSV isolated from single plaques (~$10^5$ plaque forming units) were used to infect a monolayer of BHK cells (~80% confluent) on a 10 cm dish in 10 ml DME plus 5% FBS. After 24 h, cell debris and nuclei were removed by centrifugation at 1,250× g for 5 min, and virus was then pelleted from the medium at 35,000 RPM in a Beckman SW41 rotor for one hour. Virus pellets were resuspended in 0.5 ml 10 mM Tris-HCl, pH 7.4 for protein analysis. For RNA isolation, virus was resuspended in 0.2 ml of 0.5% SDS/0.2M sodium acetate, pH 8.0, followed by extraction with phenol/$CHCl_3$. RNA was precipitated with 95% ethanol and 5 μg carrier tRNA. RNA was pelleted by centrifugation at 12,000× g for 15 min and resuspended in water with 1 unit RNasin (Promega). For analysis of RNA by RT-PCR, primer pairs flanking either the novel Nhe I or Mlu I sites were used. The first strand DNA synthesis reaction was carried out in 50 μl of PCR buffer (Promega) containing 5 mM $MgCl_2$, 1 mM dNTPs, 1 unit RNAs in (Promega), 1 unit avian myeloblastosis virus reverse transcriptase (ANV RT; Promega) 0.75 μM primer and approximately 0.25 μg of VSV genomic RNA. Incubation was at 42° C. for 15 min followed by 5 min at 99° C. and 5 min at 5° C. PCR was carried out by addition of 0.5 U Taq polymerase, adjustment of $MgCl_2$ concentration to 1.25 mM, and addition of the second primer (0.75 μM). The reaction was subjected to 20 thermal cycles: 95° C., 1 min; 60° C. 1.5 min. The reaction was then incubated at 60° C. for 7 min.

Direct sequencing of VSV genomic RNA was performed according to a previously described protocol based on the dideoxy chain termination method (Mierendorf and Pfeffer, 1987, Methods in Enzymology 152:563–566) except that [α-$^{33}$P]dATP (Amersham, Inc.) was used. Each reaction included approximately 0.25 μg of VSV genomic RNA.

6.2. RESULTS

To construct a cDNA clone encoding the entire 11,161 VSV genome, individual cDNA clones of the VSV mRNAs were initially joined using small DNA fragments generated by RT-PCR that covered the four gene junctions. Correct genomic terminal sequences were also generated by RT-PCR of the VSV genome, and these were joined to the other DNAs using restriction sites. This initial clone was constructed with a T7 promoter directing synthesis of the full-length negative strand VSV RNA. Despite numerous attempts, we were unable to recover VSV from cells expressing the VSV genomic RNA and the VSV N, P, and L proteins. The VSV constructed was thus redesigned to express the VSV antigenomic DNA. The construction strategy is described in Materials and Methods and in FIGS. 4A–B. The entire VSV sequence as well as a T7 promoter, terminator and HDV ribozyme sequence were cloned in pBluescript SK+ between the Xho I and Sac I sites (FIG. 4B; FIG. 1). An additional T7 promoter is also present upstream of the Xho I site in the plasmid. A slightly different cloning strategy was used to generate plasmids lacking the upstream T7 promoter and VSV has also been recovered from these constructs. Recovery of VSV from DNA. To determine if we could recover VSV from plasmid DNA, we infected cells with vaccinia vTF7-3 (Fuerst et al., 1986, Proc. Natl. Acad. Sci. USA 83:8122–8126) to provide cytoplasmic T7 RNA polymerase. These cells were then transfected with pVSVFL (+), which expresses the antigenomic VSV RNA from a T7 promoter, and three other plasmids which express the VSV N, P, and L proteins. Expression of the N protein was required to assemble nascent VSV antigenomic RNA into nucleocapsids. Once formed, these nucleocapsids should serve as templates for synthesis of minus strand RNA by the L/P polymerase complex. Encapsidated minus strand RNA should then be a template for transcription, initiating the VSV infectious cycle.

The initial recovery experiment employed two 10 cm plates of BHK cells (~5×10$^6$ cells each). At 24 hours after the infection with vTF7-3 and transfection with the four plasmids, cells and medium were frozen and thawed to release any cell-associated VSV, and the clarified lysates were added to fresh BHK cells. After 48 hours, both plates showed severe cytopathic effects that could have been due either to vaccinia virus or to recovered VSV. One ml of each supernatant was then added to small dishes of BHK cells on coverslips. After two hours, one of these coverslips showed rounded cells characteristic of a VSV infection, while the other did not. After 4 hours, cells on both coverslips were fixed, stained with appropriate antibodies, and examined by indirect immunofluorescence microscopy to detect the VSV G protein. All cells on the coverslip showing rounded cells revealed intense fluorescence characteristic of G protein expression during VSV infection (data not shown). Subsequent passaging and analysis described below showed that VSV had been recovered from the transfection. The other coverslip showed no G expression, and no VSV could be recovered after passaging.

Based on the frequency with which rabies virus (Schnell et al., 1994, EMBO J. 13:4195–4203) and VSV minigenomes (Stillman et al., manuscript submitted) were recovered, we anticipated that recovery of complete VSV, if obtainable, would be a rare event. The initial recovery of VSV from only one of two transfections suggested the possibility that the initial titer in the positive lysate was very low. To examine this titer, we infected BHK cells on coverslips with one tenth of the lysate (1 ml) derived from each initial transfection. After eight hours, the cells were examined for expression of G protein by indirect immunofluorescence. A scan of the entire coverslip revealed no VSV infection from the negative lysate, and only five small areas of infection (2–6 cells each) from the lysate that gave rise to VSV G expression on subsequent passaging.

The initial titer was therefore very low as we suspected, and likely represented a total of about 50 infectious particles, probably derived from a VSV infection initiated in only one cell out of 2×10$^7$ transfected. This low rate of recovery of infectious VSV is typical of that observed in several experiments.

Analysis of viral proteins. Subsequent passages and plaque assays of VSV recovered in three independent experiments revealed plaques that were detectable in less than 16 hours and titers up to 2×10$^9$ pfu/ml characteristic of VSV. For further verification that VSV had been recovered, the proteins in virus pelleted from the medium ere examined by SDS polyacrylamide gel electrophoresis (PAGE). FIG. 5 shows the Coomassie stained gel of proteins of VSV recovered from recombinant DNA (rVSV) and wildtype VSV. The mobilities and relative amounts of the five viral proteins were indistinguishable in the wildtype and recombinant virus.

Identification of sequence tags. In pVSVFL(+), the VSV nucleotide sequence was altered by oligonucleotide-directed mutagenesis to generate unique Mlu I and Nhe I restriction enzyme sites in the 5' and 3' non-coding regions of the glycoprotein gene. To verify that these sites were present in recovered virus, we carried out reverse transcription of genomic RNA purified from wild-type or recombinant virions using primers upstream of each restriction site. The reverse transcription products were then amplified by PCR using an additional primer downstream of each restriction site. The presence of the genetic tag in the recombinant virus was verified by digestion of the PCR products with the appropriate restriction enzymes. Using this method, the presence of both the Mlu I and Nhe I sequences in the recovered virus RNA was verified, and the results for the Nhe I site are shown in FIG. 6. Sequences from wild-type VSV and recombinant VSV were amplified in parallel and a 620 nucleotide fragment was obtained in both cases (lanes 3 and 5). No product was obtained when reverse transcriptase was omitted from the reactions prior to PCR (lanes 1 and 2), indicating that the PCR product was derived from RNA, not from contaminating DNA. After digestion with Nhe I, expected fragments of 273 and 347 base pairs were obtained from recombinant VSV RNA, while the DNA derived from the wildtype RNA remained undigested (lanes 4 and 6).

Direct sequencing of tagged genomic RNA. The presence of new restriction sites in the DNA generated by PCR provided strong evidence that VSV had been recovered from DNA. To ensure that identification of the genetic tags by PCR had not resulted from inadvertent contamination by plasmid DNA, we carried out direct sequence analysis of the genomic RNA using reverse transcriptase and a primer hybridizing upstream of the Nhe I site. The sequence from the autoradiogram shown in FIG. 7 is in exact agreement with the published sequence of the VSV G mRNA (Rose and Gallione, 1981, J. Virol. 39:519–528) except that the four nucleotide changes used to generate the Nhe I site (GC ACAA to GCTAGC) are present. These results show unequivocally that the sequence tag is present in the genomic RNA.

Recombinant VSV Indiana virus carrying the glycoprotein of the New Jersey serotype. There are two serotypes of VSV designated Indiana and New Jersey. The glycoproteins of the two serotypes share approximately 50% sequence identity (Gallione and Rose, 1983, J. Virol. 46:162–169). In earlier studies we found that the glycoprotein of the New Jersey serotype could complement a mutant of the VSV, serotype that makes a defective glycoprotein (Whitt et al., 1989, J. Virol. 63:3569–3578). It therefore seemed likely that a recombinant VSV in which the Indiana glycoprotein ($G_I$) gene was replaced by the New Jersey glycoprotein ($G_{NJ}$) gene would be viable despite the extensive sequence divergence. To generate such a recombinant, the $G_{NJ}$ cDNA was amplified by PCR using primers that introduced Mlu I and Nhe I sites within the 5' and 3' non-coding regions at each end of the gene. The amplified DNA was cloned into pBluescript and the $G_{NJ}$ protein was expressed in BHK cells using the vaccinia-T7 system. The protein expressed was shown to have membrane fusion activity below pH 6.0 indicating that it was functional (data not shown). This $G_{NJ}$ cDNA was then cloned into the unique Mlu I and Nhe I sites of the full-length construct after removal of sequences encoding $G_I$. Recombinant VSV was recovered essentially as described above except that the initial transfection was allowed to proceed for 48 hours before the freeze-thaw step. After the first passage, expression of the $G_{NJ}$ protein was verified by indirect immunofluorescence using a monoclonal antibody specific to $G_{NJ}$ (Bricker et al., 1987, Virology 161:533–540). The virus was then plaque purified and grown. To examine the proteins present in the recombinant virus, virus recovered from cells infected with $VSV_I$, $VSV_{NJ}$, and the recombinant $VSV_{I/INJG}$ was analyzed by SDS-PAGE followed by Coomassie staining. The $VSV_I$, G, N, P, and M proteins each have mobilities distinct from their $VSV_{NJ}$ counterparts (FIG. 8, lanes 1 and 3). The recombinant $VSV_{I/INJG}$ shows the mobility difference in only the G protein as expected (lane 2). The presence of the novel Nhe I and Mlu I sites in the recombinant was also verified (data not shown).

6.3. DISCUSSION

The results presented here establish that infectious VSV can be recovered from recombinant DNA. We believe that expressing the positive strand, antigenomic RNA in the presence of the N, P and L proteins was critical to our success because we have not recovered virus starting with an equivalent construct encoding the genomic RNA.

Why is the initial event of generating VSV so rare, apparently occurring in only 1 in $10^7$ to $10^8$ transfected cells? One possibility is that our clone contains a sequence error that is only corrected by a rare mutational event. We believe this is not the case because the clone was completely sequenced prior to assembly and differences from published sequences were corrected, or the proteins were shown to be functional in complementation assays. Also, the frequency of recovery is actually higher than expected based on our observations with minigenomes encoding one or two VSV proteins (Stillman et al., manuscript submitted). In these cases we found that a transcribing and replicating minigenome (~2 kb RNA) was recovered in about 1 in $10^2$ transfected cells expressing the RNA with the N,P and L proteins. Addition of a second cistron (0.85 kb additional RNA) encoding the M protein dropped the recovery rate to approximately 1 in $10^3$ transfected cells. If there is a ten-fold drop in recovery rate for each additional kilobase of RNA added, one can easily rationalize an even lower frequency of recovery for the 11, 161 kb genome than we observed. Although these minigenomes encode negative sense RNAs, the comparison of the frequency of recovery to that of the full length plus construct is probably valid because expression of the N, P and L mRNAs would not generate mRNAs complementary to the minigenome.

Although the rate limiting step in generation of infectious VSV is not known, it is likely to be at the level of synthesis and encapsidation of the large antigenomic RNA, which must occur prior to replication and transcription. The complete encapsidation with N protein probably has to occur on the nascent RNA to protect it from degradation, and the cells in which this occurs must also produce appropriate amounts of L and P proteins to initiate replication. Once this has occurred, however, the transcription and translation of the genome should generate additional N, P, and L proteins as well as the G and M proteins required for budding of infectious virus.

The recovery of VSV from DNA opens numerous aspects of the viral life cycle to genetic analysis. The studies of the genetic signals involved in transcription and replication have so far been confined to analysis of defective RNAs that do not encode viral proteins (Pattnaik et al., 1992, Cell 69:1011–1120; Wertz et al., 1994, Proc. Natl. Acad. Sci. USA 91:8587–8591). These and other signals can be now examined in the context of a VSV infection occurring in the absence of a vaccinia virus infection. The system we have described also provides an opportunity to study the roles of individual viral protein domains and modifications in viral assembly and replication. Previously these analyses have been confined to in vitro systems or to analysis employing the complementation of naturally occurring mutants where synthesis of the mutant protein can complicate the analysis.

Perhaps even more exciting is the ability to use VSV as a vector to express other proteins. The experiment in which we recovered VSV Indiana carrying the glycoprotein from the New Jersey serotype (FIG. 8) illustrates that viable recombinants can be made. For reasons that are unclear the titers of recombinant virus were at least ten-fold lower than those obtained with either parent. The lower titer apparently did not result from a defect in viral assembly because the amounts of proteins in wildtype and recombinant virions at the end of the infection were comparable (FIG. 8). Our previous experiments showed that a foreign glycoprotein carrying the appropriate cytoplasmic tail signal could be incorporated into the VSV envelope (Owens and Rose, 1993, J. Virol. 67:360–365). This suggests that one may generate recombinant VSVs carrying novel proteins in their envelopes. If these were appropriately attenuated, they can be used as vaccines against other viral diseases.

The truncated genomes of defective interfering particles are replicated and packaged very well, thus we suspect that there will be flexibility in the maximum length of the genome that can be packaged as well. Presumably a longer nucleocapsid can be packaged as a longer bullet-shaped particle. Because of the modular nature of the VSV genome, with conserved gene end and start sequences at the gene junctions (Rose and Schubert, 1987, in The Viruses: The Rhabdoviruses, Plenum Publishing Corp., NY, pp. 129–166), it should be relatively easy to engineer additional genes into VSV.

7. THE MINIMAL CONSERVED TRANSCRIPTION STOP-START SIGNAL PROMOTES STABLE EXPRESSION OF A FOREIGN GENE IN VESICULAR STOMATITUS VIRUS

As described herein, a new transcription unit was generated in the 3'-noncoding region of the vesicular stomatitis virus (VSV) glycoprotein gene by introducing the smallest conserved sequence found at each VSV gene junction (described hereinabove in Section 5.1). This sequence was introduced into a DNA copy of the VSV genome from which infectious VSV can be derived. It contained an eleven nucleotide putative transcription stop/polyadenylation signal for the glycoprotein mRNA, an intergenic dinucleotide, and a ten nucleotide putative transcription start sequence preceding a downstream foreign gene encoding the bacterial enzyme chloramphenicol acetyltransferase (CAT). Infectious recombinant VSV was recovered from this construct and was found to express high levels of functional CAT mRNA and protein. The recombinant virus grew to wild-type titers of $5\times10^9$/ml and expression of the foreign gene was completely stable for at least 15 passages involving $10^6$-fold expansion at each passage. These results define functionally the transcription stop/polyadenylation and start sequences for VSV and also illustrate the utility of VSV as a stable vector that should have wide application in cell biology and vaccine development.

VSV transcription proceeds sequentially from the 3' end of the genomic RNA to generate a short leader RNA followed by the five mRNAs (Abraham and Banerjee, 1976, Proc. Natl. Acad. Sci. USA 73:1504–1508; Ball and White, 1976, Proc. Natl. Acad. Sci. USA 73:442–446; Iverson and Rose, 1981, Cell 23:477–484). The mechanism of sequential transcription involves an obligatory polymerase start at the 3' end of the genome, which is apparently followed by sequential stops and re-starts at each gene junction. We will assume that this stop/start mechanism is in fact used, although an RNA cleavage mechanism has not been completely ruled out (Rose and Schubert, 1987, Rhabdovirus genomes and their products, p.129–166, in R. R. Wagner (ed.), The Rhabdoviruses. Plenum Publishing Corp., NY). Nucleotide sequence analysis of the VSV genome showed conserved 23 nucleotide sequences present at each of the gene end and gene start sequences (McGeoch, 1979, Cell 17:673–681; Rose, 1980, Cell 19:415–421). These sequences in the negative sense (genomic) consist of (see Section 5.1) a putative transcription stop/polyadenylation motif 3'-AUACUUUUUUU (portion of SEQ ID NO:34) that apparently signals repetitive copying of the seven-residue U sequence to generate poly(A). This sequence is followed by an intergenic dinucleotide CA or GA that is not transcribed, and a putative transcription start signal 3'-UUGUCNNUAG (portion of SEQ ID NO:34) complementary to the $m^7$GpppAACAGNNAUC (SED ID NO:42) sequence present at the 5' end of all VSV mRNAs. Related conserved sequences are found at the gene junctions in all RNA viruses having single, negative-strand RNA genomes.

In the study described here we show that insertion of this minimal conserved sequence in the 3' non-coding region of a gene is sufficient to terminate transcription of the gene, and promote transcription of a foreign gene (chloramphenical acetyltransferase (CAT)) introduced downstream. Therefore, no additional unrecognized features of VSV genomic structure are required to promote efficient transcription termination and reinitiation.

The high spontaneous mutation rate in VSV (Steinhauer et al., 1989, J. Virol 63:2063–2071) was a major concern in using VSV to express foreign proteins because expression of the unselected foreign sequence might be lost rapidly through mutation. Surprisingly, we found that the unselected CAT gene is maintained quite stably. Given this stability of expression, the ease with which VSVs expressing foreign proteins can be constructed, and the very wide host range of the virus, this system is likely to be an important vehicle for expression of foreign genes in cells and in animals.

7.1. MATERIALS AND METHODS

Plasmid Construction. The starting plasmid, designated pVSVFL-2, was similar to pVSVFL(+) described in Section 6 hereof, but contained only a single T7 promoter immediately preceding the sequence encoding the 5' end of the VSV positive strand and was used because it lacked the XhoI site present in pVSVFL(+). The single NheI site in the 3' noncoding region of the G gene was used as the target site for introduction of a linker containing the putative VSV polymerase stop-start sequence and an XhoI site (see FIG. 9B). The linker was prepared from two complementary oligonucleotides, which were annealed and cloned into the unique NheI site of pVSV. Introduction of this linker in the correct orientation restored the NheI site immediately next to the XhoI site and eliminated the upstream NheI site. The resulting plasmid was designated pVSV-XN1, and the presence of the correct sequence was confirmed.

The CAT gene was amplified by PCR with VENT polymerase (Stratagene) from the pSV2-CAT plasmid (Gorman et al., 1982, Mol. Cell. Biol. 2:1044–1051) using the primers 5,-GCTCCCCCGGGCTCGAGAAA ATGGAGAAGAAAATCACTGGAT-3' (SEQ ID NO:43) and 5'-GCGGCCGCTCTAG ATTACGCCCCGCCCGCCCTGCCACT-3' (SEQ ID NO:44). The first primer contains a XhoI site (boldface letters) and the first 21 nucleotides of the coding region of the CAT gene (underlined letters), the second primer contains an XbaI site (boldface letters) and the last 21 nucleotides of the CAT gene (underlined letters). The PCR product was digested with XhoI and XbaI and cloned in PVSV-XN1 that was digested with XhoI and NheI. The resulting plasmid was called pVSV-CAT.

Transfection and Recovery of VSV-CAT. Baby hamster kidney cells (BHK-21, ATCC) were maintained in DMEM (Dulbecco's modified Eagle's medium) supplemented with 5% fetal bovine serum (FBS). Cells (~80% confluent) on 10 cm diameter dishes were infected with vTF7-3 (Fuerst et al., 1986, Proc. Natl. Acad. Sci. USA 83:8122–8126) at a multiplicity of infection (MOI) of 10. After 1 h, plasmids encoding the N, P, and L proteins (see Section 6) and the VSV-CAT RNA were transfected into the cells with TransfectACE (Bethesda Research Laboratories) (Rose et al., 1991, BioTechniques 10:520–525) as previously described. Plasmids and amounts were as follows: 10 $\mu$g of pVSV-CAT, 3 $\mu$g of pBS-N, 5 $\mu$g of pBS-P, and 2 $\mu$g of pBS-L. After 48 h of incubation at 37° C. in 5% $CO_2$, supernatants from transfected cells were collected and debris was pelleted from the cell lysates by centrifugation at 1,250× g for 5 min. Lysates were filtered through 0.2 $\mu$m pore-size syringe filters (Acrodisc) to remove vaccinia virus, and 5 ml of this lysate was added to approximately $10^6$ BHK cells on a 6 cm diameter plate. After 24 h, the medium was clarified by centrifugation at 1,250× g for 10 min, and 1 ml was then added directly to BHK cells that had been plated on a coverslip in a 35 mm diameter dish. After four hours, the cells were fixed in 3% paraformaldehyde and stained with monoclonal antibody I1 to the VSV G protein (Lefrancois and Lyles, 1982, Virology 121:168–174) followed by goat anti-mouse rhodamine conjugated antibody (Jackson Research). Cells were then examined by indirect immunofluorescence using a Nikon Microphot-FX microscope equipped with a ×10 planapochromat objective.

Preparation and analysis of VSV-CAT Protein and mRNA. For metabolic labeling of the VSV proteins, BHK cells (~80% confluent) on a 3.5 cm diameter plate were infected with VSV-CAT or wild-type (wt) VSV at an MOI of ~20. After 4 h, cells were washed with DMEM minus methionine and incubated for 1 h at 37° C. in 1 ml of DMEM lacking unlabeled methionine and containing 80 $\mu$Ci of [$^{35}$S]methionine. Cell extracts (2% of the total) were analyzed by sodium dodecyl sulfate-polyacrylamide gel electrophoresis (SDS-PAGE) and on a PhosphorImager (Molecular Dynamics). For isolation of VSV-CAT and wild-type VSV virions, a monolayer of BHK cells (~80% confluent) on a 10 cm diameter dish in 10 ml of DMEM plus 5% FBS were infected with virus at an MOI of 0.1. After 24 h, cell debris and nuclei were removed by centrifugation at 1,250× g for 5 min, and virus was then pelleted from the medium over a 10% sucrose gradient at 38,000 rpm in a Beckman SW41 rotor for 1 h. Virus pellets were resuspended in 0.5 ml of 10 mM Tris-HCl, pH 7.4, and pelleted a second time before separation by SDS-PAGE and staining with Coomassie blue.

For analysis of VSV-CAT virus after fifteen passages, virus isolated from 12 single plaques (~$10^5$ plaque forming units (PFU)) was used to infect twelve 3.5 cm diameter dishes of BHK cells. After 24 h, cells were harvested and analyzed for CAT activity. Supernatants were clarified by centrifugation at 1,250× g for 5 min, and virus was pelleted from the medium at 15,000 rpm in a TOMY MTX-150 centrifuge for 1 h. Virus pellets were resuspended in 0.2 ml of 0.5% SDS-0.2 M sodium acetate, pH 8.0, followed by extraction with phenol-chloroform. RNA was precipitated with 95% ethanol and 5 µg of carrier tRNA, pelleted by centrifugation at 12,000× g for 15 min, and resuspended in water with 1 U of RNasin (Promega). For reverse transcriptase PCR (RT-PCR), the first-strand DNA synthesis reaction was carried out in 50 µl of PCR buffer (Promega) containing 5 mM $MgCl_2$, 1 mM (each) deoxynucleotide triphosphate, 1 U of RNAsin (Promega), 1 U of avian myeloblastosis virus reverse transcriptase (AMV RT; Promega) 0.75 µM positive-strand CAT primer (described above), and approximately 0.25 µg of VSV genomic RNA. Incubation was at 42° C. for 15 min followed by 5 min at 99° C. and 5 min at 5° C. PCR was carried out by addition of 0.5 U Vent polymerase and addition of the second CAT primer. The reaction was subjected to 20 thermal cycles: 95° C., 1 min; 60° C. 1.5 min; and then incubated at 60° C. for 7 min. For sequencing the resulting PCR products were gel purified and sequence was determined by the Yale oligonucleotide sequencing facility using positive-strand CAT primer.

A CAT enzyme-linked immunosorbent assay (ELISA) kit was purchased from Boehringer Mannheim and used according to the manufacturer's instructions. Total protein in lysates was assayed using the bicinchonimic acid reagent (Pierce).

Northern (RNA) hybridization. Total RNA was isolated from infected cells at 6 h post-infection with the TRIZOL (GIBCO-BRL) reagent used according to the protocol recommended by the manufacturer. Total RNA (1 µg) was analyzed by denaturing agarose gel electrophoresis and Northern hybridizations with $^{32}$P-labeled pVSVFL-2 or pSV2-CAT as probes.

CAT enzyme assay. For analysis of CAT activity, VSV-CAT- or wt VSV-infected cells were washed twice with phosphate-buffered saline (PBS) and cell extracts were prepared by scraping the cells from the dish following three rounds of freeze-thawing (−700 and 37° C.) in 500 µl of Tris-HCl (pH 7.5). Cells extracts (10%) were analyzed in CAT assays by standard procedures adapted from Gorman (Gorman et al., 1982, Mol. Cell. Biol. 2:1044–1051).

Immunofluorescence microscopy. Cells on 3.5 cm diameter plates were infected for 4 h, fixed in 3% paraformaldehyde, and double stained with monoclonal antibody I1 to the VSV G, protein (Lefrancois and Lyles, 1982, Virology 121:168–174) and a polyclonal rabbit antibody directed against the CAT protein (5'–3', Inc.) followed by fluorescein isothiocyanate (FITC)-conjugated goat anti-mouse antibody (Jackson Research) and rhodamine-conjugated goat anti-rabbit antibody (Jackson Research). Cells were examined by indirect immunofluorescence with a Nikon Microphot-FX microscope equipped with a ×40 planapochromat objective.

7.2. RESULTS

To construct a DNA clone allowing insertion and expression of a foreign gene in the genome of VSV, we generated a synthetic DNA linker containing the sequence illustrated in FIG. 9A. This DNA contains the indicated minimal sequence elements that are conserved at all four VSV gene junctions: a transcription stop/polyadenylation signal, an intergenic dinucleotide, and the conserved transcription start sequence, all of which are shown in the positive-strand (mRNA) sense. These sequences were followed by unique XhoI and NheI sites to allow insertion of a foreign gene. The linker was inserted at the unique NheI site that we had engineered in the 3' non-coding region of the VSV G mRNA (Section 6).

We next inserted the complete sequence encoding the bacterial CAT protein (Gorman et al., 1982, Mol. Cell. Biol. 2:1044–1051) between the XhoI and NheI sites. The complete construct encoding the VSV-CAT positive-strand RNA, along with the T7 RNA polymerase promoter, ribozyme, and T7 terminator, is diagrammed in FIG. 9B. If the stop-start signals preceding the CAT gene junction sequence were functional in recovered virus, we anticipated that G mRNA would terminate at the new poly(A) site, and CAT mRNA would initiate at the new start site and terminate at the original G poly(A) site. This particular site downstream of G was chosen for insertion of the new transcription unit because it was likely to have minimal effects on viral replication, perhaps only reducing L expression slightly because of a polar effect on downstream transcription.

Recovery of VSV-CAT from DNA. The recovery of VSV from DNA involves simultaneous transfection of the plasmid encoding the full-length antigenomic RNA along with three plasmids encoding the VSV N, P, and L proteins into cells infected with the vaccinia virus vector vTF7-3 (Section 6). VSV nucleocapsids are assembled in these cells, but because the assembly of the VSV nucleocapsid is a relatively inefficient process, recoveries are not obtained in all transfections (Section 6). We therefore set up ten transfections to recover VSV-CAT virus. We found in other experiments that recoveries of VSV from DNA were obtained just as frequently by transfection with a cationic liposome reagent (Rose et al., 1991, BioTechniques 10:520–525) as with $CaPO_4$; therefore, the simpler liposome transfection method was adopted. After two days, supernatants from the initial transfections were filtered to remove vaccinia virus and added to BHK cells. Infection of BHK cells with supernatants from this first passage showed typical VSV cytopathic effects for 9 out of the 10 transfections. Further passage of these supernatants and analysis of infected cells by indirect immunofluorescence revealed surface expression of VSV G protein and a diffuse cytoplasmic fluorescence of CAT protein. Examples of the immunofluorescence results for a low-multiplicity VSV-CAT infection are shown at low multiplicity are shown so that some uninfected cells are visible (FIGS. 10A and B).

Proteins expressed by VSV-CAT. Immunofluorescence showed that CAT protein sequences were expressed in cells infected with VSV-CAT, and the results in FIG. 11A show that the CAT protein expressed was functional. To determine if a full-length CAT protein was being produced and to quantitate expression, we infected BHK cells for four hours with two independently derived VSV-CAT viruses or with wild-type VSV. Infected cells were then labeled with [$^{35}$S]-methionine, and crude lysates were fractionated by SDS-PAGE. Because VSV infection shuts off host mRNA translation, the viral proteins can be visualized without immunoprecipitation. The results in FIG. 11B show that the VSV L, G, N, P and M proteins as well as an additional protein of the size expected for CAT were synthesized in VSV-CAT-infected cells. The CAT band is not seen in the VSV-infected cells. There are also two proteins of unknown identity flanking CAT that are seen in the wild-type infection also. Quantitation of CAT protein expression on the PhosphorImager (correcting for the number of methionine residues) showed that CAT was expressed at a level of 58% of VSV G protein.

VSV-CAT expresses CAT protein from a sixth mRNA. To determine if CAT protein was being expressed from an mRNA of the expected size (~800 nucleotides without poly(A) including the untranslated portion from G), we electrophoresed RNA from cells infected with VSV-CAT or VSV and carried out the Northern blot shown in FIG. 12. Using a probe generated from the complete pVSVFL-2 plasmid, we detected similar mRNA patterns from both VSV- and VSV-CAT-infected cells. The specific probe for CAT sequences showed an mRNA comigrating with the VSV M and P mRNAs, which are both approximately the same size as CAT. The faint RNA bands migrating above the 9.5 kb marker are probably the full length genomic and antigenomic RNAs.

VSV-CAT grows to the same titer and produces the same number of particles as VSV. Two different VSV-CAT isolates were plaque purified and then grown on BHK cells. Final titers on BHK cells were 2×10$^9$ or 5×10$^9$ plaque forming units (PFU)/ml, equivalent to those obtained with wild-type VSV. To determine if there were any differences in the protein compositions or amounts of total protein produced by VSV or VSV-CAT, identical numbers of BHK cells (5×10$^6$) were infected with virus from single plaques of either VSV or VSV-CAT. After 24 hours when the infection was complete, the virus was pelleted from the supernatants and 5% of the total from each pellet was fractionated by SDS-PAGE and subjected to Coomassie staining. The photograph of the gel (FIG. 11C) shows identical protein compositions and amounts for both viruses, with no CAT protein present in the particles. We conclude that the presence of the CAT gene does not have a detectable effect on the growth of VSV, although VSV-CAT presumably replicates marginally more slowly than wild-type VSV because of its longer genome.

CAT protein is expressed in high levels. To determine the amount and the time course of CAT protein expression by VSV-CAT, cells were infected with VSV-CAT at an MOI of ~20 and after 4, 6, 8 and 24 hours cell lysates were prepared from cell pellets. The amount of CAT protein as a percentage of cell protein was determined by an ELISA with a CAT protein standard. The results showed that CAT protein was already 1% of total cellular protein at 4 hours and was 1.7, 1.6, and 1.3% of total cellular protein after 6, 8, and 24 hours, respectively.

Stability of the CAT gene and protein expression over fifteen passages. Because RNA viruses including VSV are known to have high spontaneous mutation rates (Steinhauer et al., 1989, J. Virol 63:2063–2071), we were concerned that expression of the CAT protein might be lost rapidly during passaging of VSV-CAT. To determine genomic stability, we passaged a VSV-CAT stock obtained from a single recovery. Virus (10$^5$ PFU) was then added to 10$^7$ BHK cells and grown for 24 hours, yielding 10$^{11}$ infectious VSV particles. Approximately 10$^5$ particles from this stock were then added to fresh cells, and the entire process was repeated for a total of fifteen low multiplicity passages. We then infected BHK cells with the passaged virus at an MOI of 1 and carried out double-label immunofluorescence microscopy for CAT protein and VSV G protein as shown in FIG. 10. Scanning of over 10,000 infected cells expressing G protein revealed none that had lost CAT expression.

We next carried out a plaque assay on the passaged virus and picked 12 individual plaques. Virus from these plaques was used to infect separate dishes of BHK cells, and CAT assays were performed on the cell lysates from each dish (FIG. 13). This experiment showed that all cells expressed functional CAT protein and suggested that no major changes such as frameshift mutations or deletions of the CAT sequence had occurred, but they did not rule out minor base changes that might affect CAT sequence without eliminating enzyme activity. To look for such changes, we used RT-PCR with VENT polymerase to amplify the CAT sequences from six of the individual plaques and carried out direct sequencing of the PCR products. At least 400 bases could be read reliably from each PCR product. Four of the sequences agreed completely with the sequence of the starting pVSV-CAT plasmid. In two sequences we found different single base changes that would change single amino acids in CAT at positions 79 and 88, but these mutations apparently did not eliminate CAT activity. Thus, even after 15 passages involving 10$^6$-fold expansion at each passage, functional CAT expression was not lost in a significant proportion of the virus population and nucleotide sequence changes were still relatively rare.

7.3. DISCUSSION

The homologies among the sequences at the junctions of the VSV genes have been known for many years (McGeoch, 1979, Cell 17:673–681; Rose, 1980, Cell 19:415–421) but until the instant invention it has not been possible to test the function of these conserved sequences as terminators and promoters for expression of foreign genes. Here, we have described a modified VSV containing the minimal 23-nucleotide conserved sequence, and we report that it is sufficient to direct expression of a foreign gene from a new mRNA species in VSV. Therefore no other special features of VSV genome structure, such as transcription termination, polyadenylation, or reinitiation signals, are required.

We chose the bacterial CAT gene for these studies because it is small (~700 nucleotides) and might fit within any existing packaging constraint. In other recent studies, we have found that VSV can accommodate and express extra genes of at least 2.5 kb and still produce normal yields of virus particles. VSV virions contain a helical nucleocapsid with approximately 35 turns that is tightly packed within a membrane-enveloped, bullet-shaped particle (Rose and Schubert, 1987, Rhabdovirus genomes and their products, p.129–166, in R. R. Wagner (ed.), The Rhabdoviruses. Plenum Publishing Corp., NY). Defective VSVs have been known for many years, and these contain shorter nucleocapsids packed in shorter, bullet-shaped particles. Thus, it is not unreasonable that a longer RNA might simply be accommodated in a longer nucleocapsid. In fact, other rhabdoviruses do contain an extra gene between G and L (Kurath et al., 1985, J. Virol. 53:469–476). Based on our results to date, we believe that there is no strict packaging limit in VSV, although packaging of very large nucleocapsids will likely become inefficient at some point.

There is a polarity in VSV transcription that follows the gene order, N,P,M,G,L. As polymerase proceeds along the genome during transcription, it apparently terminates after polyadenylating each mRNA. This is followed by reinitiation of about 70 to 80% of the polymerases on the next gene (Iverson and Rose, 1981, Cell 23:477–484). The level of expression of the CAT protein was less than that of G, consistent with such a polarity. We might also expect that inclusion of the CAT gene between G and L would reduce levels of L expression relative to those of the other genes. Although a 20 to 25% reduction in levels of L expression relative to those of N or P was noted for the recombinants compared with those of wild-type VSV in the experiment shown (FIG. 11B), this difference does not appreciably affect the growth of the recombinant virus.

VSV offers a number of advantages over other live virus-based expression systems. First, the virus life cycle is so rapid that recombinants expressing the protein of interest can be generated in one to two days after the gene to be expressed is cloned into the pVSVXN1 vector. Virus plaque assays require only 12 to 18 hours, and stocks with titers of $5 \times 10^9$ per ml can be prepared overnight from single plaques. The very useful live-virus expression systems based on vaccinia virus recombinants require significantly more time and effort, because recombination in vivo is used and then recombinants must be screened or selected (Moss and Flexner, 1987, Annu. Rev. Immunol. 5:305–324). Second, the gene to be included in the VSV vector needs only an effective translation initiation site and a termination codon because it is expressed from a new mRNA species. This contrasts with expression in positive-strand RNA viruses such as poliovirus, which cleave all proteins from a larger polyprotein.

Proteolytic cleavage sites must therefore be introduced on either side of protein to be expressed, and the polyprotein structure is also important (Harris et al., 1990, Semin. Virol. 1:323–333). Third, the expression level in VSV is quite high. CAT protein was 1.7% of total cell protein after six hours, and it is expressed with only the five other VSV proteins because host protein synthesis is shut off. In contrast, vaccinia virus expresses a very large number of additional polypeptides from its 190 kb genome (Moss and Flexner, 1987, Annu. Rev. Immunol. 5:305–324). For the generation of specific immune responses in vaccine applications it will likely prove advantageous to have only a limited number of proteins expressed.

There are also other very useful expression systems based on defective alphaviruses derived from Sindbis and Semliki Forest viruses. Because of RNA packaging limits in these viruses, mostly defective derivatives expressing the gene of interest replacing the viral structural genes are normally employed. These defective viruses are generally packaged by employing a helper virus, and are limited to a single cycle of replication (Liljestrum and Garoff, 1991, Bio/Technology 9:1356–1361; Xiong et al., 1989, Science 243:1188–1191).

Recently, the use of a nondefective Sindbis virus as a vaccine vector was described. However, in this system expression of the foreign gene is lost after one to five passages and the recombinant viruses grow to lower titers then the wild-type virus (Pugachev et al., 1995, Virology 212:587–594).

Polymerase errors during replication were a major concern in using an RNA virus such as VSV to express a foreign gene. Neutral mutation frequencies in VSV have been estimated at 1 in $10^3$ to $10^4$ for specific nucleotides in the genome (Holland et al., 1989, J. Virol 63:5030–5036; Steinhauer et al., 1989, J. Virol 63:2063–2071). However, there are examples of remarkable VSV genome sequence stability based on analysis of VSV genome sequence evolution in nature. For example, a region of the P gene that is highly variable in sequence among VSV strains isolated from diverse geographical areas is extremely stable over seven years of replication in sandflies and pigs in one enzootic focus (Nichol et al., 1993, Proc. Natl. Acad. Sci. USA 90:10424–10428).

Our results show that an additional unselected gene is very stable in VSV. Even after 15 low multiplicity passages, all viruses examined expressed functional CAT protein. We did, however, find single base changes in the CAT gene in two out of six viruses after 15 low-multiplicity passages. Extensive analysis of the number of sequence changes in this CAT gene occurring over a very large number of passages could be useful for obtaining an accurate measure of the neutral mutation rate in VSV.

Most importantly, the mutation rate in VSV is so low that it does not present a problem when using the virus to express foreign genes, even during extensive passaging. In a single overnight passage on $10^7$ BHK cells, virus from a single VSV plaque ($\sim 10^5$ infectious particles) is amplified to $\sim 10^{11}$ infectious particles, corresponding to $\sim 200$ $\mu$g of virus protein. This single passage thus yields enough virus to carry out infections on an industrial scale. A second passage of $10^6$-fold amplification would produce 200 grams of virus.

8. DEPOSIT OF MICROORGANISMS

Plasmid pVSVFL(+) was deposited on May 2, 1995 with the American Type Culture Collection (ATCC), 1201 Parklawn Drive, Rockville, Md. 20852, under the provisions of the Budapest Treaty on the International Recognition of the Deposit of Microorganisms for the Purposes of Patent Procedures, and assigned accession no. 97134.

The present invention is not to be limited in scope by the microorganism deposited or the specific embodiments described herein. Indeed, various modifications of the invention in addition to those described herein will become apparent to those skilled in the art from the foregoing description and accompanying figures. Such modifications are intended to fall within the scope of the appended claims.

Various publications are cited herein, the disclosures of which are incorporated by reference in their entireties.

What is claimed is:

1. A method of producing a recombinant replicable vesiculovirus comprising culturing a cell containing
    (a) a first recombinant nucleic acid that can be transcribed to produce an RNA molecule comprising (A) a vesiculovirus antigenomic (+) RNA containing the vesiculovirus promoter for replication, and (B) a ribozyme sequence immediately downstream of said antigenomic (+) RNA, that cleaves at the 3' terminus of the antigenomic (+) RNA, in which a region of the RNA nonessential for replication of the vesiculovirus has been inserted into or replaced by a foreign RNA sequence, said first recombinant nucleic acid having the following operatively linked components:
        (i) a first promoter;
        (ii) a first DNA sequence that can be transcribed under the control of the first promoter in the cell to produce said RNA molecule; and
        (iii) a first transcription termination signal;
    (b) a second recombinant nucleic acid encoding a vesiculovirus N protein and having the following operatively linked components:
        (i) a second promoter which controls the expression of the N protein;
        (ii) a first translation initiation signal; and
        (iii) a second DNA sequence encoding the N protein;
    (c) a third recombinant nucleic acid encoding a vesiculovirus L protein and having the following operatively linked components:
        (i) a third promoter which controls the expression of the L protein;
        (ii) a second translation initiation signal; and
        (iii) a third DNA sequence encoding the L protein;
    (d) a fourth recombinant nucleic acid encoding a vesiculovirus P protein and having the following operatively linked components:
        (i) a fourth promoter which controls the expression of the P protein;
        (ii) a third translation initiation signal; and
        (iii) a fourth DNA sequence encoding the P protein;
whereby the first recombinant nucleic acid is transcribed in the cell to produce said RNA molecule, and the N, L and P proteins are expressed in the cell, and a recombinant replicable vesiculovirus is produced that has a genome that is the complement of said antigenomic RNA comprising said foreign RNA sequence, in which said foreign RNA sequence encodes a peptide or protein that is expressed and induces an immune response to said peptide or protein in a suitable host infected by the vesiculovirus.

2. The method according to claim 1 in which the cell is a mammalian cell.

3. The method according to claim 1 in which the first recombinant nucleic acid is a DNA plasmid vector.

4. The method according to claim 1 or 3 in which the second recombinant nucleic acid is a DNA plasmid vector; and in which the third recombinant nucleic acid is a DNA plasmid vector; and in which the fourth recombinant nucleic acid is a DNA plasmid vector.

5. The method according to claim 4 in which the first recombinant nucleic acid, the second recombinant nucleic acid, the third recombinant nucleic acid, and the fourth recombinant nucleic acid, each further comprises a selectable marker.

6. The method according to claim 1 in which the second, third and fourth recombinant nucleic acids form part of a single recombinant nucleic acid that does not also contain said first recombinant nucleic acid.

7. The method according to claim 1 in which the first, second, third and fourth promoter sequences are RNA polymerase promoter sequences for the same RNA polymerase, and in which the cell also contains a cytoplasmic source of said RNA polymerase.

8. The method according to claim 7 in which the cytoplasmic source of said RNA polymerase is a recombinant vaccinia virus expressing said RNA polymerase in the cell.

9. A method of producing a recombinant replicable vesiculovirus comprising culturing a mammalian cell containing:
    (a) a first DNA plasmid vector comprising the following operatively linked components:
        (i) a bacteriophage RNA polymerase promoter;
        (ii) a first DNA sequence that is transcribed in the cell to produce an RNA molecule comprising (A) a vesiculovirus antigenomic (+) RNA containing the vesiculovirus promoter for replication, in which a region of the RNA nonessential for replication of the vesiculovirus has been inserted into or replaced by a foreign RNA sequence, and (B) a ribozyme sequence immediately downstream of said antigenomic (+) RNA, that cleaves at the 3' terminus of the antigenomic RNA; and
        (iii) a transcription termination signal for the RNA polymerase;
    (b) a second DNA plasmid vector comprising the following operatively linked components:
        (i) the bacteriophage RNA polymerase promoter;
        (ii) a second DNA sequence encoding an N protein of the vesiculovirus; and
        (iii) a second transcription termination signal for the RNA polymerase;
    (c) a third DNA plasmid vector comprising the following operatively linked components:
        (i) the bacteriophage RNA polymerase promoter;
        (ii) a third DNA sequence encoding a P protein of the vesiculovirus; and
        (iii) a third transcription termination signal for the RNA polymerase;
    (d) a fourth DNA plasmid vector comprising the following operatively linked components:

(i) the bacteriophage RNA polymerase promoter;
(ii) a fourth DNA sequence encoding an L protein of the vesiculovirus; and
(iii) a fourth transcription termination signal for the RNA polymerase; and (e) a recombinant vaccinia virus comprising a sequence encoding the bacteriophage RNA polymerase; whereby in said cell the first DNA sequence is transcribed to produce said RNA molecule, the N, P, and L proteins and the bacteriophage RNA polymerase are expressed, and a recombinant replicable vesiculovirus is produced that has a genome that is the complement of said antigenomic RNA comprising said foreign RNA sequence, in which said foreign RNA sequence encodes a peptide or protein that is expressed and induces an immune response to said peptide or protein in a suitable host infected by the vesiculovirus.

10. The method according to claim 9 in which the ribozyme sequence is the sequence of the hepatitis delta virus ribozyme, and the bacteriophage RNA polymerase is the T7 RNA polymerase.

11. The method according to claim 1 or 9 in which the protein or peptide displays at least an immunogenic portion of an antigen of a pathogenic microorganism.

12. The method according to claim 1 or 9 in which the protein or peptide displays at least an immunogenic portion of a tumor specific antigen.

13. The method according to claim 9 which further comprises before step (a) the step of introducing said first, second, third and fourth plasmid vectors and said recombinant vaccinia virus into said cell.

* * * * *

UNITED STATES PATENT AND TRADEMARK OFFICE
CERTIFICATE OF CORRECTION

PATENT NO. : 6,168,943 B1
DATED : January 2, 2001
INVENTOR(S) : John K. Rose

Figure 2A:
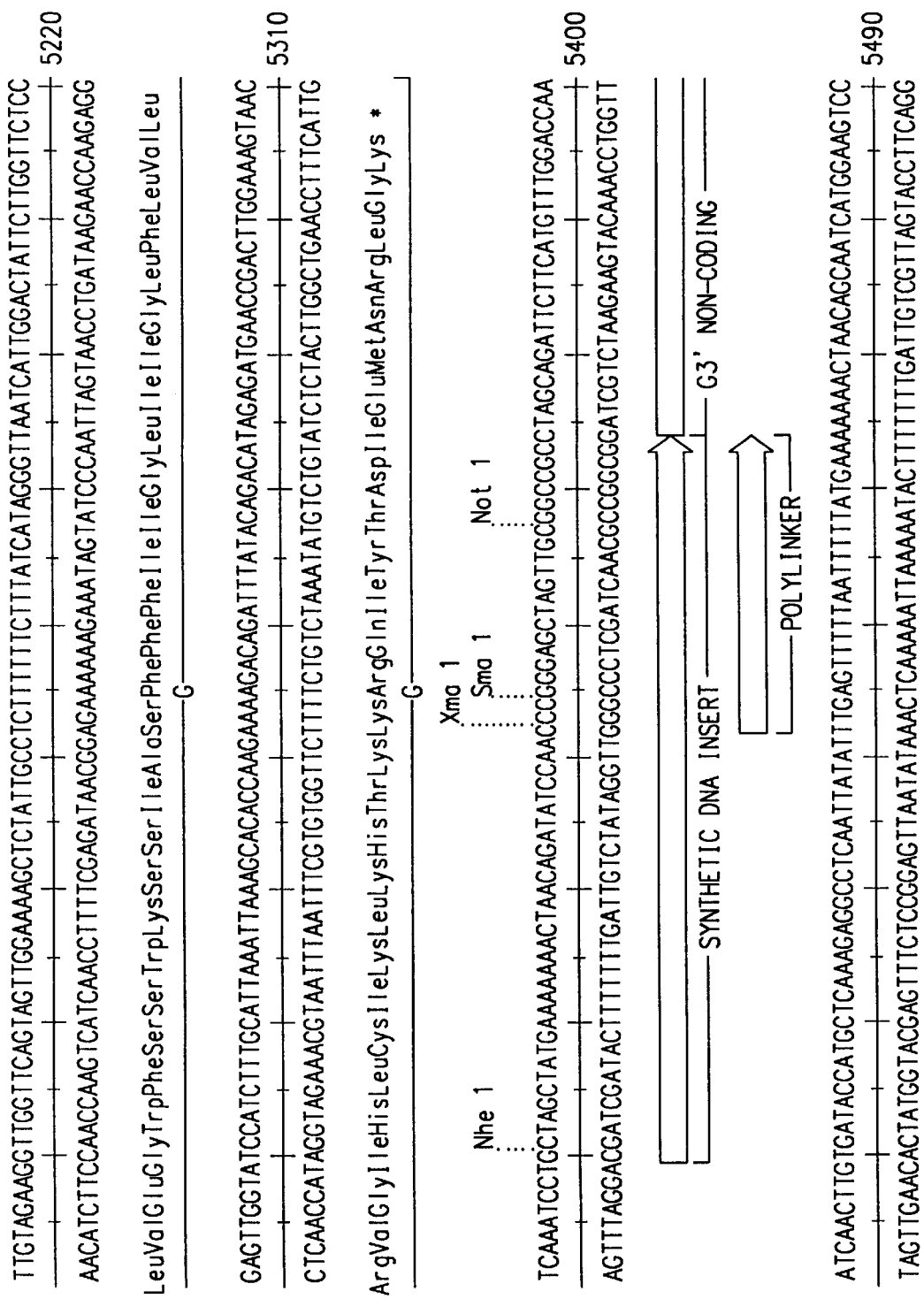

It is certified that error appears in the above-identified patent and that said Letters Patent is hereby corrected as shown below:

Column 4,
Line 51, please replace "FIGS. 1A-1S" with -- FIGS. 1A-1P1 --;

Column 5,
Line 1, please replace "FIG. 2" with -- FIGS. 2A-2B --;

Column 123,
Lines 16-26, please replace sub-paragraph (a) of claim 1 beginning with "(a)" to and including "components" with the following rewritten sub-paragraph (a):

-- (a) a first recombinant nucleic acid that can be transcribed to porduce an RNA molecule comprising (A) a vesiculovirus antigenomic (+) RNA containing the vesiculovirus promoter for replication, and (B) a ribozyme sequence immediately downstream of said antigenomic (+) RNA, that cleaves at the 3' terminus of the antigenomic (+) RNA, in which a foreign RNA sequence is inserted into or replaces a region of the RNA nonessential for replication of the vesiculovirus, said first recombinant nucleic acid having the following operatively linked components: --.

Column 124,
Lines 39-49, please replace the sub-paragraph (ii) of claim 9 beginning with "(ii)" to and including "and" with the following rewritten sub-paragraph (ii):

UNITED STATES PATENT AND TRADEMARK OFFICE
CERTIFICATE OF CORRECTION

PATENT NO.    : 6,168,943 B1
DATED         : January 2, 2001
INVENTOR(S)   : John K. Rose It is certified that error appears in the above-identified patent and that said Letters Patent is hereby corrected as shown below:

Column 124 (cont'd),

-- (ii) a first DNA sequence that is transcribed in the cell to produce an RNA molecule comprising (A) a vesiculovirus antigenomic (+) RNA containing the vesiculovirus promoter for replication, in which a foreign RNA sequence is inserted into or replaces a region of the RNA nonessentail for replication of the vesiculovirus, and (B) a ribozyme sequence immediately downstream of said antigenomic (+) RNA, that cleaves at the 3' terminus of the antigenomic RNA; and --.

Signed and Sealed this

Nineteenth Day of August, 2003

JAMES E. ROGAN
*Director of the United States Patent and Trademark Office*

SEQUENCE LISTING (1) GENERAL INFORMATION:

(iii) NUMBER OF SEQUENCES: 44

(2) INFORMATION FOR SEQ ID NO:1:

(i) SEQUENCE CHARACTERISTICS:
      (A) LENGTH: 14311 base pairs
      (B) TYPE: nucleic acid
      (C) STRANDEDNESS: double
      (D) TOPOLOGY: linear (ii) MOLECULE TYPE: DNA (ix) FEATURE:
      (A) NAME/KEY: CDS
      (B) LOCATION: 760..2025

(ix) FEATURE:
      (A) NAME/KEY: CDS
      (B) LOCATION: 2092..2886

(ix) FEATURE:
      (A) NAME/KEY: CDS
      (B) LOCATION: 2946..3632

(ix) FEATURE:
      (A) NAME/KEY: CDS
      (B) LOCATION: 3774..5306

(ix) FEATURE:
      (A) NAME/KEY: CDS
      (B) LOCATION: 5429..11755

(xi) SEQUENCE DESCRIPTION: SEQ ID NO:1:

```
CACCTAAATT GTAAGCGTTA ATATTTTGTT AAAATTCGCG TTAAATTTTT GTTAAATCAG      60

CTCATTTTTT AACCAATAGG CCGAAATCGG CAAAATCCCT TATAAATCAA AAGAATAGAC     120

CGAGATAGGG TTGAGTGTTG TTCCAGTTTG GAACAAGAGT CCACTATTAA AGAACGTGGA     180

CTCCAACGTC AAAGGGCGAA AAACCGTCTA TCAGGGCGAT GGCCCACTAC GTGAACCATC     240

ACCCTAATCA AGTTTTTTGG GGTCGAGGTG CCGTAAAGCA CTAAATCGGA ACCCTAAAGG     300

GAGCCCCCGA TTTAGAGCTT GACGGGGAAA GCCGGCGAAC GTGGCGAGAA AGGAAGGGAA     360

GAAAGCGAAA GGAGCGGGCG CTAGGGCGCT GGCAAGTGTA GCGGTCACGC TGCGCGTAAC     420

CACCACACCC GCCGCGCTTA ATGCGCCGCT ACAGGGCGCG TCCCATTCGC CATTCAGGCT     480

GCGCAACTGT TGGGAAGGGC GATCGGTGCG GGCCTCTTCG CTATTACGCC AGCTGGCGAA     540

AGGGGGATGT GCTGCAAGGC GATTAAGTTG GGTAACGCCA GGGTTTTCCC AGTCACGACG     600

TTGTAAAACG ACGGCCAGTG AATTGTAATA CGACTCACTA TAGGGCGAAT TGGGTACCGG     660

GCCCCCCCTC GAGTTGTAAT ACGACTCACT ATAGGGACGA AGACAAACAA ACCATTATTA     720

TCATTAAAAG GCTCAGGAGA AACTTTAACA GTAATCAAA ATG TCT GTT ACA GTC       774
                                              Met Ser Val Thr Val
                                                1               5

AAG AGA ATC ATT GAC AAC ACA GTC ATA GTT CCA AAA CTT CCT GCA AAT      822
Lys Arg Ile Ile Asp Asn Thr Val Ile Val Pro Lys Leu Pro Ala Asn
             10                  15                  20

GAG GAT CCA GTG GAA TAC CCG GCA GAT TAC TTC AGA AAA TCA AAG GAG      870
Glu Asp Pro Val Glu Tyr Pro Ala Asp Tyr Phe Arg Lys Ser Lys Glu
         25                  30                  35

ATT CCT CTT TAC ATC AAT ACT ACA AAA AGT TTG TCA GAT CTA AGA GGA      918
Ile Pro Leu Tyr Ile Asn Thr Thr Lys Ser Leu Ser Asp Leu Arg Gly
```

```
                    40                  45                  50
TAT GTC TAC CAA GGC CTC AAA TCC GGA AAT GTA TCA ATC ATA CAT GTC    966
Tyr Val Tyr Gln Gly Leu Lys Ser Gly Asn Val Ser Ile Ile His Val
         55                  60                  65

AAC AGC TAC TTG TAT GGA GCA TTA AAG GAC ATC CGG GGT AAG TTG GAT    1014
Asn Ser Tyr Leu Tyr Gly Ala Leu Lys Asp Ile Arg Gly Lys Leu Asp
 70                  75                  80                  85

AAA GAT TGG TCA AGT TTC GGA ATA AAC ATC GGG AAA GCA GGG GAT ACA    1062
Lys Asp Trp Ser Ser Phe Gly Ile Asn Ile Gly Lys Ala Gly Asp Thr
                 90                  95                 100

ATC GGA ATA TTT GAC CTT GTA TCC TTG AAA GCC CTG GAC GGC GTA CTT    1110
Ile Gly Ile Phe Asp Leu Val Ser Leu Lys Ala Leu Asp Gly Val Leu
                105                 110                 115

CCA GAT GGA GTA TCG GAT GCT TCC AGA ACC AGC GCA GAT GAC AAA TGG    1158
Pro Asp Gly Val Ser Asp Ala Ser Arg Thr Ser Ala Asp Asp Lys Trp
        120                 125                 130

TTG CCT TTG TAT CTA CTT GGC TTA TAC AGA GTG GGC AGA ACA CAA ATG    1206
Leu Pro Leu Tyr Leu Leu Gly Leu Tyr Arg Val Gly Arg Thr Gln Met
        135                 140                 145

CCT GAA TAC AGA AAA AAG CTC ATG GAT GGG CTG ACA AAT CAA TGC AAA    1254
Pro Glu Tyr Arg Lys Lys Leu Met Asp Gly Leu Thr Asn Gln Cys Lys
150                 155                 160                 165

ATG ATC AAT GAA CAG TTT GAA CCT CTT GTG CCA GAA GGT CGT GAC ATT    1302
Met Ile Asn Glu Gln Phe Glu Pro Leu Val Pro Glu Gly Arg Asp Ile
                170                 175                 180

TTT GAT GTG TGG GGA AAT GAC AGT AAT TAC ACA AAA ATT GTC GCT GCA    1350
Phe Asp Val Trp Gly Asn Asp Ser Asn Tyr Thr Lys Ile Val Ala Ala
                185                 190                 195

GTG GAC ATG TTC TTC CAC ATG TTC AAA AAA CAT GAA TGT GCC TCG TTC    1398
Val Asp Met Phe Phe His Met Phe Lys Lys His Glu Cys Ala Ser Phe
        200                 205                 210

AGA TAC GGA ACT ATT GTT TCC AGA TTC AAA GAT TGT GCT GCA TTG GCA    1446
Arg Tyr Gly Thr Ile Val Ser Arg Phe Lys Asp Cys Ala Ala Leu Ala
215                 220                 225

ACA TTT GGA CAC CTC TGC AAA ATA ACC GGA ATG TCT ACA GAA GAT GTA    1494
Thr Phe Gly His Leu Cys Lys Ile Thr Gly Met Ser Thr Glu Asp Val
230                 235                 240                 245

ACG ACC TGG ATC TTG AAC CGA GAA GTT GCA GAT GAA ATG GTC CAA ATG    1542
Thr Thr Trp Ile Leu Asn Arg Glu Val Ala Asp Glu Met Val Gln Met
                250                 255                 260

ATG CTT CCA GGC CAA GAA ATT GAC AAG GCC GAT TCA TAC ATG CCT TAT    1590
Met Leu Pro Gly Gln Glu Ile Asp Lys Ala Asp Ser Tyr Met Pro Tyr
        265                 270                 275

TTG ATC GAC TTT GGA TTG TCT TCT AAG TCT CCA TAT TCT TCC GTC AAA    1638
Leu Ile Asp Phe Gly Leu Ser Ser Lys Ser Pro Tyr Ser Ser Val Lys
        280                 285                 290

AAC CCT GCC TTC CAC TTC TGG GGG CAA TTG ACA GCT CTT CTG CTC AGA    1686
Asn Pro Ala Phe His Phe Trp Gly Gln Leu Thr Ala Leu Leu Leu Arg
        295                 300                 305

TCC ACC AGA GCA AGG AAT GCC CGA CAG CCT GAT GAC ATT GAG TAT ACA    1734
Ser Thr Arg Ala Arg Asn Ala Arg Gln Pro Asp Asp Ile Glu Tyr Thr
310                 315                 320                 325

TCT CTT ACT ACA GCA GGT TTG TTG TAC GCT TAT GCA GTA GGA TCC TCT    1782
Ser Leu Thr Thr Ala Gly Leu Leu Tyr Ala Tyr Ala Val Gly Ser Ser
                330                 335                 340

GCC GAC TTG GCA CAA CAG TTT TGT GTT GGA GAT AAC AAA TAC ACT CCA    1830
Ala Asp Leu Ala Gln Gln Phe Cys Val Gly Asp Asn Lys Tyr Thr Pro
        345                 350                 355

GAT GAT AGT ACC GGA GGA TTG ACG ACT AAT GCA CCG CCA CAA GGC AGA    1878
```

-continued

```
Asp Asp Ser Thr Gly Gly Leu Thr Thr Asn Ala Pro Pro Gln Gly Arg
        360                 365                 370

GAT GTG GTC GAA TGG CTC GGA TGG TTT GAA GAT CAA AAC AGA AAA CCG        1926
Asp Val Val Glu Trp Leu Gly Trp Phe Glu Asp Gln Asn Arg Lys Pro
        375                 380                 385

ACT CCT GAT ATG ATG CAG TAT GCG AAA AGA GCA GTC ATG TCA CTG CAA        1974
Thr Pro Asp Met Met Gln Tyr Ala Lys Arg Ala Val Met Ser Leu Gln
390                 395                 400                 405

GGC CTA AGA GAG AAG ACA ATT GGC AAG TAT GCT AAG TCA GAA TTT GAC        2022
Gly Leu Arg Glu Lys Thr Ile Gly Lys Tyr Ala Lys Ser Glu Phe Asp
                410                 415                 420

AAA TGA CCCTATAATT CTCAGATCAC CTATTATATA TTATGCTACA TATGAAAAAA        2078
Lys

ACTAACAGAT ATC ATG GAT AAT CTC ACA AAA GTT CGT GAG TAT CTC AAG        2127
            Met Asp Asn Leu Thr Lys Val Arg Glu Tyr Leu Lys
             1               5                   10

TCC TAT TCT CGT CTG GAT CAG GCG GTA GGA GAG ATA GAT GAG ATC GAA        2175
Ser Tyr Ser Arg Leu Asp Gln Ala Val Gly Glu Ile Asp Glu Ile Glu
            15                  20                  25

GCA CAA CGA GCT GAA AAG TCC AAT TAT GAG TTG TTC CAA GAG GAT GGA        2223
Ala Gln Arg Ala Glu Lys Ser Asn Tyr Glu Leu Phe Gln Glu Asp Gly
        30                  35                  40

GTG GAA GAG CAT ACT AAG CCC TCT TAT TTT CAG GCA GCA GAT GAT TCT        2271
Val Glu Glu His Thr Lys Pro Ser Tyr Phe Gln Ala Ala Asp Asp Ser
45                  50                  55                  60

GAC ACA GAA TCT GAA CCA GAA ATT GAA GAC AAT CAA GGT TTG TAT GCA        2319
Asp Thr Glu Ser Glu Pro Glu Ile Glu Asp Asn Gln Gly Leu Tyr Ala
                65                  70                  75

CCA GAT CCA GAA GCT GAG CAA GTT GAA GGC TTT ATA CAG GGG CCT TTA        2367
Pro Asp Pro Glu Ala Glu Gln Val Glu Gly Phe Ile Gln Gly Pro Leu
            80                  85                  90

GAT GAC TAT GCA GAT GAG GAA GTG GAT GTT GTA TTT ACT TCG GAC TGG        2415
Asp Asp Tyr Ala Asp Glu Glu Val Asp Val Val Phe Thr Ser Asp Trp
        95                  100                 105

AAA CAG CCT GAG CTT GAA TCT GAC GAG CAT GGA AAG ACC TTA CGG TTG        2463
Lys Gln Pro Glu Leu Glu Ser Asp Glu His Gly Lys Thr Leu Arg Leu
110                 115                 120

ACA TCG CCA GAG GGT TTA AGT GGA GAG CAG AAA TCC CAG TGG CTT TCG        2511
Thr Ser Pro Glu Gly Leu Ser Gly Glu Gln Lys Ser Gln Trp Leu Ser
125                 130                 135                 140

ACG ATT AAA GCA GTC GTG CAA AGT GCC AAA TAC TGG AAT CTG GCA GAG        2559
Thr Ile Lys Ala Val Val Gln Ser Ala Lys Tyr Trp Asn Leu Ala Glu
                145                 150                 155

TGC ACA TTT GAA GCA TCG GGA GAA GGG GTC ATT ATG AAG GAG CGC CAG        2607
Cys Thr Phe Glu Ala Ser Gly Glu Gly Val Ile Met Lys Glu Arg Gln
            160                 165                 170

ATA ACT CCG GAT GTA TAT AAG GTC ACT CCA GTG ATG AAC ACA CAT CCG        2655
Ile Thr Pro Asp Val Tyr Lys Val Thr Pro Val Met Asn Thr His Pro
        175                 180                 185

TCC CAA TCA GAA GCA GTA TCA GAT GTT TGG TCT CTC TCA AAG ACA TCC        2703
Ser Gln Ser Glu Ala Val Ser Asp Val Trp Ser Leu Ser Lys Thr Ser
    190                 195                 200

ATG ACT TTC CAA CCC AAG AAA GCA AGT CTT CAG CCT CTC ACC ATA TCC        2751
Met Thr Phe Gln Pro Lys Lys Ala Ser Leu Gln Pro Leu Thr Ile Ser
205                 210                 215                 220

TTG GAT GAA TTG TTC TCA TCT AGA GGA GAG TTC ATC TCT GTC GGA GGT        2799
Leu Asp Glu Leu Phe Ser Ser Arg Gly Glu Phe Ile Ser Val Gly Gly
                225                 230                 235

GAC GGA CGA ATG TCT CAT AAA GAG GCC ATC CTG CTC GGC CTG AGA TAC        2847
```

```
Asp Gly Arg Met Ser His Lys Glu Ala Ile Leu Leu Gly Leu Arg Tyr
            240                 245                 250

AAA AAG TTG TAC AAT CAG GCG AGA GTC AAA TAT TCT CTG TAG                    2889
Lys Lys Leu Tyr Asn Gln Ala Arg Val Lys Tyr Ser Leu
            255                 260                 265

ACTATGAAAA AAAGTAACAG ATATCACGAT CTAAGTGTTA TCCCAATCCA TTCATC              2945

ATG AGT TCC TTA AAG AAG ATT CTC GGT CTG AAG GGG AAA GGT AAG AAA            2993
Met Ser Ser Leu Lys Lys Ile Leu Gly Leu Lys Gly Lys Gly Lys Lys
 1               5                  10                 15

TCT AAG AAA TTA GGG ATC GCA CCA CCC CCT TAT GAA GAG GAC ACT AGC            3041
Ser Lys Lys Leu Gly Ile Ala Pro Pro Pro Tyr Glu Glu Asp Thr Ser
            20                  25                  30

ATG GAG TAT GCT CCG AGC GCT CCA ATT GAC AAA TCC TAT TTT GGA GTT            3089
Met Glu Tyr Ala Pro Ser Ala Pro Ile Asp Lys Ser Tyr Phe Gly Val
        35                  40                  45

GAC GAG ATG GAC ACC TAT GAT CCG AAT CAA TTA AGA TAT GAG AAA TTC            3137
Asp Glu Met Asp Thr Tyr Asp Pro Asn Gln Leu Arg Tyr Glu Lys Phe
    50                  55                  60

TTT TTT ACA GTG AAA ATG ACG GTT AGA TCT AAT CGT CCG TTC AGA ACA            3185
Phe Phe Thr Val Lys Met Thr Val Arg Ser Asn Arg Pro Phe Arg Thr
65                  70                  75                  80

TAC TCA GAT GTG GCA GCC GCT GTA TCC CAT TGG GAT CAC ATG TAC ATC            3233
Tyr Ser Asp Val Ala Ala Ala Val Ser His Trp Asp His Met Tyr Ile
                85                  90                  95

GGA ATG GCA GGG AAA CGT CCC TTC TAC AAA ATC TTG GCT TTT TTG GGT            3281
Gly Met Ala Gly Lys Arg Pro Phe Tyr Lys Ile Leu Ala Phe Leu Gly
            100                 105                 110

TCT TCT AAT CTA AAG GCC ACT CCA GCG GTA TTG GCA GAT CAA GGT CAA            3329
Ser Ser Asn Leu Lys Ala Thr Pro Ala Val Leu Ala Asp Gln Gly Gln
        115                 120                 125

CCA GAG TAT CAC ACT CAC TGC GAA GGC AGG GCT TAT TTG CCA CAT AGG            3377
Pro Glu Tyr His Thr His Cys Glu Gly Arg Ala Tyr Leu Pro His Arg
    130                 135                 140

ATG GGG AAG ACC CCT CCC ATG CTC AAT GTA CCA GAG CAC TTC AGA AGA            3425
Met Gly Lys Thr Pro Pro Met Leu Asn Val Pro Glu His Phe Arg Arg
145                 150                 155                 160

CCA TTC AAT ATA GGT CTT TAC AAG GGA ACG ATT GAG CTC ACA ATG ACC            3473
Pro Phe Asn Ile Gly Leu Tyr Lys Gly Thr Ile Glu Leu Thr Met Thr
                165                 170                 175

ATC TAC GAT GAT GAG TCA CTG GAA GCA GCT CCT ATG ATC TGG GAT CAT            3521
Ile Tyr Asp Asp Glu Ser Leu Glu Ala Ala Pro Met Ile Trp Asp His
            180                 185                 190

TTC AAT TCT TCC AAA TTT TCT GAT TTC AGA GAG AAG GCC TTA ATG TTT            3569
Phe Asn Ser Ser Lys Phe Ser Asp Phe Arg Glu Lys Ala Leu Met Phe
        195                 200                 205

GGC CTG ATT GTC GAG AAA AAG GCA TCT GGA GCG TGG GTC CTG GAT TCT            3617
Gly Leu Ile Val Glu Lys Lys Ala Ser Gly Ala Trp Val Leu Asp Ser
    210                 215                 220

ATC AGC CAC TTC AAA TGA GCTAGTCTAA CTTCTAGCTT CTGAACAATC                   3665
Ile Ser His Phe Lys
225

CCCGGTTTAC TCAGTCTCTC CTAATTCCAG CCTCTCGAAC AACTAATATC CTGTCTTTTC          3725

TATCCCTATG AAAAAAACTA ACAGAGATCG ATCTGTTTAC GCGTCACT ATG AAG TGC           3782
                                                    Met Lys Cys
                                                     1

CTT TTG TAC TTA GCC TTT TTA TTC ATT GGG GTG AAT TGC AAG TTC ACC            3830
Leu Leu Tyr Leu Ala Phe Leu Phe Ile Gly Val Asn Cys Lys Phe Thr
            5                   10                  15
```

```
ATA GTT TTT CCA CAC AAC CAA AAA GGA AAC TGG AAA AAT GTT CCT TCT    3878
Ile Val Phe Pro His Asn Gln Lys Gly Asn Trp Lys Asn Val Pro Ser
 20              25                  30                  35

AAT TAC CAT TAT TGC CCG TCA AGC TCA GAT TTA AAT TGG CAT AAT GAC    3926
Asn Tyr His Tyr Cys Pro Ser Ser Ser Asp Leu Asn Trp His Asn Asp
             40                  45                  50

TTA ATA GGC ACA GCC ATA CAA GTC AAA ATG CCC AAG AGT CAC AAG GCT    3974
Leu Ile Gly Thr Ala Ile Gln Val Lys Met Pro Lys Ser His Lys Ala
         55                  60                  65

ATT CAA GCA GAC GGT TGG ATG TGT CAT GCT TCC AAA TGG GTC ACT ACT    4022
Ile Gln Ala Asp Gly Trp Met Cys His Ala Ser Lys Trp Val Thr Thr
     70                  75                  80

TGT GAT TTC CGC TGG TAT GGA CCG AAG TAT ATA ACA CAG TCC ATC CGA    4070
Cys Asp Phe Arg Trp Tyr Gly Pro Lys Tyr Ile Thr Gln Ser Ile Arg
 85                  90                  95

TCC TTC ACT CCA TCT GTA GAA CAA TGC AAG GAA AGC ATT GAA CAA ACG    4118
Ser Phe Thr Pro Ser Val Glu Gln Cys Lys Glu Ser Ile Glu Gln Thr
100                 105                 110                 115

AAA CAA GGA ACT TGG CTG AAT CCA GGC TTC CCT CCT CAA AGT TGT GGA    4166
Lys Gln Gly Thr Trp Leu Asn Pro Gly Phe Pro Pro Gln Ser Cys Gly
             120                 125                 130

TAT GCA ACT GTG ACG GAT GCC GAA GCA GTG ATT GTC CAG GTG ACT CCT    4214
Tyr Ala Thr Val Thr Asp Ala Glu Ala Val Ile Val Gln Val Thr Pro
         135                 140                 145

CAC CAT GTG CTG GTT GAT GAA TAC ACA GGA GAA TGG GTT GAT TCA CAG    4262
His His Val Leu Val Asp Glu Tyr Thr Gly Glu Trp Val Asp Ser Gln
     150                 155                 160

TTC ATC AAC GGA AAA TGC AGC AAT TAC ATA TGC CCC ACT GTC CAT AAC    4310
Phe Ile Asn Gly Lys Cys Ser Asn Tyr Ile Cys Pro Thr Val His Asn
165                 170                 175

TCT ACA ACC TGG CAT TCT GAC TAT AAG GTC AAA GGG CTA TGT GAT TCT    4358
Ser Thr Thr Trp His Ser Asp Tyr Lys Val Lys Gly Leu Cys Asp Ser
180                 185                 190                 195

AAC CTC ATT TCC ATG GAC ATC ACC TTC TTC TCA GAG GAC GGA GAG CTA    4406
Asn Leu Ile Ser Met Asp Ile Thr Phe Phe Ser Glu Asp Gly Glu Leu
             200                 205                 210

TCA TCC CTG GGA AAG GAG GGC ACA GGG TTC AGA AGT AAC TAC TTT GCT    4454
Ser Ser Leu Gly Lys Glu Gly Thr Gly Phe Arg Ser Asn Tyr Phe Ala
         215                 220                 225

TAT GAA ACT GGA GGC AAG GCC TGC AAA ATG CAA TAC TGC AAG CAT TGG    4502
Tyr Glu Thr Gly Gly Lys Ala Cys Lys Met Gln Tyr Cys Lys His Trp
     230                 235                 240

GGA GTC AGA CTC CCA TCA GGT GTC TGG TTC GAG ATG GCT GAT AAG GAT    4550
Gly Val Arg Leu Pro Ser Gly Val Trp Phe Glu Met Ala Asp Lys Asp
245                 250                 255

CTC TTT GCT GCA GCC AGA TTC CCT GAA TGC CCA GAA GGG TCA AGT ATC    4598
Leu Phe Ala Ala Ala Arg Phe Pro Glu Cys Pro Glu Gly Ser Ser Ile
260                 265                 270                 275

TCT GCT CCA TCT CAG ACC TCA GTG GAT GTA AGT CTA ATT CAG GAC GTT    4646
Ser Ala Pro Ser Gln Thr Ser Val Asp Val Ser Leu Ile Gln Asp Val
             280                 285                 290

GAG AGG ATC TTG GAT TAT TCC CTC TGC CAA GAA ACC TGG AGC AAA ATC    4694
Glu Arg Ile Leu Asp Tyr Ser Leu Cys Gln Glu Thr Trp Ser Lys Ile
         295                 300                 305

AGA GCG GGT CTT CCA ATC TCT CCA GTG GAT CTC AGC TAT CTT GCT CCT    4742
Arg Ala Gly Leu Pro Ile Ser Pro Val Asp Leu Ser Tyr Leu Ala Pro
     310                 315                 320

AAA AAC CCA GGA ACC GGT CCT GCT TTC ACC ATA ATC AAT GGT ACC CTA    4790
Lys Asn Pro Gly Thr Gly Pro Ala Phe Thr Ile Ile Asn Gly Thr Leu
325                 330                 335
```

```
AAA TAC TTT GAG ACC AGA TAC ATC AGA GTC GAT ATT GCT GCT CCA ATC      4838
Lys Tyr Phe Glu Thr Arg Tyr Ile Arg Val Asp Ile Ala Ala Pro Ile
340                 345                 350                 355

CTC TCA AGA ATG GTC GGA ATG ATC AGT GGA ACT ACC ACA GAA AGG GAA      4886
Leu Ser Arg Met Val Gly Met Ile Ser Gly Thr Thr Thr Glu Arg Glu
                360                 365                 370

CTG TGG GAT GAC TGG GCA CCA TAT GAA GAC GTG GAA ATT GGA CCC AAT      4934
Leu Trp Asp Asp Trp Ala Pro Tyr Glu Asp Val Glu Ile Gly Pro Asn
            375                 380                 385

GGA GTT CTG AGG ACC AGT TCA GGA TAT AAG TTT CCT TTA TAC ATG ATT      4982
Gly Val Leu Arg Thr Ser Ser Gly Tyr Lys Phe Pro Leu Tyr Met Ile
        390                 395                 400

GGA CAT GGT ATG TTG GAC TCC GAT CTT CAT CTT AGC TCA AAG GCT CAG      5030
Gly His Gly Met Leu Asp Ser Asp Leu His Leu Ser Ser Lys Ala Gln
    405                 410                 415

GTG TTC GAA CAT CCT CAC ATT CAA GAC GCT GCT TCG CAA CTT CCT GAT      5078
Val Phe Glu His Pro His Ile Gln Asp Ala Ala Ser Gln Leu Pro Asp
420                 425                 430                 435

GAT GAG AGT TTA TTT TTT GGT GAT ACT GGG CTA TCC AAA AAT CCA ATC      5126
Asp Glu Ser Leu Phe Phe Gly Asp Thr Gly Leu Ser Lys Asn Pro Ile
                440                 445                 450

GAG CTT GTA GAA GGT TGG TTC AGT AGT TGG AAA AGC TCT ATT GCC TCT      5174
Glu Leu Val Glu Gly Trp Phe Ser Ser Trp Lys Ser Ser Ile Ala Ser
            455                 460                 465

TTT TTC TTT ATC ATA GGG TTA ATC ATT GGA CTA TTC TTG GTT CTC CGA      5222
Phe Phe Phe Ile Ile Gly Leu Ile Ile Gly Leu Phe Leu Val Leu Arg
        470                 475                 480

GTT GGT ATC CAT CTT TGC ATT AAA TTA AAG CAC ACC AAG AAA AGA CAG      5270
Val Gly Ile His Leu Cys Ile Lys Leu Lys His Thr Lys Lys Arg Gln
    485                 490                 495

ATT TAT ACA GAC ATA GAG ATG AAC CGA CTT GGA AAG TAA CTCAAATCCT       5319
Ile Tyr Thr Asp Ile Glu Met Asn Arg Leu Gly Lys
500                 505                 510

GCTAGCCAGA TTCTTCATGT TTGGACCAAA TCAACTTGTG ATACCATGCT CAAAGAGGCC    5379

TCAATTATAT TTGAGTTTTT AATTTTTATG AAAAAAACTA ACAGCAATC ATG GAA        5434
                                                      Met Glu
                                                       1

GTC CAC GAT TTT GAG ACC GAC GAG TTC AAT GAT TTC AAT GAA GAT GAC      5482
Val His Asp Phe Glu Thr Asp Glu Phe Asn Asp Phe Asn Glu Asp Asp
            5                   10                  15

TAT GCC ACA AGA GAA TTC CTG AAT CCC GAT GAG CGC ATG ACG TAC TTG      5530
Tyr Ala Thr Arg Glu Phe Leu Asn Pro Asp Glu Arg Met Thr Tyr Leu
        20                  25                  30

AAT CAT GCT GAT TAC AAT TTG AAT TCT CCT CTA ATT AGT GAT GAT ATT      5578
Asn His Ala Asp Tyr Asn Leu Asn Ser Pro Leu Ile Ser Asp Asp Ile
    35                  40                  45                  50

GAC AAT TTG ATC AGG AAA TTC AAT TCT CTT CCG ATT CCC TCG ATG TGG      5626
Asp Asn Leu Ile Arg Lys Phe Asn Ser Leu Pro Ile Pro Ser Met Trp
                55                  60                  65

GAT AGT AAG AAC TGG GAT GGA GTT CTT GAG ATG TTA ACA TCA TGT CAA      5674
Asp Ser Lys Asn Trp Asp Gly Val Leu Glu Met Leu Thr Ser Cys Gln
            70                  75                  80

GCC AAT CCC ATC TCA ACA TCT CAG ATG CAT AAA TGG ATG GGA AGT TGG      5722
Ala Asn Pro Ile Ser Thr Ser Gln Met His Lys Trp Met Gly Ser Trp
        85                  90                  95

TTA ATG TCT GAT AAT CAT GAT GCC AGT CAA GGG TAT AGT TTT TTA CAT      5770
Leu Met Ser Asp Asn His Asp Ala Ser Gln Gly Tyr Ser Phe Leu His
    100                 105                 110
```

```
GAA GTG GAC AAA GAG GCA GAA ATA ACA TTT GAC GTG GTG GAG ACC TTC    5818
Glu Val Asp Lys Glu Ala Glu Ile Thr Phe Asp Val Val Glu Thr Phe
115                 120                 125                 130

ATC CGC GGC TGG GGC AAC AAA CCA ATT GAA TAC ATC AAA AAG GAA AGA    5866
Ile Arg Gly Trp Gly Asn Lys Pro Ile Glu Tyr Ile Lys Lys Glu Arg
            135                 140                 145

TGG ACT GAC TCA TTC AAA ATT CTC GCT TAT TTG TGT CAA AAG TTT TTG    5914
Trp Thr Asp Ser Phe Lys Ile Leu Ala Tyr Leu Cys Gln Lys Phe Leu
                150                 155                 160

GAC TTA CAC AAG TTG ACA TTA ATC TTA AAT GCT GTC TCT GAG GTG GAA    5962
Asp Leu His Lys Leu Thr Leu Ile Leu Asn Ala Val Ser Glu Val Glu
            165                 170                 175

TTG CTC AAC TTG GCG AGG ACT TTC AAA GGC AAA GTC AGA AGA AGT TCT    6010
Leu Leu Asn Leu Ala Arg Thr Phe Lys Gly Lys Val Arg Arg Ser Ser
180                 185                 190

CAT GGA ACG AAC ATA TGC AGG ATT AGG GTT CCC AGC TTG GGT CCT ACT    6058
His Gly Thr Asn Ile Cys Arg Ile Arg Val Pro Ser Leu Gly Pro Thr
195                 200                 205                 210

TTT ATT TCA GAA GGA TGG GCT TAC TTC AAG AAA CTT GAT ATT CTA ATG    6106
Phe Ile Ser Glu Gly Trp Ala Tyr Phe Lys Lys Leu Asp Ile Leu Met
            215                 220                 225

GAC CGA AAC TTT CTG TTA ATG GTC AAA GAT GTG ATT ATA GGG AGG ATG    6154
Asp Arg Asn Phe Leu Leu Met Val Lys Asp Val Ile Ile Gly Arg Met
                230                 235                 240

CAA ACG GTG CTA TCC ATG GTA TGT AGA ATA GAC AAC CTG TTC TCA GAG    6202
Gln Thr Val Leu Ser Met Val Cys Arg Ile Asp Asn Leu Phe Ser Glu
            245                 250                 255

CAA GAC ATC TTC TCC CTT CTA AAT ATC TAC AGA ATT GGA GAT AAA ATT    6250
Gln Asp Ile Phe Ser Leu Leu Asn Ile Tyr Arg Ile Gly Asp Lys Ile
260                 265                 270

GTG GAG AGG CAG GGA AAT TTT TCT TAT GAC TTG ATT AAA ATG GTG GAA    6298
Val Glu Arg Gln Gly Asn Phe Ser Tyr Asp Leu Ile Lys Met Val Glu
275                 280                 285                 290

CCG ATA TGC AAC TTG AAG CTG ATG AAA TTA GCA AGA GAA TCA AGG CCT    6346
Pro Ile Cys Asn Leu Lys Leu Met Lys Leu Ala Arg Glu Ser Arg Pro
            295                 300                 305

TTA GTC CCA CAA TTC CCT CAT TTT GAA AAT CAT ATC AAG ACT TCT GTT    6394
Leu Val Pro Gln Phe Pro His Phe Glu Asn His Ile Lys Thr Ser Val
                310                 315                 320

GAT GAA GGG GCA AAA ATT GAC CGA GGT ATA AGA TTC CTC CAT GAT CAG    6442
Asp Glu Gly Ala Lys Ile Asp Arg Gly Ile Arg Phe Leu His Asp Gln
            325                 330                 335

ATA ATG AGT GTG AAA ACA GTG GAT CTC ACA CTG GTG ATT TAT GGA TCG    6490
Ile Met Ser Val Lys Thr Val Asp Leu Thr Leu Val Ile Tyr Gly Ser
340                 345                 350

TTC AGA CAT TGG GGT CAT CCT TTT ATA GAT TAT TAC ACT GGA CTA GAA    6538
Phe Arg His Trp Gly His Pro Phe Ile Asp Tyr Tyr Thr Gly Leu Glu
355                 360                 365                 370

AAA TTA CAT TCC CAA GTA ACC ATG AAG AAA GAT ATT GAT GTG TCA TAT    6586
Lys Leu His Ser Gln Val Thr Met Lys Lys Asp Ile Asp Val Ser Tyr
            375                 380                 385

GCA AAA GCA CTT GCA AGT GAT TTA GCT CGG ATT GTT CTA TTT CAA CAG    6634
Ala Lys Ala Leu Ala Ser Asp Leu Ala Arg Ile Val Leu Phe Gln Gln
                390                 395                 400

TTC AAT GAT CAT AAA AAG TGG TTC GTG AAT GGA GAC TTG CTC CCT CAT    6682
Phe Asn Asp His Lys Lys Trp Phe Val Asn Gly Asp Leu Leu Pro His
            405                 410                 415

GAT CAT CCC TTT AAA AGT CAT GTT AAA GAA AAT ACA TGG CCC ACA GCT    6730
Asp His Pro Phe Lys Ser His Val Lys Glu Asn Thr Trp Pro Thr Ala
420                 425                 430
```

```
GCT CAA GTT CAA GAT TTT GGA GAT AAA TGG CAT GAA CTT CCG CTG ATT        6778
Ala Gln Val Gln Asp Phe Gly Asp Lys Trp His Glu Leu Pro Leu Ile
435                 440                 445                 450

AAA TGT TTT GAA ATA CCC GAC TTA CTA GAC CCA TCG ATA ATA TAC TCT        6826
Lys Cys Phe Glu Ile Pro Asp Leu Leu Asp Pro Ser Ile Ile Tyr Ser
                455                 460                 465

GAC AAA AGT CAT TCA ATG AAT AGG TCA GAG GTG TTG AAA CAT GTC CGA        6874
Asp Lys Ser His Ser Met Asn Arg Ser Glu Val Leu Lys His Val Arg
            470                 475                 480

ATG AAT CCG AAC ACT CCT ATC CCT AGT AAA AAG GTG TTG CAG ACT ATG        6922
Met Asn Pro Asn Thr Pro Ile Pro Ser Lys Lys Val Leu Gln Thr Met
        485                 490                 495

TTG GAC ACA AAG GCT ACC AAT TGG AAA GAA TTT CTT AAA GAG ATT GAT        6970
Leu Asp Thr Lys Ala Thr Asn Trp Lys Glu Phe Leu Lys Glu Ile Asp
    500                 505                 510

GAG AAG GGC TTA GAT GAT GAT GAT CTA ATT ATT GGT CTT AAA GGA AAG        7018
Glu Lys Gly Leu Asp Asp Asp Asp Leu Ile Ile Gly Leu Lys Gly Lys
515                 520                 525                 530

GAG AGG GAA CTG AAG TTG GCA GGT AGA TTT TTC TCC CTA ATG TCT TGG        7066
Glu Arg Glu Leu Lys Leu Ala Gly Arg Phe Phe Ser Leu Met Ser Trp
                535                 540                 545

AAA TTG CGA GAA TAC TTT GTA ATT ACC GAA TAT TTG ATA AAG ACT CAT        7114
Lys Leu Arg Glu Tyr Phe Val Ile Thr Glu Tyr Leu Ile Lys Thr His
                550                 555                 560

TTC GTC CCT ATG TTT AAA GGC CTG ACA ATG GCG GAC GAT CTA ACT GCA        7162
Phe Val Pro Met Phe Lys Gly Leu Thr Met Ala Asp Asp Leu Thr Ala
            565                 570                 575

GTC ATT AAA AAG ATG TTA GAT TCC TCA TCC GGC CAA GGA TTG AAG TCA        7210
Val Ile Lys Lys Met Leu Asp Ser Ser Ser Gly Gln Gly Leu Lys Ser
        580                 585                 590

TAT GAG GCA ATT TGC ATA GCC AAT CAC ATT GAT TAC GAA AAA TGG AAT        7258
Tyr Glu Ala Ile Cys Ile Ala Asn His Ile Asp Tyr Glu Lys Trp Asn
595                 600                 605                 610

AAC CAC CAA AGG AAG TTA TCA AAC GGC CCA GTG TTC CGA GTT ATG GGC        7306
Asn His Gln Arg Lys Leu Ser Asn Gly Pro Val Phe Arg Val Met Gly
                615                 620                 625

CAG TTC TTA GGT TAT CCA TCC TTA ATC GAG AGA ACT CAT GAA TTT TTT        7354
Gln Phe Leu Gly Tyr Pro Ser Leu Ile Glu Arg Thr His Glu Phe Phe
                630                 635                 640

GAG AAA AGT CTT ATA TAC TAC AAT GGA AGA CCA GAC TTG ATG CGT GTT        7402
Glu Lys Ser Leu Ile Tyr Tyr Asn Gly Arg Pro Asp Leu Met Arg Val
            645                 650                 655

CAC AAC AAC ACA CTG ATC AAT TCA ACC TCC CAA CGA GTT TGT TGG CAA        7450
His Asn Asn Thr Leu Ile Asn Ser Thr Ser Gln Arg Val Cys Trp Gln
        660                 665                 670

GGA CAA GAG GGT GGA CTG GAA GGT CTA CGG CAA AAA GGA TGG ACT ATC        7498
Gly Gln Glu Gly Gly Leu Glu Gly Leu Arg Gln Lys Gly Trp Thr Ile
675                 680                 685                 690

CTC AAT CTA CTG GTT ATT CAA AGA GAG GCT AAA ATC AGA AAC ACT GCT        7546
Leu Asn Leu Leu Val Ile Gln Arg Glu Ala Lys Ile Arg Asn Thr Ala
                695                 700                 705

GTC AAA GTC TTG GCA CAA GGT GAT AAT CAA GTT ATT TGC ACA CAG TAT        7594
Val Lys Val Leu Ala Gln Gly Asp Asn Gln Val Ile Cys Thr Gln Tyr
            710                 715                 720

AAA ACG AAG AAA TCG AGA AAC GTT GTA GAA TTA CAG GGT GCT CTC AAT        7642
Lys Thr Lys Lys Ser Arg Asn Val Val Glu Leu Gln Gly Ala Leu Asn
        725                 730                 735

CAA ATG GTT TCT AAT AAT GAG AAA ATT ATG ACT GCA ATC AAA ATA GGG        7690
Gln Met Val Ser Asn Asn Glu Lys Ile Met Thr Ala Ile Lys Ile Gly
```

```
                740                      745                      750
ACA GGG AAG TTA GGA CTT TTG ATA AAT GAC GAT GAG ACT ATG CAA TCT       7738
Thr Gly Lys Leu Gly Leu Leu Ile Asn Asp Asp Glu Thr Met Gln Ser
755                 760                 765                 770

GCA GAT TAC TTG AAT TAT GGA AAA ATA CCG ATT TTC CGT GGA GTG ATT       7786
Ala Asp Tyr Leu Asn Tyr Gly Lys Ile Pro Ile Phe Arg Gly Val Ile
                    775                 780                 785

AGA GGG TTA GAG ACC AAG AGA TGG TCA CGA GTG ACT TGT GTC ACC AAT       7834
Arg Gly Leu Glu Thr Lys Arg Trp Ser Arg Val Thr Cys Val Thr Asn
                790                 795                 800

GAC CAA ATA CCC ACT TGT GCT AAT ATA ATG AGC TCA GTT TCC ACA AAT       7882
Asp Gln Ile Pro Thr Cys Ala Asn Ile Met Ser Ser Val Ser Thr Asn
            805                 810                 815

GCT CTC ACC GTA GCT CAT TTT GCT GAG AAC CCA ATC AAT GCC ATG ATA       7930
Ala Leu Thr Val Ala His Phe Ala Glu Asn Pro Ile Asn Ala Met Ile
        820                 825                 830

CAG TAC AAT TAT TTT GGG ACA TTT GCT AGA CTC TTG TTG ATG ATG CAT       7978
Gln Tyr Asn Tyr Phe Gly Thr Phe Ala Arg Leu Leu Leu Met Met His
835                 840                 845                 850

GAT CCT GCT CTT CGT CAA TCA TTG TAT GAA GTT CAA GAT AAG ATA CCG       8026
Asp Pro Ala Leu Arg Gln Ser Leu Tyr Glu Val Gln Asp Lys Ile Pro
                    855                 860                 865

GGC TTG CAC AGT TCT ACT TTC AAA TAC GCC ATG TTG TAT TTG GAC CCT       8074
Gly Leu His Ser Ser Thr Phe Lys Tyr Ala Met Leu Tyr Leu Asp Pro
                870                 875                 880

TCC ATT GGA GGA GTG TCG GGC ATG TCT TTG TCC AGG TTT TTG ATT AGA       8122
Ser Ile Gly Gly Val Ser Gly Met Ser Leu Ser Arg Phe Leu Ile Arg
            885                 890                 895

GCC TTC CCA GAT CCC GTA ACA GAA AGT CTC TCA TTC TGG AGA TTC ATC       8170
Ala Phe Pro Asp Pro Val Thr Glu Ser Leu Ser Phe Trp Arg Phe Ile
        900                 905                 910

CAT GTA CAT GCT CGA AGT GAG CAT CTG AAG GAG ATG AGT GCA GTA TTT       8218
His Val His Ala Arg Ser Glu His Leu Lys Glu Met Ser Ala Val Phe
915                 920                 925                 930

GGA AAC CCC GAG ATA GCC AAG TTT CGA ATA ACT CAC ATA GAC AAG CTA       8266
Gly Asn Pro Glu Ile Ala Lys Phe Arg Ile Thr His Ile Asp Lys Leu
                    935                 940                 945

GTA GAA GAT CCA ACC TCT CTG AAC ATC GCT ATG GGA ATG AGT CCA GCG       8314
Val Glu Asp Pro Thr Ser Leu Asn Ile Ala Met Gly Met Ser Pro Ala
                950                 955                 960

AAC TTG TTA AAG ACT GAG GTT AAA AAA TGC TTA ATC GAA TCA AGA CAA       8362
Asn Leu Leu Lys Thr Glu Val Lys Lys Cys Leu Ile Glu Ser Arg Gln
            965                 970                 975

ACC ATC AGG AAC CAG GTG ATT AAG GAT GCA ACC ATA TAT TTG TAT CAT       8410
Thr Ile Arg Asn Gln Val Ile Lys Asp Ala Thr Ile Tyr Leu Tyr His
        980                 985                 990

GAA GAG GAT CGG CTC AGA AGT TTC TTA TGG TCA ATA AAT CCT CTG TTC       8458
Glu Glu Asp Arg Leu Arg Ser Phe Leu Trp Ser Ile Asn Pro Leu Phe
995                 1000                1005                1010

CCT AGA TTT TTA AGT GAA TTC AAA TCA GGC ACT TTT TTG GGA GTC GCA       8506
Pro Arg Phe Leu Ser Glu Phe Lys Ser Gly Thr Phe Leu Gly Val Ala
                    1015                1020                1025

GAC GGG CTC ATC AGT CTA TTT CAA AAT TCT CGT ACT ATT CGG AAC TCC       8554
Asp Gly Leu Ile Ser Leu Phe Gln Asn Ser Arg Thr Ile Arg Asn Ser
                1030                1035                1040

TTT AAG AAA AAG TAT CAT AGG GAA TTG GAT GAT TTG ATT GTG AGG AGT       8602
Phe Lys Lys Lys Tyr His Arg Glu Leu Asp Asp Leu Ile Val Arg Ser
            1045                1050                1055

GAG GTA TCC TCT TTG ACA CAT TTA GGG AAA CTT CAT TTG AGA AGG GGA       8650
```

```
Glu Val Ser Ser Leu Thr His Leu Gly Lys Leu His Leu Arg Arg Gly
    1060                1065                1070

TCA TGT AAA ATG TGG ACA TGT TCA GCT ACT CAT GCT GAC ACA TTA AGA      8698
Ser Cys Lys Met Trp Thr Cys Ser Ala Thr His Ala Asp Thr Leu Arg
1075                1080                1085                1090

TAC AAA TCC TGG GGC CGT ACA GTT ATT GGG ACA ACT GTA CCC CAT CCA      8746
Tyr Lys Ser Trp Gly Arg Thr Val Ile Gly Thr Thr Val Pro His Pro
                1095                1100                1105

TTA GAA ATG TTG GGT CCA CAA CAT CGA AAA GAG ACT CCT TGT GCA CCA      8794
Leu Glu Met Leu Gly Pro Gln His Arg Lys Glu Thr Pro Cys Ala Pro
        1110                1115                1120

TGT AAC ACA TCA GGG TTC AAT TAT GTT TCT GTG CAT TGT CCA GAC GGG      8842
Cys Asn Thr Ser Gly Phe Asn Tyr Val Ser Val His Cys Pro Asp Gly
            1125                1130                1135

ATC CAT GAC GTC TTT AGT TCA CGG GGA CCA TTG CCT GCT TAT CTA GGG      8890
Ile His Asp Val Phe Ser Ser Arg Gly Pro Leu Pro Ala Tyr Leu Gly
                1140                1145                1150

TCT AAA ACA TCT GAA TCT ACA TCT ATT TTG CAG CCT TGG GAA AGG GAA      8938
Ser Lys Thr Ser Glu Ser Thr Ser Ile Leu Gln Pro Trp Glu Arg Glu
1155                1160                1165                1170

AGC AAA GTC CCA CTG ATT AAA AGA GCT ACA CGT CTT AGA GAT GCT ATC      8986
Ser Lys Val Pro Leu Ile Lys Arg Ala Thr Arg Leu Arg Asp Ala Ile
                1175                1180                1185

TCT TGG TTT GTT GAA CCC GAC TCT AAA CTA GCA ATG ACT ATA CTT TCT      9034
Ser Trp Phe Val Glu Pro Asp Ser Lys Leu Ala Met Thr Ile Leu Ser
        1190                1195                1200

AAC ATC CAC TCT TTA ACA GGC GAA GAA TGG ACC AAA AGG CAG CAT GGG      9082
Asn Ile His Ser Leu Thr Gly Glu Glu Trp Thr Lys Arg Gln His Gly
            1205                1210                1215

TTC AAA AGA ACA GGG TCT GCC CTT CAT AGG TTT TCG ACA TCT CGG ATG      9130
Phe Lys Arg Thr Gly Ser Ala Leu His Arg Phe Ser Thr Ser Arg Met
    1220                1225                1230

AGC CAT GGT GGG TTC GCA TCT CAG AGC ACT GCA GCA TTG ACC AGG TTG      9178
Ser His Gly Gly Phe Ala Ser Gln Ser Thr Ala Ala Leu Thr Arg Leu
1235                1240                1245                1250

ATG GCA ACT ACA GAC ACC ATG AGG GAT CTG GGA GAT CAG AAT TTC GAC      9226
Met Ala Thr Thr Asp Thr Met Arg Asp Leu Gly Asp Gln Asn Phe Asp
                1255                1260                1265

TTT TTA TTC CAA GCA ACG TTG CTC TAT GCT CAA ATT ACC ACC ACT GTT      9274
Phe Leu Phe Gln Ala Thr Leu Leu Tyr Ala Gln Ile Thr Thr Thr Val
        1270                1275                1280

GCA AGA GAC GGA TGG ATC ACC AGT TGT ACA GAT CAT TAT CAT ATT GCC      9322
Ala Arg Asp Gly Trp Ile Thr Ser Cys Thr Asp His Tyr His Ile Ala
            1285                1290                1295

TGT AAG TCC TGT TTG AGA CCC ATA GAA GAG ATC ACC CTG GAC TCA AGT      9370
Cys Lys Ser Cys Leu Arg Pro Ile Glu Glu Ile Thr Leu Asp Ser Ser
1300                1305                1310

ATG GAC TAC ACG CCC CCA GAT GTA TCC CAT GTG CTG AAG ACA TGG AGG      9418
Met Asp Tyr Thr Pro Pro Asp Val Ser His Val Leu Lys Thr Trp Arg
                1315                1320                1325                1330

AAT GGG GAA GGT TCG TGG GGA CAA GAG ATA AAA CAG ATC TAT CCT TTA      9466
Asn Gly Glu Gly Ser Trp Gly Gln Glu Ile Lys Gln Ile Tyr Pro Leu
                1335                1340                1345

GAA GGG AAT TGG AAG AAT TTA GCA CCT GCT GAG CAA TCC TAT CAA GTC      9514
Glu Gly Asn Trp Lys Asn Leu Ala Pro Ala Glu Gln Ser Tyr Gln Val
        1350                1355                1360

GGC AGA TGT ATA GGT TTT CTA TAT GGA GAC TTG GCG TAT AGA AAA TCT      9562
Gly Arg Cys Ile Gly Phe Leu Tyr Gly Asp Leu Ala Tyr Arg Lys Ser
            1365                1370                1375
```

-continued

```
ACT CAT GCC GAG GAC AGT TCT CTA TTT CCT CTA TCT ATA CAA GGT CGT      9610
Thr His Ala Glu Asp Ser Ser Leu Phe Pro Leu Ser Ile Gln Gly Arg
    1380                1385                1390

ATT AGA GGT CGA GGT TTC TTA AAA GGG TTG CTA GAC GGA TTA ATG AGA      9658
Ile Arg Gly Arg Gly Phe Leu Lys Gly Leu Leu Asp Gly Leu Met Arg
1395                1400                1405                1410

GCA AGT TGC TGC CAA GTA ATA CAC CGG AGA AGT CTG GCT CAT TTG AAG      9706
Ala Ser Cys Cys Gln Val Ile His Arg Arg Ser Leu Ala His Leu Lys
                1415                1420                1425

AGG CCG GCC AAC GCA GTG TAC GGA GGT TTG ATT TAC TTG ATT GAT AAA      9754
Arg Pro Ala Asn Ala Val Tyr Gly Gly Leu Ile Tyr Leu Ile Asp Lys
            1430                1435                1440

TTG AGT GTA TCA CCT CCA TTC CTT TCT CTT ACT AGA TCA GGA CCT ATT      9802
Leu Ser Val Ser Pro Pro Phe Leu Ser Leu Thr Arg Ser Gly Pro Ile
            1445                1450                1455

AGA GAC GAA TTA GAA ACG ATT CCC CAC AAG ATC CCA ACC TCC TAT CCG      9850
Arg Asp Glu Leu Glu Thr Ile Pro His Lys Ile Pro Thr Ser Tyr Pro
        1460                1465                1470

ACA AGC AAC CGT GAT ATG GGG GTG ATT GTC AGA AAT TAC TTC AAA TAC      9898
Thr Ser Asn Arg Asp Met Gly Val Ile Val Arg Asn Tyr Phe Lys Tyr
1475                1480                1485                1490

CAA TGC CGT CTA ATT GAA AAG GGA AAA TAC AGA TCA CAT TAT TCA CAA      9946
Gln Cys Arg Leu Ile Glu Lys Gly Lys Tyr Arg Ser His Tyr Ser Gln
                1495                1500                1505

TTA TGG TTA TTC TCA GAT GTC TTA TCC ATA GAC TTC ATT GGA CCA TTC      9994
Leu Trp Leu Phe Ser Asp Val Leu Ser Ile Asp Phe Ile Gly Pro Phe
            1510                1515                1520

TCT ATT TCC ACC ACC CTC TTG CAA ATC CTA TAC AAG CCA TTT TTA TCT     10042
Ser Ile Ser Thr Thr Leu Leu Gln Ile Leu Tyr Lys Pro Phe Leu Ser
            1525                1530                1535

GGG AAA GAT AAG AAT GAG TTG AGA GAG CTG GCA AAT CTT TCT TCA TTG     10090
Gly Lys Asp Lys Asn Glu Leu Arg Glu Leu Ala Asn Leu Ser Ser Leu
        1540                1545                1550

CTA AGA TCA GGA GAG GGG TGG GAA GAC ATA CAT GTG AAA TTC TTC ACC     10138
Leu Arg Ser Gly Glu Gly Trp Glu Asp Ile His Val Lys Phe Phe Thr
1555                1560                1565                1570

AAG GAC ATA TTA TTG TGT CCA GAG GAA ATC AGA CAT GCT TGC AAG TTC     10186
Lys Asp Ile Leu Leu Cys Pro Glu Glu Ile Arg His Ala Cys Lys Phe
                1575                1580                1585

GGG ATT GCT AAG GAT AAT AAT AAA GAC ATG AGC TAT CCC CCT TGG GGA     10234
Gly Ile Ala Lys Asp Asn Asn Lys Asp Met Ser Tyr Pro Pro Trp Gly
            1590                1595                1600

AGG GAA TCC AGA GGG ACA ATT ACA ACA ATC CCT GTT TAT TAT ACG ACC     10282
Arg Glu Ser Arg Gly Thr Ile Thr Thr Ile Pro Val Tyr Tyr Thr Thr
        1605                1610                1615

ACC CCT TAC CCA AAG ATG CTA GAG ATG CCT CCA AGA ATC CAA AAT CCC     10330
Thr Pro Tyr Pro Lys Met Leu Glu Met Pro Pro Arg Ile Gln Asn Pro
1620                1625                1630

CTG CTG TCC GGA ATC AGG TTG GGC CAA TTA CCA ACT GGC GCT CAT TAT     10378
Leu Leu Ser Gly Ile Arg Leu Gly Gln Leu Pro Thr Gly Ala His Tyr
1635                1640                1645                1650

AAA ATT CGG AGT ATA TTA CAT GGA ATG GGA ATC CAT TAC AGG GAC TTC     10426
Lys Ile Arg Ser Ile Leu His Gly Met Gly Ile His Tyr Arg Asp Phe
                1655                1660                1665

TTG AGT TGT GGA GAC GGC TCC GGA GGG ATG ACT GCT GCA TTA CTA CGA     10474
Leu Ser Cys Gly Asp Gly Ser Gly Gly Met Thr Ala Ala Leu Leu Arg
            1670                1675                1680

GAA AAT GTG CAT AGC AGA GGA ATA TTC AAT AGT CTG TTA GAA TTA TCA     10522
Glu Asn Val His Ser Arg Gly Ile Phe Asn Ser Leu Leu Glu Leu Ser
        1685                1690                1695
```

```
GGG TCA GTC ATG CGA GGC GCC TCT CCT GAG CCC CCC AGT GCC CTA GAA        10570
Gly Ser Val Met Arg Gly Ala Ser Pro Glu Pro Pro Ser Ala Leu Glu
    1700                1705                1710

ACT TTA GGA GGA GAT AAA TCG AGA TGT GTA AAT GGT GAA ACA TGT TGG        10618
Thr Leu Gly Gly Asp Lys Ser Arg Cys Val Asn Gly Glu Thr Cys Trp
1715                1720                1725                1730

GAA TAT CCA TCT GAC TTA TGT GAC CCA AGG ACT TGG GAC TAT TTC CTC        10666
Glu Tyr Pro Ser Asp Leu Cys Asp Pro Arg Thr Trp Asp Tyr Phe Leu
                1735                1740                1745

CGA CTC AAA GCA GGC TTG GGG CTT CAA ATT GAT TTA ATT GTA ATG GAT        10714
Arg Leu Lys Ala Gly Leu Gly Leu Gln Ile Asp Leu Ile Val Met Asp
            1750                1755                1760

ATG GAA GTT CGG GAT TCT TCT ACT AGC CTG AAA ATT GAG ACG AAT GTT        10762
Met Glu Val Arg Asp Ser Ser Thr Ser Leu Lys Ile Glu Thr Asn Val
        1765                1770                1775

AGA AAT TAT GTG CAC CGG ATT TTG GAT GAG CAA GGA GTT TTA ATC TAC        10810
Arg Asn Tyr Val His Arg Ile Leu Asp Glu Gln Gly Val Leu Ile Tyr
    1780                1785                1790

AAG ACT TAT GGA ACA TAT ATT TGT GAG AGC GAA AAG AAT GCA GTA ACA        10858
Lys Thr Tyr Gly Thr Tyr Ile Cys Glu Ser Glu Lys Asn Ala Val Thr
1795                1800                1805                1810

ATC CTT GGT CCC ATG TTC AAG ACG GTC GAC TTA GTT CAA ACA GAA TTT        10906
Ile Leu Gly Pro Met Phe Lys Thr Val Asp Leu Val Gln Thr Glu Phe
                1815                1820                1825

AGT AGT TCT CAA ACG TCT GAA GTA TAT ATG GTA TGT AAA GGT TTG AAG        10954
Ser Ser Ser Gln Thr Ser Glu Val Tyr Met Val Cys Lys Gly Leu Lys
            1830                1835                1840

AAA TTA ATC GAT GAA CCC AAT CCC GAT TGG TCT TCC ATC AAT GAA TCC        11002
Lys Leu Ile Asp Glu Pro Asn Pro Asp Trp Ser Ser Ile Asn Glu Ser
        1845                1850                1855

TGG AAA AAC CTG TAC GCA TTC CAG TCA TCA GAA CAG GAA TTT GCC AGA        11050
Trp Lys Asn Leu Tyr Ala Phe Gln Ser Ser Glu Gln Glu Phe Ala Arg
    1860                1865                1870

GCA AAG AAG GTT AGT ACA TAC TTT ACC TTG ACA GGT ATT CCC TCC CAA        11098
Ala Lys Lys Val Ser Thr Tyr Phe Thr Leu Thr Gly Ile Pro Ser Gln
1875                1880                1885                1890

TTC ATT CCT GAT CCT TTT GTA AAC ATT GAG ACT ATG CTA CAA ATA TTC        11146
Phe Ile Pro Asp Pro Phe Val Asn Ile Glu Thr Met Leu Gln Ile Phe
                1895                1900                1905

GGA GTA CCC ACG GGT GTG TCT CAT GCG GCT GCC TTA AAA TCA TCT GAT        11194
Gly Val Pro Thr Gly Val Ser His Ala Ala Ala Leu Lys Ser Ser Asp
            1910                1915                1920

AGA CCT GCA GAT TTA TTG ACC ATT AGC CTT TTT TAT ATG GCG ATT ATA        11242
Arg Pro Ala Asp Leu Leu Thr Ile Ser Leu Phe Tyr Met Ala Ile Ile
        1925                1930                1935

TCG TAT TAT AAC ATC AAT CAT ATC AGA GTA GGA CCG ATA CCT CCG AAC        11290
Ser Tyr Tyr Asn Ile Asn His Ile Arg Val Gly Pro Ile Pro Pro Asn
    1940                1945                1950

CCC CCA TCA GAT GGA ATT GCA CAA AAT GTG GGG ATC GCT ATA ACT GGT        11338
Pro Pro Ser Asp Gly Ile Ala Gln Asn Val Gly Ile Ala Ile Thr Gly
1955                1960                1965                1970

ATA AGC TTT TGG CTG AGT TTG ATG GAG AAA GAC ATT CCA CTA TAT CAA        11386
Ile Ser Phe Trp Leu Ser Leu Met Glu Lys Asp Ile Pro Leu Tyr Gln
                1975                1980                1985

CAG TGT TTA GCA GTT ATC CAG CAA TCA TTC CCG ATT AGG TGG GAG GCT        11434
Gln Cys Leu Ala Val Ile Gln Gln Ser Phe Pro Ile Arg Trp Glu Ala
            1990                1995                2000

GTT TCA GTA AAA GGA GGA TAC AAG CAG AAG TGG AGT ACT AGA GGT GAT        11482
Val Ser Val Lys Gly Gly Tyr Lys Gln Lys Trp Ser Thr Arg Gly Asp
```

|  |  |  |  |  |  |  |  |  |  |  |
|---|---|---|---|---|---|---|---|---|---|---|
|  |  | 2005 |  |  |  | 2010 |  |  | 2015 |  |
| GGG | CTC | CCA | AAA | GAT | ACC | CGA | ACT | TCA | GAC | TCC | TTG | GCC | CCA | ATC | GGG | 11530 |
| Gly | Leu | Pro | Lys | Asp | Thr | Arg | Thr | Ser | Asp | Ser | Leu | Ala | Pro | Ile | Gly |  |
|  |  | 2020 |  |  |  | 2025 |  |  | 2030 |  |
| AAC | TGG | ATC | AGA | TCT | CTG | GAA | TTG | GTC | CGA | AAC | CAA | GTT | CGT | CTA | AAT | 11578 |
| Asn | Trp | Ile | Arg | Ser | Leu | Glu | Leu | Val | Arg | Asn | Gln | Val | Arg | Leu | Asn |  |
| 2035 |  |  |  | 2040 |  |  | 2045 |  |  |  | 2050 |  |
| CCA | TTC | AAT | GAG | ATC | TTG | TTC | AAT | CAG | CTA | TGT | CGT | ACA | GTG | GAT | AAT | 11626 |
| Pro | Phe | Asn | Glu | Ile | Leu | Phe | Asn | Gln | Leu | Cys | Arg | Thr | Val | Asp | Asn |  |
|  |  |  | 2055 |  |  |  | 2060 |  |  |  | 2065 |  |
| CAT | TTG | AAA | TGG | TCA | AAT | TTG | CGA | AGA | AAC | ACA | GGA | ATG | ATT | GAA | TGG | 11674 |
| His | Leu | Lys | Trp | Ser | Asn | Leu | Arg | Arg | Asn | Thr | Gly | Met | Ile | Glu | Trp |  |
|  |  | 2070 |  |  |  | 2075 |  |  |  | 2080 |  |
| ATC | AAT | AGA | CGA | ATT | TCA | AAA | GAA | GAC | CGG | TCT | ATA | CTG | ATG | TTG | AAG | 11722 |
| Ile | Asn | Arg | Arg | Ile | Ser | Lys | Glu | Asp | Arg | Ser | Ile | Leu | Met | Leu | Lys |  |
|  |  | 2085 |  |  |  | 2090 |  |  |  | 2095 |  |
| AGT | GAC | CTA | CAC | GAG | GAA | AAC | TCT | TGG | AGA | GAT | TAA | AAAATCATGA |  |  |  | 11768 |
| Ser | Asp | Leu | His | Glu | Glu | Asn | Ser | Trp | Arg | Asp |  |  |
|  |  | 2100 |  |  |  | 2105 |  |  |

```
GGAGACTCCA AACTTTAAGT ATGAAAAAAA CTTTGATCCT TAAGACCCTC TTGTGGTTTT    11828
TATTTTTTAT CTGGTTTTGT GGTCTTCGTG GGTCGGCATG GCATCTCCAC CTCCTCGCGG    11888
TCCGACCTGG GCATCCGAAG GAGGACGTCG TCCACTCGGA TGGCTAAGGG AGGGGCCCCC    11948
GCGGGGCTGC TAACAAAGCC CGAAAGGAAG CTGAGTTGGC TGCTGCCACC GCTGAGCAAT    12008
AACTAGCATA ACCCCTTGGG GCCTCTAAAC GGGTCTTGAG GGGTTTTTTG CTGAAAGGAG    12068
GAACTATATC CGGATCGAGA CCTCGATACT AGTGCGGTGG AGCTCCAGCT TTTGTTCCCT    12128
TTAGTGAGGG TTAATTTCGA GCTTGGCGTA ATCATGGTCA TAGCTGTTTC CTGTGTGAAA    12188
TTGTTATCCG CTCACAATTC CACACAACAT ACGAGCCGGA AGCATAAAGT GTAAAGCCTG    12248
GGGTGCCTAA TGAGTGAGCT AACTCACATT AATTGCGTTG CGCTCACTGC CCGCTTTCCA    12308
GTCGGGAAAC CTGTCGTGCC AGCTGCATTA ATGAATCGGC CAACGCGCGG GGAGAGGCGG    12368
TTTGCGTATT GGGCGCTCTT CCGCTTCCTC GCTCACTGAC TCGCTGCGCT CGGTCGTTCG    12428
GCTGCGGCGA GCGGTATCAG CTCACTCAAA GGCGGTAATA CGGTTATCCA CAGAATCAGG    12488
GGATAACGCA GGAAAGAACA TGTGAGCAAA AGGCCAGCAA AAGGCCAGGA ACCGTAAAAA    12548
GGCCGCGTTG CTGGCGTTTT TCCATAGGCT CCGCCCCCCT GACGAGCATC ACAAAAATCG    12608
ACGCTCAAGT CAGAGGTGGC GAAACCCGAC AGGACTATAA AGATACCAGG CGTTTCCCCC    12668
TGGAAGCTCC CTCGTGCGCT CTCCTGTTCC GACCCTGCCG CTTACCGGAT ACCTGTCCGC    12728
CTTTCTCCCT TCGGGAAGCG TGGCGCTTTC TCATAGCTCA CGCTGTAGGT ATCTCAGTTC    12788
GGTGTAGGTC GTTCGCTCCA AGCTGGGCTG TGTGCACGAA CCCCCCGTTC AGCCCGACCG    12848
CTGCGCCTTA TCCGGTAACT ATCGTCTTGA GTCCAACCCG GTAAGACACG ACTTATCGCC    12908
ACTGGCAGCA GCCACTGGTA ACAGGATTAG CAGAGCGAGG TATGTAGGCG GTGCTACAGA    12968
GTTCTTGAAG TGGTGGCCTA ACTACGGCTA CACTAGAAGG ACAGTATTTG GTATCTGCGC    13028
TCTGCTGAAG CCAGTTACCT TCGGAAAAAG AGTTGGTAGC TCTTGATCCG GCAAACAAAC    13088
CACCGCTGGT AGCGGTGGTT TTTTGTTTG CAAGCAGCAG ATTACGCGCA GAAAAAAGG    13148
ATCTCAAGAA GATCCTTTGA TCTTTTCTAC GGGGTCTGAC GCTCAGTGGA ACGAAAACTC    13208
ACGTTAAGGG ATTTTGGTCA TGAGATTATC AAAAAGGATC TTCACCTAGA TCCTTTTAAA    13268
TTAAAAATGA AGTTTTAAAT CAATCTAAAG TATATATGAG TAAACTTGGT CTGACAGTTA    13328
CCAATGCTTA ATCAGTGAGG CACCTATCTC AGCGATCTGT CTATTTCGTT CATCCATAGT    13388
```

```
TGCCTGACTC CCCGTCGTGT AGATAACTAC GATACGGGAG GGCTTACCAT CTGGCCCCAG    13448

TGCTGCAATG ATACCGCGAG ACCCACGCTC ACCGGCTCCA GATTTATCAG CAATAAACCA    13508

GCCAGCCGGA AGGGCCGAGC GCAGAAGTGG TCCTGCAACT TTATCCGCCT CCATCCAGTC    13568

TATTAATTGT TGCCGGGAAG CTAGAGTAAG TAGTTCGCCA GTTAATAGTT TGCGCAACGT    13628

TGTTGCCATT GCTACAGGCA TCGTGGTGTC ACGCTCGTCG TTTGGTATGG CTTCATTCAG    13688

CTCCGGTTCC CAACGATCAA GGCGAGTTAC ATGATCCCCC ATGTTGTGCA AAAAAGCGGT    13748

TAGCTCCTTC GGTCCTCCGA TCGTTGTCAG AAGTAAGTTG GCCGCAGTGT TATCACTCAT    13808

GGTTATGGCA GCACTGCATA ATTCTCTTAC TGTCATGCCA TCCGTAAGAT GCTTTTCTGT    13868

GACTGGTGAG TACTCAACCA AGTCATTCTG AGAATAGTGT ATGCGGCGAC CGAGTTGCTC    13928

TTGCCCGGCG TCAATACGGG ATAATACCGC GCCACATAGC AGAACTTTAA AAGTGCTCAT    13988

CATTGGAAAA CGTTCTTCGG GGCGAAAACT CTCAAGGATC TTACCGCTGT TGAGATCCAG    14048

TTCGATGTAA CCCACTCGTG CACCCAACTG ATCTTCAGCA TCTTTTACTT TCACCAGCGT    14108

TTCTGGGTGA GCAAAAACAG GAAGGCAAAA TGCCGCAAAA AAGGGAATAA GGGCGACACG    14168

GAAATGTTGA ATACTCATAC TCTTCCTTTT TCAATATTAT TGAAGCATTT ATCAGGGTTA    14228

TTGTCTCATG AGCGGATACA TATTTGAATG TATTTAGAAA AATAAACAAA TAGGGGTTCC    14288

GCGCACATTT CCCCGAAAAG TGC                                             14311

(2) INFORMATION FOR SEQ ID NO:2:

(i) SEQUENCE CHARACTERISTICS:
        (A) LENGTH: 422 amino acids
        (B) TYPE: amino acid
        (D) TOPOLOGY: linear (ii) MOLECULE TYPE: protein (xi) SEQUENCE DESCRIPTION: SEQ ID NO:2:

Met Ser Val Thr Val Lys Arg Ile Ile Asp Asn Thr Val Ile Val Pro
 1               5                  10                  15

Lys Leu Pro Ala Asn Glu Asp Pro Val Glu Tyr Pro Ala Asp Tyr Phe
                20                  25                  30

Arg Lys Ser Lys Glu Ile Pro Leu Tyr Ile Asn Thr Thr Lys Ser Leu
            35                  40                  45

Ser Asp Leu Arg Gly Tyr Val Tyr Gln Gly Leu Lys Ser Gly Asn Val
        50                  55                  60

Ser Ile Ile His Val Asn Ser Tyr Leu Tyr Gly Ala Leu Lys Asp Ile
65                  70                  75                  80

Arg Gly Lys Leu Asp Lys Asp Trp Ser Ser Phe Gly Ile Asn Ile Gly
                85                  90                  95

Lys Ala Gly Asp Thr Ile Gly Ile Phe Asp Leu Val Ser Leu Lys Ala
            100                 105                 110

Leu Asp Gly Val Leu Pro Asp Gly Val Ser Asp Ala Ser Arg Thr Ser
        115                 120                 125

Ala Asp Asp Lys Trp Leu Pro Leu Tyr Leu Leu Gly Leu Tyr Arg Val
    130                 135                 140

Gly Arg Thr Gln Met Pro Glu Tyr Arg Lys Leu Met Asp Gly Leu
145                 150                 155                 160

Thr Asn Gln Cys Lys Met Ile Asn Glu Gln Phe Glu Pro Leu Val Pro
                165                 170                 175

Glu Gly Arg Asp Ile Phe Asp Val Trp Gly Asn Asp Ser Asn Tyr Thr
```

-continued

```
                180                 185                 190
Lys Ile Val Ala Ala Val Asp Met Phe Phe His Met Phe Lys Lys His
                195                 200                 205
Glu Cys Ala Ser Phe Arg Tyr Gly Thr Ile Val Ser Arg Phe Lys Asp
    210                 215                 220
Cys Ala Ala Leu Ala Thr Phe Gly His Leu Cys Lys Ile Thr Gly Met
225                 230                 235                 240
Ser Thr Glu Asp Val Thr Thr Trp Ile Leu Asn Arg Glu Val Ala Asp
                245                 250                 255
Glu Met Val Gln Met Met Leu Pro Gly Gln Glu Ile Asp Lys Ala Asp
                260                 265                 270
Ser Tyr Met Pro Tyr Leu Ile Asp Phe Gly Leu Ser Ser Lys Ser Pro
            275                 280                 285
Tyr Ser Ser Val Lys Asn Pro Ala Phe His Phe Trp Gly Gln Leu Thr
    290                 295                 300
Ala Leu Leu Leu Arg Ser Thr Arg Ala Arg Asn Ala Arg Gln Pro Asp
305                 310                 315                 320
Asp Ile Glu Tyr Thr Ser Leu Thr Thr Ala Gly Leu Leu Tyr Ala Tyr
                325                 330                 335
Ala Val Gly Ser Ser Ala Asp Leu Ala Gln Gln Phe Cys Val Gly Asp
                340                 345                 350
Asn Lys Tyr Thr Pro Asp Asp Ser Thr Gly Gly Leu Thr Thr Asn Ala
            355                 360                 365
Pro Pro Gln Gly Arg Asp Val Val Glu Trp Leu Gly Trp Phe Glu Asp
    370                 375                 380
Gln Asn Arg Lys Pro Thr Pro Asp Met Met Gln Tyr Ala Lys Arg Ala
385                 390                 395                 400
Val Met Ser Leu Gln Gly Leu Arg Glu Lys Thr Ile Gly Lys Tyr Ala
                405                 410                 415
Lys Ser Glu Phe Asp Lys
                420

(2) INFORMATION FOR SEQ ID NO:3:

(i) SEQUENCE CHARACTERISTICS:
        (A) LENGTH: 265 amino acids
        (B) TYPE: amino acid
        (D) TOPOLOGY: linear (ii) MOLECULE TYPE: protein (xi) SEQUENCE DESCRIPTION: SEQ ID NO:3:

Met Asp Asn Leu Thr Lys Val Arg Glu Tyr Leu Lys Ser Tyr Ser Arg
1               5                   10                  15
Leu Asp Gln Ala Val Gly Glu Ile Asp Glu Ile Glu Ala Gln Arg Ala
                20                  25                  30
Glu Lys Ser Asn Tyr Glu Leu Phe Gln Glu Asp Gly Val Glu Glu His
            35                  40                  45
Thr Lys Pro Ser Tyr Phe Gln Ala Ala Asp Asp Ser Asp Thr Glu Ser
        50                  55                  60
Glu Pro Glu Ile Glu Asp Asn Gln Gly Leu Tyr Ala Pro Asp Pro Glu
65                  70                  75                  80
Ala Glu Gln Val Glu Gly Phe Ile Gln Gly Pro Leu Asp Asp Tyr Ala
                85                  90                  95
Asp Glu Glu Val Asp Val Val Phe Thr Ser Asp Trp Lys Gln Pro Glu
                100                 105                 110
```

```
Leu Glu Ser Asp Glu His Gly Lys Thr Leu Arg Leu Thr Ser Pro Glu
            115                 120                 125

Gly Leu Ser Gly Glu Gln Lys Ser Gln Trp Leu Ser Thr Ile Lys Ala
        130                 135                 140

Val Val Gln Ser Ala Lys Tyr Trp Asn Leu Ala Glu Cys Thr Phe Glu
145                 150                 155                 160

Ala Ser Gly Glu Gly Val Ile Met Lys Glu Arg Gln Ile Thr Pro Asp
                165                 170                 175

Val Tyr Lys Val Thr Pro Val Met Asn Thr His Pro Ser Gln Ser Glu
            180                 185                 190

Ala Val Ser Asp Val Trp Ser Leu Ser Lys Thr Ser Met Thr Phe Gln
            195                 200                 205

Pro Lys Lys Ala Ser Leu Gln Pro Leu Thr Ile Ser Leu Asp Glu Leu
        210                 215                 220

Phe Ser Ser Arg Gly Glu Phe Ile Ser Val Gly Gly Asp Gly Arg Met
225                 230                 235                 240

Ser His Lys Glu Ala Ile Leu Leu Gly Leu Arg Tyr Lys Lys Leu Tyr
                245                 250                 255

Asn Gln Ala Arg Val Lys Tyr Ser Leu
            260                 265

(2) INFORMATION FOR SEQ ID NO:4:

(i) SEQUENCE CHARACTERISTICS:
        (A) LENGTH: 229 amino acids
        (B) TYPE: amino acid
        (D) TOPOLOGY: linear (ii) MOLECULE TYPE: protein (xi) SEQUENCE DESCRIPTION: SEQ ID NO:4:

Met Ser Ser Leu Lys Lys Ile Leu Gly Leu Lys Gly Lys Gly Lys Lys
  1               5                  10                  15

Ser Lys Lys Leu Gly Ile Ala Pro Pro Tyr Glu Glu Asp Thr Ser
            20                  25                  30

Met Glu Tyr Ala Pro Ser Ala Pro Ile Asp Lys Ser Tyr Phe Gly Val
        35                  40                  45

Asp Glu Met Asp Thr Tyr Asp Pro Asn Gln Leu Arg Tyr Glu Lys Phe
    50                  55                  60

Phe Phe Thr Val Lys Met Thr Val Arg Ser Asn Arg Pro Phe Arg Thr
65                  70                  75                  80

Tyr Ser Asp Val Ala Ala Ala Val Ser His Trp Asp His Met Tyr Ile
                85                  90                  95

Gly Met Ala Gly Lys Arg Pro Phe Tyr Lys Ile Leu Ala Phe Leu Gly
            100                 105                 110

Ser Ser Asn Leu Lys Ala Thr Pro Ala Val Leu Ala Asp Gln Gly Gln
        115                 120                 125

Pro Glu Tyr His Thr His Cys Glu Gly Arg Ala Tyr Leu Pro His Arg
    130                 135                 140

Met Gly Lys Thr Pro Pro Met Leu Asn Val Pro Glu His Phe Arg Arg
145                 150                 155                 160

Pro Phe Asn Ile Gly Leu Tyr Lys Gly Thr Ile Glu Leu Thr Met Thr
                165                 170                 175

Ile Tyr Asp Asp Glu Ser Leu Glu Ala Ala Pro Met Ile Trp Asp His
            180                 185                 190
```

```
Phe Asn Ser Ser Lys Phe Ser Asp Phe Arg Glu Lys Ala Leu Met Phe
        195                 200                 205

Gly Leu Ile Val Glu Lys Lys Ala Ser Gly Ala Trp Val Leu Asp Ser
        210                 215                 220

Ile Ser His Phe Lys
225

(2) INFORMATION FOR SEQ ID NO:5:

(i) SEQUENCE CHARACTERISTICS:
        (A) LENGTH: 511 amino acids
        (B) TYPE: amino acid
        (D) TOPOLOGY: linear (ii) MOLECULE TYPE: protein (xi) SEQUENCE DESCRIPTION: SEQ ID NO:5:

Met Lys Cys Leu Leu Tyr Leu Ala Phe Leu Phe Ile Gly Val Asn Cys
  1               5                  10                  15

Lys Phe Thr Ile Val Phe Pro His Asn Gln Lys Gly Asn Trp Lys Asn
                 20                  25                  30

Val Pro Ser Asn Tyr His Tyr Cys Pro Ser Ser Ser Asp Leu Asn Trp
             35                  40                  45

His Asn Asp Leu Ile Gly Thr Ala Ile Gln Val Lys Met Pro Lys Ser
 50                  55                  60

His Lys Ala Ile Gln Ala Asp Gly Trp Met Cys His Ala Ser Lys Trp
 65                  70                  75                  80

Val Thr Thr Cys Asp Phe Arg Trp Tyr Gly Pro Lys Tyr Ile Thr Gln
                 85                  90                  95

Ser Ile Arg Ser Phe Thr Pro Ser Val Glu Gln Cys Lys Glu Ser Ile
                100                 105                 110

Glu Gln Thr Lys Gln Gly Thr Trp Leu Asn Pro Gly Phe Pro Pro Gln
                115                 120                 125

Ser Cys Gly Tyr Ala Thr Val Thr Asp Ala Glu Ala Val Ile Val Gln
            130                 135                 140

Val Thr Pro His His Val Leu Val Asp Glu Tyr Thr Gly Glu Trp Val
145                 150                 155                 160

Asp Ser Gln Phe Ile Asn Gly Lys Cys Ser Asn Tyr Ile Cys Pro Thr
                165                 170                 175

Val His Asn Ser Thr Thr Trp His Ser Asp Tyr Lys Val Lys Gly Leu
            180                 185                 190

Cys Asp Ser Asn Leu Ile Ser Met Asp Ile Thr Phe Phe Ser Glu Asp
                195                 200                 205

Gly Glu Leu Ser Ser Leu Gly Lys Glu Gly Thr Gly Phe Arg Ser Asn
        210                 215                 220

Tyr Phe Ala Tyr Glu Thr Gly Gly Lys Ala Cys Lys Met Gln Tyr Cys
225                 230                 235                 240

Lys His Trp Gly Val Arg Leu Pro Ser Gly Val Trp Phe Glu Met Ala
                245                 250                 255

Asp Lys Asp Leu Phe Ala Ala Ala Arg Phe Pro Glu Cys Pro Glu Gly
                260                 265                 270

Ser Ser Ile Ser Ala Pro Ser Gln Thr Ser Val Asp Val Ser Leu Ile
            275                 280                 285

Gln Asp Val Glu Arg Ile Leu Asp Tyr Ser Leu Cys Gln Glu Thr Trp
        290                 295                 300

Ser Lys Ile Arg Ala Gly Leu Pro Ile Ser Pro Val Asp Leu Ser Tyr
```

```
                    305                 310                 315                 320
Leu Ala Pro Lys Asn Pro Gly Thr Gly Pro Ala Phe Thr Ile Ile Asn
                325                 330                 335
Gly Thr Leu Lys Tyr Phe Glu Thr Arg Tyr Ile Arg Val Asp Ile Ala
                340                 345                 350
Ala Pro Ile Leu Ser Arg Met Val Gly Met Ile Ser Gly Thr Thr Thr
                355                 360                 365
Glu Arg Glu Leu Trp Asp Asp Trp Ala Pro Tyr Glu Asp Val Glu Ile
            370                 375                 380
Gly Pro Asn Gly Val Leu Arg Thr Ser Ser Gly Tyr Lys Phe Pro Leu
385                 390                 395                 400
Tyr Met Ile Gly His Gly Met Leu Asp Ser Asp Leu His Leu Ser Ser
                405                 410                 415
Lys Ala Gln Val Phe Glu His Pro His Ile Gln Asp Ala Ala Ser Gln
                420                 425                 430
Leu Pro Asp Asp Glu Ser Leu Phe Phe Gly Asp Thr Gly Leu Ser Lys
                435                 440                 445
Asn Pro Ile Glu Leu Val Glu Gly Trp Phe Ser Ser Trp Lys Ser Ser
            450                 455                 460
Ile Ala Ser Phe Phe Phe Ile Ile Gly Leu Ile Ile Gly Leu Phe Leu
465                 470                 475                 480
Val Leu Arg Val Gly Ile His Leu Cys Ile Lys Leu Lys His Thr Lys
                485                 490                 495
Lys Arg Gln Ile Tyr Thr Asp Ile Glu Met Asn Arg Leu Gly Lys
                500                 505                 510

(2) INFORMATION FOR SEQ ID NO:6:

(i) SEQUENCE CHARACTERISTICS:
        (A) LENGTH: 2109 amino acids
        (B) TYPE: amino acid
        (D) TOPOLOGY: linear (ii) MOLECULE TYPE: protein (xi) SEQUENCE DESCRIPTION: SEQ ID NO:6:

Met Glu Val His Asp Phe Glu Thr Asp Glu Phe Asn Asp Phe Asn Glu
  1               5                  10                  15
Asp Asp Tyr Ala Thr Arg Glu Phe Leu Asn Pro Asp Glu Arg Met Thr
                20                  25                  30
Tyr Leu Asn His Ala Asp Tyr Asn Leu Asn Ser Pro Leu Ile Ser Asp
            35                  40                  45
Asp Ile Asp Asn Leu Ile Arg Lys Phe Asn Ser Leu Pro Ile Pro Ser
        50                  55                  60
Met Trp Asp Ser Lys Asn Trp Asp Gly Val Leu Glu Met Leu Thr Ser
 65                  70                  75                  80
Cys Gln Ala Asn Pro Ile Ser Thr Ser Gln Met His Lys Trp Met Gly
                85                  90                  95
Ser Trp Leu Met Ser Asp Asn His Asp Ala Ser Gln Gly Tyr Ser Phe
                100                 105                 110
Leu His Glu Val Asp Lys Glu Ala Glu Ile Thr Phe Asp Val Val Glu
            115                 120                 125
Thr Phe Ile Arg Gly Trp Gly Asn Lys Pro Ile Glu Tyr Ile Lys Lys
        130                 135                 140
Glu Arg Trp Thr Asp Ser Phe Lys Ile Leu Ala Tyr Leu Cys Gln Lys
145                 150                 155                 160
```

```
Phe Leu Asp Leu His Lys Leu Thr Leu Ile Leu Asn Ala Val Ser Glu
                165                 170                 175
Val Glu Leu Leu Asn Leu Ala Arg Thr Phe Lys Gly Lys Val Arg Arg
            180                 185                 190
Ser Ser His Gly Thr Asn Ile Cys Arg Ile Arg Val Pro Ser Leu Gly
        195                 200                 205
Pro Thr Phe Ile Ser Glu Gly Trp Ala Tyr Phe Lys Lys Leu Asp Ile
    210                 215                 220
Leu Met Asp Arg Asn Phe Leu Met Val Lys Asp Val Ile Ile Gly
225                 230                 235                 240
Arg Met Gln Thr Val Leu Ser Met Val Cys Arg Ile Asp Asn Leu Phe
                245                 250                 255
Ser Glu Gln Asp Ile Phe Ser Leu Leu Asn Ile Tyr Arg Ile Gly Asp
            260                 265                 270
Lys Ile Val Glu Arg Gln Gly Asn Phe Ser Tyr Asp Leu Ile Lys Met
        275                 280                 285
Val Glu Pro Ile Cys Asn Leu Lys Leu Met Lys Leu Ala Arg Glu Ser
    290                 295                 300
Arg Pro Leu Val Pro Gln Phe Pro His Phe Glu Asn His Ile Lys Thr
305                 310                 315                 320
Ser Val Asp Glu Gly Ala Lys Ile Asp Arg Gly Ile Arg Phe Leu His
                325                 330                 335
Asp Gln Ile Met Ser Val Lys Thr Val Asp Leu Thr Leu Val Ile Tyr
            340                 345                 350
Gly Ser Phe Arg His Trp Gly His Pro Phe Ile Asp Tyr Tyr Thr Gly
        355                 360                 365
Leu Glu Lys Leu His Ser Gln Val Thr Met Lys Lys Asp Ile Asp Val
    370                 375                 380
Ser Tyr Ala Lys Ala Leu Ala Ser Asp Leu Ala Arg Ile Val Leu Phe
385                 390                 395                 400
Gln Gln Phe Asn Asp His Lys Lys Trp Phe Val Asn Gly Asp Leu Leu
                405                 410                 415
Pro His Asp His Pro Phe Lys Ser His Val Lys Glu Asn Thr Trp Pro
            420                 425                 430
Thr Ala Ala Gln Val Gln Asp Phe Gly Asp Lys Trp His Glu Leu Pro
        435                 440                 445
Leu Ile Lys Cys Phe Glu Ile Pro Asp Leu Leu Asp Pro Ser Ile Ile
    450                 455                 460
Tyr Ser Asp Lys Ser His Ser Met Asn Arg Ser Glu Val Leu Lys His
465                 470                 475                 480
Val Arg Met Asn Pro Asn Thr Pro Ile Pro Ser Lys Lys Val Leu Gln
                485                 490                 495
Thr Met Leu Asp Thr Lys Ala Thr Asn Trp Lys Glu Phe Leu Lys Glu
            500                 505                 510
Ile Asp Glu Lys Gly Leu Asp Asp Asp Leu Ile Ile Gly Leu Lys
        515                 520                 525
Gly Lys Glu Arg Glu Leu Lys Leu Ala Gly Arg Phe Phe Ser Leu Met
    530                 535                 540
Ser Trp Lys Leu Arg Glu Tyr Phe Val Ile Thr Glu Tyr Leu Ile Lys
545                 550                 555                 560
Thr His Phe Val Pro Met Phe Lys Gly Leu Thr Met Ala Asp Asp Leu
                565                 570                 575
```

-continued

```
Thr Ala Val Ile Lys Lys Met Leu Asp Ser Ser Gly Gln Gly Leu
            580                 585                 590

Lys Ser Tyr Glu Ala Ile Cys Ile Ala Asn His Ile Asp Tyr Glu Lys
            595                 600                 605

Trp Asn Asn His Gln Arg Lys Leu Ser Asn Gly Pro Val Phe Arg Val
            610                 615                 620

Met Gly Gln Phe Leu Gly Tyr Pro Ser Leu Ile Glu Arg Thr His Glu
625                 630                 635                 640

Phe Phe Glu Lys Ser Leu Ile Tyr Tyr Asn Gly Arg Pro Asp Leu Met
                645                 650                 655

Arg Val His Asn Asn Thr Leu Ile Asn Ser Thr Ser Gln Arg Val Cys
                660                 665                 670

Trp Gln Gly Gln Glu Gly Gly Leu Glu Gly Leu Arg Gln Lys Gly Trp
            675                 680                 685

Thr Ile Leu Asn Leu Leu Val Ile Gln Arg Glu Ala Lys Ile Arg Asn
            690                 695                 700

Thr Ala Val Lys Val Leu Ala Gln Gly Asp Asn Gln Val Ile Cys Thr
705                 710                 715                 720

Gln Tyr Lys Thr Lys Lys Ser Arg Asn Val Val Glu Leu Gln Gly Ala
                725                 730                 735

Leu Asn Gln Met Val Ser Asn Asn Glu Lys Ile Met Thr Ala Ile Lys
            740                 745                 750

Ile Gly Thr Gly Lys Leu Gly Leu Leu Ile Asn Asp Asp Glu Thr Met
            755                 760                 765

Gln Ser Ala Asp Tyr Leu Asn Tyr Gly Lys Ile Pro Ile Phe Arg Gly
            770                 775                 780

Val Ile Arg Gly Leu Glu Thr Lys Arg Trp Ser Arg Val Thr Cys Val
785                 790                 795                 800

Thr Asn Asp Gln Ile Pro Thr Cys Ala Asn Ile Met Ser Ser Val Ser
                805                 810                 815

Thr Asn Ala Leu Thr Val Ala His Phe Ala Glu Asn Pro Ile Asn Ala
            820                 825                 830

Met Ile Gln Tyr Asn Tyr Phe Gly Thr Phe Ala Arg Leu Leu Leu Met
            835                 840                 845

Met His Asp Pro Ala Leu Arg Gln Ser Leu Tyr Glu Val Gln Asp Lys
            850                 855                 860

Ile Pro Gly Leu His Ser Ser Thr Phe Lys Tyr Ala Met Leu Tyr Leu
865                 870                 875                 880

Asp Pro Ser Ile Gly Gly Val Ser Gly Met Ser Leu Ser Arg Phe Leu
                885                 890                 895

Ile Arg Ala Phe Pro Asp Pro Val Thr Glu Ser Leu Ser Phe Trp Arg
            900                 905                 910

Phe Ile His Val His Ala Arg Ser Glu His Leu Lys Glu Met Ser Ala
            915                 920                 925

Val Phe Gly Asn Pro Glu Ile Ala Lys Phe Arg Ile Thr His Ile Asp
            930                 935                 940

Lys Leu Val Glu Asp Pro Thr Ser Leu Asn Ile Ala Met Gly Met Ser
945                 950                 955                 960

Pro Ala Asn Leu Leu Lys Thr Glu Val Lys Lys Cys Leu Ile Glu Ser
                965                 970                 975

Arg Gln Thr Ile Arg Asn Gln Val Ile Lys Asp Ala Thr Ile Tyr Leu
            980                 985                 990

Tyr His Glu Glu Asp Arg Leu Arg Ser Phe Leu Trp Ser Ile Asn Pro
```

-continued

```
                 995                 1000                1005
Leu Phe Pro Arg Phe Leu Ser Glu Phe Lys Ser Gly Thr Phe Leu Gly
        1010                1015                1020

Val Ala Asp Gly Leu Ile Ser Leu Phe Gln Asn Ser Arg Thr Ile Arg
1025                1030                1035                1040

Asn Ser Phe Lys Lys Lys Tyr His Arg Glu Leu Asp Asp Leu Ile Val
                1045                1050                1055

Arg Ser Glu Val Ser Ser Leu Thr His Leu Gly Lys Leu His Leu Arg
        1060                1065                1070

Arg Gly Ser Cys Lys Met Trp Thr Cys Ser Ala Thr His Ala Asp Thr
        1075                1080                1085

Leu Arg Tyr Lys Ser Trp Gly Arg Thr Val Ile Gly Thr Thr Val Pro
        1090                1095                1100

His Pro Leu Glu Met Leu Gly Pro Gln His Arg Lys Glu Thr Pro Cys
1105                1110                1115                1120

Ala Pro Cys Asn Thr Ser Gly Phe Asn Tyr Val Ser Val His Cys Pro
                1125                1130                1135

Asp Gly Ile His Asp Val Phe Ser Ser Arg Gly Pro Leu Pro Ala Tyr
        1140                1145                1150

Leu Gly Ser Lys Thr Ser Glu Ser Thr Ser Ile Leu Gln Pro Trp Glu
        1155                1160                1165

Arg Glu Ser Lys Val Pro Leu Ile Lys Arg Ala Thr Arg Leu Arg Asp
        1170                1175                1180

Ala Ile Ser Trp Phe Val Glu Pro Asp Ser Lys Leu Ala Met Thr Ile
1185                1190                1195                1200

Leu Ser Asn Ile His Ser Leu Thr Gly Glu Glu Trp Thr Lys Arg Gln
                1205                1210                1215

His Gly Phe Lys Arg Thr Gly Ser Ala Leu His Arg Phe Ser Thr Ser
                1220                1225                1230

Arg Met Ser His Gly Gly Phe Ala Ser Gln Ser Thr Ala Ala Leu Thr
        1235                1240                1245

Arg Leu Met Ala Thr Thr Asp Thr Met Arg Asp Leu Gly Asp Gln Asn
        1250                1255                1260

Phe Asp Phe Leu Phe Gln Ala Thr Leu Leu Tyr Ala Gln Ile Thr Thr
1265                1270                1275                1280

Thr Val Ala Arg Asp Gly Trp Ile Thr Ser Cys Thr Asp His Tyr His
                1285                1290                1295

Ile Ala Cys Lys Ser Cys Leu Arg Pro Ile Glu Glu Ile Thr Leu Asp
                1300                1305                1310

Ser Ser Met Asp Tyr Thr Pro Pro Asp Val Ser His Val Leu Lys Thr
        1315                1320                1325

Trp Arg Asn Gly Glu Gly Ser Trp Gly Gln Glu Ile Lys Gln Ile Tyr
        1330                1335                1340

Pro Leu Glu Gly Asn Trp Lys Asn Leu Ala Pro Ala Glu Gln Ser Tyr
1345                1350                1355                1360

Gln Val Gly Arg Cys Ile Gly Phe Leu Tyr Gly Asp Leu Ala Tyr Arg
                1365                1370                1375

Lys Ser Thr His Ala Glu Asp Ser Ser Leu Phe Pro Leu Ser Ile Gln
        1380                1385                1390

Gly Arg Ile Arg Gly Arg Gly Phe Leu Lys Gly Leu Leu Asp Gly Leu
        1395                1400                1405

Met Arg Ala Ser Cys Cys Gln Val Ile His Arg Arg Ser Leu Ala His
        1410                1415                1420
```

-continued

```
Leu Lys Arg Pro Ala Asn Ala Val Tyr Gly Gly Leu Ile Tyr Leu Ile
1425                1430                1435                1440

Asp Lys Leu Ser Val Ser Pro Pro Phe Leu Ser Leu Thr Arg Ser Gly
            1445                1450                1455

Pro Ile Arg Asp Glu Leu Glu Thr Ile Pro His Lys Ile Pro Thr Ser
        1460                1465                1470

Tyr Pro Thr Ser Asn Arg Asp Met Gly Val Ile Val Arg Asn Tyr Phe
    1475                1480                1485

Lys Tyr Gln Cys Arg Leu Ile Glu Lys Gly Lys Tyr Arg Ser His Tyr
1490                1495                1500

Ser Gln Leu Trp Leu Phe Ser Asp Val Leu Ser Ile Asp Phe Ile Gly
1505                1510                1515                1520

Pro Phe Ser Ile Ser Thr Thr Leu Leu Gln Ile Leu Tyr Lys Pro Phe
            1525                1530                1535

Leu Ser Gly Lys Asp Lys Asn Glu Leu Arg Glu Leu Ala Asn Leu Ser
        1540                1545                1550

Ser Leu Leu Arg Ser Gly Glu Gly Trp Glu Asp Ile His Val Lys Phe
    1555                1560                1565

Phe Thr Lys Asp Ile Leu Leu Cys Pro Glu Ile Arg His Ala Cys
1570                1575                1580

Lys Phe Gly Ile Ala Lys Asp Asn Asn Lys Asp Met Ser Tyr Pro Pro
1585                1590                1595                1600

Trp Gly Arg Glu Ser Arg Gly Thr Ile Thr Thr Ile Pro Val Tyr Tyr
            1605                1610                1615

Thr Thr Thr Pro Tyr Pro Lys Met Leu Glu Met Pro Pro Arg Ile Gln
        1620                1625                1630

Asn Pro Leu Leu Ser Gly Ile Arg Leu Gly Gln Leu Pro Thr Gly Ala
    1635                1640                1645

His Tyr Lys Ile Arg Ser Ile Leu His Gly Met Gly Ile His Tyr Arg
1650                1655                1660

Asp Phe Leu Ser Cys Gly Asp Gly Ser Gly Met Thr Ala Ala Leu
1665                1670                1675                1680

Leu Arg Glu Asn Val His Ser Arg Gly Ile Phe Asn Ser Leu Leu Glu
            1685                1690                1695

Leu Ser Gly Ser Val Met Arg Gly Ala Ser Pro Glu Pro Pro Ser Ala
        1700                1705                1710

Leu Glu Thr Leu Gly Gly Asp Lys Ser Arg Cys Val Asn Gly Glu Thr
    1715                1720                1725

Cys Trp Glu Tyr Pro Ser Asp Leu Cys Asp Pro Arg Thr Trp Asp Tyr
1730                1735                1740

Phe Leu Arg Leu Lys Ala Gly Leu Gly Leu Gln Ile Asp Leu Ile Val
1745                1750                1755                1760

Met Asp Met Glu Val Arg Asp Ser Ser Thr Ser Leu Lys Ile Glu Thr
            1765                1770                1775

Asn Val Arg Asn Tyr Val His Arg Ile Leu Asp Glu Gln Gly Val Leu
        1780                1785                1790

Ile Tyr Lys Thr Tyr Gly Thr Tyr Ile Cys Glu Ser Glu Lys Asn Ala
    1795                1800                1805

Val Thr Ile Leu Gly Pro Met Phe Lys Thr Val Asp Leu Val Gln Thr
1810                1815                1820

Glu Phe Ser Ser Ser Gln Thr Ser Glu Val Tyr Met Val Cys Lys Gly
1825                1830                1835                1840
```

```
Leu Lys Lys Leu Ile Asp Glu Pro Asn Pro Asp Trp Ser Ser Ile Asn
            1845                1850                1855

Glu Ser Trp Lys Asn Leu Tyr Ala Phe Gln Ser Ser Glu Gln Glu Phe
        1860                1865                1870

Ala Arg Ala Lys Lys Val Ser Thr Tyr Phe Thr Leu Thr Gly Ile Pro
    1875                1880                1885

Ser Gln Phe Ile Pro Asp Pro Phe Val Asn Ile Glu Thr Met Leu Gln
    1890                1895                1900

Ile Phe Gly Val Pro Thr Gly Val Ser His Ala Ala Leu Lys Ser
1905                1910                1915                1920

Ser Asp Arg Pro Ala Asp Leu Leu Thr Ile Ser Leu Phe Tyr Met Ala
            1925                1930                1935

Ile Ile Ser Tyr Tyr Asn Ile Asn His Ile Arg Val Gly Pro Ile Pro
            1940                1945                1950

Pro Asn Pro Pro Ser Asp Gly Ile Ala Gln Asn Val Gly Ile Ala Ile
            1955                1960                1965

Thr Gly Ile Ser Phe Trp Leu Ser Leu Met Glu Lys Asp Ile Pro Leu
    1970                1975                1980

Tyr Gln Gln Cys Leu Ala Val Ile Gln Gln Ser Phe Pro Ile Arg Trp
1985                1990                1995                2000

Glu Ala Val Ser Val Lys Gly Gly Tyr Lys Gln Lys Trp Ser Thr Arg
            2005                2010                2015

Gly Asp Gly Leu Pro Lys Asp Thr Arg Thr Ser Asp Ser Leu Ala Pro
            2020                2025                2030

Ile Gly Asn Trp Ile Arg Ser Leu Glu Leu Val Arg Asn Gln Val Arg
            2035                2040                2045

Leu Asn Pro Phe Asn Glu Ile Leu Phe Asn Gln Leu Cys Arg Thr Val
    2050                2055                2060

Asp Asn His Leu Lys Trp Ser Asn Leu Arg Arg Asn Thr Gly Met Ile
2065                2070                2075                2080

Glu Trp Ile Asn Arg Arg Ile Ser Lys Glu Asp Arg Ser Ile Leu Met
            2085                2090                2095

Leu Lys Ser Asp Leu His Glu Glu Asn Ser Trp Arg Asp
            2100                2105

(2) INFORMATION FOR SEQ ID NO:7:

(i) SEQUENCE CHARACTERISTICS:
        (A) LENGTH: 14311 base pairs
        (B) TYPE: nucleic acid
        (C) STRANDEDNESS: double
        (D) TOPOLOGY: linear (ii) MOLECULE TYPE: DNA (xi) SEQUENCE DESCRIPTION: SEQ ID NO:7:

GCACTTTTCG GGGAAATGTG CGCGGAACCC CTATTTGTTT ATTTTTCTAA ATACATTCAA      60

ATATGTATCC GCTCATGAGA CAATAACCCT GATAAATGCT TCAATAATAT TGAAAAAGGA    120

AGAGTATGAG TATTCAACAT TTCCGTGTCG CCCTTATTCC CTTTTTTGCG GCATTTTGCC    180

TTCCTGTTTT TGCTCACCCA GAAACGCTGG TGAAAGTAAA AGATGCTGAA GATCAGTTGG    240

GTGCACGAGT GGGTTACATC GAACTGGATC TCAACAGCGG TAAGATCCTT GAGAGTTTTC    300

GCCCCGAAGA ACGTTTTCCA ATGATGAGCA CTTTTAAAGT TCTGCTATGT GGCGCGGTAT    360

TATCCCGTAT TGACGCCGGG CAAGAGCAAC TCGGTCGCCG CATACACTAT TCTCAGAATG    420

ACTTGGTTGA GTACTCACCA GTCACAGAAA AGCATCTTAC GGATGGCATG ACAGTAAGAG    480
```

-continued

```
AATTATGCAG TGCTGCCATA ACCATGAGTG ATAACACTGC GGCCAACTTA CTTCTGACAA    540

CGATCGGAGG ACCGAAGGAG CTAACCGCTT TTTTGCACAA CATGGGGGAT CATGTAACTC    600

GCCTTGATCG TTGGGAACCG GAGCTGAATG AAGCCATACC AAACGACGAG CGTGACACCA    660

CGATGCCTGT AGCAATGGCA ACAACGTTGC GCAAACTATT AACTGGCGAA CTACTTACTC    720

TAGCTTCCCG GCAACAATTA ATAGACTGGA TGGAGGCGGA TAAAGTTGCA GGACCACTTC    780

TGCGCTCGGC CCTTCCGGCT GGCTGGTTTA TTGCTGATAA ATCTGGAGCC GGTGAGCGTG    840

GGTCTCGCGG TATCATTGCA GCACTGGGGC CAGATGGTAA GCCCTCCCGT ATCGTAGTTA    900

TCTACACGAC GGGGAGTCAG GCAACTATGG ATGAACGAAA TAGACAGATC GCTGAGATAG    960

GTGCCTCACT GATTAAGCAT TGGTAACTGT CAGACCAAGT TTACTCATAT ATACTTTAGA    1020

TTGATTTAAA ACTTCATTTT TAATTTAAAA GGATCTAGGT GAAGATCCTT TTTGATAATC    1080

TCATGACCAA AATCCCTTAA CGTGAGTTTT CGTTCCACTG AGCGTCAGAC CCCGTAGAAA    1140

AGATCAAAGG ATCTTCTTGA GATCCTTTTT TTCTGCGCGT AATCTGCTGC TTGCAAACAA    1200

AAAAACCACC GCTACCAGCG GTGGTTTGTT TGCCGGATCA AGAGCTACCA ACTCTTTTTC    1260

CGAAGGTAAC TGGCTTCAGC AGAGCGCAGA TACCAAATAC TGTCCTTCTA GTGTAGCCGT    1320

AGTTAGGCCA CCACTTCAAG AACTCTGTAG CACCGCCTAC ATACCTCGCT CTGCTAATCC    1380

TGTTACCAGT GGCTGCTGCC AGTGGCGATA AGTCGTGTCT TACCGGGTTG GACTCAAGAC    1440

GATAGTTACC GGATAAGGCG CAGCGGTCGG GCTGAACGGG GGGTTCGTGC ACACAGCCCA    1500

GCTTGGAGCG AACGACCTAC ACCGAACTGA GATACCTACA GCGTGAGCTA TGAGAAAGCG    1560

CCACGCTTCC CGAAGGGAGA AAGGCGGACA GGTATCCGGT AAGCGGCAGG GTCGGAACAG    1620

GAGAGCGCAC GAGGGAGCTT CCAGGGGGAA ACGCCTGGTA TCTTTATAGT CCTGTCGGGT    1680

TTCGCCACCT CTGACTTGAG CGTCGATTTT TGTGATGCTC GTCAGGGGGG CGGAGCCTAT    1740

GGAAAAACGC CAGCAACGCG GCCTTTTTAC GGTTCCTGGC CTTTTGCTGG CCTTTTGCTC    1800

ACATGTTCTT TCCTGCGTTA TCCCCTGATT CTGTGGATAA CCGTATTACC GCCTTTGAGT    1860

GAGCTGATAC CGCTCGCCGC AGCCGAACGA CCGAGCGCAG CGAGTCAGTG AGCGAGGAAG    1920

CGGAAGAGCG CCCAATACGC AAACCGCCTC TCCCCGCGCG TTGGCCGATT CATTAATGCA    1980

GCTGGCACGA CAGGTTTCCC GACTGGAAAG CGGGCAGTGA GCGCAACGCA ATTAATGTGA    2040

GTTAGCTCAC TCATTAGGCA CCCCAGGCTT TACACTTTAT GCTTCCGGCT CGTATGTTGT    2100

GTGGAATTGT GAGCGGATAA CAATTTCACA CAGGAAACAG CTATGACCAT GATTACGCCA    2160

AGCTCGAAAT TAACCCTCAC TAAAGGGAAC AAAAGCTGGA GCTCCACCGC ACTAGTATCG    2220

AGGTCTCGAT CCGGATATAG TTCCTCCTTT CAGCAAAAAA CCCCTCAAGA CCCGTTTAGA    2280

GGCCCCAAGG GGTTATGCTA GTTATTGCTC AGCGGTGGCA GCAGCCAACT CAGCTTCCTT    2340

TCGGGCTTTG TTAGCAGCCC CGCGGGGGCC CCTCCCTTAG CCATCCGAGT GGACGACGTC    2400

CTCCTTCGGA TGCCCAGGTC GGACCGCGAG GAGGTGGAGA TGCCATGCCG ACCCACGAAG    2460

ACCACAAAAC CAGATAAAAA ATAAAAACCA CAAGAGGGTC TTAAGGATCA AGTTTTTTT    2520

CATACTTAAA GTTTGGAGTC TCCTCATGAT TTTTTAATCT CTCCAAGAGT TTTCCTCGTG    2580

TAGGTCACTC TTCAACATCA GTATAGACCG GTCTTCTTTT GAAATTCGTC TATTGATCCA    2640

TTCAATCATT CCTGTGTTTC TTCGCAAATT TGACCATTTC AAATGATTAT CCACTGTACG    2700

ACATAGCTGA TTGAACAAGA TCTCATTGAA TGGATTTAGA CGAACTTGGT TTCGGACCAA    2760

TTCCAGAGAT CTGATCCAGT TCCCGATTGG GGCCAAGGAG TCTGAAGTTC GGGTATCTTT    2820
```

-continued

```
TGGGAGCCCA TCACCTCTAG TACTCCACTT CTGCTTGTAT CCTCCTTTTA CTGAAACAGC   2880

CTCCCACCTA ATCGGGAATG ATTGCTGGAT AACTGCTAAA CACTGTTGAT ATAGTGGAAT   2940

GTCTTTCTCC ATCAAACTCA GCCAAAAGCT TATACCAGTT ATAGCGATCC CCACATTTTG   3000

TGCAATTCCA TCTGATGGGG GGTTCGGAGG TATCGGTCCT ACTCTGATAT GATTGATGTT   3060

ATAATACGAT ATAATCGCCA TATAAAAAAG GCTAATGGTC AATAAATCTG CAGGTCTATC   3120

AGATGATTTT AAGGCAGCCG CATGAGACAC ACCCGTGGGT ACTCCGAATA TTTGTAGCAT   3180

AGTCTCAATG TTTACAAAAG GATCAGGAAT GAATTGGGAG GGAATACCTG TCAAGGTAAA   3240

GTATGTACTA ACCTTCTTTG CTCTGGCAAA TTCCTGTTCT GATGACTGGA ATGCGTACAG   3300

GTTTTTCCAG GATTCATTGA TGGAAGACCA ATCGGGATTG GGTTCATCGA TTAATTTCTT   3360

CAAACCTTTA CATACCATAT ATACTTCAGA CGTTTGAGAA CTACTAAATT CTGTTTGAAC   3420

TAAGTCGACC GTCTTGAACA TGGGACCAAG GATTGTTACT GCATTCTTTT CGCTCTCACA   3480

AATATATGTT CCATAAGTCT TGTAGATTAA AACTCCTTGC TCATCCAAAA TCCGGTGCAC   3540

ATAATTTCTA ACATTCGTCT CAATTTTCAG GCTAGTAGAA GAATCCCGAA CTTCCATATC   3600

CATTACAATT AAATCAATTT GAAGCCCCAA GCCTGCTTTG AGTCGGAGGA AATAGTCCCA   3660

AGTCCTTGGG TCACATAAGT CAGATGGATA TTCCCAACAT GTTTCACCAT TTACACATCT   3720

CGATTTATCT CCTCCTAAAG TTTCTAGGGC ACTGGGGGGC TCAGGAGAGG CGCCTCGCAT   3780

GACTGACCCT GATAATTCTA ACAGACTATT GAATATTCCT CTGCTATGCA CATTTTCTCG   3840

TAGTAATGCA GCAGTCATCC CTCCGGAGCC GTCTCCACAA CTCAAGAAGT CCCTGTAATG   3900

GATTCCCATT CCATGTAATA TACTCCGAAT TTTATAATGA GCGCCAGTTG GTAATTGGCC   3960

CAACCTGATT CCGGACAGCA GGGGATTTTG GATTCTTGGA GGCATCTCTA GCATCTTTGG   4020

GTAAGGGGTG GTCGTATAAT AAACAGGGAT TGTTGTAATT GTCCCTCTGG ATTCCCTTCC   4080

CCAAGGGGGA TAGCTCATGT CTTTATTATT ATCCTTAGCA ATCCCGAACT TGCAAGCATG   4140

TCTGATTTCC TCTGGACACA ATAATATGTC CTTGGTGAAG AATTTCACAT GTATGTCTTC   4200

CCACCCCTCT CCTGATCTTA GCAATGAAGA AAGATTTGCC AGCTCTCTCA ACTCATTCTT   4260

ATCTTTCCCA GATAAAAATG GCTTGTATAG GATTTGCAAG AGGGTGGTGG AAATAGAGAA   4320

TGGTCCAATG AAGTCTATGG ATAAGACATC TGAGAATAAC CATAATTGTG AATAATGTGA   4380

TCTGTATTTT CCCTTTTCAA TTAGACGGCA TTGGTATTTG AAGTAATTTC TGACAATCAC   4440

CCCCATATCA CGGTTGCTTG TCGGATAGGA GGTTGGGATC TTGTGGGGAA TCGTTTCTAA   4500

TTCGTCTCTA ATAGGTCCTG ATCTAGTAAG AGAAAGGAAT GGAGGTGATA CACTCAATTT   4560

ATCAATCAAG TAAATCAAAC CTCCGTACAC TGCGTTGGCC GGCCTCTTCA AATGAGCCAG   4620

ACTTCTCCGG TGTATTACTT GGCAGCAACT TGCTCTCATT AATCCGTCTA GCAACCCTTT   4680

TAAGAAACCT CGACCTCTAA TACGACCTTG TATAGATAGA GGAAATAGAG AACTGTCCTC   4740

GGCATGAGTA GATTTTCTAT ACGCCAAGTC TCCATATAGA AAACCTATAC ATCTGCCGAC   4800

TTGATAGGAT TGCTCAGCAG GTGCTAAATT CTTCCAATTC CCTTCTAAAG GATAGATCTG   4860

TTTTATCTCT TGTCCCCACG AACCTTCCCC ATTCCTCCAT GTCTTCAGCA CATGGGATAC   4920

ATCTGGGGC GTGTAGTCCA TACTTGAGTC CAGGGTGATC TCTTCTATGG GTCTCAAACA   4980

GGACTTACAG GCAATATGAT AATGATCTGT ACAACTGGTG ATCCATCCGT CTCTTGCAAC   5040

AGTGGTGGTA ATTTGAGCAT AGAGCAACGT TGCTTGGAAT AAAAAGTCGA AATTCTGATC   5100

TCCCAGATCC CTCATGGTGT CTGTAGTTGC CATCAACCTG GTCAATGCTG CAGTGCTCTG   5160

AGATGCGAAC CCACCATGGC TCATCCGAGA TGTCGAAAAC CTATGAAGGG CAGACCCTGT   5220
```

```
TCTTTTGAAC CCATGCTGCC TTTTGGTCCA TTCTTCGCCT GTTAAAGAGT GGATGTTAGA    5280

AAGTATAGTC ATTGCTAGTT TAGAGTCGGG TTCAACAAAC CAAGAGATAG CATCTCTAAG    5340

ACGTGTAGCT CTTTTAATCA GTGGGACTTT GCTTTCCCTT TCCCAAGGCT GCAAAATAGA    5400

TGTAGATTCA GATGTTTTAG ACCCTAGATA AGCAGGCAAT GGTCCCCGTG AACTAAAGAC    5460

GTCATGGATC CCGTCTGGAC AATGCACAGA ACATAATTG AACCCTGATG TGTTACATGG     5520

TGCACAAGGA GTCTCTTTTC GATGTTGTGG ACCCAACATT TCTAATGGAT GGGGTACAGT    5580

TGTCCCAATA ACTGTACGGC CCCAGGATTT GTATCTTAAT GTGTCAGCAT GAGTAGCTGA    5640

ACATGTCCAC ATTTTACATG ATCCCCTTCT CAAATGAAGT TTCCCTAAAT GTGTCAAAGA    5700

GGATACCTCA CTCCTCACAA TCAAATCATC CAATTCCCTA TGATACTTTT TCTTAAAGGA    5760

GTTCCGAATA GTACGAGAAT TTTGAAATAG ACTGATGAGC CCGTCTGCGA CTCCCAAAAA    5820

AGTGCCTGAT TTGAATTCAC TTAAAAATCT AGGGAACAGA GGATTTATTG ACCATAAGAA    5880

ACTTCTGAGC CGATCCTCTT CATGATACAA ATATATGGTT GCATCCTTAA TCACCTGGTT    5940

CCTGATGGTT TGTCTTGATT CGATTAAGCA TTTTTTAACC TCAGTCTTTA ACAAGTTCGC    6000

TGGACTCATT CCCATAGCGA TGTTCAGAGA GGTTGGATCT TCTACTAGCT TGTCTATGTG    6060

AGTTATTCGA AACTTGGCTA TCTCGGGGTT TCCAAATACT GCACTCATCT CCTTCAGATG    6120

CTCACTTCGA GCATGTACAT GGATGAATCT CCAGAATGAG AGACTTTCTG TTACGGGATC    6180

TGGGAAGGCT CTAATCAAAA ACCTGGACAA AGACATGCCC GACACTCCTC CAATGGAAGG    6240

GTCCAAATAC AACATGGCGT ATTTGAAAGT AGAACTGTGC AAGCCCGGTA TCTTATCTTG    6300

AACTTCATAC AATGATTGAC GAAGAGCAGG ATCATGCATC ATCAACAAGA GTCTAGCAAA    6360

TGTCCCAAAA TAATTGTACT GTATCATGGC ATTGATTGGG TTCTCAGCAA AATGAGCTAC    6420

GGTGAGAGCA TTTGTGGAAA CTGAGCTCAT TATATTAGCA CAAGTGGGTA TTTGGTCATT    6480

GGTGACACAA GTCACTCGTG ACCATCTCTT GGTCTCTAAC CCTCTAATCA CTCCACGGAA    6540

AATCGGTATT TTTCCATAAT TCAAGTAATC TGCAGATTGC ATAGTCTCAT CGTCATTTAT    6600

CAAAAGTCCT AACTTCCCTG TCCCTATTTT GATTGCAGTC ATAATTTTCT CATTATTAGA    6660

AACCATTTGA TTGAGAGCAC CCTGTAATTC TACAACGTTT CTCGATTTCT TCGTTTTATA    6720

CTGTGTGCAA ATAACTTGAT TATCACCTTG TGCCAAGACT TTGACAGCAG TGTTTCTGAT    6780

TTTAGCCTCT CTTTGAATAA CCAGTAGATT GAGGATAGTC CATCCTTTTT GCCGTAGACC    6840

TTCCAGTCCA CCCTCTTGTC CTTGCCAACA AACTCGTTGG GAGGTTGAAT TGATCAGTGT    6900

GTTGTTGTGA ACACGCATCA AGTCTGGTCT TCCATTGTAG TATATAAGAC TTTTCTCAAA    6960

AAATTCATGA GTTCTCTCGA TTAAGGATGG ATAACCTAAG AACTGGCCCA TAACTCGGAA    7020

CACTGGGCCG TTTGATAACT TCCTTTGGTG GTTATTCCAT TTTTCGTAAT CAATGTGATT    7080

GGCTATGCAA ATTGCCTCAT ATGACTTCAA TCCTTGGCCG GATGAGGAAT CTAACATCTT    7140

TTTAATGACT GCAGTTAGAT CGTCCGCCAT TGTCAGGCCT TTAAACATAG GGACGAAATG    7200

AGTCTTTATC AAATATTCGG TAATTACAAA GTATTCTCGC AATTTCCAAG ACATTAGGGA    7260

GAAAAATCTA CCTGCCAACT TCAGTTCCCT CTCCTTTCCT TTAAGACCAA TAATTAGATC    7320

ATCATCATCT AAGCCCTTCT CATCAATCTC TTTAAGAAAT TCTTTCCAAT TGGTAGCCTT    7380

TGTGTCCAAC ATAGTCTGCA ACACCTTTTT ACTAGGGATA GGAGTGTTCG GATTCATTCG    7440

GACATGTTTC AACACCTCTG ACCTATTCAT TGAATGACTT TTGTCAGAGT ATATTATCGA    7500

TGGGTCTAGT AAGTCGGGTA TTTCAAAACA TTTAATCAGC GGAAGTTCAT GCCATTTATC    7560
```

-continued

```
TCCAAAATCT TGAACTTGAG CAGCTGTGGG CCATGTATTT TCTTTAACAT GACTTTTAAA      7620

GGGATGATCA TGAGGGAGCA AGTCTCCATT CACGAACCAC TTTTTATGAT CATTGAACTG      7680

TTGAAATAGA ACAATCCGAG CTAAATCACT TGCAAGTGCT TTTGCATATG ACACATCAAT      7740

ATCTTTCTTC ATGGTTACTT GGGAATGTAA TTTTTCTAGT CCAGTGTAAT AATCTATAAA      7800

AGGATGACCC CAATGTCTGA ACGATCCATA AATCACCAGT GTGAGATCCA CTGTTTTCAC      7860

ACTCATTATC TGATCATGGA GGAATCTTAT ACCTCGGTCA ATTTTTGCCC CTTCATCAAC      7920

AGAAGTCTTG ATATGATTTT CAAAATGAGG GAATTGTGGG ACTAAAGGCC TTGATTCTCT      7980

TGCTAATTTC ATCAGCTTCA AGTTGCATAT CGGTTCCACC ATTTTAATCA AGTCATAAGA      8040

AAAATTTCCC TGCCTCTCCA CAATTTTATC TCCAATTCTG TAGATATTTA GAAGGGAGAA      8100

GATGTCTTGC TCTGAGAACA GGTTGTCTAT TCTACATACC ATGGATAGCA CCGTTTGCAT      8160

CCTCCCTATA ATCACATCTT TGACCATTAA CAGAAAGTTT CGGTCCATTA GAATATCAAG      8220

TTTCTTGAAG TAAGCCCATC CTTCTGAAAT AAAAGTAGGA CCCAAGCTGG GAACCCTAAT      8280

CCTGCATATG TTCGTTCCAT GAGAACTTCT TCTGACTTTG CCTTTGAAAG TCCTCGCCAA      8340

GTTGAGCAAT TCCACCTCAG AGACAGCATT TAAGATTAAT GTCAACTTGT GTAAGTCCAA      8400

AAACTTTTGA CACAAATAAG CGAGAATTTT GAATGAGTCA GTCCATCTTT CCTTTTTGAT      8460

GTATTCAATT GGTTTGTTGC CCCAGCCGCG GATGAAGGTC TCCACCACGT CAAATGTTAT      8520

TTCTGCCTCT TTGTCCACTT CATGTAAAAA ACTATACCCT TGACTGGCAT CATGATTATC      8580

AGACATTAAC CAACTTCCCA TCCATTTATG CATCTGAGAT GTTGAGATGG GATTGGCTTG      8640

ACATGATGTT AACATCTCAA GAACTCCATC CCAGTTCTTA CTATCCCACA TCGAGGGAAT      8700

CGGAAGAGAA TTGAATTTCC TGATCAAATT GTCAATATCA TCACTAATTA GAGGAGAATT      8760

CAAATTGTAA TCAGCATGAT TCAAGTACGT CATGCGCTCA TCGGGATTCA GGAATTCTCT      8820

TGTGGCATAG TCATCTTCAT TGAAATCATT GAACTCGTCG GTCTCAAAAT CGTGGACTTC      8880

CATGATTGCT GTTAGTTTTT TTCATAAAAA TTAAAAACTC AAATATAATT GAGGCCTCTT      8940

TGAGCATGGT ATCACAAGTT GATTTGGTCC AAACATGAAG AATCTGGCTA GCAGGATTTG      9000

AGTTACTTTC CAAGTCGGTT CATCTCTATG TCTGTATAAA TCTGTCTTTT CTTGGTGTGC      9060

TTTAATTTAA TGCAAAGATG GATACCAACT CGGAGAACCA AGAATAGTCC AATGATTAAC      9120

CCTATGATAA AGAAAAAAGA GGCAATAGAG CTTTTCCAAC TACTGAACCA ACCTTCTACA      9180

AGCTCGATTG GATTTTTGGA TAGCCCAGTA TCACCAAAAA ATAAACTCTC ATCATCAGGA      9240

AGTTGCGAAG CAGCGTCTTG AATGTGAGGA TGTTCGAACA CCTGAGCCTT TGAGCTAAGA      9300

TGAAGATCGG AGTCCAACAT ACCATGTCCA ATCATGTATA AAGGAAACTT ATATCCTGAA      9360

CTGGTCCTCA GAACTCCATT GGGTCCAATT TCCACGTCTT CATATGGTGC CCAGTCATCC      9420

CACAGTTCCC TTTCTGTGGT AGTTCCACTG ATCATTCCGA CCATTCTTGA GAGGATTGGA      9480

GCAGCAATAT CGACTCTGAT GTATCTGGTC TCAAAGTATT TTAGGGTACC ATTGATTATG      9540

GTGAAAGCAG GACCGGTTCC TGGGTTTTTA GGAGCAAGAT AGCTGAGATC CACTGGAGAG      9600

ATTGGAAGAC CCGCTCTGAT TTTGCTCCAG GTTTCTTGGC AGAGGGAATA ATCCAAGATC      9660

CTCTCAACGT CCTGAATTAG ACTTACATCC ACTGAGGTCT GAGATGGAGC AGAGATACTT      9720

GACCCTTCTG GGCATTCAGG GAATCTGGCT GCAGCAAAGA GATCCTTATC AGCCATCTCG      9780

AACCAGACAC CTGATGGGAG TCTGACTCCC CAATGCTTGC AGTATTGCAT TTGCAGGCC      9840

TTGCCTCCAG TTTCATAAGC AAAGTAGTTA CTTCTGAACC CTGTGCCCTC CTTTCCCAGG      9900

GATGATAGCT CTCCGTCCTC TGAGAAGAAG GTGATGTCCA TGGAAATGAG GTTAGAATCA      9960
```

```
CATAGCCCTT TGACCTTATA GTCAGAATGC CAGGTTGTAG AGTTATGGAC AGTGGGCAT    10020

ATGTAATTGC TGCATTTTCC GTTGATGAAC TGTGAATCAA CCCATTCTCC TGTGTATTCA   10080

TCAACCAGCA CATGGTGAGG AGTCACCTGG ACAATCACTG CTTCGGCATC CGTCACAGTT   10140

GCATATCCAC AACTTTGAGG AGGGAAGCCT GGATTCAGCC AAGTTCCTTG TTTCGTTTGT   10200

TCAATGCTTT CCTTGCATTG TTCTACAGAT GGAGTGAAGG ATCGGATGGA CTGTGTTATA   10260

TACTTCGGTC CATACCAGCG GAAATCACAA GTAGTGACCC ATTTGGAAGC ATGCACATC    10320

CAACCGTCTG CTTGAATAGC CTTGTGACTC TTGGGCATTT TGACTTGTAT GGCTGTGCCT   10380

ATTAAGTCAT TATGCCAATT TAAATCTGAG CTTGACGGGC AATAATGGTA ATTAGAAGGA   10440

ACATTTTTCC AGTTTCCTTT TTGGTTGTGT GGAAAAACTA TGGTGAACTT GCAATTCACC   10500

CCAATGAATA AAAAGGCTAA GTACAAAAGG CACTTCATAG TGACGCGTAA ACAGATCGAT   10560

CTCTGTTAGT TTTTTTCATA GGGATAGAAA AGACAGGATA TTAGTTGTTC GAGAGGCTGG   10620

AATTAGGAGA GACTGAGTAA ACCGGGGATT GTTCAGAAGC TAGAAGTTAG ACTAGCTCAT   10680

TTGAAGTGGC TGATAGAATC CAGGACCCAC GCTCCAGATG CCTTTTTCTC GACAATCAGG   10740

CCAAACATTA AGGCCTTCTC TCTGAAATCA GAAAATTTGG AAGAATTGAA ATGATCCCAG   10800

ATCATAGGAG CTGCTTCCAG TGACTCATCA TCGTAGATGG TCATTGTGAG CTCAATCGTT   10860

CCCTTGTAAA GACCTATATT GAATGGTCTT CTGAAGTGCT CTGGTACATT GAGCATGGGA   10920

GGGGTCTTCC CCATCCTATG TGGCAAATAA GCCCTGCCTT CGCAGTGAGT GTGATACTCT   10980

GGTTGACCTT GATCTGCCAA TACCGCTGGA GTGGCCTTTA GATTAGAAGA ACCCAAAAAA   11040

GCCAAGATTT TGTAGAAGGG ACGTTTCCCT GCCATTCCGA TGTACATGTG ATCCCAATGG   11100

GATACAGCGG CTGCCACATC TGAGTATGTT CTGAACGGAC GATTAGATCT AACCGTCATT   11160

TTCACTGTAA AGAAGAATTT CTCATATCTT AATTGATTCG GATCATAGGT GTCCATCTCG   11220

TCAACTCCAA AATAGGATTT GTCAATTGGA GCGCTCGGAG CATACTCCAT GCTAGTGTCC   11280

TCTTCATAAG GGGGTGGTGC GATCCCTAAT TTCTTAGATT TCTTACCTTT CCCCTTCAGA   11340

CCGAGAATCT TCTTTAAGGA ACTCATGATG AATGGATTGG GATAACACTT AGATCGTGAT   11400

ATCTGTTACT TTTTTTCATA GTCTACAGAG AATATTTGAC TCTCGCCTGA TTGTACAACT   11460

TTTTGTATCT CAGGCCGAGC AGGATGGCCT CTTTATGAGA CATTCGTCCG TCACCTCCGA   11520

CAGAGATGAA CTCTCCTCTA GATGAGAACA ATTCATCCAA GGATATGGTG AGAGGCTGAA   11580

GACTTGCTTT CTTGGGTTGG AAAGTCATGG ATGTCTTTGA GAGAGACCAA ACATCTGATA   11640

CTGCTTCTGA TTGGGACGGA TGTGTGTTCA TCACTGGAGT GACCTTATAT ACATCCGGAG   11700

TTATCTGGCG CTCCTTCATA ATGACCCCTT CTCCCGATGC TTCAAATGTG CACTCTGCCA   11760

GATTCCAGTA TTTGGCACTT TGCACGACTG CTTTAATCGT CGAAAGCCAC TGGGATTTCT   11820

GCTCTCCACT TAAACCCTCT GGCGATGTCA ACCGTAAGGT CTTTCCATGC TCGTCAGATT   11880

CAAGCTCAGG CTGTTTCCAG TCCGAAGTAA ATACAACATC CACTTCCTCA TCTGCATAGT   11940

CATCTAAAGG CCCCTGTATA AAGCCTTCAA CTTGCTCAGC TTCTGGATCT GGTGCATACA   12000

AACCTTGATT GTCTTCAATT TCTGGTTCAG ATTCTGTGTC AGAATCATCT GCTGCCTGAA   12060

AATAAGAGGG CTTAGTATGC TCTTCCACTC CATCCTCTTG GAACAACTCA TAATTGGACT   12120

TTTCAGCTCG TTGTGCTTCG ATCTCATCTA TCTCTCCTAC CGCCTGATCC AGACGAGAAT   12180

AGGACTTGAG ATACTCACGA ACTTTTGTGA GATTATCCAT GATATCTGTT AGTTTTTTTC   12240

ATATGTAGCA TAATATATAA TAGGTGATCT GAGAATTATA GGGTCATTTG TCAAATTCTG   12300
```

-continued

```
ACTTAGCATA CTTGCCAATT GTCTTCTCTC TTAGGCCTTG CAGTGACATG ACTGCTCTTT    12360

TCGCATACTG CATCATATCA GGAGTCGGTT TTCTGTTTTG ATCTTCAAAC CATCCGAGCC    12420

ATTCGACCAC ATCTCTGCCT TGTGGCGGTG CATTAGTCGT CAATCCTCCG GTACTATCAT    12480

CTGGAGTGTA TTTGTTATCT CCAACACAAA ACTGTTGTGC CAAGTCGGCA GAGGATCCTA    12540

CTGCATAAGC GTACAACAAA CCTGCTGTAG TAAGAGATGT ATACTCAATG TCATCAGGCT    12600

GTCGGGCATT CCTTGCTCTG GTGGATCTGA GCAGAAGAGC TGTCAATTGC CCCCAGAAGT    12660

GGAAGGCAGG GTTTTTGACG GAAGAATATG GAGACTTAGA AGACAATCCA AAGTCGATCA    12720

AATAAGGCAT GTATGAATCG GCCTTGTCAA TTTCTTGGCC TGGAAGCATC ATTTGGACCA    12780

TTTCATCTGC AACTTCTCGG TTCAAGATCC AGGTCGTTAC ATCTTCTGTA GACATTCCGG    12840

TTATTTTGCA GAGGTGTCCA AATGTTGCCA ATGCAGCACA ATCTTTGAAT CTGGAAACAA    12900

TAGTTCCGTA TCTGAACGAG GCACATTCAT GTTTTTTGAA CATGTGGAAG AACATGTCCA    12960

CTGCAGCGAC AATTTTTGTG TAATTACTGT CATTTCCCCA CACATCAAAA ATGTCACGAC    13020

CTTCTGGCAC AAGAGGTTCA AACTGTTCAT TGATCATTTT GCATTGATTT GTCAGCCCAT    13080

CCATGAGCTT TTTTCTGTAT TCAGGCATTT GTGTTCTGCC CACTCTGTAT AAGCCAAGTA    13140

GATACAAAGG CAACCATTTG TCATCTGCGC TGGTTCTGGA AGCATCCGAT ACTCCATCTG    13200

GAAGTACGCC GTCCAGGGCT TTCAAGGATA CAAGGTCAAA TATTCCGATT GTATCCCCTG    13260

CTTTCCCGAT GTTTATTCCG AAACTTGACC AATCTTTATC CAACTTACCC CGGATGTCCT    13320

TTAATGCTCC ATACAAGTAG CTGTTGACAT GTATGATTGA TACATTTCCG GATTTGAGGC    13380

CTTGGTAGAC ATATCCTCTT AGATCTGACA AACTTTTTGT AGTATTGATG TAAAGAGGAA    13440

TCTCCTTTGA TTTTCTGAAG TAATCTGCCG GGTATTCCAC TGGATCCTCA TTTGCAGGAA    13500

GTTTTGGAAC TATGACTGTG TTGTCAATGA TTCTCTTGAC TGTAACAGAC ATTTTGATTA    13560

CTGTTAAAGT TTCTCCTGAG CCTTTTAATG ATAATAATGT TTTGTTTGTC TTCGTCCCTA    13620

TAGTGAGTCG TATTACAACT CGAGGGGGGG CCCGGTACCC AATTCGCCCT ATAGTGAGTC    13680

GTATTACAAT TCACTGGCCG TCGTTTTACA ACGTCGTGAC TGGGAAAACC CTGGCGTTAC    13740

CCAACTTAAT CGCCTTGCAG CACATCCCCC TTTCGCCAGC TGGCGTAATA GCGAAGAGGC    13800

CCGCACCGAT CGCCCTTCCC AACAGTTGCG CAGCCTGAAT GGCGAATGGG ACGCGCCCTG    13860

TAGCGGCGCA TTAAGCGCGG CGGGTGTGGT GGTTACGCGC AGCGTGACCG CTACACTTGC    13920

CAGCGCCCTA GCGCCCGCTC CTTTCGCTTT CTTCCCTTCC TTTCTCGCCA CGTTCGCCGG    13980

CTTTCCCCGT CAAGCTCTAA ATCGGGGGCT CCCTTTAGGG TTCCGATTTA GTGCTTTACG    14040

GCACCTCGAC CCCAAAAAAC TTGATTAGGG TGATGGTTCA CGTAGTGGGC CATCGCCCTG    14100

ATAGACGGTT TTTCGCCCTT TGACGTTGGA GTCCACGTTC TTTAATAGTG GACTCTTGTT    14160

CCAAACTGGA ACAACACTCA ACCCTATCTC GGTCTATTCT TTTGATTTAT AAGGGATTTT    14220

GCCGATTTCG GCCTATTGGT TAAAAAATGA GCTGATTTAA CAAAAATTTA ACGCGAATTT    14280

TAACAAAATA TTAACGCTTA CAATTTAGGT G                                  14311
```

(2) INFORMATION FOR SEQ ID NO:8:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:8:

TTGTAATACG ACTCACTATA GGG                                                   23

(2) INFORMATION FOR SEQ ID NO:9:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:9:

TTGTAATACG ACTCACTATA GGG                                                   23

(2) INFORMATION FOR SEQ ID NO:10:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:10:

ACGAAGACAA ACAAACCATT ATTATCATTA AAAGGCTCAG GAGAAACTTT                       50

(2) INFORMATION FOR SEQ ID NO:11:

(i) SEQUENCE CHARACTERISTICS:
        (A) LENGTH: 136 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:11:

GGCTGCTAAC AAAGCCCGAA AGGAAGCTGA GTTGGCTGCT GCCACCGCTG AGCAATAACT            60

AGCATAACCC CTTGGGGCCT CTAAACGGGT CTTGAGGGGT TTTTTGCTGA AAGGAGGAAC           120

TATATCCGGA TCGAGA                                                          136

(2) INFORMATION FOR SEQ ID NO:12:

(i) SEQUENCE CHARACTERISTICS:
        (A) LENGTH: 83 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:12:

GGGTCGGCAT GGCATCTCCA CCTCCTCGCG GTCCGACCTG GCATCCGAA GGAGGACGTC             60

GTCCACTCGG ATGGCTAAGG GAG                                                   83

(2) INFORMATION FOR SEQ ID NO:13:

(i) SEQUENCE CHARACTERISTICS:
        (A) LENGTH: 630 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:13:

| | | | | | |
|---|---|---|---|---|---|
| TTGTAGAAGG | TTGGTTCAGT | AGTTGGAAAA | GCTCTATTGC | CTCTTTTTTC | TTTATCATAG | 60 |
| GGTTAATCAT | TGGACTATTC | TTGGTTCTCC | GAGTTGGTAT | CCATCTTTGC | ATTAAATTAA | 120 |
| AGCACACCAA | GAAAAGACAG | ATTTATACAG | ACATAGAGAT | GAACCGACTT | GGAAAGTAAC | 180 |
| TCAAATCCTG | CTAGCTATGA | AAAAAACTAA | CAGATATCCA | ACCCGGGAGC | TAGTTGCGGC | 240 |
| CGCCTAGCAG | ATTCTTCATG | TTTGGACCAA | ATCAACTTGT | GATACCATGC | TCAAAGAGGC | 300 |
| CTCAATTATA | TTTGAGTTTT | TAATTTTTAT | GAAAAAAACT | AACAGCAATC | ATGGAAGTCC | 360 |
| ACGATTTTGA | GACCGACGAG | TTCAATGATT | TCAATGAAGA | TGACTATGCC | ACAAGAGAAT | 420 |
| TCCTGAATCC | CGATGAGCGC | ATGACGTACT | TGAATCATGC | TGATTACAAT | TTGAATTCTC | 480 |
| CTCTAATTAG | TGATGATATT | GACAATTTGA | TCAGGAAATT | CAATTCTCTT | CCGATTCCCT | 540 |
| CGATGTGGGA | TAGTAAGAAC | TGGGATGGAG | TTCTTGAGAT | GTTAACATCA | TGTCAAGCCA | 600 |
| ATCCCATCTC | AACATCTCAG | ATGCATAAAT | | | | 630 |

(2) INFORMATION FOR SEQ ID NO:14:

(i) SEQUENCE CHARACTERISTICS:
    (A) LENGTH: 630 base pairs
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO:14:

| | | | | | |
|---|---|---|---|---|---|
| ATTTATGCAT | CTGAGATGTT | GAGATGGGAT | TGGCTTGACA | TGATGTTAAC | ATCTCAAGAA | 60 |
| CTCCATCCCA | GTTCTTACTA | TCCCACATCG | AGGGAATCGG | AAGAGAATTG | AATTTCCTGA | 120 |
| TCAAATTGTC | AATATCATCA | CTAATTAGAG | GAGAATTCAA | ATTGTAATCA | GCATGATTCA | 180 |
| AGTACGTCAT | GCGCTCATCG | GGATTCAGGA | ATTCTCTTGT | GGCATAGTCA | TCTTCATTGA | 240 |
| AATCATTGAA | CTCGTCGGTC | TCAAAATCGT | GGACTTCCAT | GATTGCTGTT | AGTTTTTTTC | 300 |
| ATAAAAATTA | AAAACTCAAA | TATAATTGAG | GCCTCTTTGA | GCATGGTATC | ACAAGTTGAT | 360 |
| TTGGTCCAAA | CATGAAGAAT | CTGCTAGGCG | GCCGCAACTA | GCTCCCGGGT | TGGATATCTG | 420 |
| TTAGTTTTTT | TCATAGCTAG | CAGGATTTGA | GTTACTTTCC | AAGTCGGTTC | ATCTCTATGT | 480 |
| CTGTATAAAT | CTGTCTTTTC | TTGGTGTGCT | TAATTTAAT | GCAAAGATGG | ATACCAACTC | 540 |
| GGAGAACCAA | GAATAGTCCA | ATGATTAACC | CTATGATAAA | GAAAAAGAG | GCAATAGAGC | 600 |
| TTTTCCAACT | ACTGAACCAA | CCTTCTACAA | | | | 630 |

(2) INFORMATION FOR SEQ ID NO:15:

(i) SEQUENCE CHARACTERISTICS:
    (A) LENGTH: 11 base pairs
    (B) TYPE: nucleic acid
    (C) STRANDEDNESS: single
    (D) TOPOLOGY: unknown (ii) MOLECULE TYPE: RNA (xi) SEQUENCE DESCRIPTION: SEQ ID NO:15:

| | |
|---|---|
| UCAGGAGAAA C | 11 |

(2) INFORMATION FOR SEQ ID NO:16:

```
    (i) SEQUENCE CHARACTERISTICS:
        (A) LENGTH: 10 base pairs
        (B) TYPE: nucleic acid
        (C) STRANDEDNESS: single
        (D) TOPOLOGY: unknown (ii) MOLECULE TYPE: RNA (ix) FEATURE:
        (A) NAME/KEY: 5' Gppp
        (B) LOCATION: 1

(xi) SEQUENCE DESCRIPTION: SEQ ID NO:16:

AACAGUAAUC                                                              10

(2) INFORMATION FOR SEQ ID NO:17:

(i) SEQUENCE CHARACTERISTICS:
        (A) LENGTH: 24 base pairs
        (B) TYPE: nucleic acid
        (C) STRANDEDNESS: single
        (D) TOPOLOGY: unknown (ii) MOLECULE TYPE: RNA (xi) SEQUENCE DESCRIPTION: SEQ ID NO:17:

GAUUACUGUU AAAGUUUCUC CUGA                                              24

(2) INFORMATION FOR SEQ ID NO:18:

(i) SEQUENCE CHARACTERISTICS:
        (A) LENGTH: 10 base pairs
        (B) TYPE: nucleic acid
        (C) STRANDEDNESS: single
        (D) TOPOLOGY: unknown (ii) MOLECULE TYPE: RNA (ix) FEATURE:
        (A) NAME/KEY: polyA
        (B) LOCATION: 10

(xi) SEQUENCE DESCRIPTION: SEQ ID NO:18:

GCUACAUAUG                                                              10

(2) INFORMATION FOR SEQ ID NO:19:

(i) SEQUENCE CHARACTERISTICS:
        (A) LENGTH: 10 base pairs
        (B) TYPE: nucleic acid
        (C) STRANDEDNESS: single
        (D) TOPOLOGY: unknown (ii) MOLECULE TYPE: RNA (ix) FEATURE:
        (A) NAME/KEY: 5' Gppp
        (B) LOCATION: 1

(xi) SEQUENCE DESCRIPTION: SEQ ID NO:19:

AACAGAUAUC                                                              10

(2) INFORMATION FOR SEQ ID NO:20:

(i) SEQUENCE CHARACTERISTICS:
        (A) LENGTH: 29 base pairs
        (B) TYPE: nucleic acid
        (C) STRANDEDNESS: single
        (D) TOPOLOGY: unknown (ii) MOLECULE TYPE: RNA
```

(xi) SEQUENCE DESCRIPTION: SEQ ID NO:20:

GAUAUCUGUU AGUUUUUUC AUAUGUAGC                                      29

(2) INFORMATION FOR SEQ ID NO:21:

(i) SEQUENCE CHARACTERISTICS:
        (A) LENGTH: 10 base pairs
        (B) TYPE: nucleic acid
        (C) STRANDEDNESS: single
        (D) TOPOLOGY: unknown (ii) MOLECULE TYPE: RNA (ix) FEATURE:
        (A) NAME/KEY: polyA
        (B) LOCATION: 10

(xi) SEQUENCE DESCRIPTION: SEQ ID NO:21:

GUAGACUAUG                                                          10

(2) INFORMATION FOR SEQ ID NO:22:

(i) SEQUENCE CHARACTERISTICS:
        (A) LENGTH: 10 base pairs
        (B) TYPE: nucleic acid
        (C) STRANDEDNESS: single
        (D) TOPOLOGY: unknown (ii) MOLECULE TYPE: RNA (ix) FEATURE:
        (A) NAME/KEY: 5' Gppp
        (B) LOCATION: 1

(xi) SEQUENCE DESCRIPTION: SEQ ID NO:22:

AACAGAUAUC                                                          10

(2) INFORMATION FOR SEQ ID NO:23:

(i) SEQUENCE CHARACTERISTICS:
        (A) LENGTH: 29 base pairs
        (B) TYPE: nucleic acid
        (C) STRANDEDNESS: single
        (D) TOPOLOGY: unknown (ii) MOLECULE TYPE: RNA (xi) SEQUENCE DESCRIPTION: SEQ ID NO:23:

GAUAUCUGUU ACUUUUUUC AUAGUCUAC                                      29

(2) INFORMATION FOR SEQ ID NO:24:

(i) SEQUENCE CHARACTERISTICS:
        (A) LENGTH: 10 base pairs
        (B) TYPE: nucleic acid
        (C) STRANDEDNESS: single
        (D) TOPOLOGY: unknown (ii) MOLECULE TYPE: RNA (ix) FEATURE:
        (A) NAME/KEY: polyA
        (B) LOCATION: 10

(xi) SEQUENCE DESCRIPTION: SEQ ID NO:24:

UAUCCCUAUG                                                          10

(2) INFORMATION FOR SEQ ID NO:25:

(i) SEQUENCE CHARACTERISTICS:
            (A) LENGTH: 10 base pairs
            (B) TYPE: nucleic acid
            (C) STRANDEDNESS: single
            (D) TOPOLOGY: unknown (ii) MOLECULE TYPE: RNA (ix) FEATURE:
            (A) NAME/KEY: 5' Gppp
            (B) LOCATION: 1

(xi) SEQUENCE DESCRIPTION: SEQ ID NO:25:

AACAGAGAUC                                                                  10

(2) INFORMATION FOR SEQ ID NO:26:

(i) SEQUENCE CHARACTERISTICS:
            (A) LENGTH: 29 base pairs
            (B) TYPE: nucleic acid
            (C) STRANDEDNESS: single
            (D) TOPOLOGY: unknown (ii) MOLECULE TYPE: RNA (xi) SEQUENCE DESCRIPTION: SEQ ID NO:26:

GAUCUCUGUU AGUUUUUUUC AUAGGGAUA                                             29

(2) INFORMATION FOR SEQ ID NO:27:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: RNA (ix) FEATURE:
            (A) NAME/KEY: polyA
            (B) LOCATION: 10

(xi) SEQUENCE DESCRIPTION: SEQ ID NO:27:

AAUUUUUAUG                                                                  10

(2) INFORMATION FOR SEQ ID NO:28:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: RNA (ix) FEATURE:
            (A) NAME/KEY: 5' Gppp
            (B) LOCATION: 1

(xi) SEQUENCE DESCRIPTION: SEQ ID NO:28:

AACAGCAAUC                                                                  10

(2) INFORMATION FOR SEQ ID NO:29:

(i) SEQUENCE CHARACTERISTICS:
            (A) LENGTH: 29 base pairs
            (B) TYPE: nucleic acid
            (C) STRANDEDNESS: single
            (D) TOPOLOGY: unknown

```
    (ii) MOLECULE TYPE: RNA (xi) SEQUENCE DESCRIPTION: SEQ ID NO:29:

GAUUGCUGUU AGUUUUUUC AUAAAAAUU                                              29

(2) INFORMATION FOR SEQ ID NO:30:

(i) SEQUENCE CHARACTERISTICS:
        (A) LENGTH: 10 base pairs
        (B) TYPE: nucleic acid
        (C) STRANDEDNESS: single
        (D) TOPOLOGY: unknown (ii) MOLECULE TYPE: RNA (ix) FEATURE:
        (A) NAME/KEY: polyA
        (B) LOCATION: 10

(xi) SEQUENCE DESCRIPTION: SEQ ID NO:30:

UUUAAGUAUG                                                                  10

(2) INFORMATION FOR SEQ ID NO:31:

(i) SEQUENCE CHARACTERISTICS:
        (A) LENGTH: 27 base pairs
        (B) TYPE: nucleic acid
        (C) STRANDEDNESS: single
        (D) TOPOLOGY: unknown (ii) MOLECULE TYPE: RNA (xi) SEQUENCE DESCRIPTION: SEQ ID NO:31:

AGGAUCAAAG UUUUUUUCAU ACUUAAA                                               27

(2) INFORMATION FOR SEQ ID NO:32:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:32:

CATTCAAGAC GCTGCTTCGC AACTTCC                                               27

(2) INFORMATION FOR SEQ ID NO:33:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:33:

CATGAATGTT AACATCTCAA GA                                                    22

(2) INFORMATION FOR SEQ ID NO:34:

(i) SEQUENCE CHARACTERISTICS:
        (A) LENGTH: 23 base pairs
        (B) TYPE: nucleic acid
        (C) STRANDEDNESS: single
        (D) TOPOLOGY: linear
```

(ii) MOLECULE TYPE: RNA (ix) FEATURE:
            (A) NAME/KEY: miscellaneous feature
            (B) LOCATION: 11..12
            (D) OTHER INFORMATION: Intergenic dinucleotide (xi) SEQUENCE DESCRIPTION: SEQ ID NO:34:

GAUNNCUGUU ANUUUUUUC AUA                                           23

(2) INFORMATION FOR SEQ ID NO:35:

(i) SEQUENCE CHARACTERISTICS:
            (A) LENGTH: 11 base pairs
            (B) TYPE: nucleic acid
            (C) STRANDEDNESS: single
            (D) TOPOLOGY: unknown (ii) MOLECULE TYPE: RNA (xi) SEQUENCE DESCRIPTION: SEQ ID NO:35:

UAUGAAAAAA A                                                        11

(2) INFORMATION FOR SEQ ID NO:36:

(i) SEQUENCE CHARACTERISTICS:
            (A) LENGTH: 11 base pairs
            (B) TYPE: nucleic acid
            (C) STRANDEDNESS: single
            (D) TOPOLOGY: unknown (ii) MOLECULE TYPE: RNA (xi) SEQUENCE DESCRIPTION: SEQ ID NO:36:

UUUUUUUCAU A                                                        11

(2) INFORMATION FOR SEQ ID NO:37:

(i) SEQUENCE CHARACTERISTICS:
            (A) LENGTH: 11 base pairs
            (B) TYPE: nucleic acid
            (C) STRANDEDNESS: single
            (D) TOPOLOGY: unknown (ii) MOLECULE TYPE: DNA (xi) SEQUENCE DESCRIPTION: SEQ ID NO:37:

TATGAAAAAA A                                                        11

(2) INFORMATION FOR SEQ ID NO:38:

(i) SEQUENCE CHARACTERISTICS:
            (A) LENGTH: 59 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:38:

CCGGCTCGAG TTGTAATACG ACTCACTATA GGGACGAAGA CAAACAAACC ATTATTATC    59

(2) INFORMATION FOR SEQ ID NO:39:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:39:

GAACTCTCCT CTAGATGAGA AC                                                    22

(2) INFORMATION FOR SEQ ID NO:40:

(i) SEQUENCE CHARACTERISTICS:
         (A) LENGTH: 58 base pairs
         (B) TYPE: nucleic acid
         (C) STRANDEDNESS: single
         (D) TOPOLOGY: linear (ii) MOLECULE TYPE: DNA (xi) SEQUENCE DESCRIPTION: SEQ ID NO:40:

AGGTCGGACC GCGAGGAGGT GGAGATGCCA TGCCGACCCA CGAAGACCAC AAAACCAG             58

(2) INFORMATION FOR SEQ ID NO:41:

(i) SEQUENCE CHARACTERISTICS:
         (A) LENGTH: 22 base pairs
         (B) TYPE: nucleic acid
         (C) STRANDEDNESS: single
         (D) TOPOLOGY: linear (ii) MOLECULE TYPE: DNA (xi) SEQUENCE DESCRIPTION: SEQ ID NO:41:

ATGTTGAAGA GTGACCTACA CG                                                    22

(2) INFORMATION FOR SEQ ID NO:42:

(i) SEQUENCE CHARACTERISTICS:
         (A) LENGTH: 11 base pairs
         (B) TYPE: nucleic acid
         (C) STRANDEDNESS: single
         (D) TOPOLOGY: unknown (ii) MOLECULE TYPE: RNA (ix) FEATURE:
         (A) NAME/KEY: modified_base
         (B) LOCATION: 1
         (D) OTHER INFORMATION: /mod_base= m7g  /note= "The
             7-methylguanosine has three phosphates attached to
             it."

(xi) SEQUENCE DESCRIPTION: SEQ ID NO:42:

NAACAGNNAU C                                                                11

(2) INFORMATION FOR SEQ ID NO:43:

(i) SEQUENCE CHARACTERISTICS:
         (A) LENGTH: 42 base pairs
         (B) TYPE: nucleic acid
         (C) STRANDEDNESS: single
         (D) TOPOLOGY: unknown (ii) MOLECULE TYPE: DNA (xi) SEQUENCE DESCRIPTION: SEQ ID NO:43:

GCTCCCCCGG GCTCGAGAAA ATGGAGAAGA AAATCACTGG AT                              42

(2) INFORMATION FOR SEQ ID NO:44:

(i) SEQUENCE CHARACTERISTICS:
         (A) LENGTH: 38 base pairs

-continued

```
        (B) TYPE: nucleic acid
        (C) STRANDEDNESS: single
        (D) TOPOLOGY: unknown (ii) MOLECULE TYPE: DNA (xi) SEQUENCE DESCRIPTION: SEQ ID NO:44:

GCGGCCGCTC TAGATTACGC CCCGCCCGCC CTGCCACT                                      38
```